(12) United States Patent
Bojarski et al.

(10) Patent No.: US 8,771,365 B2
(45) Date of Patent: Jul. 8, 2014

(54) PATIENT-ADAPTED AND IMPROVED ORTHOPEDIC IMPLANTS, DESIGNS, AND RELATED TOOLS

(75) Inventors: Raymond A. Bojarski, Attleboro, MA (US); Philipp Lang, Lexington, MA (US); Nam Chao, Marlborough, MA (US); Wolfgang Fitz, Sherborn, MA (US); John Slamin, Wrentham, MA (US); Daniel Steines, Lexington, MA (US); Thomas Minas, Dover, MA (US)

(73) Assignee: ConforMIS, Inc., Bedford, MA (US)

( * ) Notice: Subject to any disclaimer, the term of this patent is extended or adjusted under 35 U.S.C. 154(b) by 50 days.

(21) Appl. No.: 12/821,301

(22) Filed: Jun. 23, 2010

(65) Prior Publication Data

US 2011/0029091 A1  Feb. 3, 2011

Related U.S. Application Data

(63) Continuation-in-part of application No. 12/660,529, filed on Feb. 25, 2010.

(60) Provisional application No. 61/269,405, filed on Jun. 24, 2009, provisional application No. 61/220,726, filed on Jun. 26, 2009, provisional application No. 61/273,216, filed on Jul. 31, 2009, provisional application No. 61/275,174, filed on Aug. 26, 2009, provisional application No. 61/280,493, filed on Nov. 4, 2009, provisional application No. 61/284,458, filed on Dec. 18, 2009, provisional application No. 61/155,362, filed on Feb. 25, 2009.

(51) Int. Cl.
*A61F 2/38* (2006.01)

(52) U.S. Cl.
USPC ..................... 623/20.32; 606/86 R

(58) Field of Classification Search
USPC ............ 623/20.21, 20.32, 20.33, 20.34, 20.3, 623/13.11, 13.14; 606/86 R
See application file for complete search history.

(56) References Cited

U.S. PATENT DOCUMENTS

| 3,314,420 | A | 4/1967 | Smith et al. ..................... 128/92 |
| 3,605,123 | A | 9/1971 | Hahn .................................. 3/1 |

(Continued)

FOREIGN PATENT DOCUMENTS

| CN | 86209787 | 11/1987 | ................ A61F 2/38 |
| CN | 2305966 | 2/1999 | ................ A61F 2/28 |

(Continued)

OTHER PUBLICATIONS

European Patent Office, Extended European Search Report—European Application No. 09717686.1-2310 dated Mar. 6, 2012, 7 pages.

(Continued)

*Primary Examiner* — Pedro Philogene
(74) *Attorney, Agent, or Firm* — Sunstein Kann Murphy & Timbers LLP

(57) ABSTRACT

Methods and devices are disclosed relating improved articular models, implant components, and related guide tools and procedures. In addition, methods and devices are disclosed relating articular models, implant components, and/or related guide tools and procedures that include one or more features derived from patient-data, for example, images of the patient's joint. The data can be used to create a model for analyzing a patient's joint and to devise and evaluate a course of corrective action. The data also can be used to create patient-adapted implant components and related tools and procedures.

66 Claims, 42 Drawing Sheets

(56) References Cited

U.S. PATENT DOCUMENTS

| | | | |
|---|---|---|---|
| 3,694,820 A | 10/1972 | Scales et al. ............................ 3/1 |
| 3,798,679 A | 3/1974 | Ewald ..................................... 3/1 |
| 3,808,606 A | 5/1974 | Tronzo ................................... 3/1 |
| 3,816,855 A | 6/1974 | Saleh ...................................... 3/1 |
| 3,843,975 A | 10/1974 | Tronzo ................................... 3/1 |
| 3,852,830 A | 12/1974 | Marmor ................................. 3/1 |
| 3,855,638 A | 12/1974 | Pilliar ................................... 3/1 |
| 3,938,198 A | 2/1976 | Kahn et al. ......................... 3/1.912 |
| 3,987,499 A | 10/1976 | Scharbach et al. ................. 3/1.91 |
| 3,991,425 A | 11/1976 | Martin et al. ....................... 3/1.91 |
| 4,052,753 A | 10/1977 | Dedo ..................................... 3/1 |
| 4,055,862 A | 11/1977 | Farling ............................... 3/1.91 |
| 4,085,466 A | 4/1978 | Goodfellow et al. ............. 3/1.91 |
| 4,098,626 A | 7/1978 | Graham et al. ................... 149/19.4 |
| 4,164,793 A | 8/1979 | Swanson ............................ 3/1.91 |
| 4,178,641 A | 12/1979 | Grundei et al. ................. 3/1.911 |
| 4,203,444 A | 5/1980 | Bonnell et al. ................... 128/276 |
| 4,207,627 A * | 6/1980 | Cloutier ....................... 623/20.21 |
| 4,211,228 A | 7/1980 | Cloutier .......................... 128/303 R |
| 4,213,816 A | 7/1980 | Morris .............................. 156/245 |
| 4,219,893 A | 9/1980 | Noiles ............................... 3/1.911 |
| 4,280,231 A | 7/1981 | Swanson ............................ 3/1.91 |
| 4,309,778 A | 1/1982 | Buechel et al. .................. 3/1.911 |
| 4,340,978 A | 7/1982 | Buechel et al. .................. 3/1.911 |
| 4,344,193 A | 8/1982 | Kenny .............................. 3/1.911 |
| 4,368,040 A | 1/1983 | Weissman .......................... 433/36 |
| 4,436,684 A | 3/1984 | White ................................ 264/138 |
| 4,459,985 A | 7/1984 | McKay et al. ............... 128/303 R |
| 4,502,161 A | 3/1985 | Wall .................................. 3/1.91 |
| 4,575,805 A | 3/1986 | Moermann et al. ............. 364/474 |
| 4,586,496 A | 5/1986 | Keller ............................. 128/92 E |
| 4,594,380 A | 6/1986 | Chapin et al. .................... 524/144 |
| 4,601,290 A | 7/1986 | Effron et al. ..................... 128/305 |
| 4,609,551 A | 9/1986 | Caplan et al. ...................... 424/95 |
| 4,627,853 A | 12/1986 | Campbell et al. .................. 623/16 |
| 4,655,227 A | 4/1987 | Gracovetsky ..................... 128/781 |
| 4,699,156 A | 10/1987 | Gracovetsky ..................... 128/781 |
| 4,714,472 A | 12/1987 | Averill et al. ...................... 623/20 |
| 4,714,474 A | 12/1987 | Brooks, Jr. et al. ............... 623/20 |
| 4,769,040 A | 9/1988 | Wevers .............................. 623/20 |
| 4,813,436 A | 3/1989 | Au .................................... 128/779 |
| 4,822,365 A | 4/1989 | Walker et al. ..................... 623/20 |
| 4,823,807 A | 4/1989 | Russell et al. ................... 128/773 |
| 4,846,835 A | 7/1989 | Grande .............................. 623/11 |
| 4,865,607 A | 9/1989 | Witzel et al. ..................... 623/20 |
| 4,872,452 A | 10/1989 | Alexson ........................ 128/92 VJ |
| 4,880,429 A | 11/1989 | Stone ................................. 623/18 |
| 4,883,488 A | 11/1989 | Bloebaum et al. |
| 4,888,021 A | 12/1989 | Forte et al. ........................ 623/20 |
| 4,936,853 A | 6/1990 | Fabian et al. ...................... 623/20 |
| 4,936,862 A | 6/1990 | Walker et al. ..................... 623/23 |
| 4,944,757 A | 7/1990 | Martinez et al. .................. 623/20 |
| 5,019,103 A | 5/1991 | Van Zile et al. .................. 623/20 |
| 5,021,061 A | 6/1991 | Wevers et al. .................... 623/20 |
| 5,041,138 A | 8/1991 | Vacanti et al. .................... 623/16 |
| 5,047,057 A | 9/1991 | Lawes ............................... 623/20 |
| 5,059,216 A | 10/1991 | Winters ............................. 623/20 |
| 5,067,964 A | 11/1991 | Richmond et al. ............... 623/18 |
| 5,099,859 A | 3/1992 | Bell .................................. 128/781 |
| 5,108,452 A | 4/1992 | Fallin et al. ....................... 623/23 |
| 5,123,927 A | 6/1992 | Duncan et al. .................... 623/20 |
| 5,129,908 A | 7/1992 | Peterson ............................ 606/88 |
| 5,133,759 A | 7/1992 | Turner ............................... 623/20 |
| 5,150,304 A | 9/1992 | Berchem et al. ............. 364/474.24 |
| 5,154,178 A | 10/1992 | Shah ............................. 128/653.2 |
| 5,162,430 A | 11/1992 | Rhee et al. ..................... 525/54.1 |
| 5,171,244 A | 12/1992 | Caspari et al. .................... 606/88 |
| 5,171,322 A | 12/1992 | Kenny ............................... 623/18 |
| 5,197,985 A | 3/1993 | Caplan et al. ..................... 623/16 |
| 5,206,023 A | 4/1993 | Hunziker ......................... 424/423 |
| 5,226,914 A | 7/1993 | Caplan et al. ..................... 623/16 |
| 5,234,433 A | 8/1993 | Bert et al. .......................... 606/88 |
| 5,245,282 A | 9/1993 | Mugler, III et al. ............. 324/309 |
| 5,246,013 A | 9/1993 | Frank et al. ...................... 128/774 |
| 5,246,530 A | 9/1993 | Bugle et al. ...................... 156/643 |
| 5,270,300 A | 12/1993 | Hunziker ........................... 514/12 |
| 5,274,565 A | 12/1993 | Reuben ........................ 364/474.24 |
| 5,282,868 A | 2/1994 | Bahler .............................. 623/20 |
| 5,288,797 A | 2/1994 | Khalil et al. ..................... 524/872 |
| 5,303,148 A | 4/1994 | Mattson et al. ............ 364/413.01 |
| 5,306,307 A | 4/1994 | Senter et al. ...................... 623/17 |
| 5,306,311 A | 4/1994 | Stone et al. ....................... 623/18 |
| 5,314,478 A | 5/1994 | Oka et al. .......................... 623/18 |
| 5,314,482 A | 5/1994 | Goodfellow et al. ............. 623/20 |
| 5,320,102 A | 6/1994 | Paul et al. ..................... 128/653.2 |
| 5,326,363 A | 7/1994 | Aikins ............................... 623/20 |
| 5,326,365 A | 7/1994 | Alvine ............................... 623/21 |
| 5,344,459 A | 9/1994 | Swartz .............................. 623/18 |
| 5,360,446 A | 11/1994 | Kennedy ........................... 623/16 |
| 5,365,996 A | 11/1994 | Crook ............................... 164/45 |
| 5,368,858 A | 11/1994 | Hunziker ......................... 424/423 |
| 5,403,319 A | 4/1995 | Matsen, III et al. .............. 606/88 |
| 5,413,116 A | 5/1995 | Radke et al. ..................... 128/777 |
| 5,423,828 A | 6/1995 | Benson ............................ 606/102 |
| 5,433,215 A | 7/1995 | Athanasiou et al. ............ 128/774 |
| 5,445,152 A | 8/1995 | Bell ............................. 128/653.5 |
| 5,448,489 A | 9/1995 | Reuben ........................ 364/474.05 |
| 5,468,787 A | 11/1995 | Braden et al. ................... 523/113 |
| 5,478,739 A | 12/1995 | Slivka et al. ............... 435/240.23 |
| 5,489,309 A | 2/1996 | Lackey et al. .................... 623/19 |
| 5,501,687 A | 3/1996 | Willert et al. ..................... 606/94 |
| 5,503,162 A | 4/1996 | Athanasiou et al. ............ 128/774 |
| 5,507,820 A | 4/1996 | Pappas .............................. 623/20 |
| 5,510,121 A | 4/1996 | Rhee et al. ...................... 424/520 |
| 5,522,900 A | 6/1996 | Hollister ........................... 623/18 |
| 5,523,843 A | 6/1996 | Yamane et al. ................. 356/363 |
| 5,541,515 A | 7/1996 | Tsujita ............................. 324/318 |
| 5,549,690 A | 8/1996 | Hollister et al. .................. 623/21 |
| 5,554,190 A | 9/1996 | Draenert .......................... 623/16 |
| 5,556,432 A | 9/1996 | Kubein-Meesenburg et al. ..................................... 623/20 |
| 5,560,096 A | 10/1996 | Stephens .......................... 29/558 |
| 5,564,437 A | 10/1996 | Bainville et al. ............... 128/774 |
| 5,571,191 A | 11/1996 | Fitz .................................... 623/17 |
| 5,571,205 A | 11/1996 | James ................................ 623/24 |
| 5,609,640 A | 3/1997 | Johnson ............................ 623/20 |
| 5,611,802 A | 3/1997 | Samuelson et al. .............. 606/86 |
| 5,616,146 A | 4/1997 | Murray ............................. 606/80 |
| 5,632,745 A | 5/1997 | Schwartz .......................... 606/75 |
| 5,671,741 A | 9/1997 | Lang et al. .................. 128/653.2 |
| 5,681,354 A | 10/1997 | Eckhoff ............................ 623/20 |
| 5,682,886 A | 11/1997 | Delp et al. .................. 128/653.1 |
| 5,683,466 A | 11/1997 | Vitale ................................ 623/18 |
| 5,683,468 A | 11/1997 | Pappas .............................. 623/20 |
| 5,684,562 A | 11/1997 | Fujieda ............................ 351/212 |
| 5,687,210 A | 11/1997 | Maitrejean et al. .............. 378/57 |
| 5,690,635 A | 11/1997 | Matsen, III et al. .............. 606/88 |
| 5,702,463 A | 12/1997 | Pothier et al. .................... 623/20 |
| 5,702,464 A | 12/1997 | Lackey et al. .................... 623/20 |
| 5,723,331 A | 3/1998 | Tubo et al. ....................... 435/366 |
| 5,728,162 A | 3/1998 | Eckhoff ............................ 623/20 |
| 5,735,277 A | 4/1998 | Schuster ..................... 128/653.1 |
| 5,749,362 A | 5/1998 | Funda et al. ................ 128/653.1 |
| 5,749,874 A | 5/1998 | Schwartz .......................... 606/75 |
| 5,749,876 A | 5/1998 | Duvillier et al. ................. 606/88 |
| 5,759,205 A | 6/1998 | Valentini .......................... 623/16 |
| 5,768,134 A | 6/1998 | Swaelens et al. ........... 364/468.28 |
| 5,769,899 A | 6/1998 | Schwartz et al. ................. 623/18 |
| 5,772,595 A | 6/1998 | Votruba et al. .................. 600/415 |
| 5,779,651 A | 7/1998 | Buschmann et al. ........... 600/587 |
| 5,786,217 A | 7/1998 | Tubo et al. ....................... 435/402 |
| 5,810,006 A | 9/1998 | Votruba et al. .............. 128/653.2 |
| 5,824,085 A | 10/1998 | Sahay et al. ...................... 623/16 |
| 5,824,102 A | 10/1998 | Buscayret ......................... 623/20 |
| 5,827,289 A | 10/1998 | Reiley et al. ..................... 606/86 |
| 5,832,422 A | 11/1998 | Wiedenhoefer ................. 702/154 |
| 5,835,619 A | 11/1998 | Morimoto et al. .............. 382/132 |
| 5,842,477 A | 12/1998 | Naughton et al. ............... 128/898 |
| 5,847,804 A | 12/1998 | Sarver et al. .................... 351/206 |
| 5,853,746 A | 12/1998 | Hunziker ......................... 424/426 |
| 5,871,018 A | 2/1999 | Delp et al. ....................... 128/898 |
| 5,871,540 A | 2/1999 | Weissman et al. ................ 623/20 |
| 5,871,542 A | 2/1999 | Goodfellow et al. ............. 623/20 |
| 5,871,546 A | 2/1999 | Colleran et al. .................. 623/20 |

(56) References Cited

U.S. PATENT DOCUMENTS

| | | | |
|---|---|---|---|
| 5,879,390 A | 3/1999 | Kubein-Meesenburg et al. ............... 623/20 |
| 5,880,976 A | 3/1999 | DiGioia, III et al. ......... 364/578 |
| 5,885,296 A | 3/1999 | Masini ........................... 606/86 |
| 5,885,298 A | 3/1999 | Herrington et al. ............. 606/88 |
| 5,897,559 A | 4/1999 | Masini ........................... 606/86 |
| 5,899,859 A | 5/1999 | Votruba et al. ................ 600/415 |
| 5,900,245 A | 5/1999 | Sawhney et al. .............. 424/426 |
| 5,906,643 A | 5/1999 | Walker ........................... 623/20 |
| 5,906,934 A | 5/1999 | Grande et al. ................ 435/325 |
| 5,913,821 A | 6/1999 | Farese et al. ................. 600/425 |
| 5,916,220 A | 6/1999 | Masini ........................... 606/88 |
| 5,928,945 A | 7/1999 | Seliktar et al. ............... 435/395 |
| 5,939,323 A | 8/1999 | Valentini et al. .............. 435/395 |
| 5,957,979 A | 9/1999 | Beckman et al. ............... 623/20 |
| 5,961,523 A | 10/1999 | Masini ........................... 606/86 |
| 5,968,051 A | 10/1999 | Luckman et al. .............. 606/88 |
| 5,968,099 A | 10/1999 | Badorf et al. ................... 623/20 |
| 5,972,385 A | 10/1999 | Liu et al. ...................... 424/486 |
| 5,995,738 A | 11/1999 | DiGioia, III et al. .... 395/500.32 |
| 6,002,859 A | 12/1999 | DiGioia, III et al. .... 395/500.32 |
| 6,013,103 A | 1/2000 | Kaufman et al. ................ 623/20 |
| 6,046,379 A | 4/2000 | Stone et al. ..................... 623/11 |
| 6,057,927 A | 5/2000 | Levesque et al. ......... 356/432 T |
| 6,078,680 A | 6/2000 | Yoshida et al. ............... 382/128 |
| 6,081,577 A | 6/2000 | Webber ........................... 378/23 |
| 6,082,364 A | 7/2000 | Balian et al. .................. 128/898 |
| 6,090,144 A | 7/2000 | Letot et al. ...................... 623/20 |
| 6,093,204 A | 7/2000 | Stone ......................... 623/14.12 |
| 6,102,916 A | 8/2000 | Masini ........................... 606/88 |
| 6,102,955 A | 8/2000 | Mendes et al. .................. 623/20 |
| 6,110,209 A | 8/2000 | Stone ......................... 623/16.11 |
| 6,112,109 A | 8/2000 | D'Urso .......................... 600/407 |
| 6,120,541 A | 9/2000 | Johnson ..................... 623/14.12 |
| 6,120,543 A | 9/2000 | Kubein-Meesenburg et al. ............... 623/20 |
| 6,126,690 A | 10/2000 | Ateshian et al. ................ 623/18 |
| 6,139,578 A | 10/2000 | Lee et al. .................... 623/16.11 |
| 6,146,422 A | 11/2000 | Lawson ..................... 623/17.16 |
| 6,151,521 A | 11/2000 | Guo et al. ..................... 600/407 |
| 6,152,960 A | 11/2000 | Pappas ....................... 623/20.31 |
| 6,156,069 A | 12/2000 | Amstutz ..................... 623/22.11 |
| 6,161,080 A | 12/2000 | Aouni-Ateshian et al. ..... 703/11 |
| 6,162,208 A | 12/2000 | Hipps ............................... 606/1 |
| 6,165,221 A | 12/2000 | Schmotzer ................. 623/20.11 |
| 6,171,340 B1 | 1/2001 | McDowell .................. 623/18.11 |
| 6,175,655 B1 | 1/2001 | George, III et al. ........... 382/257 |
| 6,178,225 B1 | 1/2001 | Zur et al. ..................... 378/98.2 |
| 6,187,010 B1 | 2/2001 | Masini ........................... 606/86 |
| 6,197,064 B1 | 3/2001 | Haines et al. .............. 623/20.31 |
| 6,197,325 B1 | 3/2001 | MacPhee et al. ............. 424/426 |
| 6,200,606 B1 | 3/2001 | Peterson et al. .............. 424/574 |
| 6,203,576 B1 | 3/2001 | Afriat et al. ................ 623/20.27 |
| 6,205,411 B1 | 3/2001 | DiGioia, III et al. ........... 703/11 |
| 6,206,927 B1 | 3/2001 | Fell et al. .................... 623/20.29 |
| 6,214,369 B1 | 4/2001 | Grande et al. ................ 424/423 |
| 6,217,894 B1 | 4/2001 | Sawhney et al. .............. 424/426 |
| 6,219,571 B1 | 4/2001 | Hargreaves et al. .......... 600/410 |
| 6,224,632 B1 | 5/2001 | Pappas et al. .............. 623/20.34 |
| 6,235,060 B1 | 5/2001 | Kubein-Meesenburg et al. ............... 623/20.31 |
| 6,249,692 B1 | 6/2001 | Cowin .......................... 600/407 |
| 6,251,143 B1 | 6/2001 | Schwartz et al. ........... 623/23.72 |
| 6,254,639 B1 | 7/2001 | Peckitt ....................... 623/11.11 |
| 6,261,296 B1 | 7/2001 | Aebi et al. ...................... 606/90 |
| 6,277,151 B1 | 8/2001 | Lee et al. .................... 623/23.61 |
| 6,281,195 B1 | 8/2001 | Rueger et al. .................. 514/21 |
| 6,283,980 B1 | 9/2001 | Vibe-Hansen et al. ........ 606/151 |
| 6,289,115 B1 | 9/2001 | Takeo .......................... 382/130 |
| 6,289,753 B1 | 9/2001 | Basser et al. ................... 73/866 |
| 6,299,645 B1 | 10/2001 | Ogden ....................... 623/20.21 |
| 6,299,905 B1 | 10/2001 | Peterson et al. .............. 424/486 |
| 6,302,582 B1 | 10/2001 | Nord et al. .................... 378/207 |
| 6,310,477 B1 | 10/2001 | Schneider .................... 324/307 |
| 6,310,619 B1 | 10/2001 | Rice ............................. 345/420 |
| 6,316,153 B1 | 11/2001 | Goodman et al. ................. 430/8 |
| 6,319,712 B1 | 11/2001 | Meenen et al. ............... 435/395 |
| 6,322,588 B1 | 11/2001 | Ogle et al. .................... 623/1.46 |
| 6,328,765 B1 | 12/2001 | Hardwick et al. .......... 623/23.72 |
| 6,334,006 B1 | 12/2001 | Tanabe ........................... 385/12 |
| 6,334,066 B1 | 12/2001 | Rupprecht et al. ............ 600/411 |
| 6,342,075 B1 | 1/2002 | MacArthur ................ 623/20.14 |
| 6,344,043 B1 | 2/2002 | Pappas ........................... 606/96 |
| 6,344,059 B1 | 2/2002 | Krakovits et al. .......... 623/20.31 |
| 6,352,558 B1 | 3/2002 | Spector ...................... 623/18.11 |
| 6,358,253 B1 | 3/2002 | Torrie et al. ..................... 606/96 |
| 6,365,405 B1 | 4/2002 | Salzmann et al. ............. 435/366 |
| 6,371,958 B1 | 4/2002 | Overaker ........................ 606/72 |
| 6,373,250 B1 | 4/2002 | Tsoref et al. .................. 324/309 |
| 6,375,658 B1 | 4/2002 | Hangody et al. ................ 606/80 |
| 6,379,367 B1 | 4/2002 | Vibe-Hansen et al. ........ 606/151 |
| 6,379,388 B1 | 4/2002 | Ensign et al. ............... 623/20.34 |
| 6,382,028 B1 | 5/2002 | Wooh et al. ..................... 73/602 |
| 6,383,228 B1 | 5/2002 | Schmotzer ................. 623/23.35 |
| 6,387,131 B1 | 5/2002 | Miehlke et al. ............. 623/20.15 |
| 6,429,013 B1 | 8/2002 | Halvorsen et al. ............. 435/377 |
| 6,443,988 B2 | 9/2002 | Felt et al. .................... 623/17.12 |
| 6,443,991 B1 | 9/2002 | Running .................... 623/20.27 |
| 6,444,222 B1 | 9/2002 | Asculai et al. ................. 424/484 |
| 6,450,978 B1 | 9/2002 | Brosseau et al. .............. 600/595 |
| 6,459,948 B1 | 10/2002 | Ateshian et al. .............. 700/117 |
| 6,468,314 B2 | 10/2002 | Schwartz et al. ........... 623/23.72 |
| 6,479,996 B1 | 11/2002 | Hoogeveen et al. .......... 324/309 |
| 6,482,209 B1 | 11/2002 | Engh et al. ...................... 606/79 |
| 6,510,334 B1 | 1/2003 | Schuster et al. .............. 600/407 |
| 6,514,514 B1 | 2/2003 | Atkinson et al. .............. 424/423 |
| 6,520,964 B2 | 2/2003 | Tallarida et al. .............. 396/567 |
| 6,533,737 B1 | 3/2003 | Brosseau et al. .............. 600/595 |
| 6,556,855 B2 | 4/2003 | Thesen ......................... 600/419 |
| 6,558,421 B1 | 5/2003 | Fell et al. .................... 623/14.12 |
| 6,560,476 B1 | 5/2003 | Pelletier et al. ............... 600/410 |
| 6,575,980 B1 | 6/2003 | Robie et al. .................... 606/88 |
| 6,591,581 B2 | 7/2003 | Schmieding .................... 53/396 |
| 6,592,624 B1 | 7/2003 | Fraser et al. ................ 623/17.16 |
| 6,623,526 B1 | 9/2003 | Lloyd ......................... 623/20.28 |
| 6,626,945 B2 | 9/2003 | Simon et al. ............... 623/17.19 |
| 6,632,235 B2 | 10/2003 | Weikel et al. .................. 606/192 |
| 6,652,587 B2 | 11/2003 | Felt et al. .................... 623/20.16 |
| 6,679,917 B2 | 1/2004 | Ek ............................. 623/20.14 |
| 6,690,816 B2 | 2/2004 | Aylward et al. ............... 382/128 |
| 6,692,448 B2 | 2/2004 | Tanaka et al. ................. 600/587 |
| 6,702,821 B2 | 3/2004 | Bonutti ........................... 606/88 |
| 6,712,856 B1 * | 3/2004 | Carignan et al. ............ 623/20.35 |
| 6,719,794 B2 | 4/2004 | Gerber et al. ............... 623/17.11 |
| 6,770,078 B2 | 8/2004 | Bonutti ........................... 606/88 |
| 6,772,026 B2 | 8/2004 | Bradbury et al. ............... 700/98 |
| 6,799,066 B2 | 9/2004 | Steines et al. ................. 600/407 |
| 6,816,607 B2 | 11/2004 | O'Donnell et al. ............ 382/131 |
| 6,835,377 B2 | 12/2004 | Goldberg et al. ............. 424/93.7 |
| 6,855,165 B2 | 2/2005 | Fell et al. .................... 623/14.12 |
| 6,873,741 B2 | 3/2005 | Li ................................. 382/266 |
| 6,893,463 B2 | 5/2005 | Fell et al. .................... 623/14.12 |
| 6,893,467 B1 | 5/2005 | Bercovy ..................... 623/20.14 |
| 6,902,582 B2 | 6/2005 | Kubein-Meesenburg et al. ............... 623/20.31 |
| 6,905,514 B2 | 6/2005 | Carignan et al. ........... 623/20.35 |
| 6,911,044 B2 | 6/2005 | Fell et al. .................... 623/14.12 |
| 6,916,341 B2 | 7/2005 | Rolston ....................... 623/20.3 |
| 6,923,831 B2 | 8/2005 | Fell et al. .................... 623/14.12 |
| 6,932,842 B1 | 8/2005 | Litschko et al. ............ 623/16.11 |
| 6,964,687 B1 | 11/2005 | Bernard et al. ............. 623/17.16 |
| 6,966,928 B2 | 11/2005 | Fell et al. .................... 623/14.12 |
| 6,984,981 B2 | 1/2006 | Tamez-Peña et al. ......... 324/309 |
| 6,998,841 B1 | 2/2006 | Tamez-Peña et al. ......... 324/302 |
| 7,020,314 B1 | 3/2006 | Suri et al. ..................... 382/130 |
| 7,050,534 B2 | 5/2006 | Lang ............................... 378/54 |
| 7,058,159 B2 | 6/2006 | Lang et al. ...................... 378/54 |
| 7,058,209 B2 | 6/2006 | Chen et al. .................... 382/117 |
| 7,060,101 B2 * | 6/2006 | O'Connor et al. .......... 623/20.32 |
| 7,105,026 B2 * | 9/2006 | Johnson et al. ............. 623/20.14 |
| 7,115,131 B2 | 10/2006 | Engh et al. ...................... 606/79 |
| 7,174,282 B2 | 2/2007 | Hollister et al. .................. 703/2 |
| 7,184,814 B2 | 2/2007 | Lang et al. ................... 600/416 |
| 7,204,807 B2 | 4/2007 | Tsoref ........................... 600/438 |

(56) References Cited

U.S. PATENT DOCUMENTS

| | | | |
|---|---|---|---|
| 7,238,203 B2 | 7/2007 | Bagga et al. | 623/17.11 |
| 7,239,908 B1 | 7/2007 | Alexander et al. | 600/427 |
| 7,244,273 B2 | 7/2007 | Pedersen et al. | 623/14.12 |
| 7,245,697 B2 | 7/2007 | Lang | 378/54 |
| 7,292,674 B2 | 11/2007 | Lang | 378/54 |
| 7,326,252 B2 * | 2/2008 | Otto et al. | 623/20.15 |
| 7,379,529 B2 | 5/2008 | Lang | 378/54 |
| 7,438,685 B2 | 10/2008 | Burdette et al. | 600/439 |
| 7,467,892 B2 | 12/2008 | Lang et al. | 378/207 |
| 7,468,075 B2 | 12/2008 | Lang et al. | 623/16.11 |
| 7,517,358 B2 | 4/2009 | Petersen | 606/247 |
| 7,520,901 B2 | 4/2009 | Engh et al. | 623/20.21 |
| 7,534,263 B2 | 5/2009 | Burdulis, Jr. et al. | 623/14.12 |
| 7,603,192 B2 | 10/2009 | Martin et al. | 700/98 |
| 7,611,519 B2 | 11/2009 | Lefevre et al. | 606/102 |
| 7,611,653 B1 | 11/2009 | Elsner et al. | 264/255 |
| 7,615,054 B1 | 11/2009 | Bonutti | 606/88 |
| 7,618,451 B2 | 11/2009 | Berez et al. | 623/14.12 |
| 7,634,119 B2 | 12/2009 | Tsougarakis et al. | 382/128 |
| 7,796,791 B2 | 9/2010 | Tsougarakis et al. | 382/128 |
| 7,799,077 B2 | 9/2010 | Lang et al. | 623/14.12 |
| 7,806,896 B1 | 10/2010 | Bonutti | 606/86 R |
| 7,842,092 B2 | 11/2010 | Otto et al. | 623/18.11 |
| 7,881,768 B2 | 2/2011 | Lang et al. | 600/407 |
| 7,914,582 B2 | 3/2011 | Felt et al. | 623/20.16 |
| 7,935,151 B2 | 5/2011 | Haines | 623/20.35 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/86 |
| 8,070,821 B2 | 12/2011 | Roger | 623/20.17 |
| 8,077,950 B2 | 12/2011 | Tsougarakis et al. | 382/128 |
| 8,083,745 B2 | 12/2011 | Lang et al. | 606/87 |
| 8,094,900 B2 | 1/2012 | Steines et al. | 382/128 |
| 8,105,330 B2 | 1/2012 | Fitz et al. | 606/88 |
| 8,112,142 B2 | 2/2012 | Alexander et al. | 600/407 |
| RE43,282 E | 3/2012 | Alexander et al. | 600/427 |
| 8,192,498 B2 | 6/2012 | Wagner et al. | 623/20.21 |
| 8,211,181 B2 | 7/2012 | Walker | 623/20.21 |
| 8,234,097 B2 | 7/2012 | Steines et al. | 703/1 |
| 8,236,061 B2 | 8/2012 | Heldreth et al. | 623/20.31 |
| 8,265,730 B2 | 9/2012 | Alexander et al. | 600/410 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | 606/86 R |
| 8,337,507 B2 | 12/2012 | Lang et al. | 606/102 |
| 8,343,218 B2 | 1/2013 | Lang et al. | 623/16.11 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,129 B2 | 2/2013 | Fitz et al. | 623/14.12 |
| 8,380,471 B2 | 2/2013 | Iannotti et al. | 703/6 |
| 8,407,067 B2 | 3/2013 | Uthgenannt et al. | 705/2 |
| 8,439,926 B2 | 5/2013 | Bojarski et al. | 606/88 |
| 8,457,930 B2 | 6/2013 | Schroeder | 703/1 |
| 8,460,304 B2 | 6/2013 | Fitz et al. | 606/88 |
| 8,473,305 B2 | 6/2013 | Belcher et al. | 705/2 |
| 8,480,754 B2 | 7/2013 | Bojarski et al. | 623/20.35 |
| 8,486,150 B2 | 7/2013 | White et al. | 623/20.21 |
| 8,500,740 B2 | 8/2013 | Bojarski et al. | 606/86 R |
| 8,521,492 B2 | 8/2013 | Otto et al. | 703/6 |
| 8,529,568 B2 | 9/2013 | Bouadi | 606/84 |
| 8,529,630 B2 | 9/2013 | Bojarski et al. | 623/20.14 |
| 8,532,807 B2 | 9/2013 | Metzger | 700/98 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,617,172 B2 | 12/2013 | Fitz et al. | 606/88 |
| 8,617,242 B2 | 12/2013 | Philipp | 623/16.11 |
| 8,623,026 B2 | 1/2014 | Wong et al. | 606/96 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0016543 A1 | 2/2002 | Tyler | 600/410 |
| 2002/0022884 A1 | 2/2002 | Mansmann | 623/14.12 |
| 2002/0045940 A1 | 4/2002 | Giannetti et al. | 623/11.11 |
| 2002/0059049 A1 | 5/2002 | Bradbury et al. | 703/11 |
| 2002/0067798 A1 | 6/2002 | Lang et al. | 378/54 |
| 2002/0068979 A1 | 6/2002 | Brown et al. | 623/20.3 |
| 2002/0072821 A1 | 6/2002 | Baker | 700/98 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0111694 A1 | 8/2002 | Ellingsen et al. | 623/23.57 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0147392 A1 | 10/2002 | Steines et al. | 600/407 |
| 2002/0151986 A1 | 10/2002 | Asculai et al. | 424/484 |
| 2002/0156150 A1 | 10/2002 | Williams et al. | 523/113 |
| 2002/0173852 A1 | 11/2002 | Felt et al. | 623/20.32 |
| 2002/0177770 A1 | 11/2002 | Lang et al. | 600/410 |
| 2002/0183850 A1 | 12/2002 | Felt et al. | 623/20.16 |
| 2003/0015208 A1 | 1/2003 | Lang et al. | 128/922 |
| 2003/0031292 A1 | 2/2003 | Lang | 378/54 |
| 2003/0035773 A1 | 2/2003 | Totterman et al. | 424/9.1 |
| 2003/0045935 A1 | 3/2003 | Angelucci et al. | 623/17.11 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0063704 A1 | 4/2003 | Lang | 378/54 |
| 2003/0069591 A1 | 4/2003 | Carson et al. | 606/130 |
| 2003/0100953 A1 | 5/2003 | Rosa et al. | 623/20.3 |
| 2003/0158606 A1 | 8/2003 | Coon et al. | 623/20.15 |
| 2003/0216669 A1 | 11/2003 | Lang et al. | 600/587 |
| 2003/0225457 A1 | 12/2003 | Justin et al. | 623/20.14 |
| 2003/0236473 A1 | 12/2003 | Dore et al. | 600/587 |
| 2004/0006393 A1 | 1/2004 | Burkinshaw | 623/20.3 |
| 2004/0062358 A1 | 4/2004 | Lang et al. | 378/207 |
| 2004/0081287 A1 | 4/2004 | Lang et al. | 378/210 |
| 2004/0098132 A1 | 5/2004 | Andriacchi et al. | 623/20.35 |
| 2004/0098133 A1 | 5/2004 | Carignan et al. | 623/20.35 |
| 2004/0102851 A1 | 5/2004 | Saladino | 623/20.15 |
| 2004/0102852 A1 | 5/2004 | Johnson et al. | 623/20.15 |
| 2004/0102866 A1 | 5/2004 | Harris et al. | 700/117 |
| 2004/0117015 A1 | 6/2004 | Biscup | 623/16.11 |
| 2004/0117023 A1 | 6/2004 | Gerbec et al. | 623/18.11 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0138755 A1 | 7/2004 | O'Connor et al. | 623/20.32 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0204766 A1 | 10/2004 | Siebel | 623/20.31 |
| 2004/0236424 A1 | 11/2004 | Berez et al. | 623/14.12 |
| 2005/0010106 A1 | 1/2005 | Lang et al. | 600/425 |
| 2005/0015153 A1 | 1/2005 | Goble et al. | 623/23.46 |
| 2005/0021042 A1 | 1/2005 | Marnay et al. | 606/99 |

(56) References Cited

U.S. PATENT DOCUMENTS

| | | | |
|---|---|---|---|
| 2005/0033424 A1 | 2/2005 | Fell | 623/14.12 |
| 2005/0043807 A1 | 2/2005 | Wood | 623/20.14 |
| 2005/0055028 A1 | 3/2005 | Haines | 606/79 |
| 2005/0078802 A1 | 4/2005 | Lang et al. | 387/207 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0125029 A1 | 6/2005 | Bernard et al. | 606/205 |
| 2005/0148843 A1 | 7/2005 | Roose | 600/407 |
| 2005/0154471 A1 | 7/2005 | Aram et al. | 623/20.15 |
| 2005/0171612 A1 | 8/2005 | Rolston | 623/20.19 |
| 2005/0203384 A1 | 9/2005 | Sati et al. | 600/426 |
| 2005/0216305 A1 | 9/2005 | Funderud | 705/2 |
| 2005/0226374 A1 | 10/2005 | Lang et al. | 378/54 |
| 2005/0234461 A1 | 10/2005 | Burdulis, Jr. et al. | 606/79 |
| 2005/0267584 A1 | 12/2005 | Burdulis et al. | 623/20.19 |
| 2005/0278034 A1 | 12/2005 | Johnson et al. | 623/20.15 |
| 2006/0009853 A1 | 1/2006 | Justin et al. | 623/20.3 |
| 2006/0069318 A1 | 3/2006 | Keaveny et al. | 600/300 |
| 2006/0111722 A1 | 5/2006 | Bouadi | 606/79 |
| 2006/0111726 A1 | 5/2006 | Felt et al. | 606/86 |
| 2006/0129246 A1 | 6/2006 | Steffensmeier | 623/20.29 |
| 2006/0149374 A1 | 7/2006 | Winslow et al. | 623/17.11 |
| 2006/0190086 A1 | 8/2006 | Clemow et al. | 623/20.15 |
| 2006/0210017 A1 | 9/2006 | Lang | 378/54 |
| 2006/0210018 A1 | 9/2006 | Lang | 378/54 |
| 2006/0265078 A1 | 11/2006 | McMinn | 623/20.14 |
| 2007/0015995 A1 | 1/2007 | Lang | 600/407 |
| 2007/0047794 A1 | 3/2007 | Lang et al. | 378/132 |
| 2007/0067032 A1 | 3/2007 | Felt et al. | 623/14.12 |
| 2007/0083266 A1 | 4/2007 | Lang | 623/17.11 |
| 2007/0100462 A1 | 5/2007 | Lang et al. | 623/20.29 |
| 2007/0118055 A1 | 5/2007 | McCombs | 600/587 |
| 2007/0118222 A1 | 5/2007 | Lang | 623/17.12 |
| 2007/0118243 A1 | 5/2007 | Schroeder et al. | 700/118 |
| 2007/0156171 A1 | 7/2007 | Lang et al. | 606/205 |
| 2007/0190108 A1 | 8/2007 | Datta et al. | 424/423 |
| 2007/0198022 A1* | 8/2007 | Lang et al. | 606/88 |
| 2007/0203430 A1 | 8/2007 | Lang et al. | 600/587 |
| 2007/0233156 A1 | 10/2007 | Metzger | 606/130 |
| 2007/0233269 A1 | 10/2007 | Steines et al. | 623/20.21 |
| 2007/0239165 A1 | 10/2007 | Amirouche | 606/86 |
| 2007/0250169 A1 | 10/2007 | Lang | 623/17.12 |
| 2007/0255288 A1 | 11/2007 | Mahfouz et al. | 606/102 |
| 2007/0274444 A1 | 11/2007 | Lang | 378/54 |
| 2007/0276224 A1 | 11/2007 | Lang et al. | 600/410 |
| 2007/0276501 A1 | 11/2007 | Betz et al. | 623/17.16 |
| 2008/0009950 A1 | 1/2008 | Richardson | 623/20.29 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1* | 3/2008 | Hajaj et al. | 623/20.14 |
| 2008/0119938 A1 | 5/2008 | Oh | 623/20.14 |
| 2008/0119940 A1 | 5/2008 | Otto et al. | 623/20.31 |
| 2008/0147072 A1 | 6/2008 | Park et al. | 606/87 |
| 2008/0170659 A1 | 7/2008 | Lang et al. | 378/56 |
| 2008/0172125 A1 | 7/2008 | Ek | 623/14.12 |
| 2008/0195108 A1 | 8/2008 | Bhatnagar et al. | 606/87 |
| 2008/0195216 A1 | 8/2008 | Philipp | 623/18.11 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Fitz et al. | 623/17.16 |
| 2008/0281426 A1 | 11/2008 | Fitz et al. | 623/17.16 |
| 2008/0319448 A1 | 12/2008 | Lavallee et al. | 606/102 |
| 2009/0076371 A1 | 3/2009 | Lang et al. | 600/407 |
| 2009/0076508 A1 | 3/2009 | Weinans et al. | 606/62 |
| 2009/0118830 A1 | 5/2009 | Fell | 623/14.12 |
| 2009/0131941 A1 | 5/2009 | Park et al. | 606/87 |
| 2009/0149977 A1 | 6/2009 | Schendel | 700/98 |
| 2009/0222103 A1 | 9/2009 | Fitz et al. | 623/18.11 |
| 2009/0226068 A1 | 9/2009 | Fitz et al. | 382/131 |
| 2009/0228111 A1 | 9/2009 | Otto | 623/20.19 |
| 2009/0228113 A1 | 9/2009 | Lang et al. | 623/20.32 |
| 2009/0265013 A1 | 10/2009 | Mandell | 623/20.21 |
| 2009/0270868 A1 | 10/2009 | Park et al. | 606/87 |
| 2009/0276045 A1 | 11/2009 | Lang | 623/14.12 |
| 2009/0299481 A9 | 12/2009 | Romagnoli | 623/20.3 |
| 2009/0306676 A1 | 12/2009 | Lang et al. | 606/102 |
| 2009/0312805 A1 | 12/2009 | Lang et al. | 606/86 R |
| 2009/0326666 A1 | 12/2009 | Wyss et al. | 623/20.39 |
| 2010/0054572 A1 | 3/2010 | Tsougarakis et al. | 382/131 |
| 2010/0063594 A1 | 3/2010 | Hazebrouck et al. | 623/20.29 |
| 2010/0274534 A1 | 10/2010 | Steines et al. | 703/1 |
| 2010/0303313 A1 | 12/2010 | Lang et al. | 382/128 |
| 2010/0303317 A1 | 12/2010 | Tsougarakis et al. | 382/128 |
| 2010/0303324 A1 | 12/2010 | Lang et al. | 382/131 |
| 2010/0305708 A1 | 12/2010 | Lang et al. | 623/20.18 |
| 2010/0305907 A1 | 12/2010 | Fitz et al. | 703/1 |
| 2010/0329530 A1 | 12/2010 | Lang et al. | 382/131 |
| 2010/0331991 A1 | 12/2010 | Wilkinson et al. | 623/20.32 |
| 2011/0022179 A1 | 1/2011 | Andriacchi et al. | 623/20.18 |
| 2011/0029091 A1 | 2/2011 | Bojarski et al. | 623/20.32 |
| 2011/0029093 A1 | 2/2011 | Bojarski et al. | 623/20.35 |
| 2011/0046735 A1 | 2/2011 | Metzger et al. | 623/14.12 |
| 2011/0066245 A1 | 3/2011 | Lang et al. | 623/18.11 |
| 2011/0071645 A1 | 3/2011 | Bojarski et al. | 623/20.35 |
| 2011/0071802 A1 | 3/2011 | Bojarski et al. | 703/1 |
| 2011/0087332 A1 | 4/2011 | Bojarski et al. | 623/20.32 |
| 2011/0087465 A1 | 4/2011 | Mahfouz | 703/1 |
| 2011/0092804 A1 | 4/2011 | Schoenefeld et al. | 600/416 |
| 2011/0125009 A1 | 5/2011 | Lang et al. | 600/425 |
| 2011/0144760 A1 | 6/2011 | Wong et al. | 623/20.14 |
| 2011/0218635 A1 | 9/2011 | Amis et al. | 623/20.18 |
| 2011/0266265 A1 | 11/2011 | Lang | 219/121.72 |
| 2011/0288669 A1 | 11/2011 | Sanford et al. | 700/103 |
| 2011/0295378 A1 | 12/2011 | Bojarski et al. | 623/20.35 |
| 2011/0305379 A1 | 12/2011 | Mahfouz | 382/131 |
| 2012/0093377 A1 | 4/2012 | Tsougarakis et al. | 382/128 |
| 2012/0116203 A1 | 5/2012 | Vancraen et al. | 600/407 |
| 2012/0191205 A1 | 7/2012 | Bojarski et al. | 623/20.32 |
| 2012/0191420 A1 | 7/2012 | Bojarski et al. | 703/1 |
| 2012/0197408 A1 | 8/2012 | Lang et al. | 623/18.11 |
| 2012/0201440 A1 | 8/2012 | Steines et al. | 382/131 |
| 2012/0209394 A1 | 8/2012 | Bojarski et al. | 623/20.32 |
| 2012/0232669 A1 | 9/2012 | Bojarski et al. | 623/20.3 |
| 2012/0232670 A1 | 9/2012 | Bojarski et al. | 623/20.35 |
| 2012/0232671 A1 | 9/2012 | Bojarski et al. | 623/20.35 |
| 2012/0265496 A1 | 10/2012 | Mahfouz | 703/1 |
| 2013/0006598 A1 | 1/2013 | Alexander et al. | 703/11 |
| 2013/0071828 A1 | 3/2013 | Lang et al. | 434/274 |
| 2013/0103363 A1 | 4/2013 | Lang et al. | 703/1 |
| 2013/0110471 A1 | 5/2013 | Lang et al. | 703/1 |
| 2013/0144570 A1 | 6/2013 | Axelson, Jr. et al. | 703/1 |
| 2013/0158671 A1 | 6/2013 | Uthgenannt et al. | 623/20.35 |
| 2013/0165939 A1 | 6/2013 | Ries et al. | 606/88 |
| 2013/0197870 A1 | 8/2013 | Steines et al. | 703/1 |
| 2013/0199259 A1 | 8/2013 | Smith | 72/362 |
| 2013/0203031 A1 | 8/2013 | Mckinnon et al. | 434/262 |
| 2013/0211531 A1 | 8/2013 | Steines et al. | 623/20.35 |
| 2013/0245803 A1 | 9/2013 | Lang | 700/98 |
| 2013/0297031 A1 | 11/2013 | Hafez | 623/20.14 |
| 2014/0005792 A1 | 1/2014 | Lang et al. | 623/20.32 |

FOREIGN PATENT DOCUMENTS

| | | | |
|---|---|---|---|
| DE | 2306552 | 8/1974 | A61F 1/00 |
| DE | 3516743 | 11/1986 | A61F 2/36 |
| DE | 8909091 | 9/1989 | A61F 2/35 |
| DE | 44 34 539 | 4/1996 | A61F 2/38 |
| DE | 19803673 | 8/1999 | A61L 27/54 |
| DE | 19926083 | 12/2000 | A61L 27/54 |
| DE | 10135771 | 2/2003 | A61B 17/70 |
| EP | 0528080 | 2/1993 | A61F 2/30 |
| EP | 0600806 | 6/1994 | A61L 25/00 |
| EP | 0672397 | 9/1995 | A61F 2/38 |
| EP | 0 704 193 | 4/1996 | A61F 2/30 |
| EP | 0626156 | 7/1997 | A61F 2/38 |
| EP | 0613380 | 12/1999 | A61L 27/00 |
| EP | 1074229 | 2/2001 | A61F 2/38 |

(56) References Cited

FOREIGN PATENT DOCUMENTS

| | | | |
|---|---|---|---|
| EP | 1077253 | 2/2001 | ............... C12N 5/00 |
| EP | 1120087 | 8/2001 | ............ A61B 17/06 |
| EP | 1129675 | 9/2001 | ............. A61F 2/30 |
| EP | 0732091 | 12/2001 | ............. A61F 2/38 |
| EP | 0896825 | 7/2002 | ............ A61L 27/00 |
| EP | 0814731 | 8/2002 | ............. A61F 2/30 |
| EP | 1234552 | 8/2002 | ............. A61F 2/00 |
| EP | 1234555 | 8/2002 | ............. A61F 2/30 |
| EP | 0809987 | 10/2002 | ............. A61F 2/38 |
| EP | 0833620 | 10/2002 | ............ A61K 9/22 |
| EP | 1327423 | 7/2003 | ............. A61F 2/38 |
| EP | 1329205 | 7/2003 | ............. A61F 2/38 |
| EP | 0530804 | 6/2004 | ............ A61L 25/00 |
| EP | 1437101 | 7/2004 | ............. A61F 2/08 |
| EP | 1070487 | 9/2005 | ............. A61F 2/08 |
| EP | 1754457 | 2/2007 | ............. A61F 2/38 |
| EP | 1886640 | 2/2008 | ............ A61B 19/00 |
| EP | 2324799 | 5/2011 | ............. A61F 2/38 |
| FR | 2589720 | 11/1985 | ............. A61F 2/38 |
| FR | 2740326 | 4/1997 | ............. A61F 2/38 |
| GB | 1451283 | 9/1976 | ............. A61F 1/24 |
| GB | 2291355 | 1/1996 | ............. A61F 2/38 |
| GB | 2304051 | 3/1997 | ............. A61F 2/38 |
| GB | 2348373 | 10/2000 | ............. A61F 2/38 |
| JP | 56-083343 | 7/1981 | ............. A61F 1/03 |
| JP | 61-247448 | 11/1986 | ............. A61F 2/30 |
| JP | 1-249049 | 10/1989 | ............. A61F 2/38 |
| JP | 05-184612 | 7/1993 | ............. A61F 2/30 |
| JP | 7-236648 | 9/1995 | ............. A61F 2/28 |
| JP | 8-173465 | 7/1996 | ............. A61F 2/38 |
| JP | 9-206322 | 8/1997 | ............. A61F 2/36 |
| JP | 11-19104 | 1/1999 | ............. A61F 2/28 |
| JP | 11-276510 | 10/1999 | ............. A61F 2/28 |
| JP | 2007-521881 | 8/2007 | ............. A61F 2/44 |
| WO | WO 87/02882 | 5/1987 | ............. A61F 2/38 |
| WO | WO 90/09769 | 9/1990 | ............. A61F 2/28 |
| WO | WO 93/04710 | 3/1993 | ............ A61L 25/00 |
| WO | WO 93/09819 | 5/1993 | ............ A61L 27/00 |
| WO | WO 93/25157 | 12/1993 | ............ A61B 17/56 |
| WO | WO 95/27450 | 10/1995 | ............. A61F 2/38 |
| WO | WO 95/28688 | 10/1995 | ............ G06T 15/00 |
| WO | WO 95/30390 | 11/1995 | ............. A61F 2/38 |
| WO | WO 95/32623 | 12/1995 | ............. A01N 1/02 |
| WO | WO 96/24302 | 8/1996 | ............ A61B 17/90 |
| WO | WO 97/25942 | 7/1997 | ............. A61F 2/32 |
| WO | WO 97/27885 | 8/1997 | ............ A61L 27/00 |
| WO | WO 97/38676 | 10/1997 | ............. A61K 9/10 |
| WO | WO 97/46665 | 12/1997 | ............. C12N 5/06 |
| WO | WO 98/08469 | 3/1998 | ............. A61F 2/30 |
| WO | WO 98/12994 | 4/1998 | ............. A61F 2/28 |
| WO | WO 98/20816 | 5/1998 | ............. A61F 2/38 |
| WO | WO 98/30617 | 7/1998 | ............ C08G 63/12 |
| WO | WO 98/52498 | 11/1998 | ............. A61F 2/28 |
| WO | WO 99/02654 | 1/1999 | ............. C12N 5/00 |
| WO | WO 99/08598 | 2/1999 | ............. A61B 8/00 |
| WO | WO 99/08728 | 2/1999 | ............ A61L 27/00 |
| WO | WO 99/42061 | 8/1999 | ............. A61F 2/38 |
| WO | WO 99/47186 | 9/1999 | ............ A61L 27/00 |
| WO | WO 99/51719 | 10/1999 | ............. C12M 3/00 |
| WO | WO 00/09179 | 2/2000 | ............ A61L 25/00 |
| WO | WO 00/15153 | 3/2000 | ............. A61L 2/38 |
| WO | WO 00/19911 | 4/2000 | ............ A61B 17/02 |
| WO | WO 00/35346 | 6/2000 | ............. A61B 5/11 |
| WO | WO 00/48550 | 8/2000 | |
| WO | WO 00/59411 | 10/2000 | ............. A61F 2/38 |
| WO | WO 00/68749 | 11/2000 | ......... G05B 19/4099 |
| WO | WO 00/74554 | 12/2000 | |
| WO | WO 00/74741 | 12/2000 | ............ A61L 27/00 |
| WO | WO 00/76428 | 12/2000 | ............. A61F 2/38 |
| WO | WO 01/10356 | 2/2001 | ............. A61F 2/46 |
| WO | WO 01/17463 | 3/2001 | ............. A61F 2/30 |
| WO | WO 01/19254 | 3/2001 | ............ A61B 17/00 |
| WO | WO 01/35968 | 5/2001 | ............ A61K 35/00 |
| WO | WO 01/45764 | 6/2001 | ............ A61L 27/36 |
| WO | WO 01/68800 | 9/2001 | ............. C12M 3/00 |
| WO | WO 01/70142 | 9/2001 | ............. A61F 2/38 |
| WO | WO 01/77988 | 10/2001 | ............ G06F 19/00 |
| WO | WO 01/82677 | 11/2001 | |
| WO | WO 01/91672 | 12/2001 | ............. A61F 2/36 |
| WO | WO 02/02021 | 1/2002 | ............ A61B 17/56 |
| WO | WO 02/09623 | 2/2002 | ............. A61F 2/38 |
| WO | WO 02/22013 | 3/2002 | ............. A61B 5/55 |
| WO | WO 02/22014 | 3/2002 | ............. A61B 5/55 |
| WO | WO 02/23483 | 3/2002 | ............. A61B 5/55 |
| WO | WO 02/34310 | 5/2002 | ............ A61L 31/04 |
| WO | WO 02/36147 | 5/2002 | ............ A61K 31/04 |
| WO | WO 02/37423 | 5/2002 | ............ G06T 17/00 |
| WO | WO 02/096268 | 12/2002 | |
| WO | WO 03/007788 | 1/2003 | |
| WO | WO 03/037192 | 5/2003 | ............ A61B 17/15 |
| WO | WO 03/047470 | 6/2003 | ............. A61F 2/34 |
| WO | WO 03/051210 | 6/2003 | ............ A61B 17/58 |
| WO | WO 03/061522 | 7/2003 | |
| WO | WO 03/099106 | 12/2003 | |
| WO | WO 2004/006811 | 1/2004 | ............. A61F 2/46 |
| WO | WO 2004/032806 | 4/2004 | ............. A61F 2/30 |
| WO | WO 2004/043305 | 5/2004 | ............. A61F 2/30 |
| WO | WO 2004/049981 | 6/2004 | ............. A61F 2/46 |
| WO | WO 2004/051301 | 6/2004 | ............ G01R 33/56 |
| WO | WO 2004/073550 | 9/2004 | |
| WO | WO 2005/016175 | 2/2005 | |
| WO | WO 2005/020850 | 3/2005 | |
| WO | WO 2005/051239 | 6/2005 | ............. A61F 2/08 |
| WO | WO 2005/051240 | 6/2005 | ............. A61F 2/08 |
| WO | WO 2005/067521 | 7/2005 | |
| WO | WO 2005/076974 | 8/2005 | |
| WO | WO 2006/058057 | 6/2006 | ............. A61F 2/38 |
| WO | WO 2006/060795 | 6/2006 | ............ A61B 17/17 |
| WO | WO 2006/065774 | 6/2006 | ............. A61F 2/44 |
| WO | WO2006/092600 | 9/2006 | ............ A61B 19/00 |
| WO | WO 2007/041375 | 4/2007 | ............. A61F 2/38 |
| WO | WO 2007/062079 | 5/2007 | ............. A61F 2/30 |
| WO | WO 2007/090784 | 8/2007 | ............. A61F 2/38 |
| WO | WO 2007/092841 | 8/2007 | ............ A61B 17/15 |
| WO | WO 2007/109641 | 9/2007 | ............. A61F 2/30 |
| WO | WO 2008/021494 | 2/2008 | ............ G06F 19/00 |
| WO | WO 2008/055161 | 5/2008 | ............. A61F 2/44 |
| WO | WO 2008/101090 | 8/2008 | ............. A61F 2/38 |
| WO | WO 2008/117028 | 10/2008 | ............ A61B 17/15 |
| WO | WO 2008/157412 | 12/2008 | ............ A61B 17/17 |
| WO | WO 2009/111656 | 9/2009 | ............. A61F 2/38 |
| WO | WO 2009/140294 | 11/2009 | ............. A61F 2/30 |
| WO | WO 2010/099231 | 9/2010 | ............. A61F 2/38 |
| WO | WO 2010/099353 | 9/2010 | ............. A61F 2/30 |
| WO | WO 2010/099359 | 9/2010 | ............. A61F 2/00 |
| WO | WO 2010/140036 | 12/2010 | ............. A61F 2/38 |
| WO | WO 2010/151564 | 12/2010 | ............. A61F 2/38 |
| WO | WO 2011/028624 | 3/2011 | ............. A61F 2/38 |
| WO | WO 2011/056995 | 5/2011 | ............. A61F 2/38 |
| WO | WO 2011/072235 | 6/2011 | ............. A61F 2/38 |
| WO | WO 2011/075697 | 6/2011 | ............. A61F 2/38 |
| WO | WO 2011/101474 | 8/2011 | ............ G06F 19/00 |
| WO | WO 2012/027150 | 3/2012 | ............ G06F 19/00 |
| WO | WO 2012/027185 | 3/2012 | ............ G06T 17/00 |
| WO | WO 2012/112694 | 8/2012 | ............. A61B 6/00 |
| WO | WO 2012/112698 | 8/2012 | ............. A61F 2/30 |
| WO | WO 2012/112701 | 8/2012 | ............. A61F 2/30 |
| WO | WO 2012/112702 | 8/2012 | ............. A61F 2/30 |
| WO | WO 2013/020026 | 2/2013 | ............. A61F 2/30 |
| WO | WO 2013/025814 | 2/2013 | ............. A61F 2/38 |
| WO | WO 2013/056036 | 4/2013 | ............. A61F 2/38 |
| WO | WO 2013/119790 | 8/2013 | ............. A61F 2/38 |

OTHER PUBLICATIONS

International Searching Authority, International Search Report—International Application No. PCT/US2009/036218, dated Apr. 28, 2009, together with the Written Opinion of the International Searching Authority, 10 pages.

International Searching Authority, International Search Report—International Application No. PCT/US2010/061141, dated Aug. 31, 2011, together with the Written Opinion of the International Searching Authority, 8 pages.

(56) References Cited

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.

Adam et al., "MR Imaging of the Knee: Three-Dimensional Volume Imaging Combined with Fast Processing," J. Compt. Asst. Tomogr., 13(6): 984-988 (1989).

Adams et al., "Quantitative Imaging of Osteoarthritis," Semin Arthritis Rheum, 20(6) Suppl. 2: 26-39 (Jun. 1991).

Ahmad et al., "Biomechanical and Topographic Considerations for Autologous Osteochondral Grafting in the Knee," Am J Sports Med, 29(2): 201-206 (Mar.-Apr. 2001).

Alexander, "Estimating the motion of bones from markers on the skin," University of Illinois at Chicago (Doctoral Dissertation) (1998).

Alexander et al., "Correcting for deformation in skin-based marker systems," Proceedings of the 3rd Annual Gait and Clinical Movement Analysis Meeting, San Diego, CA (1998).

Alexander et al., "Internal to external correspondence in the analysis of lower limb bone motion," Proceedings of the 1999 ASME Summer Bioengineering Conference, Big Sky, Montana (1999).

Alexander et al., "State estimation theory in human movement analysis," Proceedings of the ASME International Mechanical Engineering Congress (1998).

Alexander et al., "Optimization techniques for skin deformation correction," International Symposium on 3-D Human Movement Conference, Chattanooga, TN, (1998).

Alexander et al., "Dynamic Functional Imaging of the Musculoskeletal System," ASME Winter International Congress and Exposition, Nashville, TN (1999).

Allen et al., "Late degenerative changes after meniscectomy 5 factors affecting the knee after operations," J Bone Joint Surg 66B: 666-671 (1984).

Alley et al., "Ultrafast contrast-enhanced three dimensional MR Aagiography: State of the art," Radiographics 18: 273-285 (1998).

Andersson et al., "MacIntosh Arthroplasty in Rheumatoid Arthritis," Acta. Orthrop. Scand. 45(2):245-259 (1974).

Andriacchi, "Dynamics of knee Malalignment," Orthop Clin North Am 25: 395-403 (1994).

Andriacchi, et al., "A point cluster method for in vivo motion analysis: Applied to a study of knee kinematics," J. Biomech Eng 120(12): 743-749 (1998).

Andriacchi, et al., "Methods for evaluating the progression of Osterarthiritis," Journal of Rehabilitation Research and Development 37(2): 163-170 (2000).

Andriacchi et al., "Gait analysis as a tool to assess joint kinetics biomechanics of normal and pathological human articulating joints," Nijhoff, Series E 93: 83-102 (1985).

Andriacchi et al., "In vivo measurement of six-degrees-of-freedom knee movement during functional testing," Transactions of the Orthopedic Research Society 698 (1995).

Argenson et al., "Is There a Place for Patellofemoral Arthroplasty?," Clinical Orthopaedics and Related Research No. 321, pp. 162-167 (1995).

Aro et al., "Clinical Use of Bone Allografts," Ann Med 25:403-412 (1993).

Bashir, "Validation of Gadolinium-Enhanced MRI of FAF Measurement in Human Cartilage," Intl. Soc. Mag. Resonance Med. (1998).

Beaulieu et al., "Glenohumeral relationships during physiological shoulder motion and stress testing: Initial experience with open MRI and active Scan-25 plane registration," Radiology (1999).

Beaulieu et al., "Dynamic imaging of glenohumeral instability with open MRI," Int. Society for Magnetic Resonance in Medicine Sydney, Australia (1998).

Beckmann et al. "Noninvasive 3D MR Microscopy as Tool in Pharmacological Research: Application to a Model of Rheumatoid Arthritis," Magn Reson Imaging 13(7): 1013-1017 (1995).

Billet, Philippe, French Version—"Gliding Knee Prostheses—Analysis of Mechanical Failures", Thesis, Medical School of Marseilles, 1982, 64 pages.

Billet, Philippe, Translated Version—"Gliding Knee Prostheses—Analysis of Mechanical Failures", Thesis, Medical School of Marseilles, 1982, 93 pages.

Blazina et al., "Patellofemoral replacement: Utilizing a customized femoral groove replacement," 5(1)53-55 (1990).

Blum et al., "Knee Arthroplasty in Patients with Rheumatoid Arthritis," ANN. Rheum. Dis. 33 (1): 1-11 (1974).

Bobic, "Arthroscopic osteochondral autogaft transplantation in anterior cruciate ligament reconstruction: a preliminary clinical study," Knee Surg Sports Traumatol Arthrosc 3(4): 262-264 (1996).

Boe et al., "Arthroscopic partial meniscectomy in patients aged over 50," J. Bone Joint Surg 68B: 707 (1986).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Borthakur et al., "In Vivo Triple Quantum Filtered Sodium MRI of Human Articular Cartilage," Proc. Intl. Soc. Mag. Resonance Med., 7:549 (1999).

Brandt et al., In German: "CRIGOS—Development of a Compact Robot System for Image-Guided Orthopedic Surgery," Der Orthopäde, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," Der Orthopäde, Springer-Verlag, vol. 29, No. 7, pp. 645-649 (Jul. 2000).

Bregler et al., "Recovering non-rigid 3D shape from image streams," Proc. IEEE Conference on Computer Vision and Pattern Recognition (Jun. 2000).

Brett et al., "Quantitative Analysis of Biomedical Images," Univ. of Manchester, Zeneca Pharmaceuticals, IBM UK, http://www.wiau.man.ac.uk/~ads/imv (1998).

Brittberg et al., "A critical analysis of cartilage repair," Acta Orthop Scand 68(2): 186-191 (1997).

Brittberg et al., "Treatment of deep cartilage defects in the knee with autologous chrondrocyte transplantation," N Engl J Med 331(14): 889-895 (1994).

Broderick et al., "Severity of articular cartilage abnormality in patients with osteoarthritis: evaluation with fast spin-echo MR vs. arthroscopy," AJR 162: 99-103 (1994).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Burgkart et al., "Magnetic Resonance Imaging-Based Assessment of Cartilage Loss in Severe Osteoarthritis," Arth Rheum; 44(9): 2072-2077 (Sep. 2001).

Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).

Butts et al., "Real-Time MR imaging of joint motion on an open MR imaging scanner," Radiological Society of North America, 83rd Scientific Assembly and Annual Meeting, Chicago, IL (1997).

Cameron, et al., "Review of a Failed Knee Replacement and Some Observations on the Design of a Knee Resurfacing Prosthesis," Arch. Orthop Trauma Surg. 97(2):87-89 (1980).

CAOS, "MIS meets CAOS Spring 2005 Symposium Schedule", *CAOS Spring 2005 Symposium*, pp. 1-9, May 19, 2005.

Carano et al., "Estimation of Erosive Changes In Rheumatoid Arthritis by Temporal Multispectral Analysis," Proc. Intl. Soc. Mag. Resonance Med., 7:408 (1999).

Carr et al., "Surface Interpolation with Radial Basis Functions for Medical Imaging," IEEE Transactions on Medical Imaging, IEEE, Inc. New York, vol. 16, pp. 96-107 (Feb. 1997).

Castriota-Scanderbeg et al., "Precision of Sonographic Measurement of Articular Cartilage: Inter-and Intraobserver Analysis," Skeletal Radiol 25: 545-549 (1996).

(56) References Cited

OTHER PUBLICATIONS

Chan et al., "Osteoarthritis of the Knee: Comparison of Radiography, CT and MR Imaging to Asses Extent and Severity," AJR Am J Roentgenol 157(4): 799-806 (1991).

Chelule et al., "Patient-Specific Template to Preserve Bone Stock in Total Knee Replacement: Preliminary Results", *15th Annual ISTA Symposium*, Sep. 2002, 1 page.

Clarke et al., "Human Hip Joint Geometry and Hemiarthroplasty Selection," The Hip. C.V. Mosby, St. Louis 63-89 (1975).

Clary et al., "Experience with the MacIntosh Knee Prosthesis," South Med. J. 65(3):265-272 (1972).

Cohen et al., "Knee cartilage topography, thickness, and contact areas from MRI: in-vitro calibration and in-vivo measurements," Osteoarthritis and Cartilage 7: 95-109 (1999).

Cohen et al., "Computer-Aided Planning of Patellofemoral Joint OA Surgery: Developing Physical Models from Patient MRI", MICCAI, Oct. 11-13, 1998, 13 pages.

Conaty, et al., "Surgery of the Hip and Knee in Patients with Rheumatoid Arthritis," J. Bone Joint Surg. Am. 55(2):301-314 (1973).

Creamer et al., "Quantitative Magnetic Resonance Imaging of the Knee: A Method of Measuring Response to Intra-Articular Treatments," Ann Rheum Dis. 378-381 (1997).

Daniel et al., "Breast cancer-gadolinium-enhanced MR imaging with a 0.5T open imager and three-point Dixon technique," Radiology 207(1): 183-190 (1998).

Dardzinski et al., "Entropy Mapping of Articular Cartilage", ISMRM Seventh Scientific Meeting, Philadelphia, PA (1999) T. 41, V. II.

Dardzinski et al., "T1-T2 Comparison in Adult Articular Cartilage," ISMRM Seventh Scientific Meeting, Philadelphia, PA (May 22-28, 1999).

De Winter et al., "The Richards Type II Patellofemoral Arthroplasty", Acta Orthop Scand 2001; 72 (5): 487-490.

Disler, "Fat-suppressed three-dimensional spoiled gradient-recalled MR imaging: assessment of articular and physeal hyaline cartilage," AJR 169: 1117-1123 (1997).

Disler et al., "Fat-suppressed three-dimensional spoiled gradient-echo MR imaging of hyaline cartilage defects in the knee: comparison with standard MR imaging and arthroscopy," AJR 167: 127-132 (1996).

Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).

Doherty et al., Osteoarthritis, Oxford Textbook of Rheumatology, Oxford University Press 959-983 (1993).

Dougados et al., "Longitudinal radiologic evaluation of osteoarthritis of the knee," J Rheumatol 19: 378-384 (1992).

Du et al., "Vessel enhancement filtering in three-dimensional MR angiography," J. Magn Res Imaging 5: 151-157 (1995).

Du et al., "Reduction of partial-volume artifacts with zero filled interpolation in three-dimensional MR Angiography," J Magn Res Imaging 4: 733-741 (1994).

Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).

Dumoulin et al., "Real-time position monitoring of invasive devises using magnetic resonance," Magn Reson Med 29: 411-5 (1993).

Dupuy et al., "Quantification of Articular Cartilage in the Knee with Three-Dimensional MR Imaging," Acad Radiol 3: 919-924 (1996).

Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).

Eckstein et al., "Effect of Gradient and Section Orientation on Quantitative Analyses of Knee Joint Cartilage," Journal of Magnetic Resonance Imaging 11: 161-167 (2000).

Eckstein et al., "Effect of Physical Exercise on Cartilage Volume And Thickness In Vivo: An MR Imaging Study," Radiology 207: 243-248 (1998).

Eckstein et al., "Functional Analysis Of Articular Cartilage Deformation, Recovery, and Fluid Flow Following Dynamic Exercise In Vivo," Anatomy and Embryology 200: 419-424 (1999).

Eckstein et al., "In Vivo Reproducibility of Three-Dimensional Cartilage Volume And Thickness Measurements With MR Imaging", AJR 170(3): 593-597 (1998).

Eckstein et al., "New Quantitative Approaches With 3-D MRI: Cartilage Morphology, Function and Degeneration", Medical Imaging International, Nov.-Dec. 1998.

Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).

Eckstein et al., Accuracy of Cartilage Volume and Thickness Measurements with Magnetic Resonance Imaging, Clin. Orthop. 1998; 352: 137-148 T. 60 V. II.

Eckstein et al., "Magnetic Resonance Chondro-Crassometry (MR CCM): A Method for Accurate Determination of Articular Cartilage Thickness?" Magn. Reson. Med. 35: 89-96 (1996).

Eckstein et al., "The Influence of Geometry on the Stress Distribution in Joints—A Finite Element Analysis," Anat Embryol, 189: 545-552 (1994).

Eckstein et al., "The Morphology of Articular Cartilage Assessed by Magnetic Resonance Imaging: Reproducibility and Anatomical Correlation," Sur. Radiol Anat 16: 429-438 (1994).

Elting et al., "Unilateral frame distraction: proximal tibial valgus osteotomy for medial gonarthritis," Contemp Orthrop 27(6): 522-524 (1993).

Faber et al., "Gender Differences in Knee Joint Cartilage Thickness, Volume And Articular Surface Areas: Assessment With Quantitative Three-Dimensional MR Imaging," Skeletal Radiology 30 (3): 144-150 (2001).

Faber et al., "Quantitative Changes of Articular Cartilage Microstructure During Compression of an Intact Joint," Proc. Intl. Soc. Mag. Resonance Med., 7:547 (1999).

Falcao et al., "User-steered image segmentation paradigms. Live wire and live lane," Graphical Models and Image Processing 60: 233-260 (1998).

Felson et al., "Weight Loss Reduces the risk for symptomatic knee osteoarthritis in women: the Framingham study," Ann Intern Med 116: 535-539 (1992).

Gandy et al., "One-Year Longitudinal Study of Femoral Cartilage Lesions in Knee Arthritis," Proc. Intl. Soc. Mag. Resonance Med., 7:1032 (1999).

Garrett, "Osteochondral allografts for reconstruction of articular defects of the knee," Instr Course Lect 47: 517-522 (1998).

Gerscovich, "A Radiologist's Guide to the Imaging in the Diagnosis and Treatment of Developmental Dysplasia of the Hip," Skeletal Radiol 26: 447-456 (1997).

Ghelman et al., "Kinematics of the Knee After Prosthetic Replacements", Clin. Orthop. May 1975: (108): 149-157.

Ghosh et al., "Watershed Segmentation of High Resolution Articular Cartilage Images for Assessment of Osteoarthritis," International Society for Magnetic Resonance in Medicine, Philadelphia, (1999).

Glaser et al., "Optimization and Validation of a Rapid Highresolution T1-W 3-D Flash Waterexcitation MR Sequence for the Quantitative Assessment of Articular Cartilage Volume and Thickness," Magnetic Resonance Imaging 19: 177-185 (2001).

Goodwin et al., "MR Imaging of Articular Cartilage: Striations in the Radial Layer Reflect the Fibrous Structure of Cartilage," Proc. Intl. Soc. Mag. Resonance Med., 7:546 (1999).

Gouraud, "Continuous shading of curved surfaces," IEEE Trans on Computers C-20(6) (1971).

Graichen et al., "Three-Dimensional Analysis of the Width of the Subacromial Space in Healthy Subjects and Patients With Impingement Syndrome," American Journal of Roentgenology 172: 1081-1086 (1999).

Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).

(56) References Cited

OTHER PUBLICATIONS

Hafez et al., "Computer-assisted Total Knee Arthroplasty Using Patient-specific Templating," *Clinical Orthopaedics and Related Research*, No. 444, pp. 184-192 (Mar. 2006).

Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).

Hardy et al., "Measuring the Thickness of Articular Cartilage From MR Images," J. Magnetic Resonance Imaging 13: 120-126 (2001).

Hardy et al., "The Influence of the Resolution and Contrast on Measuring the Articular Cartilage Volume in Magnetic Resonance Images" Magn Reson Imaging. 18(8): 965-972 (Oct. 2000).

Hargreaves et al., "MR Imaging of Articular Cartilage Using Driven Equilibrium," Magnetic Resonance in Medicine 42(4): 695-703 (Oct. 1999).

Hargreaves et al., "Technical considerations for DEFT imaging," International Society for Magnetic Resonance in Medicine, Sydney, Australia (Apr. 17-24, 1998).

Hargreaves et al., "Imaging of articular cartilage using driven equilibrium," International Society for Magnetic Resonance in Medicine, Sydney, Australia (Apr. 17-24, 1998).

Hastings et al., "Double Hemiarthroplasty of the Knee in Rheumatoid Arthritis," A Survey of Fifty Consecutive Cases, J. Bone Joint Surg. Br. 55(1):112-118 (1973).

Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).

Haut et al., "A High Accuracy Three-Dimensional Coordinate Digitizing System for Reconstructing the Geometry of Diarthrodial Joints," J. Biomechanics 31: 571-577 (1998).

Hayes et al., "Evaluation of Articular Cartilage: Radiographic and Cross-Sectional Imaging Techniques," Radiographics 12: 409-428 (1992).

Henderson et al., "Experience with the Use of the Macintosh Prosthesis in Knees of Patients with Pheumatoid Arthritis," South. Med. J. 62(11):1311-1315 (1969).

Henkelman, "Anisotropy of NMR Properties of Tissues", Magn Res Med. 32: 592-601 (1994).

Herberhold et al., "An MR-Based Technique for Quantifying the Deformation of Articular Cartilage During Mechanical Loading in an Intact Cadaver Joint," Magnetic Resonance in Medicine 39(5): 843-850 (1998).

Herberhold, "In Situ Measurement of Articular Cartilage Deformation in Intact Femorapatellar Joints Under Static Loading", Journal of biomechanics 32: 1287-1295 (1999).

Herrmann et al., "High Resolution Imaging of Normal and Osteoarthritic Cartilage with Optical Coherence Tomogrqaphy," J. Rheumatoil 26: 627-635 (1999).

High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).

Hohe, "Surface Size, Curvature Analysis, and Assessment of Knee Joint Incongruity With MR Imaging In Vivo", Magnetic Resonance in Medicine, 47: 554-561 (2002).

Holdsworth et al., "Benefits of Articular Cartilage Imaging at 4 Tesla: An In Vivo Study of Normal Volunteers," Proc. Intl. Soc. Mag. Resonance Med., 7:1028 (1999).

Hughes et al., "Technical Note: A Technique for Measuring the Surface Area of Articular Cartilage in Acetabular Fractures," Br. J. Radiol; 67: 584-588 (1994).

Husmann et al., "Three-Dimensional Morphology of the Proximal Femur," J. Arthroplasty; 12(4): 444-450 (Jun. 1997).

Hyhlik-Durr et al., "Precision of Tibial Cartilage Morphometry with a coronal water-excitation MR sequence," European Radiology 10(2): 297-303 (2000).

Ihara H., "Double-Contrast CT Arthrography of the Cartilage of the Patellofemoral Joint," Clin. Orthop.; 198: 50-55 (Sep. 1985).

Iida et al., "Socket Location in Total Hip Replacement: Preoperative Computed Tomography and Computer Simulation" Acta Orthop Scand; 59(1): 1-5 (1998).

Irarrazabal et al., "Fast three-dimensional magnetic resonance imaging," Mag Res. Med. 33: 656-662 (1995).

Jessop et al., "Follow-up of the Macintosh Arthroplasty of the Knee Joint," Rheumatol Phys. Med. 11(5):217-224 (1972).

Johnson et al., "The distribution of load across the knee. A comparison of static and dynamic measurements," J. Bone Joint Surg 62B: 346-349 (1980).

Johnson, "In vivo contact kinematics of the knee joint: Advancing the point cluster technique," Ph.D. Thesis, University of Minnesota (1999).

Johnson et al., "Development of a knee wear method based on prosthetic in vivo slip velocity," Transaction of the Orthopedic Research Society, 46th Annual Meeting (Mar. 2000).

Jonsson et al., "Precision of Hyaline Cartilage Thickness Measurements," Acta Radiol 1992; 33(3): 234-239 (1992).

Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).

Karvonen et al., "Articular Cartilage Defects of the Knee: Correlation Between Magnetic Resonance Imaging and Gross Pathology," Ann Rheum Dis. 49: 672-675 (1990).

Kass et al., "Snakes: Active contour models.," Int J Comput Vision 1: 321-331 (1988).

Kates, et al., "Experiences of Arthroplasty of the Rheumatoid Knee Using MacIntosh Prostheses," Ann. Rheum. Dis. 28(3):328 (1969).

Kaufman et al., "Articular Cartilage Sodium content as a function of compression" Seventh Scientific Meeting of ISMRM, p. 1022, 1999 T. 105, V. III.

Kay et al., The Macintosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Klosterman et al., "T2 Measurements in Adult Patellar Cartilage at 1.5 and 3.0 Tesla," ISMRM Seventh Scientific Meeting, Philadelphia, PA, (May 22-28, 1999).

Knauss et al., "Self-Diffusion of Water in Cartilage and Cartilage Components as Studied by Pulsed Field Gradient NMR," Magnetic Resonance in Medicine 41:285-292 (1999).

Koh et al., "Visualization by Magnetic Resonance Imaging of Focal Cartilage Lesions in the Excised Mini-Pig Knee," J. Orthop. Res; 14(4): 554-561 (Jul. 1996).

Korhonen et al., "Importance of the Superficial Tissue Layer for the Indentation Stiffness of Articular Cartilage," Med. Eng. Phys; 24(2): 99-108 (Mar. 2002).

Korkala et al., "Autogenous Osteoperiosteal Grafts in the Reconstruction of Full-Thickness Joint Surface Defects," Int. Orthop.; 15(3): 233-237 (1991).

Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).

Kwak et al., "Anatomy of Human Patellofemoral Joint Articular Cartilage: Surface Curvature Analysis," J. Orthop. Res.; 15: 468-472 (1997).

LaFortune et al., "Three dimensional kinematics of the human knee during walking," J. Biomechanics 25: 347-357 (1992).

Lam et al., "X-Ray Diagnosis: A Physician's Approach", Editor Lam, 1998, Springer-Verlag publishers, Title page and Index Only (ISBN 9813083267).

Lang et al., "Functional joint imaging: a new technique integrating MRI and biomotion studies," International Society for Magnetic Resonance in Medicine, Denver (Apr. 18-24, 2000).

Lang et al., Risk factors for progression of cartilage loss: a longitudinal MRI study. European Society of Musculoskeletal Radiology, 6th Annual Meeting, Edinburgh, Scotland (1999).

(56) References Cited

OTHER PUBLICATIONS

Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).

Ledingham et al., "Factors affecting radiographic progression of knee osteoarthritis," Ann Rheum Dis 54: 53-58 (1995).

Leenslag et al., "A Porous Composite for Reconstruction of Meniscus Lesions," Biological and Biomechanical Perform. of Biomaterials, Elsevier Science Publishers Amsterdam pp. 147-152 (1986).

Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).

Li et al., A Boundary Optimization Algorithm for Delineating Brain Objects from CT Scans: Nuclear Science Symposium and Medical Imaging Conference 1993 IEEE Conference Record, San Francisco, CA (1993).

Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).

Lorensen et al., "Marching cubes: a high resolution 3d surface construction algorithm," Comput Graph 21: 163-169 (1987).

Losch et al., "A non-invasive technique for 3-dimensional assessment of articular cartilage thickness based on MRI part 1: development of a computational method," Magn Res Imaging 15(7): 795-804 (1997).

Lu et al., "Bone position estimation from skin marker co-ordinates using globals optimization with joint constraints," J Biomechanics 32: 129-134 (1999).

Lu et al., "In vitro degradation of porous poly(L-lactic acid) foams", Biomaterials, 21(15):1595-1605, Aug. 2000.

Lucchetti et al., "Skin movement artefact assessment and compensation in the estimation of knee-joint kinematics," J Biomechanics 31: 977-984 (1998).

Lusse et al., "Measurement of Distribution of Water Content of Human Articular Cartilage Based on Transverse Relaxation Times: an In Vitro Study," Seventh Scientific Meeting of ISMRM, p. 1020 (1999).

Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).

MacIntosh, "Arthroplasty of the Knee in Rheumatoid Arthritis," Proceedings and Reports of Councils and Assotions, J. Bone & Joint Surg., vol. 48B No. (1): 179 (Feb. 1966).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

MacIntosh, "Hemiarthroplasty of the Knee Using a Space Occupying Prosthesis for Painful Varus and Valgus Deformities," J. Bone Joint Surg. Am. Dec. 1958:40-A:1431.

Maki et al., "SNR improvement in NMR microscopy using DEFT," J Mag Res; pp. 482-492 (1988).

Marler et al., "Soft-Tissue Augmentation with Injectable Alginate and Syngeneic Fibroblasts", Plastic & Reconstructive Surgery, 105(6):2049-2058, May, 2000.

Marshall et al., "Quantitation of Articular Cartilage Using Magnetic Resonance Imaging and Three-Dimensional Reconstruction," J. Orthop. Res.; 13: 814-823 (1995).

Matsen, III et al., "Robotic Assistance in Orthopaedic Surgery: A Proof of Principle Using Distal Femoral Arthroplasty", Clinical Ortho. and Related Research, 296:178-186 (1993).

Mattila et al., "Massive Osteoarticular Knee Allografts: Structural Changes Evaluated with CT," Radiology; 196: 657-660 (1995).

McCollum et al., "Tibial Plateau Prosthesis in Arthroplasty of the Knee," J. Bone Joint Surg. Am. 1970 52(4):827-8 (Feb. 1996).

McKeever, "The Classic Tibial Plateau Prosthesis," Clin. Orthop. Relat. Res. (192):3-12 (1985).

Merkle et al., "A Transceiver Coil Assembly for Hetero-Nuclear Investigations of Human Breast At 4T," Proc. Intl. Soc. Mag. Resonance Med., 7:170 (1999).

Meyer et al., "Simultaneous spatial and spectral selective excitation," Magn Res Med 15: 287-304 (1990).

Mills et al., "Magnetic Resonance Imaging of the Knee: Evaluation of Meniscal Disease," Curr. Opin. Radiol. 4(6): 77-82 (1992).

Milz et al., "The Thickness of the Subchondral Plate and Its Correlation with the thickness of the Uncalcified Articular Cartilage in the Human Patella," Anat. Embryol.; 192: 437-444 (1995).

Minas, "Chondrocyte Implantation in the Repair of Chondral Lesions of the Knee: Economics and Quality of Life", Am. J. Orthop. Nov. 1998; 27: 739-744.

Modest et al., "Optical Verification of a Technique for in Situ Ultrasonic Measurement of Articular Cartilage Thickness," J. Biomechanics 22(2): 171-176 (1989).

Mollica et al., "Surgical treatment of arthritic varus knee by tibial corticotomy and angular distraction with an external fixator," Ital J Orthrop Traumatol 18(1): 17-23 (1992).

Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).

Mundinger et al., "Magnetic Resonance Tomography in the Diagnosis of Peripheral Joints," Schweiz Med. Wochenschr. 121(15): 517-527 (1991) (Abstract Only).

Myers et al., "Experimental Assessment by High Frequency Ultrasound of Articular Cartilage Thickness and Osteoarthritic Changes," J. Rheumatol; 22: 109-116 (1995).

Nelson et al., "Arthroplasty and Arthrodesis of the Knee Joint," Orthop. Clin. North Am. 2 (1): 245-64 (1971).

Nieminen et al., "T2 Indicates Incompletely the Biomechanical Status of Enzymatically Degraded Articular Cartilage of 9.4T," Proc. Intl. Soc. Mag. Resonance Med., 7:551 (1999).

Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).

Nizard, "Role of tibial osteotomy in the treatment of medical femorotibial osteoarthritis," Rev Rhum Engl Ed 65(7-9): 443-446 (1998).

Noll et al., "Homodyne detection in magnetic resonance imaging," IEEE Trans Med Imag 10(2): 154-163 (1991).

Ogilvie-Harris et al., "Arthroscopic management of the degenerative knee," Arthroscopy 7: 151-157 (1991).

Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).

Pearle et al., "Use of an external MR-tracking coil for active scan plane registration during dynamic Musculoskeletal MR imaging in a vertically open MR unit," American Roentgen Ray Society, San Francisco, CA (1998).

Peterfy et al., "Quantification of the volume of articular cartilage in the metacarpophalangeal joints of the hand: accuracy and precision of three-dimensional MR imaging," AJR 165: 371-375 (1995).

Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).

Peterfy et al., "Quantification of articular cartilage in the knee with pulsed saturation transfer subtraction and fat-suppressed MR imaging: optimization and validation," Radiology 192(2): 485-491 (1994).

Peterfy et al., "Emerging Applications of Magnetic Resonance Imaging in the Evaluation of Articular Cartilage," Radiol Clin North Am.; 34(2): 195-213 (Mar. 1996).

Pilch et al., "Assessment of Cartilage Volume In the Femorotibial Joint With Magnetic Resonance Imaging and 3D Computer Reconstruction," J. Rheumatol. 21(12): 2307-2319 (1994).

(56) References Cited

OTHER PUBLICATIONS

Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates •Aspects and Analysis of Potential Applications•" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." in Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.

Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo FLASH MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028 (1999).
Robinson, "The Early Innovators of Today's Resurfacing Condylar Knees", The Journal of Arthroplasty, vol. 20, No. 1, Suppl. 1, 2005.
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an—dimensional digitized picture with applications," Pattern Recognition 27(11): 1551-1565 (1994).
Schiffers et al., In German: "Planning and execution of orthopedic surgery using individualized templates," *Der Orthopäde*, Springer-Verlag, vol. 29, No. 7, pp. 636-640, (Jul. 2000).
Schiffers et al., English Translation with Certification: "Planning and execution of orthopedic surgery using individualized templates," *Der Orthopäde*, Springer-Verlag, vol. 29, No. 7, pp. 636-640, (Jul. 2000).
Schipplein et al., "Interaction between active and passive knee stabilizers during level walking," J Orthop Res 9: 113-119 (1991).
Schorn et al. "MacIntosh Arthroplasty in Rheumatoid Arthritis," Rheumatol Rehabil. Aug. 17, 1978(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: an Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Slone et al., "Body CT: A Practical Approach", Editor Slone, 1999 McGraw-Hill publishers, Title page and Table of Contents pgs. Only (ISBN 007058219).

(56) References Cited

OTHER PUBLICATIONS

Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method for Quantifying Time Dependent Changes in MR Signal Intensity of Articular Cartilage As a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Stout et al., "X-Ray Structure Determination: A Practical Guide", $2^{nd}$ Ed. Editors Stout and Jensen, 1989, John Wiley & Sons, Title page and Table of Contents pp. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT vol. 4322, pp. 87-97, 2001.
Tebben et al., "Three-Dimensional Computerized Reconstruction. Illustration of Incremental Articular Cartilage Thinning," Invest. Radiol. 32(8): 475-484 (1997).
Thoma et al., In German: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," *Journal DGPW*, No. 17, pp. 27-28 (May 1999).
Thoma et al., In German: "Custom-made knee endoprosthetics using subtraction data of three-dimensional CT scans—A new approach," *Der Orthopäde*, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," *Der Orthopäde*, Springer-Verlag, vol. 29, No. 7, pp. 641-644, (Jul. 2000).

Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000) 8:2127.
Tsai et al., "Accurate Surface Voxelization for Manipulating Volumetric Surfaces and Solids with Application in Simulating Musculoskeletal Surgery", Inst. Of Information and Computer Engineering, pp. 234-243, 2001.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).

(56) References Cited

OTHER PUBLICATIONS

Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 6 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.
Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.

(56) References Cited

OTHER PUBLICATIONS

United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10,764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office Extended European Search Report—European Application No. 10012404.9-2310, dated Apr. 1, 2011, 7 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
International Searching Authority, International Search Report—International Application No. PCT/US2010/055483, dated Jul. 28, 2011, together with the Written Opinion of the International Searching Authority, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2012/050964 dated Oct. 22, 2012, together with the Written Opinion of the International Searching Authority, 13 pages.
European Patent Office European Search Report—Application No. 12170854.9-1526 dated Oct. 9, 2012, 6 pages.
International Searching Authority, International Search Report—International Application No. PCT/US12/59936 dated Jan. 9, 2013, together with the Written Opinion of the International Searching Authority, 11 pages.
European Patent Office, Extended European Search Report—Application No. 10792589.3-2310 dated Feb. 7, 2013, 9 pages.
European Patent Office, European Search Report—Application No. 10192339.9-1257 dated Jan. 23, 2013, 5 pages.

(56) References Cited

OTHER PUBLICATIONS

European Patent Office, Extended European Search Report—Application No. 10746859.7-1654 dated Mar. 4, 2013, 7 pages.

European Patent Office, Extended European Search Report—Application No. 12192903.8-1654 dated Apr. 17, 2013, 8 pages.

International Searching Authority, International Search Report—International Application No. PCT/US2012/025280, dated Oct. 25, 2012, together with the Written Opinion of the International Searching Authority, 11 pages.

International Searching Authority, International Search Report—International Application No. PCT/US2009/036165, dated May 7, 2009, together with the Written Opinion of the International Searching Authority, 9 pages.

International Searching Authority, International Search Report—International Application No. PCT/US2012/025274, dated Oct. 25, 2012, together with the Written Opinion of the International Searching Authority, 12 pages.

International Searching Authority, International Search Report—International Application No. PCT/US2012/025277, dated Oct. 25, 2012, together with the Written Opinion of the International Searching Authority, 12 pages.

International Searching Authority, International Search Report—International Application No. PCT/US2013/025117, dated Apr. 12, 2013, together with the Written Opinion of the International Searching Authority, 9 pages.

Delp et al. "A Graphics-Based Software System to Develop and Analyze Models of Musculoskeletal Structures," Comput. Biol. Med., vol. 25, No. 1, pp. 21-34, 1995.

Harryson et al. "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.

Lombardi, Jr. et al. "Patient-Specific Approach in Total Knee Arthroplasty", Orthopedics, vol. 31, Issue 9, Sep. 2008, 8 pages.

Overhoff et al. "Total Knee Arthroplasty: Coordinate System Definition and Planning Based on 3-D Ultrasound Image Volumes", CARS 2001, pp. 283-288.

\* cited by examiner

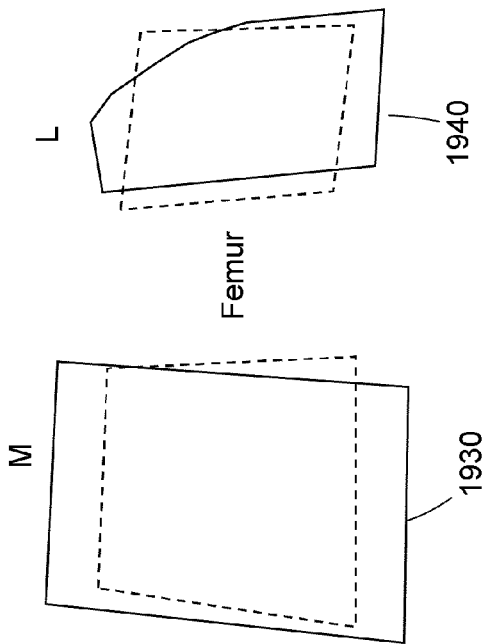
FIG. 4
FIG. 5
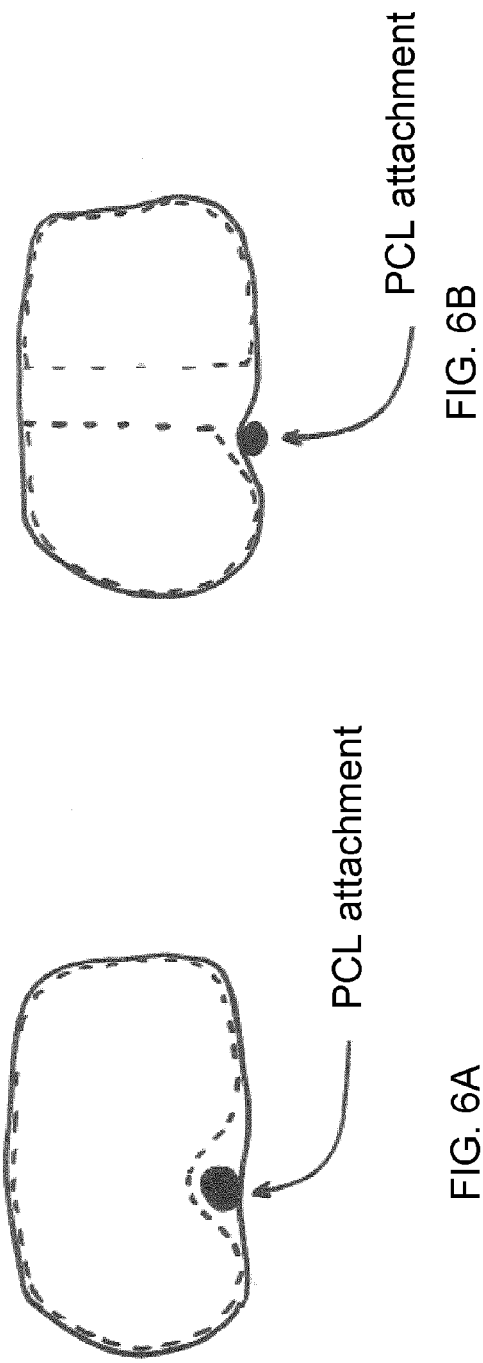
FIG. 6A
FIG. 6B

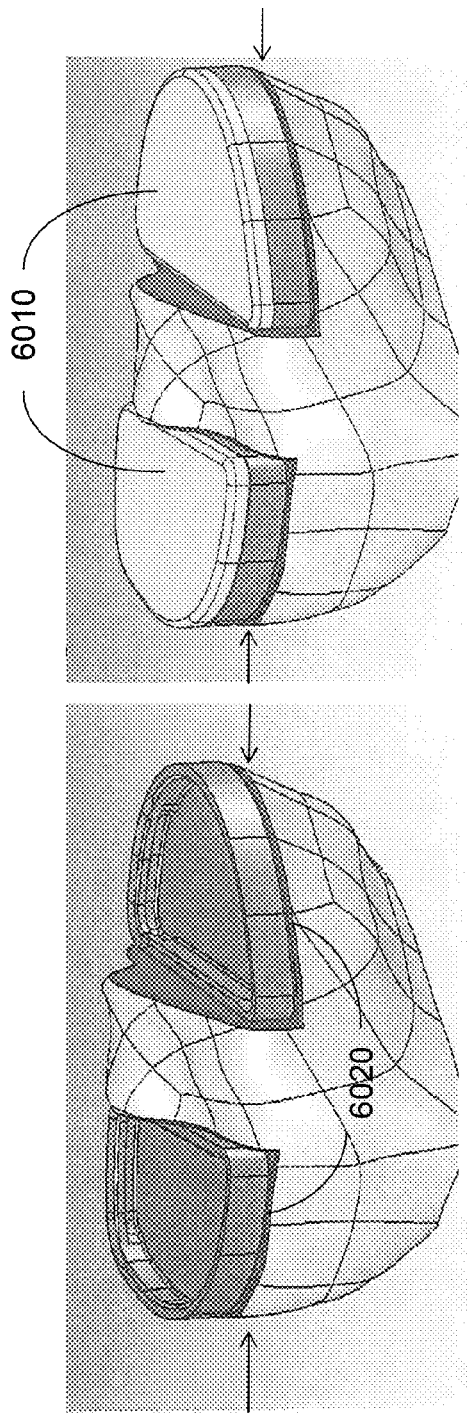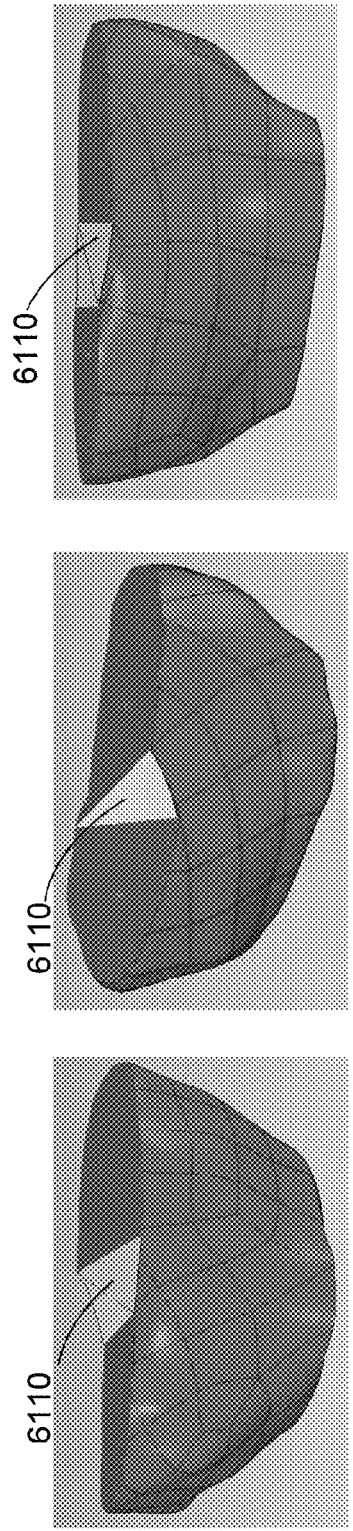

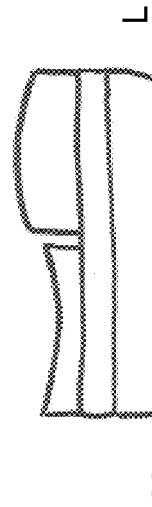
FIG. 10A — Same height medial and lateral — convex / concave
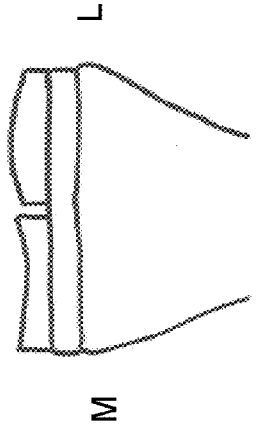
FIG. 10B — convex / flat
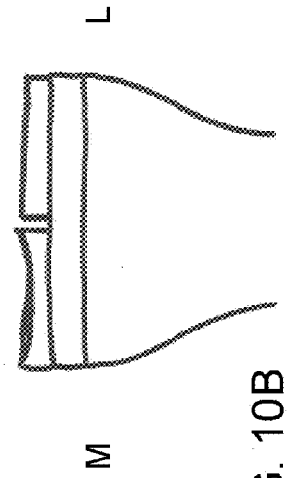
FIG. 10C — convex / convex
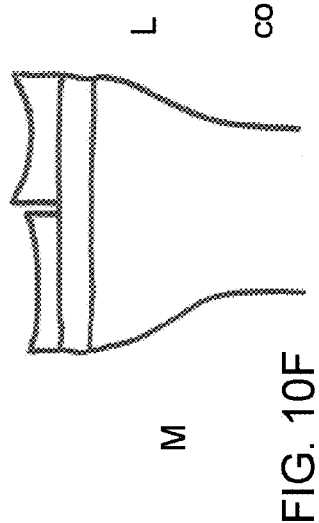
FIG. 10D — Lateral insert higher — convex / concave
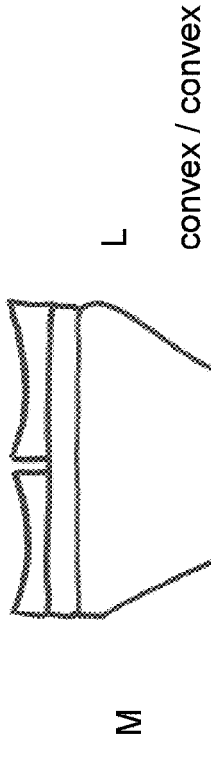
FIG. 10E — convex / flat
FIG. 10F — convex / convex

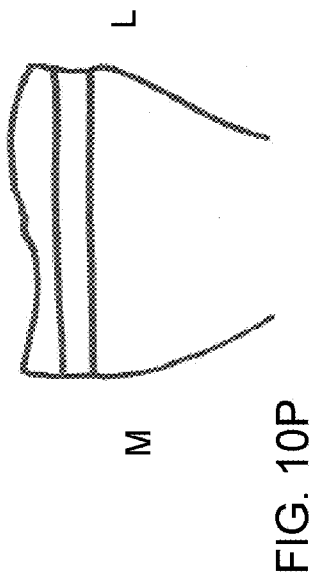
Medial insert higher
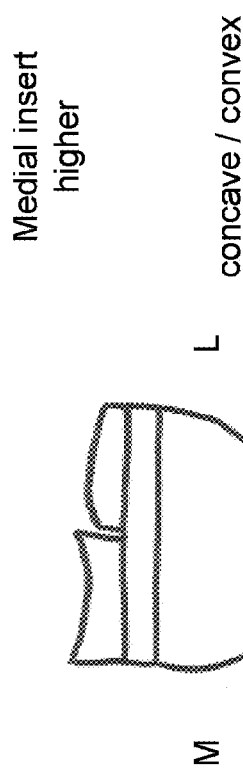
FIG. 10M
concave / convex
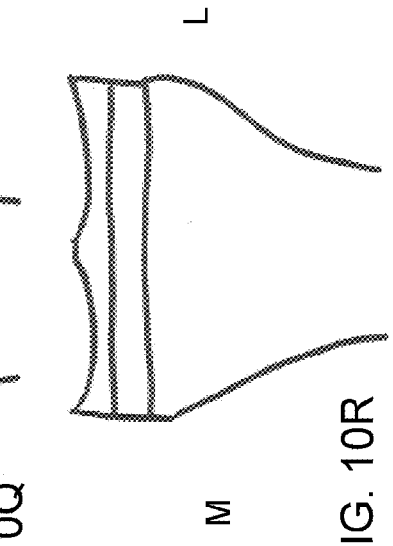
FIG. 10P
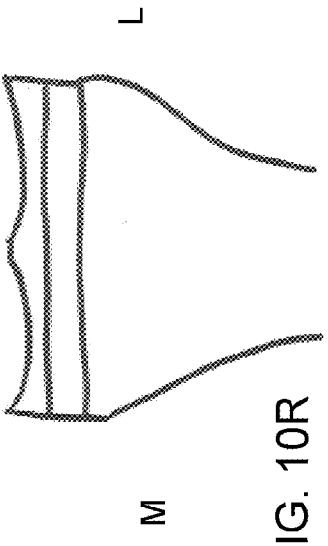
FIG. 10N
concave/ flat
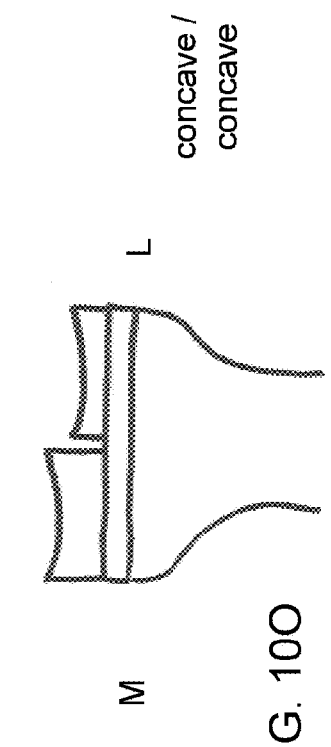
FIG. 10Q
concave / concave
FIG. 10O
FIG. 10R
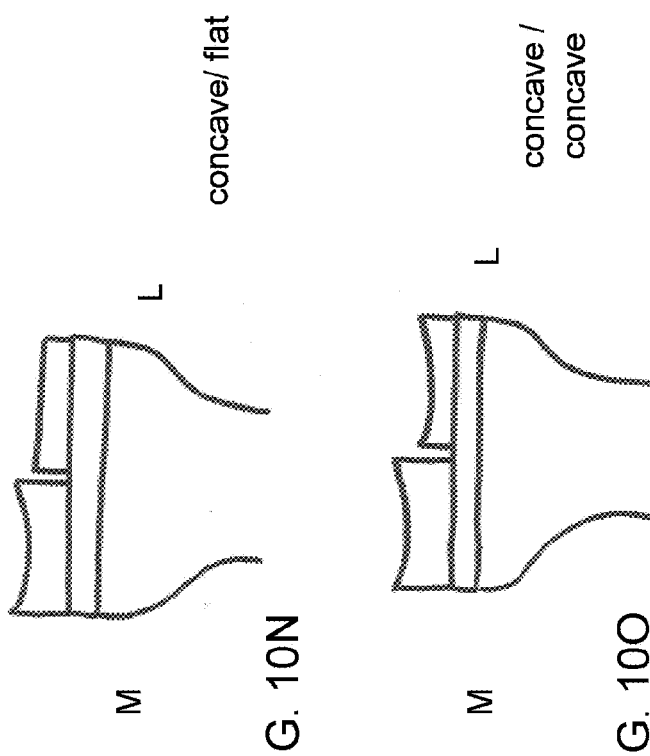

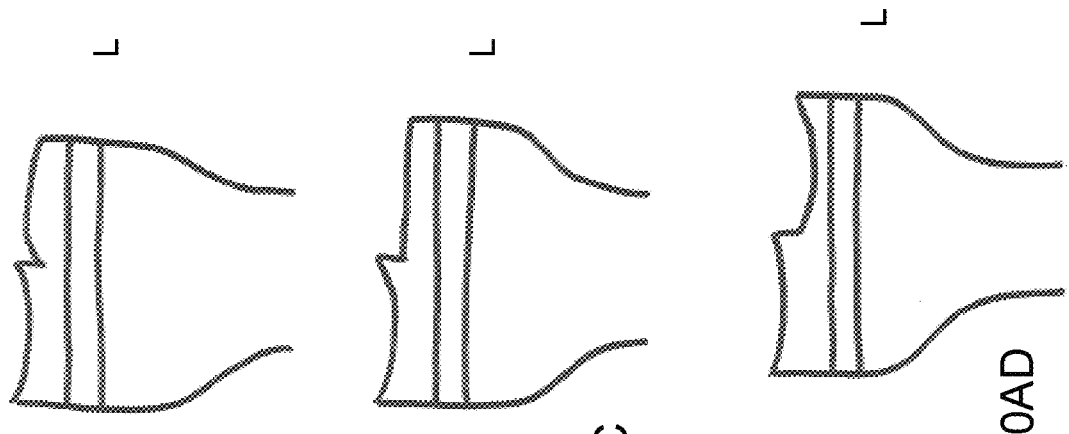
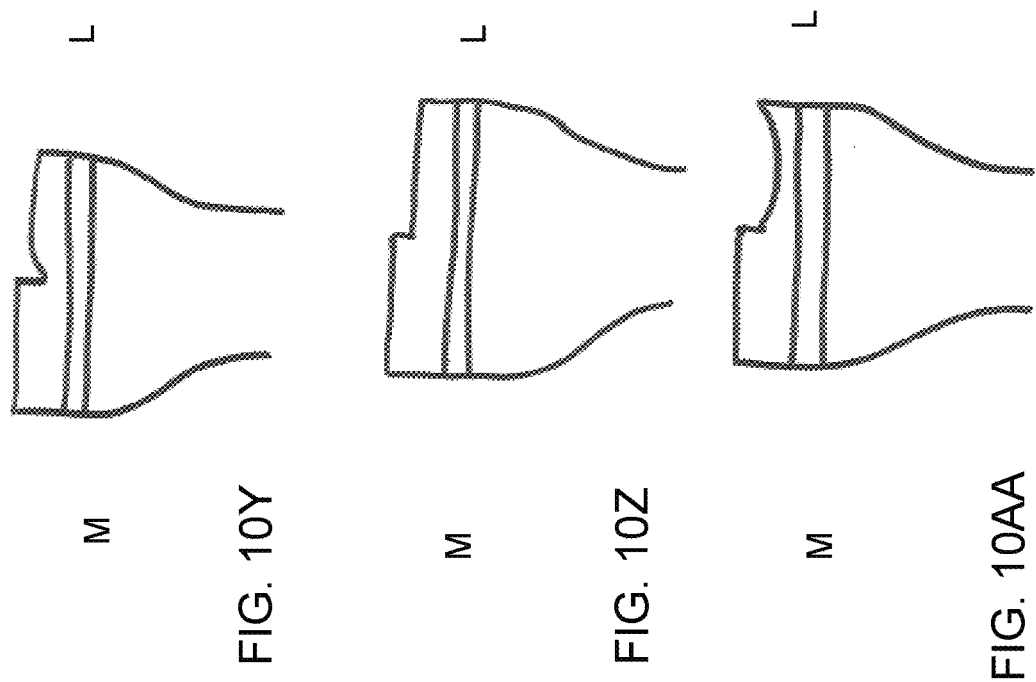

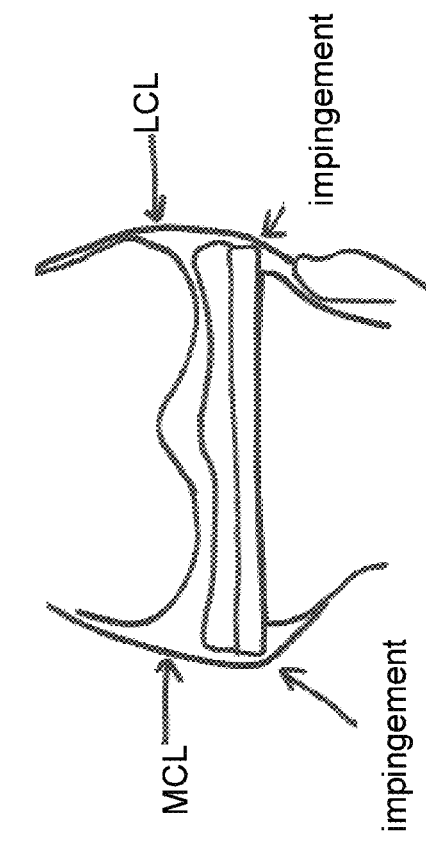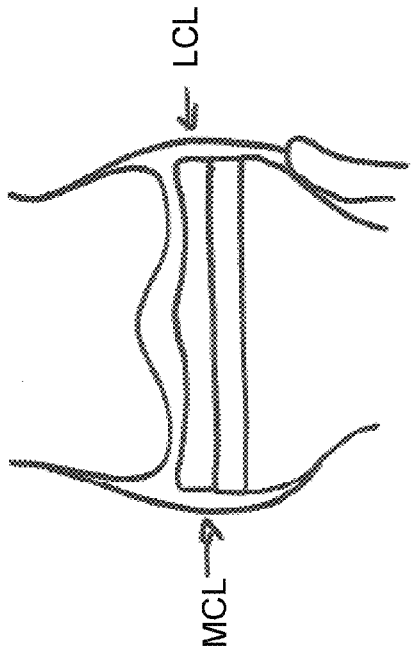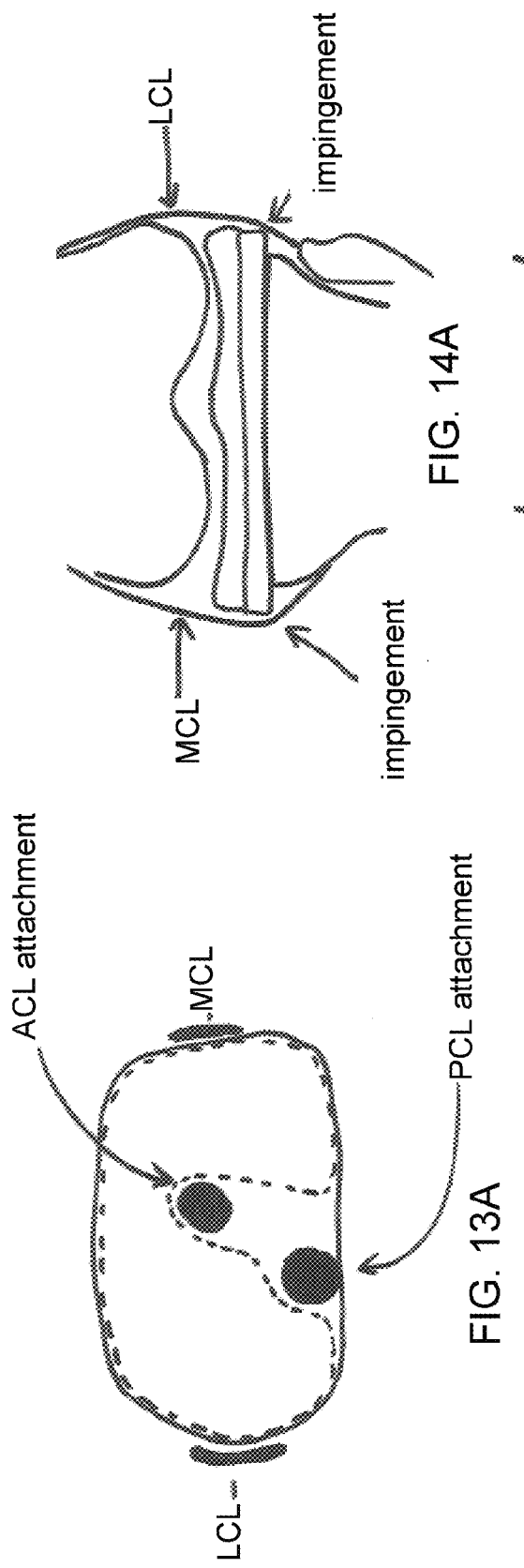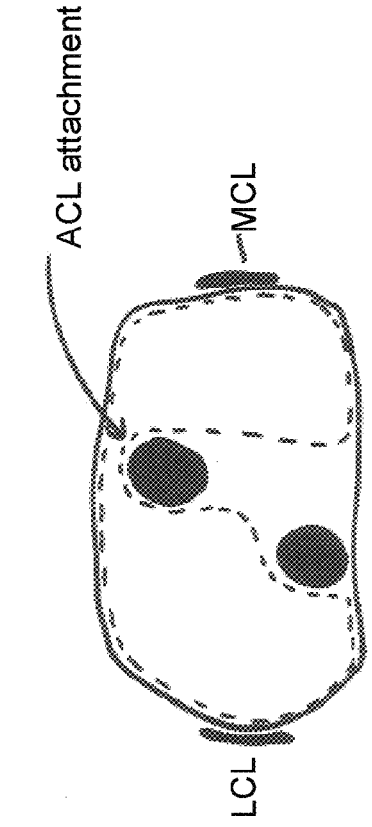
FIG. 13A
FIG. 13B
FIG. 14A
FIG. 14B (keels can be biased 5 degrees medially and 15 degrees laterally)

Tibial Cut with AP Sloped of 7°
J-Curve is tilted 7° posteriorly to
achieve a thicker poly anteriorly Tibial Cut with AP Sloped of 7°
J-Curve is the patient's natural
J-Curve

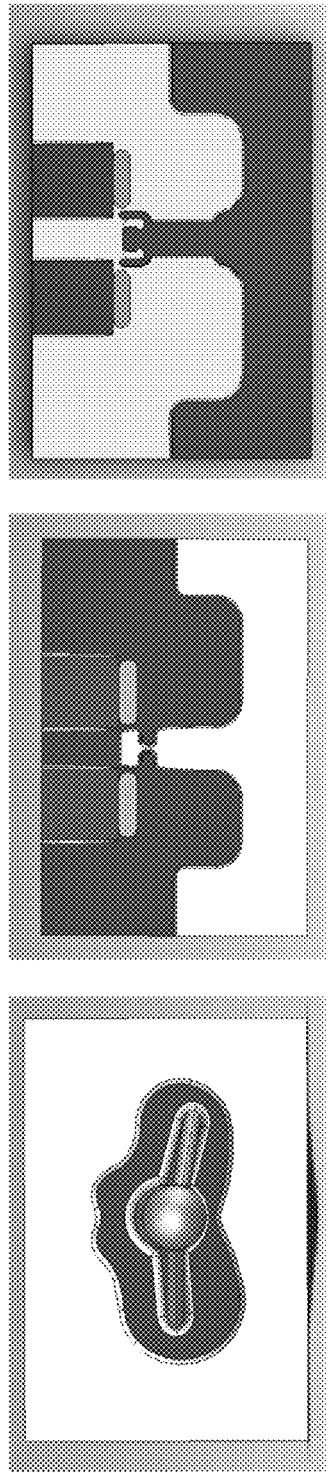
FIG. 48A
FIG. 48B
FIG. 48C
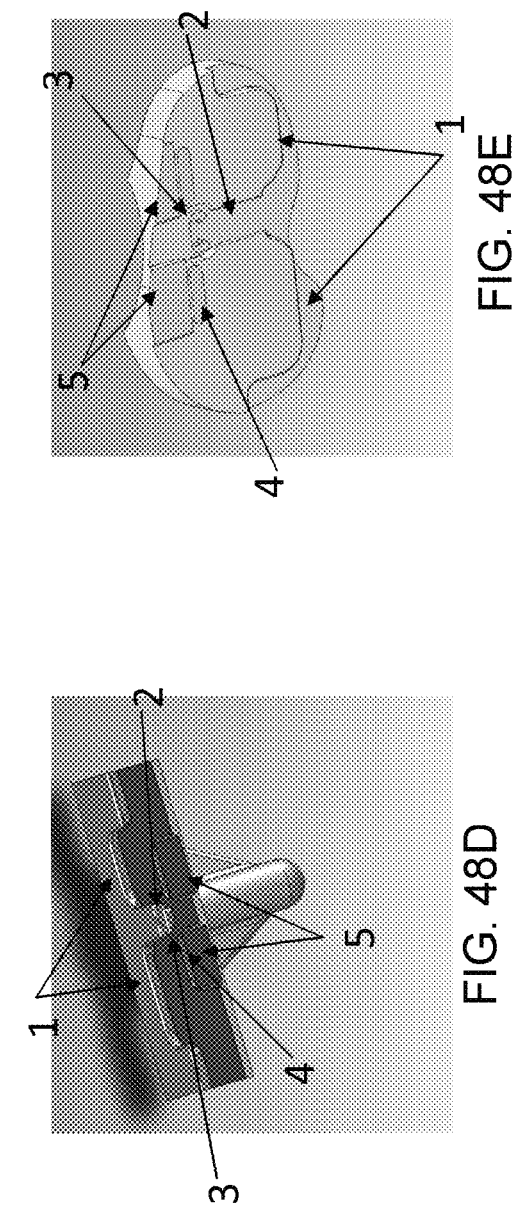
FIG. 48D
FIG. 48E

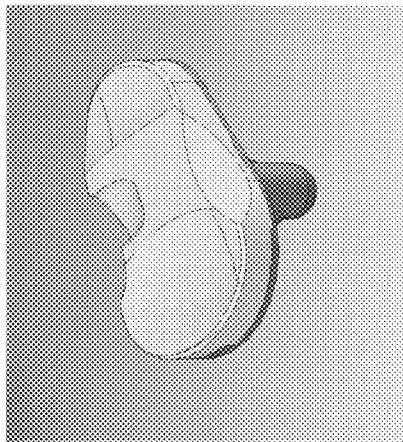
FIG. 49A
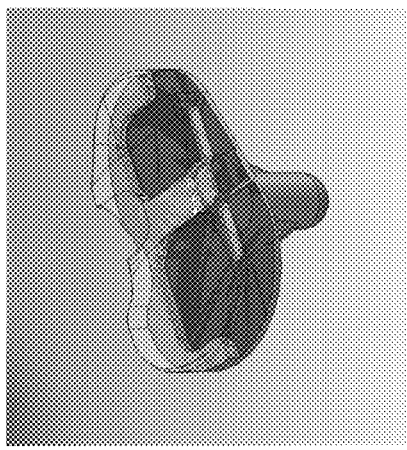
FIG. 49B
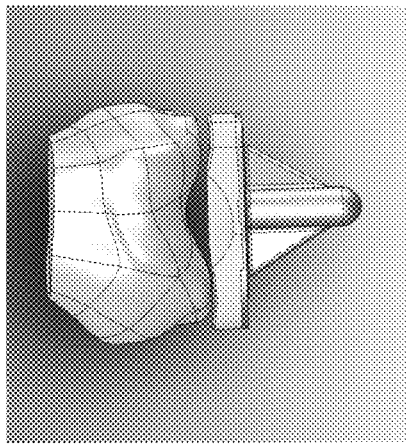
FIG. 49C
1 piece Insert
FIG. 50A
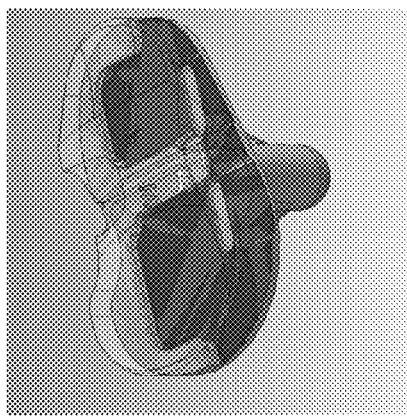
FIG. 50B
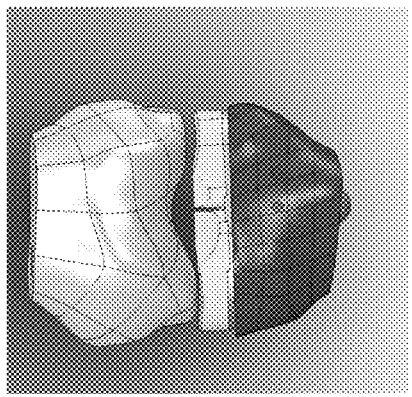
FIG. 50C
2 piece Insert Standard to Patient-Specific

Tibial Rotation

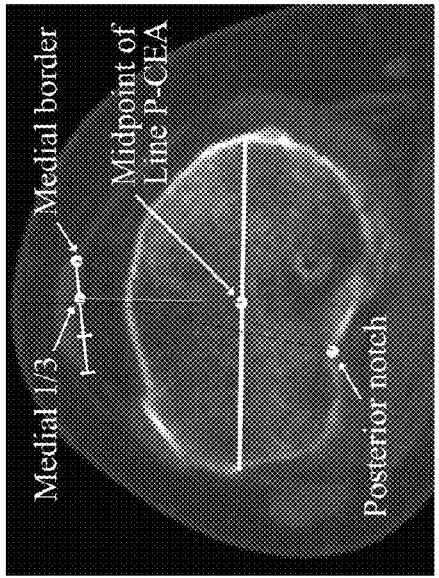

FIG. 52B

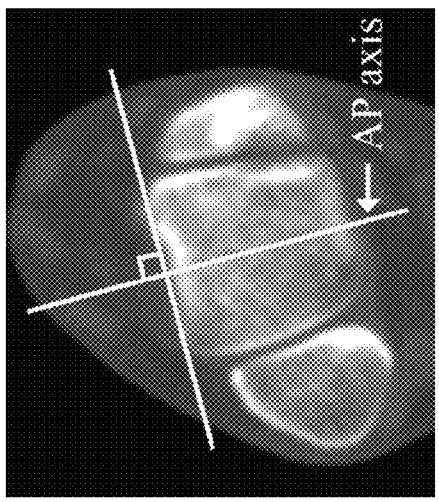

FIG. 52A

"Floating Insert" Technique
ROM technique, in which the knee is put through a full range of flexion and extension, allowing the tibial trial to orientate itself in the best position relative to the femoral component. The orientation is marked on the anterior tibial cortex and the tibial component is implanted to match this mark.

Anatomic Landmark Technique
(Mizu-uchi et al, Effect of Ankle Rotation on Cutting of the Tibia in TKA, JBJS 2006;Vol 88;Pages 2632-2636)
- AP Axis of ankle joint
- The line perpendicular to the anterior cortical line

Tibial Rotation Continues

TABLE I Data on Rotational Angle θ

| Tibial Anteroposterior Axis | Angle θ° | | |
|---|---|---|---|
| | All Knees (N = 53) | Male Patients (N = 11) | Female Patients (N = 42) |
| 1 | 16.5 +/- 7.4 (1.0 to 32.0) | 16.0 +/- 7.3 (6.1 to 26.0) | 16.7 +/- 7.5 (1.0 to 32.0) |
| 2 | 8.0 +/- 7.6 (-10.0 to 24.0) | 7.4 +/- 7.5 (-4.5 to 18.0) | 8.2 +/- 7.5 (-10.0 to 24.0) |
| 3 | 3.6 +/- 6.8 (-16.0 to 16.0) | 3.3 +/- 7.3 (-8.0 to 14.0) | 3.7 +/- 6.7 (-16.0 to 18.0) |
| 4 | 19.7 +/- 6.4 (7.0 to 33.0) | 20.5 +/- 5.9 (12.0 to 30.5) | 19.5 +/- 6.5 (7.0 to 33.0) |
| 5 | 5.9 +/- 6.6 (-7.0 to 20.0) | 5.8 +/- 5.2 (-2.0 to 16.0) | 6.0 +/- 6.9 (-7.0 to 20.0) |

*The values are given as the mean and the standard deviation, with the range in parentheses. A positive value of the angle indicates external rotation of the anteroposterior axis of the distal end of the tibia.

TABLE II Predicted Postoperative Tibial Coronal Alignment

| Tibial Anteroposterior Axis | Angle θ for All Knees (N - 53) | |
|---|---|---|
| | 7° Slope | 0° Slope |
| 1 | 4.3 +/- 1.9 (0.2 to 8.2) | 2.3 +/- 1.0 (0.1 to 4.6) |
| 2 | 2.1 +/- 2.0 (-2.6 to 6.3) | 1.1 +/- 1.1 (-1.4 to 3.5) |
| 3 | 1.0 +/- 1.8 (-4.1 to 4.3) | 0.5 +/- 1.0 (-2.2 to 2.4) |
| 4 | 5.1 +/- 1.6 (1.7 to 8.2) | 2.8 +/- 0.9 (0.9 to 4.7) |
| 5 | 1.6 +/- 1.7 (-1.7 to 5.2) | 0.9 +/- 0.9 (-0.9 to 2.5) |

*The values are given as the man and the standard deviation, with the range in parentheses. A positive value indicates varus alignment.

(Mizu-uchi et al, Effect of Ankle Rotation on Cutting of theTibia in TKA, JBJ S 2006; Vol 88; Pages 2632-2636)

FIG. 52C

Tibial Implant Profile

17100

PATIENT-ADAPTED AND IMPROVED ORTHOPEDIC IMPLANTS, DESIGNS, AND RELATED TOOLS

RELATED APPLICATIONS

This application claims the benefit of: U.S. Ser. No. 61/269,405, entitled "Patient-Specific Orthopedic Implants And Models" filed Jun. 24, 2009; U.S. Ser. No. 61/220,726, entitled "Patient-Specific Orthopedic Implants And Models," filed Jun. 26, 2009; U.S. Ser. No. 61/273,216, entitled "Patient-Specific Orthopedic Implants And Models" filed Jul. 31, 2009; U.S. Ser. No. 61/275,174, entitled "Patient-Specific Orthopedic Implants And Models" filed Aug. 26, 2009; U.S. Ser. No. 61/280,493, entitled "Patient-Adapted and Improved Orthopedic Implants, Designs and Related Tools" filed Nov. 4, 2009; U.S. Ser. No. 61/284,458, entitled "Patient-Adapted And Improved Orthopedic Implants, Designs And Related Tools" filed Dec. 18, 2009.

This application is also a continuation in part of U.S. Ser. No. 12/660,529, entitled "Patient-Adapted and Improved Orthopedic Implants, Designs, and Related Tools" filed Feb. 25, 2010, which claims priority to and the benefit of U.S. Ser. No. 61/155,362, entitled "Patient-Adapted and Improved Orthopedic Implants, Designs, and Models" filed Feb. 25, 2009.

Each of the above-described applications is hereby incorporated by reference in its entirety and for all purposes, and this application claims priority to each of the applications listed above.

TECHNICAL FIELD

This application relates to improved and/or patient-adapted (e.g., patient-specific and/or patient-engineered) orthopedic implants and guide tools, as well as related methods, designs and models.

BACKGROUND

Generally, a diseased, injured or defective joint, such as, for example, a joint exhibiting osteoarthritis, has been repaired using standard off-the-shelf implants and other surgical devices. Specific off-the-shelf implant designs have been altered over the years to address particular issues. However, in altering a design to address a particular issue, historical design changes frequently have created one or more additional issues for future designs to address. Collectively, many of these issues have arisen from one or more differences between a patient's existing or healthy joint anatomy and the corresponding features of an implant component.

SUMMARY

The patient-adapted (e.g., patient-specific and/or patient-engineered) implant components described herein can be selected (e.g., from a library), designed (e.g., preoperatively designed including, optionally, manufacturing the components or tools), and/or selected and designed (e.g., by selecting a blank component or tool having certain blank features and then altering the blank features to be patient-adapted). Moreover, related methods, such as designs and strategies for resectioning a patient's biological structure also can be selected and/or designed. For example, an implant component bone-facing surface and a resectioning strategy for the corresponding bone-facing surface can be selected and/or designed together so that an implant component's bone-facing surface matches the resected surface in one or more aspects.

In certain embodiments, patient-adapted features of an implant component, guide tool or related method can be achieved by analyzing imaging test data and selecting and/or designing (e.g., preoperatively selecting from a library and/or designing) an implant component, a guide tool, and/or a procedure having a feature that is matched and/or optimized for the particular patient's biology. The imaging test data can include data from the patient's joint, for example, data generated from an image of the joint such as x-ray imaging, cone beam CT, digital tomosynthesis, ultrasound, MRI or CT scan, or a PET or SPECT scan, is processed to generate a varied or corrected version of the joint or portions of the joint or surfaces within the joint. Certain embodiments provide methods and devices to create a desired model of a joint or portions or surfaces of a joint based on data derived from the existing joint. For example, the data also can be used to create a model that can be used to analyze the patient's joint and to devise and evaluate a course of corrective action. The data and/or model also can be used to design an implant component having one or more patient-specific features, such as a surface or curvature.

In one aspect, certain embodiments provide a tibial implant for a knee arthroplasty that includes (a) a tibial tray sized and shaped generally for placement on a proximal surface of a tibia of a patient with at least one insert locking mechanism, and (b) a first insert, a second insert, or both a first and second tibial insert. The first insert can include a first reciprocal locking mechanism, a first bottom surface for engaging a surface of the tibial tray, a first articular surface portion generally opposite the first base surface, and a first thickness extending in a generally perpendicular direction between the first bottom surface and the first articular surface. The second insert can include a second reciprocal locking mechanism, a second bottom surface for engaging a surface of the tibial tray, a second articular surface portion generally opposite the second base surface, and a second thickness extending in a generally perpendicular direction between the second bottom surface and the second articular surface. In some embodiments, the first thickness of the first insert can be greater than the second thickness of the second insert. The first and second thicknesses can be measured, for example, from geographic centers of the first and second contact areas of the first and second articular surfaces, respectively, and/or from corresponding edges of first and second contact areas of the first and second articular surfaces, respectively, and/or from central points of the first and second articular surfaces, respectively, and/or from the point of the first and second articular surfaces that are closest to the first and second bottom surfaces, respectively, and/or from the point of the first and second articular surfaces that are furthest from the first and second bottom surfaces, respectively. In some embodiments, the first and second thicknesses can be average thicknesses of the first and second inserts, respectively.

In some embodiments, the first thickness of the first insert can be substantially greater than the second thickness of the second insert. For example, the difference in the thickness of the first and second thicknesses can be a statistically significant difference. Alternatively or in addition, the first and second thicknesses can be a clinically significant difference, such as a difference in thickness that is sufficient to induce a clinical effect. A clinical effect can include an alignment of at least a portion of the knee and/or balancing of at least a portion of the knee. In addition, in some embodiments, the first and second inserts of the tibial implant can have different curvatures on respective articular surface portions and/or different slopes on respective articular surface portions.

In another aspect, certain embodiments provide a tibial implant for knee arthroplasty that can include a medial tibial insert comprising (i) a substantially planar inner surface for engaging a medial tibial tray face and (ii) an articular surface comprising an articular surface plateau and disposed therein a curved portion for opposing an articular surface of a medial femoral condyle. Alternatively or in addition, the tibial implant can include a lateral tibial insert comprising (i) a substantially planar inner surface for engaging a lateral tibial tray face and (ii) an articular surface comprising an articular surface plateau and disposed therein a curved portion for opposing an articular surface of a lateral femoral condyle. In some embodiments, the distance from the inner surface to the articular surface of the medial tibial insert can be different from the distance from the inner surface to the articular surface of the lateral tibial insert.

In some embodiments, the minimum distance from the inner surface to the articular surface of the medial tibial insert can be different from the minimum distance from the inner surface to the articular surface of the lateral tibial insert, and/or the maximum distance from the inner surface to the articular surface of the medial tibial insert can be different from the maximum distance from the inner surface to the articular surface of the lateral tibial insert, and/or the average distance from the inner surface to the articular surface of the medial tibial insert can be different from the average distance from the inner surface to the articular surface of the lateral tibial insert.

In some embodiments, the distance from the inner surface to the articular surface of the medial tibial insert can be substantially different and/or significantly different from the distance from the inner surface to the articular surface of the lateral tibial insert. For example, the distance from the inner surface to a central point of the articular surface of the medial tibial insert can be different from the distance from the inner surface to a central point of the articular surface of the lateral tibial insert. Alternatively or in addition, the distance from the inner surface to a central point of a contact area of the articular surface of the medial tibial insert is different from the distance from the inner surface to a central point of a contact area of the articular surface of the lateral tibial insert. Alternatively or in addition, the distance from the inner surface to an edge of the articular surface of the medial tibial insert is different from the distance from the inner surface to an edge the articular surface of the lateral tibial insert.

In some embodiments, the medial and lateral tibial inserts can have different curvatures in the respective curved portions, and/or different articular surface plateau slopes. In some embodiments, the slope for the articular surface plateau of the medial tibial insert can be patient-matched to the patient's medial tibial plateau slope, or it can be patient-matched to the patient's lateral tibial plateau slope. Similarly, in some embodiments, the slope for the articular surface plateau of the lateral tibial insert can be patient-matched to the patient's lateral tibial plateau slope, or it can be patient-matched to the patient's medial tibial plateau slope. In some embodiments, the tibial implant can have a first tibial tray that includes a medial tibial tray face and a second tibial tray that includes a lateral tibial tray face.

In another aspect, certain embodiments provide a method for making a tibial implant for use in repairing or replacing a knee of a patient. The method can include one or both of the steps of (a) electronically evaluating at least a portion of the knee based on image data of the of the knee, and (b) specifying one or more parameters of the tibial implant based at least in part on the evaluation. The specified parameters can define, at least in part, a tibial implant having a first articular surface higher than a second articular surface relative to a proximal end of a tibia of the knee when the tibial implant is implanted on the proximal end of the tibia. In some embodiments, the method can further include the step of planning a surgical result based on the electronic image data of a patient's knee and, optionally, the specified parameters can define, at least in part, a configuration of a tibial implant to substantially achieve a planned surgical result. The surgical result can be knee balancing during a surgical procedure and, optionally, the knee balancing can include knee balancing during extension and/or knee balancing during flexion. Alternatively or in addition, the surgical result can be knee alignment and, optionally, the knee alignment can include knee alignment of anatomical axes and/or knee alignment of biomechanical axes. In some embodiments, the knee alignment can include knee alignment of the patient's femur and tibia, for example, linear alignment and/or rotational alignment of the patient's femur and tibia. In some embodiments, the surgical result can include establishment or reestablishment of a particular joint line for the patient, for example, establishment of the joint-line of a medial compartment relative to a lateral compartment of the patient's knee.

In some embodiments, the method's step of electronically evaluating at least a portion of the knee can include determining a difference in the relative position of at least a portion of first and second articular surfaces of the knee. Alternatively and/or in addition, the step of electronically evaluating at least a portion of the knee can include determining a joint line of the knee, for example, pre-surgically determining a joint line of the knee and/or post-surgically determining a joint line of the knee.

In another aspect, certain embodiments provide a method for making a tibial implant having at least one of a medial tibial insert and a lateral tibial insert that substantially matches a patient's biological feature in one or more measurements, or as a predetermined percentage thereof. The method can include one or both of the steps of (a) preoperatively identifying a feature measurement of the patient's joint, and (b) designing at least one of the medial tibial insert and the lateral tibial insert to include substantially the same feature measurement or a predetermined percentage of the feature measurement identified in step (a). In certain embodiments, step (b) can include designing at least one of the medial tibial insert and lateral tibial insert using computer-aided design (CAD), and/or using computer-aided manufacturing (CAM), and/or cutting a blank insert or an insert having a blank feature to yield substantially the same feature measurement or a predetermined percentage of the feature measurement from step (a).

In some embodiments of the method, the substantially matching feature measurement can be selected from the group consisting of an insert mediolateral dimension substantially matching a corresponding patient mediolateral dimension or a predetermined percentage thereof, an insert thickness substantially matching a corresponding thickness of resected patient tissue or a predetermined percentage thereof, an insert perimeter shape substantially matching a corresponding patient perimeter shape or a predetermined percentage thereof, an insert surface slope substantially matching a corresponding patient slope or a predetermined percentage thereof, and an insert surface curvature substantially matching a corresponding patient curvature or a predetermined percentage thereof.

In some embodiments, designing a substantially matching or same feature measurement can include smoothing a line or curve of the patient's biological feature to derive the implant's substantially same feature measurement or a predetermined percentage of the feature measurement.

In another aspect, certain embodiments provide a method for implanting a knee implant in a patient's knee that includes one or both of the steps of (a) preparing a proximal end of a tibia to receive an implant; and (b) inserting at least one tibial implant onto the prepared proximal end of the tibia such that a first articular surface of the at least one implant engages a first articular surface of a femur or femoral implant and a second articular surface of the at least one implant engages a second articular surface of the femur or femoral implant. The first articular surface can be higher than the second articular surface relative to an anatomical axis of the tibia. In some embodiments, the tibial implant includes a single tibial implant tray, optionally with a single tibial insert, or alternatively, with dual tibial inserts. In other embodiments, the tibial implant includes dual tibial implant trays, optionally with a single tibial insert, or alternatively, with dual tibial inserts, for example, a single tibial insert for each of the two tibial implant trays.

In some embodiments, the method can further include adjusting a height of a first articular surface relative to second articular surface. In some embodiments, the method can further include one or more of aligning the patient's joint, assessing the alignment of the patient's joint, and adjusting alignment of the patient's joint. Adjusting the alignment of a patient's joint can include, for example, one or more of adjusting rotational alignment of the patient's joint, adjusting linear alignment of the patient's joint, and adjusting alignment of the patient's femur and tibia. In some embodiments, the method can include adjusting a biomechanical axis of the patient's joint and/or adjusting an anatomical axis of the patient's joint. In some embodiments, the method can further include one or more of balancing a patient's joint, assessing the balance of the patient's joint, and adjusting the balance of the patient's joint. Balancing can include, for example, balancing of the patient's joint in extension and/or in flexion.

In some embodiments, the method can further include planning a surgical procedure based on electronic image data of the patient's knee, for example, to achieve a predetermined surgical result and optionally performing the surgical procedure. In some embodiments, the method's step (b) can substantially achieve the predetermined surgical result. The surgical result can include, for example, one or more of joint balancing, joint alignment, inserting a first insert, adjusting balance with a second insert or trial insert, adjusting alignment with a second insert or trial insert, inserting a second insert, replacing a second insert or trial insert with a third insert or trial insert, adjusting balance with the third insert or trial insert, and adjusting alignment with a third insert or trial insert.

In another aspect, certain embodiments provide a method for balancing or optimizing ligament tension during implantation of a knee implant in a patient that includes one or more of the steps of (a) assessing the patient's medial joint gap distance and tension, (b) assessing the patient's lateral joint gap distance and tension, and (c) selecting independent medial and lateral tibial inserts to provide proper gap distance and tension. In some embodiments, the selected medial and lateral tibial inserts can have different thicknesses. In some embodiments, the selected medial tibial insert in step (c) is selected from among two or more medial tibial inserts having different thicknesses and/or the selected lateral tibial insert in step (c) is selected from among two or more lateral tibial inserts having different thicknesses. The selection of one or both medial and lateral tibial inserts can be used to substantially restore the patient's natural medial and/or lateral joint gaps, and/or it can be used to substantially restore the patient's natural kinematics.

In another aspect, certain embodiments provide a kit for implanting a tibial implant in a patient in need of knee replacement that includes (a) a tibial tray having a first surface for affixing the tray to the patient's tibia and an opposing second surface for engaging a medial tibial insert, and (b) two or more medial tibial inserts having different thicknesses from which to select one medial tibial insert for engaging with the tibial tray. In another aspect, certain embodiments provide a kit for implanting a tibial implant in a patient in need of knee replacement that includes (a) a tibial tray having a first surface for affixing the tray to the patient's tibia and an opposing second surface for engaging a lateral tibial insert; and (b) two or more lateral tibial inserts having different thicknesses from which to select one lateral tibial insert for engaging with the tibial tray.

It is to be understood that the features of the various embodiments described herein are not mutually exclusive and may exist in various combinations and permutations.

BRIEF DESCRIPTION OF THE DRAWINGS

The foregoing and other objects, aspects, features, and advantages of embodiments will become more apparent and may be better understood by referring to the following description, taken in conjunction with the accompanying drawings, in which:

FIG. 4 illustrates perimeters and areas of two bone surface areas for two different bone resection cut depths;

FIG. 5 is a distal view of the femur in which two different resection cuts are applied;

FIGS. 6A and 6B depict the posterior margin of an implant component selected and/or designed using imaging data or shapes derived from imaging data so that the implant component does not interfere with and stays clear of the patient's PCL;

FIGS. 7A and 7B show exemplary unicompartmental medial and lateral tibial implant components used together without (FIG. 7A) and with (FIG. 7B) a polyethylene layer or insert;

FIGS. 8A-C depict three different types of step cuts separating medial and lateral resection cut facets on a patient's proximal tibia;

FIGS. 13A and 13B depict embodiments of a tibial implant component that are ligament retaining;

FIGS. 14A and 14B depict embodiments of a tibial implant component impinge (FIG. 14A) and that do not impinge (FIG. 14B) ligaments;

FIGS. 48A to 48E illustrate various aspects of an embodiment of a tibial implant component, including a view of the tibial tray bottom (FIG. 48A), a view of the tibial tray top (FIG. 48B), a view of the tibial insert bottom (FIG. 48C), a top-front (i.e., proximal-anterior) perspective view of the tibial tray (FIG. 48D), and a bottom front (i.e., distal anterior) perspective view of the tibial insert (FIG. 48E);

FIGS. 49A-C show aspects of an embodiment of a tibial implant component that includes a tibial tray and a one-piece insert;

FIGS. 50A-C show aspects of an embodiment of a tibial implant component that includes a tibial tray and a one-piece insert;

FIGS. 52A-C show exemplary strategies for establishing proper tibial rotation for a patient;

Figure 1:
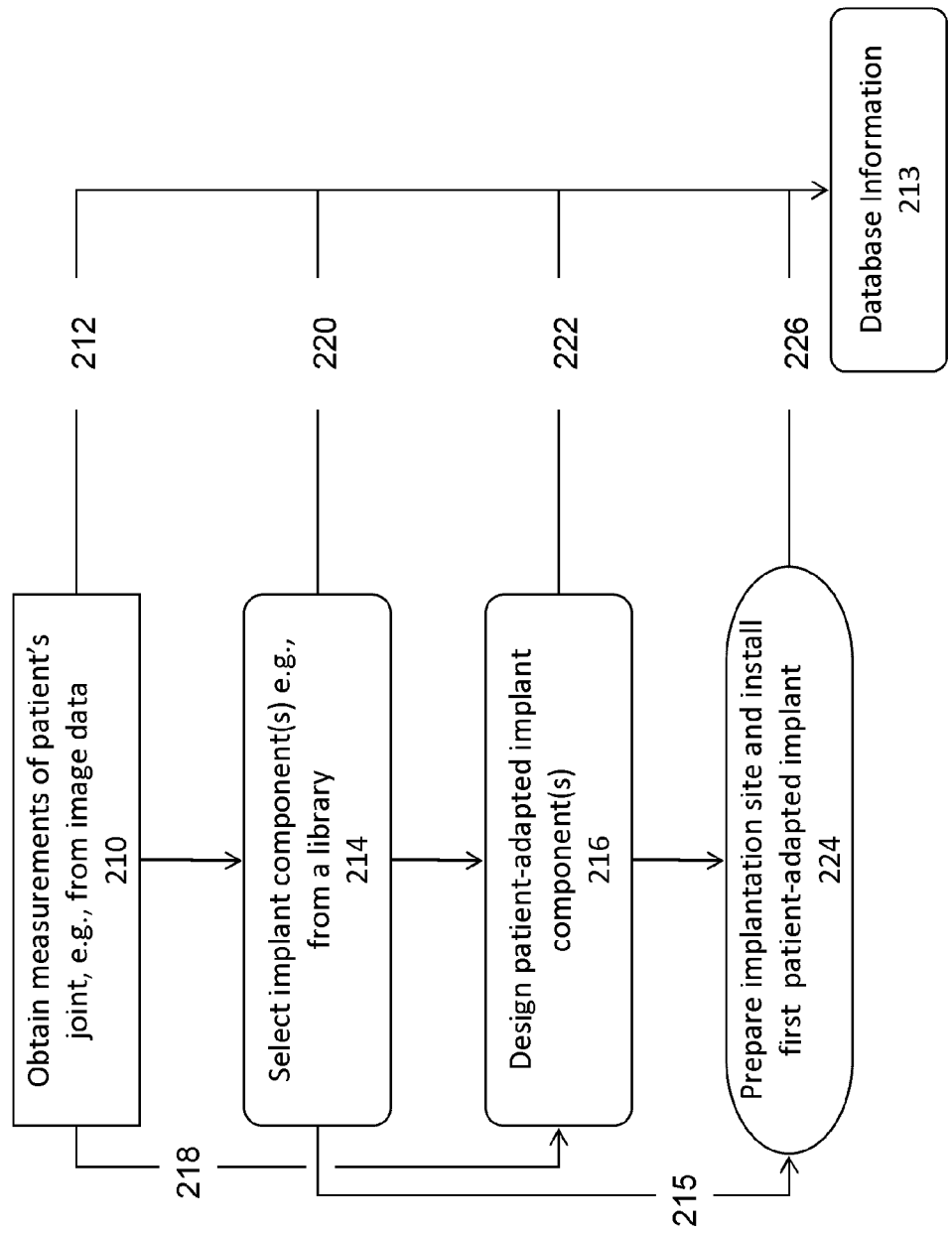
FIG. 1 is a flow chart illustrating a process that includes selecting and/or designing an initial patient-adapted implant.

Additional figure descriptions are included in the text below. Unless otherwise denoted in the description for each figure, "M" and "L" in certain figures indicate medial and lateral sides of the view; "A" and "P" in certain figures indicate anterior and posterior sides of the view, and "S" and "I" in certain figures indicate superior and inferior sides of the view.

DETAILED DESCRIPTION

Introduction

When a surgeon uses a traditional off-the-shelf implant to replace a patient's joint, for example, a knee joint, hip joint, or shoulder joint, certain features of the implant typically do not match the particular patient's biological features. These mismatches can cause various complications during and after surgery. For example, surgeons may need to extend the surgery time and apply estimates and rules of thumb during surgery to address the mismatches. For the patient, complications associated with these mismatches can include pain, discomfort, soft tissue impingement, and an unnatural feeling of the joint during motion, e.g., so-called mid-flexion instability, as well as an altered range of movement and an increased likelihood of implant failure. In order to fit a traditional implant component to a patient's articular bone, surgeons typically remove substantially more of the patient's bone than is necessary to merely clear diseased bone from the site. This removal of substantial portions of the patient's bone frequently diminishes the patient's bone stock to the point that only one subsequent revision implant is possible.

Certain embodiments of the implants, guide tools, and related methods of designing (e.g., designing and making), and using the implants and guide tools described herein can be applied to any joint including, without limitation, a spine, spinal articulations, an intervertebral disk, a facet joint, a shoulder, an elbow, a wrist, a hand, a finger, a hip, a knee, an ankle, a foot, or a toe joint. Furthermore, various embodiments described herein can apply to methods and procedures, and the design of methods and procedures, for resectioning the patient's anatomy in order to implant the implant components described herein and/or to using the guide tools described herein.

In certain embodiments, implant components and/or related methods described herein can include a combination of patient-specific and patient-engineered features. For example, patient-specific data collected preoperatively can be used to engineer one or more optimized surgical cuts to the patient's bone and to design or select a corresponding implant component having or more bone-facing surfaces or facets (i.e., "bone cuts") that specifically match one or more of the patient's resected bone surfaces. The surgical cuts to the patient's bone can be optimized (i.e., patient-engineered) to enhance one or more parameters, such as: (1) deformity correction and limb alignment (2) maximizing preservation of bone, cartilage, or ligaments, or (3) restoration and/or optimization of joint kinematics or biomechanics. Based on the optimized surgical cuts and, optionally, on other desired features of the implant component, the implant component's bone-facing surface can be designed or selected to, at least in part, negatively-match the shape of the patient's resected bone surface.

Improved Implants, Guide Tools and Related Methods

Certain embodiments are directed to implants, guide tools, and/or related methods that can be used to provide to a patient a pre-primary procedure and/or a pre-primary implant such that a subsequent, replacement implant can be performed with a second (and, optionally, a third, and optionally, a fourth) patient-adapted pre-primary implant or with a traditional primary implant. In certain embodiments, the pre-primary implant procedure can include 3, 4, 5, 6, 7, or more resection or surgical cuts to the patient's bone and the pre-primary implant can include on its corresponding bone-facing surface a matching number and orientation of bone-cut facets or surfaces.

In one illustrative embodiment, a first pre-primary joint-replacement procedure includes a patient-adapted implant component, guide tool, and/or related method. The patient-adapted implant component, guide tool, and/or related method can be preoperatively selected and/or designed from patient-specific data, such as one or more images of the patient's joint, to include one or more features that are patient-specific or patient-engineered. The features (e.g., dimensions, shape, surface contours) of the first pre-primary implant and, optionally, patient-specific data (e.g., features of the patient's resected bone surfaces and features of the patient's contralateral joint) can be stored in a database. When the first pre-primary implant fails, for example, due to bone loss or osteolysis or aseptic loosening at a later point in time (e.g., 15 years after the original implantation) a second implant can be implanted. For the second implant procedure, the amount of diseased bone can be assessed. If the amount of diseased bone to be resected is minimal, the patient-specific data can be used to select and/or design a second pre-primary procedure and/or a pre-primary implant. If the amount of diseased bone to be resected is substantial, a traditional primary procedure and a traditional implant can be employed.

Alternatively, certain embodiments are directed to implants, guide tools, and/or related methods that can be used to provide to a patient a primary procedure and/or a primary implant such that a subsequent replacement implant can be used as part of a traditional revision procedure. Certain embodiments are directed to implants, guide tools, and/or related methods that can be used to provide a patient-adapted revision implant. For example, following a traditional implant, a subsequent revision can include a patient-adapted procedure and/or a patient-adapted implant component as described herein.

FIG. 1 is a flow chart illustrating a process that includes selecting and/or designing a first patient-adapted implant, for example, a pre-primary implant. First, using the techniques described herein or those suitable and known in the art, measurements of the target joint are obtained 210. This step can be repeated multiple times, as desired. Optionally, a virtual model of the joint can be generated, for example, to determine proper joint alignment and the corresponding resection cuts and implant component features based on the determined proper alignment. This information can be collected and stored 212 in a database 213. Once measurements of the target joint are obtained and analyzed to determine resection cuts and patient-adapted implant features, the patient-adapted implant components can be selected 214 (e.g., selected from a virtual library and optionally manufactured without further design alteration 215, or selected from a physical library of implant components). Alternatively, or in addition, one or more implant components with best-fitting and/or optimized features can be selected 214 (e.g., from a library) and then further designed (e.g., designed and manufactured) 216. Alternatively or in addition, one or more implant components with best-fitting and/or optimized features can be designed (e.g., designed and manufactured) 218, 216 without an initial selection from a library. Using a virtual model to assess the selected or designed implant component(s), this process also can be repeated as desired (e.g., before one or more physical components are selected and/or generated). The information regarding the selected and/or designed implant component(s) can be collected and stored 220, 222 in a database 213. Once a desired first patient-adapted implant component or set of implant components is obtained, a surgeon can prepare the implantation site and install the first implant 224. The information regarding preparation of the implantation site and implant installation can be collected and stored 226 in a database 213. In this way, the information associated with the first pre-primary implant component is available for use by a surgeon for subsequent implantation of a second pre-primary or a primary implant.

Exemplary patient-adapted (i.e., patient-specific and/or patient-engineered) features of the implant components described herein are identified in Table 1. One or more of these implant component features can be selected and/or designed based on patient-specific data, such as image data.

TABLE 1

Exemplary implant features that can be patient-adapted based on patient-specific measurements

| Category | Exemplary feature |
|---|---|
| Implant or implant or component (applies knee, shoulder, hip, ankle, or other implant or implant component) | One or more portions of, or all of, an external implant component curvature |
| | One or more portions of, or all of, an internal implant dimension |
| | One or more portions of, or all of, an internal or external implant angle |
| | Portions or all of one or more of the ML, AP, SI dimension of the internal and external component and component features |
| | An outer locking mechanism dimension between a plastic or non-metallic insert and a metal backing component in one or more dimensions |
| | Component height |
| | Component profile |
| | Component 2D or 3D shape |
| | Component volume |
| | Composite implant height |
| | Insert width |
| | Insert shape |
| | Insert length |
| | Insert height |
| | Insert profile |
| | Insert curvature |
| | Insert angle |
| | Distance between two curvatures or concavities |
| | Polyethylene or plastic width |
| | Polyethylene or plastic shape |
| | Polyethylene or plastic length |
| | Polyethylene or plastic height |
| | Polyethylene or plastic profile |
| | Polyethylene or plastic curvature |
| | Polyethylene or plastic angle |
| | Component stem width |
| | Component stem shape |
| | Component stem length |
| | Component stem height |
| | Component stem profile |
| | Component stem curvature |
| | Component stem position |
| | Component stem thickness |
| | Component stem angle |
| | Component peg width |
| | Component peg shape |
| | Component peg length |
| | Component peg height |
| | Component peg profile |
| | Component peg curvature |
| | Component peg position |
| | Component peg thickness |
| | Component peg angle |
| | Slope of an implant surface |
| | Number of sections, facets, or cuts on an implant surface |
| Tibial implant or implant component | Slope of an implant surface |
| | Condylar distance, e.g., between tibial joint-facing surface concavities that engage femoral condyles |
| | Coronal curvature (e.g., one or more radii of curvature in the coronal plane) of one or both joint-facing surface concavities that engage each femoral condyle |
| | Sagittal curvature (e.g., one or more radii of curvature in the sagittal plane) of one or both joint-facing surface concavities that engage each femoral condyle |

The term "implant component" as used herein can include: (i) one of two or more devices that work together in an implant or implant system, or (ii) a complete implant or implant system, for example, in embodiments in which an implant is a single, unitary device. The term "match" as used herein is envisioned to include one or both of a negative-match, as a convex surface fits a concave surface, and a positive-match, as one surface is identical to another surface.

Traditional implants and implant components can have surfaces and dimensions that are a poor match to a particular patient's biological feature(s). The patient-adapted implants, guide tools, and related methods described herein improve upon these deficiencies. The following two subsections describe two particular improvements, with respect to the bone-facing surface and the joint-facing surface of an implant component; however, the principles described herein are applicable to any aspect of an implant component.

Bone-Facing Surface of an Implant Component

In certain embodiments, the bone-facing surface of an implant can be designed to substantially negatively-match one more bone surfaces. For example, in certain embodiments at least a portion of the bone-facing surface of a patient-adapted implant component can be designed to substantially negatively-match the shape of subchondral bone, cortical bone, endosteal bone, and/or bone marrow. A portion of the implant also can be designed for resurfacing, for example, by negatively-matching portions of a bone-facing surface of the implant component to the subchondral bone or cartilage. Accordingly, in certain embodiments, the bone-facing surface of an implant component can include one or more portions designed to engage resurfaced bone, for example, by having a surface that negatively-matches uncut subchondral bone or cartilage, and one or more portions designed to engage cut bone, for example, by having a surface that negatively-matches a cut subchondral bone.

In certain embodiments, the bone-facing surface of an implant component includes multiple surfaces, also referred to herein as bone cuts. One or more of the bone cuts on the bone-facing surface of the implant component can be selected and/or designed to substantially negatively-match one or more surfaces of the patient's joint, including one or more of a resected surface, a resurfaced surface, and an unaltered surface, including one or more of bone, cartilage, and other biological surfaces. For example, in certain embodiments, one or more of the bone cuts on the bone-facing surface of the implant component can be designed to substantially negatively-match (e.g., the number, depth, and/or angles of cut) one or more resected surfaces of the patient's bone. The bone-facing surface of the implant component can include any number of bone cuts, for example, two, three, four, less than five, five, more than five, six, seven, eight, nine or more bone cuts. In certain embodiments, the bone cuts of the implant component and/or the resection cuts to the patient's bone can include one or more facets on corresponding portions (e.g., medial and lateral portions) of an implant component. For example, the facets can be separated by a space or by a step cut connecting two corresponding facets that reside on parallel or non-parallel planes. These bone-facing surface features can be applied to various joint implants, including knee, hip, spine, and shoulder joint implants.

Any one or more bone cuts can include one or more facets. In some embodiments, medial and lateral facets of a bone cut can coplanar and contiguous, for example, as exemplified by coplanar and contiguous medial and lateral sections and/or anterior and posterior sections of a surface of a tibial implant component. Alternatively or in addition, facets can be separated by a space between corresponding regions of an implant component. Alternatively or in addition, facets of a bone cut can be separated by a transition such as a step cut, for example, a vertical or angled cut connecting two non-coplanar or non facets of a bone cut. In certain embodiments, one or more bone cut facets, bone cuts, and/or the entire bone-facing surface of an implant can be non-planar, for example, substantially curvilinear.

In certain embodiments, corresponding sections of an implant component can include different thicknesses (e.g., distance between the component's bone-facing surface and joint-facing surface), surface features, bone cut features, section volumes, and/or other features. For example, corresponding lateral and medial or sections of a tibial implant component surface can include different thicknesses, section volumes, bone cut angles, and bone cut surface areas. One or more of the thicknesses, section volumes, bone cut angles, bone cut surface areas, bone cut curvatures, numbers of bone cuts, peg placements, peg angles, and other features may vary between two or more sections (e.g., corresponding sections on lateral and medial condyles) of an implant component. Alternatively or in addition, one, more, or all of these features can be the same in corresponding sections of an implant component. An implant design that allows for independent features on different sections of an implant allows various options for achieving one or more goals, including, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width.

Alternatively or in addition, corresponding sections of an implant component can be designed to include the same features, for example, the same thickness or at least a threshold thickness. For example, when the corresponding implant sections are exposed to similar stress forces, similar minimum thicknesses can be used in response to those stresses. Alternatively or in addition, an implant design can include a rule, such that a quantifiable feature of one section is greater than, greater than or equal to, less than, or less than or equal to the same feature of another section of the implant component. For example, in certain embodiments, an implant design can include a lateral portion that is thicker than or equal in thickness to the corresponding medial portion. Similarly, in certain embodiments, an implant design can include a lateral height that is higher than or equal to the corresponding medial height.

In certain embodiments, one or more of an implant component's bone cut or bone cut facet features (e.g., thickness, section volume, cut angle, surface area, and/or other features) can be patient-adapted. For example, as described more fully below, patient-specific data, such as imaging data of a patient's joint, can be used to select and/or design an implant component (and, optionally, a corresponding surgical procedure and/or surgical tool) that matches a patient's anatomy and/or optimizes a parameter of that patient's anatomy. Alternatively or in addition, one or more aspects of an implant component, for example, one or more bone cuts, can be selected and/or designed to match predetermined resection cuts. Predetermined as used herein includes, for example, preoperatively determined (e.g., preoperatively selected and/or designed). For example, predetermined resection cuts can include resection cuts determined preoperatively, optionally in conjunction with a selection and/or design of one or more implant component features and/or one or more guide tool features. Similarly, a surgical guide tool can be selected and/or designed to guide the predetermined resection cuts.

Joint-Facing Surface of an Implant Component

In various embodiments described herein, the outer, joint-facing surface of an implant component includes one or more patient-adapted (e.g., patient-specific and/or patient-engineered features). For example, in certain embodiments, the joint-facing surface of an implant component can be designed to match the shape of the patient's biological structure. The joint-facing surface can include, for example, the bearing surface portion of the implant component that engages an opposing biological structure or implant component in the joint to facilitate typical movement of the joint. The patient's biological structure can include, for example, cartilage, bone, and/or one or more other biological structures.

For example, in certain embodiments, the joint-facing surface of an implant component is designed to match the shape of the patient's articular cartilage. For example, the joint-facing surface can substantially positively-match one or more features of the patient's existing cartilage surface and/or healthy cartilage surface and/or a calculated cartilage surface, on the articular surface that the component replaces. Alternatively, it can substantially negatively-match one or more features of the patient's existing cartilage surface and/or healthy cartilage surface and/or a calculated cartilage surface, on the opposing articular surface in the joint. As described below, corrections can be performed to the shape of diseased cartilage by designing surgical steps (and, optionally, patient-adapted surgical tools) to re-establish a normal or near normal cartilage shape that can then be incorporated into the shape of the joint-facing surface of the component. These corrections can be implemented and, optionally, tested in virtual two-dimensional and three-dimensional models. The corrections and testing can include kinematic analysis and/or surgical steps.

In certain embodiments, the joint-facing surface of an implant component can be designed to positively-match the shape of subchondral bone. For example, the joint-facing surface of an implant component can substantially positively-match one or more features of the patient's existing subchondral bone surface and/or healthy subchondral bone surface and/or a calculated subchondral bone surface, on the articular surface that the component attaches to on its bone-facing surface. Alternatively, it can substantially negatively-match one or more features of the patient's existing subchondral bone surface and/or healthy subchondral bone surface and/or a calculated subchondral bone surface, on the opposing articular surface in the joint. Corrections can be performed to the shape of subchondral bone to re-establish a normal or near normal articular shape that can be incorporated into the shape of the component's joint-facing surface. A standard thickness can be added to the joint-facing surface, for example, to reflect an average cartilage thickness. Alternatively, a variable thickness can be applied to the component. The variable thickness can be selected to reflect a patient's actual or healthy cartilage thickness, for example, as measured in the individual patient or selected from a standard reference database.

In certain embodiments, the joint-facing surface of an implant component can include one or more standard features. The standard shape of the joint-facing surface of the component can reflect, at least in part, the shape of typical healthy subchondral bone or cartilage. For example, the joint-facing surface of an implant component can include a curvature having standard radii or curvature of in one or more directions. Alternatively or in addition, an implant component can have a standard thickness or a standard minimum thickness in select areas. Standard thickness(es) can be added to one or more sections of the joint-facing surface of the component or, alternatively, a variable thickness can be applied to the implant component.

Certain embodiments can include, in addition to a first implant component, a second implant component having an opposing joint-facing surface. The second implant component's bone-facing surface and/or joint-facing surface can be designed as described above. Moreover, in certain embodiments, the joint-facing surface of the second component can be designed, at least in part, to match (e.g., substantially negatively-match) the joint-facing surface of the first component. Designing the joint-facing surface of the second component to complement the joint-facing surface of the first component can help reduce implant wear and optimize kinematics. Thus, in certain embodiments, the joint-facing surfaces of the first and second implant components can include features that do not match the patient's existing anatomy, but instead negatively-match or nearly negatively-match the joint-facing surface of the opposing implant component.

However, when a first implant component's joint-facing surface includes a feature adapted to a patient's biological feature, a second implant component having a feature designed to match that feature of the first implant component also is adapted to the patient's same biological feature. By way of illustration, when a joint-facing surface of a first component is adapted to a portion of the patient's cartilage shape, the opposing joint-facing surface of the second component designed to match that feature of the first implant component also is adapted to the patient's cartilage shape. When the joint-facing surface of the first component is adapted to a portion of a patient's subchondral bone shape, the opposing joint-facing surface of the second component designed to match that feature of the first implant component also is adapted to the patient's subchondral bone shape. When the joint-facing surface of the first component is adapted to a portion of a patient's cortical bone, the joint-facing surface of the second component designed to match that feature of the first implant component also is adapted to the patient's cortical bone shape. When the joint-facing surface of the first component is adapted to a portion of a patient's endosteal bone shape, the opposing joint-facing surface of the second component designed to match that feature of the first implant component also is adapted to the patient's endosteal bone shape. When the joint-facing surface of the first component is adapted to a portion of a patient's bone marrow shape, the opposing joint-facing surface of the second component designed to match that feature of the first implant component also is adapted to the patient's bone marrow shape.

The opposing joint-facing surface of a second component can substantially negatively-match the joint-facing surface of the first component in one plane or dimension, in two planes or dimensions, in three planes or dimensions, or in several planes or dimensions. For example, the opposing joint-facing surface of the second component can substantially negatively-match the joint-facing surface of the first component in the coronal plane only, in the sagittal plane only, or in both the coronal and sagittal planes.

In creating a substantially negatively-matching contour on an opposing joint-facing surface of a second component, geometric considerations can improve wear between the first and second components. For example, the radii of a concave curvature on the opposing joint-facing surface of the second component (e.g., a tibial implant component) can be selected to match or to be slightly larger in one or more dimensions than the radii of a convex curvature on the joint-facing surface of the first component (e.g., a femoral implant component). Similarly, the radii of a convex curvature on the opposing joint-facing surface of the second component can be selected to match or to be slightly smaller in one or more dimensions than the radii of a concave curvature on the joint-facing surface of the first component. In this way, contact surface area can be maximized between articulating convex and concave curvatures on the respective surfaces of first and second implant components.

The bone-facing surface of the second component can be designed to negatively-match, at least in part, the shape of articular cartilage, subchondral bone, cortical bone, endosteal bone or bone marrow (e.g., surface contour, angle, or perimeter shape of a resected or native biological structure). It can have any of the features described above for the bone-facing surface of the first component, such as having one or more patient-adapted bone cuts to match one or more predetermined resection cuts.

Many combinations of first component and second component bone-facing surfaces and joint-facing surfaces are possible. Table 2 provides illustrative combinations that may be employed.

TABLE 2

Illustrative Combinations of Implant Components

| $1^{st}$ component bone-facing surface | $1^{st}$ component joint-facing surface | $1^{st}$ component bone cut(s) | $2^{nd}$ component joint facing surface | $2^{nd}$ component bone facing surface | $2^{nd}$ component bone cuts |
|---|---|---|---|---|---|
| Example: Femur At least one bone cut | Example: Femur Cartilage | Example: Femur Yes | Example: Tibia Negative-match of $1^{st}$ component joint-facing (opposing cartilage) | Example: Tibia At least one bone cut | Example: Tibia Yes |
| At least one bone cut | Cartilage | Yes | Negative-match of $1^{st}$ component joint-facing (opposing cartilage) | Subchondral bone | Optional |
| At least one bone cut | Cartilage | Yes | Negative-match of $1^{st}$ component joint-facing (opposing cartilage) | Cartilage (same side, e.g. tibia) | Optional |
| At least one bone cut | Subchondral bone | Yes | Negative-match of $1^{st}$ component joint-facing (opposing subchondral bone) | At least one bone cut | Yes |
| At least one bone cut | Subchondral bone | Yes | Negative-match of $1^{st}$ component joint-facing (opposing subchondral bone) | Subchondral bone | Optional |

TABLE 2-continued

Illustrative Combinations of Implant Components

| 1st component bone-facing surface | 1st component joint-facing surface | 1st component bone cut(s) | 2nd component joint facing surface | 2nd component bone facing surface | 2nd component bone cuts |
|---|---|---|---|---|---|
| At least one bone cut | Subchondral bone | Yes | Negative-match of 1st component joint-facing (opposing subchondral bone) | Cartilage (same side, e.g. tibia) | Optional |
| Subchondral bone | Cartilage | Optional | Negative-match of 1st component joint-facing (opposing cartilage) | At least one bone cut | Yes |
| Subchondral bone | Cartilage | Optional | Negative-match of 1st component joint-facing (opposing cartilage) | Subchondral bone | Optional |
| Subchondral bone | Cartilage | Optional | Negative-match of 1st component joint-facing (opposing cartilage) | Cartilage (same side, e.g. tibia) | Optional |
| Subchondral bone | Subchondral bone | Optional | Negative-match of 1st component joint-facing (opposing subchondral bone) | At least one bone cut | Yes |
| Subchondral bone | Subchondral bone | Optional | Negative-match of 1st component joint-facing (opposing subchondral bone) | Subchondral bone | Optional |
| Subchondral bone | Subchondral bone | Optional | Negative-match of 1st component joint-facing (opposing subchondral bone) | Cartilage (same side, e.g. tibia) | Optional |
| Subchondral bone | Standard/Model | Optional | Negative-match of 1st component joint-facing standard | At least one bone cut | Yes |
| Subchondral bone | Standard/Model | Optional | Negative-match of 1st component joint-facing standard | Subchondral bone | Optional |
| Subchondral bone | Standard/Model | Optional | Negative-match of 1st component joint-facing standard | Cartilage (same side, e.g. tibia) | Optional |
| Subchondral bone | Subchondral bone | Optional | Non-matching standard surface | At least one bone cut | Yes |
| Subchondral bone | Cartilage | Optional | Non-matching standard surface | At least one bone cut | Yes |

Figure 2A:
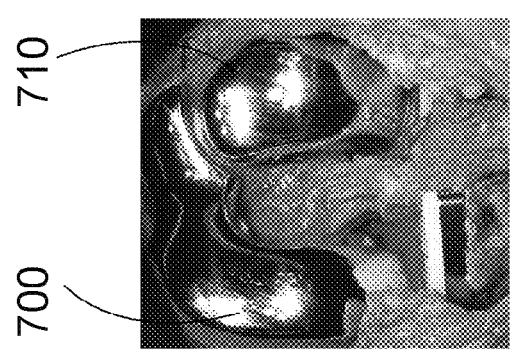
FIG. 2A is a photograph showing an exemplary knee replacement using a patient-specific bicompartmental device and a patient-specific unicompartmental device.
Figure 2C:
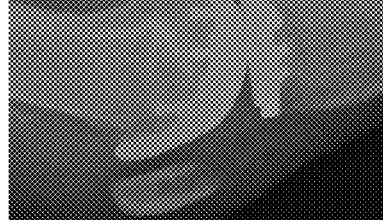
FIGS. 2B and 2C are x-ray images showing the device of FIG. 2A in the coronal plane and in the sagittal plane, respectively.
Figure 2B:
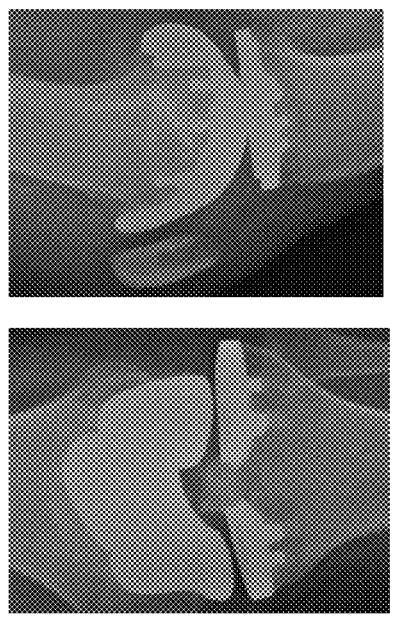

The implants and implant systems described herein include any number of patient-adapted implant components and any number of non-patient-adapted implant components. An illustrative implant or implant system is depicted in FIGS. 2A-2C. Specifically, FIG. 2A shows a photograph of a patient-adapted knee replacement implant system that includes a patient-specific bicompartmental implant component 700 and patient-specific unicompartmental implant component 710. Both components are patient-specific on both their bone-facing surfaces and on their joint-facing surfaces. FIGS. 2B and 2C show x-ray images showing the implant of FIG. 2A in the coronal plane (FIG. 2B) and the sagittal plane (FIG. 2C).

Embodiments described herein can be applied to partial or total joint replacement systems. Bone cuts or changes to an implant component dimension described herein can be applied to a portion of the dimension, or to the entire dimension.

Collecting and Modeling Patient-Specific Data

As mentioned above, certain embodiments include implant components designed and made using patient-specific data that is collected preoperatively. The patient-specific data can include points, surfaces, and/or landmarks, collectively referred to herein as "reference points." In certain embodiments, the reference points can be selected and used to derive a varied or altered surface, such as, without limitation, an ideal surface or structure. For example, the reference points can be used to create a model of the patient's relevant biological feature(s) and/or one or more patient-adapted surgical steps, tools, and implant components. For example the reference points can be used to design a patient-adapted implant component having at least one patient-specific or patient-engineered feature, such as a surface, dimension, or other feature.

Sets of reference points can be grouped to form reference structures used to create a model of a joint and/or an implant design. Designed implant surfaces can be derived from single reference points, triangles, polygons, or more complex surfaces, such as parametric or subdivision surfaces, or models of joint material, such as, for example, articular cartilage, subchondral bone, cortical bone, endosteal bone or bone marrow. Various reference points and reference structures can be selected and manipulated to derive a varied or altered surface, such as, without limitation, an ideal surface or structure.

The reference points can be located on or in the joint that receive the patient-specific implant. For example, the reference points can include weight-bearing surfaces or locations in or on the joint, a cortex in the joint, and/or an endosteal surface of the joint. The reference points also can include surfaces or locations outside of but related to the joint. Specifically, reference points can include surfaces or locations functionally related to the joint. For example, in embodiments directed to the knee joint, reference points can include one or more locations ranging from the hip down to the ankle or foot. The reference points also can include surfaces or locations homologous to the joint receiving the implant. For example, in embodiments directed to a knee, a hip, or a shoulder joint, reference points can include one or more surfaces or locations from the contralateral knee, hip, or shoulder joint.

In certain embodiments, an imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, photo-acoustic imaging, is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them.

In certain embodiments, measurements of biological features can include any one or more of the illustrative measurements identified in Table 3.

TABLE 3

Exemplary patient-specific measurements of biological features that can be used to create a model and/or to select and/or design a tibial implant component

| Anatomical feature | Exemplary measurement |
| --- | --- |
| Medullary cavity | Shape in one or more dimensions |
|  | Shape in one or more locations |
|  | Diameter of cavity |
|  | Volume of cavity |
| Subchondral bone | Shape in one or more dimensions |
|  | Shape in one or more locations |
|  | Thickness in one or more dimensions |
|  | Thickness in one or more locations |
|  | Angle, e.g., resection cut angle |
| Cortical bone | Shape in one or more dimensions |
|  | Shape in one or more locations |
|  | Thickness in one or more dimensions |
|  | Thickness in one or more locations |
|  | Angle, e.g., resection cut angle |
| Endosteal bone | Shape in one or more dimensions |
|  | Shape in one or more locations |
|  | Thickness in one or more dimensions |
|  | Thickness in one or more locations |
|  | Angle, e.g., resection cut angle |
| Cartilage | Shape in one or more dimensions |
|  | Shape in one or more locations |
|  | Thickness in one or more dimensions |
|  | Thickness in one or more locations |
|  | Angle, e.g., resection cut angle |
| Intercondylar notch | Shape in one or more dimensions |
|  | Location |
|  | Height in one or more locations |
|  | Width in one or more locations |
|  | Depth in one or more locations |
|  | Angle, e.g., resection cut angle |

TABLE 3-continued

Exemplary patient-specific measurements of biological features that can be used to create a model and/or to select and/or design a tibial implant component

| Anatomical feature | Exemplary measurement |
| --- | --- |
| Entire tibia | 2D and/or 3D shape of a portion or all |
|  | Height in one or more locations |
|  | Length in one or more locations |
|  | Width in one or more locations |
|  | Depth in one or more locations |
|  | Thickness in one or more locations |
|  | Curvature in one or more locations |
|  | Slope in one or more locations and/or directions |
|  | Angle, e.g., resection cut angle |
|  | Axes, e.g., A-P and/or M-L axes |
|  | Osteophytes |
|  | Plateau slope(s), e.g., relative slopes medial and lateral |
|  | Plateau heights(s), e.g., relative heights medial and lateral |
|  | Bearing surface radii, e.g., e.g., relative radii medial and lateral |
|  | Perimeter profile |
| Medial tibia | 2D and/or 3D shape of a portion or all |
|  | Height in one or more locations |
|  | Length in one or more locations |
|  | Width in one or more locations |
|  | Depth in one or more locations |
|  | Thickness or height in one or more locations |
|  | Curvature in one or more locations |
|  | Slope in one or more locations and/or directions |
|  | Angle, e.g., resection cut angle |
|  | Perimeter profile |
| Lateral tibia | 2D and/or 3D shape of a portion or all |
|  | Height in one or more locations |
|  | Length in one or more locations |
|  | Width in one or more locations |
|  | Depth in one or more locations |
|  | Thickness/height in one or more locations |
|  | Curvature in one or more locations |
|  | Slope in one or more locations and/or directions |
|  | Angle, e.g., resection cut angle |
|  | Perimeter profile |

In certain embodiments, the model that includes at least a portion of the patient's joint also can include or display, as part of the model, one or more resection cuts, one or more drill holes, (e.g., on a model of the patient's femur), one or more guide tools, and/or one or more implant components that have been designed for the particular patient using the model. Moreover, one or more resection cuts, one or more drill holes, one or more guide tools, and/or one or more implant components can be modeled and selected and/or designed separate from a model of a particular patient's biological feature.

Modeling and Addressing Joint Defects

In certain embodiments, the reference points and/or measurements described above can be processed using mathematical functions to derive virtual, corrected features, which may represent a restored, ideal or desired feature from which a patient-adapted implant component can be designed. For example, one or more features, such as surfaces or dimensions of a biological structure can be modeled, altered, added to, changed, deformed, eliminated, corrected and/or otherwise manipulated (collectively referred to herein as "variation" of an existing surface or structure within the joint).

Variation of the joint or portions of the joint can include, without limitation, variation of one or more external surfaces, internal surfaces, joint-facing surfaces, uncut surfaces, cut surfaces, altered surfaces, and/or partial surfaces as well as osteophytes, subchondral cysts, geodes or areas of eburnation, joint flattening, contour irregularity, and loss of normal shape. The surface or structure can be or reflect any surface or structure in the joint, including, without limitation, bone surfaces, ridges, plateaus, cartilage surfaces, ligament surfaces, or other surfaces or structures. The surface or structure derived can be an approximation of a healthy joint surface or structure or can be another variation. The surface or structure can be made to include pathological alterations of the joint. The surface or structure also can be made whereby the pathological joint changes are virtually removed in whole or in part.

Once one or more reference points, measurements, structures, surfaces, models, or combinations thereof have been selected or derived, the resultant shape can be varied, deformed or corrected. In certain embodiments, the variation can be used to select and/or design an implant component having an ideal or optimized feature or shape, e.g., corresponding to the deformed or corrected joint features or shape. For example, in one application of this embodiment, the ideal or optimized implant shape reflects the shape of the patient's joint before he or she developed arthritis.

Alternatively or in addition, the variation can be used to select and/or design a patient-adapted surgical procedure to address the deformity or abnormality. For example, the variation can include surgical alterations to the joint, such as virtual resection cuts, virtual drill holes, virtual removal of osteophytes, and/or virtual building of structural support in the joint that may be desired for a final outcome for the patient. Corrections can be used to address osteophytes, subchondral voids, and other patient-specific defects or abnormalities. In the case of osteophytes, a design for the bone-facing surface of an implant component or guide tool can be selected and/or designed after the osteophyte has been virtually removed. Alternatively, the osteophyte can be integrated into the shape of the bone-facing surface of the implant component or guide tool.

In addition to osteophytes and subchondral voids, the methods, surgical strategies, guide tools, and implant components described herein can be used to address various other patient-specific joint defects or phenomena. In certain embodiments, correction can include the virtual removal of tissue, for example, to address an articular defect, to remove subchondral cysts, and/or to remove diseased or damaged tissue (e.g., cartilage, bone, or other types of tissue), such as osteochondritic tissue, necrotic tissue, and/or torn tissue. In such embodiments, the correction can include the virtual removal of the tissue (e.g., the tissue corresponding to the defect, cyst, disease, or damage) and the bone-facing surface of the implant component can be derived after the tissue has been virtually removed. In certain embodiments, the implant component can be selected and/or designed to include a thickness or other features that substantially matches the removed tissue and/or optimizes one or more parameters of the joint. Optionally, a surgical strategy and/or one or more guide tools can be selected and/or designed to reflect the correction and correspond to the implant component.

Certain embodiments described herein include collecting and using data from imaging tests to virtually determine in one or more planes one or more of an anatomic axis and a mechanical axis and the related misalignment of a patient's limb. The imaging tests that can be used to virtually determine a patient's axis and misalignment can include one or more of such as x-ray imaging, digital tomosynthesis, cone beam CT, non-spiral or spiral CT, non-isotropic or isotropic MRI, SPECT, PET, ultrasound, laser imaging, and photoacoustic imaging, including studies utilizing contrast agents. Data from these tests can be used to determine anatomic reference points or limb alignment, including alignment angles within the same and between different joints or to simulate normal limb alignment. Using the image data, one or more mechanical or anatomical axes, angles, planes or combinations thereof can be determined In certain embodiments, such axes, angles, and/or planes can include, or be derived from, one or more of a Whiteside's line, Blumensaat's line, transepicondylar line, femoral shaft axis, femoral neck axis, acetabular angle, lines tangent to the superior and inferior acetabular margin, lines tangent to the anterior or posterior acetabular margin, femoral shaft axis, tibial shaft axis, transmalleolar axis, posterior condylar line, tangent(s) to the trochlea of the knee joint, tangents to the medial or lateral patellar facet, lines tangent or perpendicular to the medial and lateral posterior condyles, lines tangent or perpendicular to a central weight-bearing zone of the medial and lateral femoral condyles, lines transecting the medial and lateral posterior condyles, for example through their respective centerpoints, lines tangent or perpendicular to the tibial tuberosity, lines vertical or at an angle to any of the aforementioned lines, and/or lines tangent to or intersecting the cortical bone of any bone adjacent to or enclosed in a joint. Moreover, estimating a mechanical axis, an angle, or plane also can be performed using image data obtained through two or more joints, such as the knee and ankle joint, for example, by using the femoral shaft axis and a centerpoint or other point in the ankle, such as a point between the malleoli.

As one example, if surgery of the knee or hip is contemplated, the imaging test can include acquiring data through at least one of, or several of, a hip joint, knee joint or ankle joint. As another example, if surgery of the knee joint is contemplated, a mechanical axis can be determined. For example, the centerpoint of the hip knee and ankle can be determined. By connecting the centerpoint of the hip with that of the ankle, a mechanical axis can be determined in the coronal plane. The position of the knee relative to said mechanical axis can be a reflection of the degree of varus or valgus deformity. The same determinations can be made in the sagittal plane, for example to determine the degree of genu antecurvatum or recurvatum. Similarly, any of these determinations can be made in any other desired planes, in two or three dimensions.

Cartilage loss in one compartment can lead to progressive joint deformity. For example, cartilage loss in a medial compartment of the knee can lead to varus deformity. In certain embodiments, cartilage loss can be estimated in the affected compartments. The estimation of cartilage loss can be performed using an ultrasound MRI or CT scan or other imaging modality, optionally with intravenous or intra-articular contrast. The estimation of cartilage loss can be as simple as measuring or estimating the amount of joint space loss seen on x-rays. For the latter, typically standing x-rays are preferred. If cartilage loss is measured from x-rays using joint space loss, cartilage loss on one or two opposing articular surfaces can be estimated by, for example, dividing the measured or estimated joint space loss by two to reflect the cartilage loss on one articular surface. Other ratios or calculations are applicable depending on the joint or the location within the joint. Subsequently, a normal cartilage thickness can be virtually established on one or more articular surfaces by simulating normal cartilage thickness. In this manner, a normal or near normal cartilage surface can be derived. Normal cartilage thickness can be virtually simulated using a computer, for example, based on computer models, for example using the thickness of adjacent normal cartilage, cartilage in a contralateral joint, or other anatomic information including subchondral bone shape or other articular geometries. Cartilage models and estimates of cartilage thickness can also be derived from anatomic reference databases that can be matched, for example, to a patient's weight, sex, height, race, gender, or articular geometry(ies).

In certain embodiments, a patient's limb alignment can be virtually corrected by realigning the knee after establishing a normal cartilage thickness or shape in the affected compartment by moving the joint bodies, for example, femur and tibia, so that the opposing cartilage surfaces including any augmented or derived or virtual cartilage surface touch each other, typically in the preferred contact areas. These contact areas can be simulated for various degrees of flexion or extension.

Deformity Correction and Optimizing Limb Alignment

Information regarding the misalignment and the proper mechanical alignment of a patient's limb, can be used to preoperatively design and/or select one or more features of a joint implant and/or implant procedure. For example, based on the difference between the patient's misalignment and the proper mechanical axis, a knee implant and implant procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone in accordance with the preoperatively designed and/or selected resection dimensions.

In certain embodiments, the degree of deformity correction to establish a desired limb alignment is calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In a preferred embodiment, the desired deformity correction returns the leg to normal alignment, for example, a zero degree biomechanical axis in the coronal plane and absence of genu antecurvatum and recurvatum in the sagittal plane.

Figure 3:
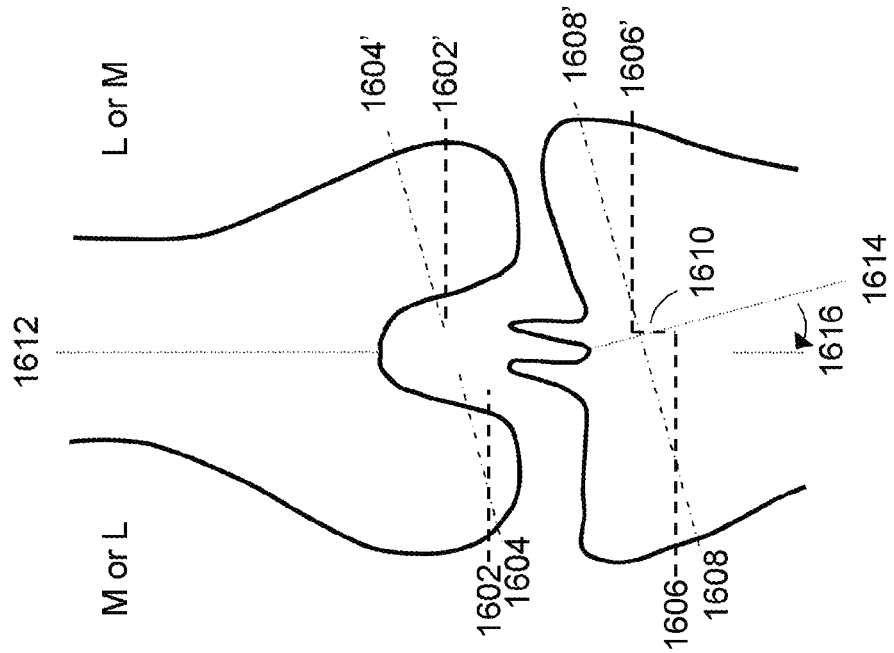
FIG. 3 illustrates a coronal plane of the knee with exemplary resection cuts that can be used to correct lower limb alignment in a knee replacement.

FIG. 3 illustrates a coronal plane of the knee with exemplary resection cuts that can be used to correct lower limb alignment in a knee replacement. As shown in the figure, the selected and/or designed resection cuts can include different cuts on different portions of a patient's biological structure. For example, resection cut facets on medial and lateral femoral condyles can be non-coplanar and parallel 1602, 1602', angled 1604, 1604', or non-coplanar and non-parallel, for example, cuts 1602 and 1604' or cuts 1602' and 1604. Similar, resection cut facets on medial and lateral portions of the tibia can be non-coplanar and parallel 1606, 1606', angled and parallel 1608, 1608', or non-coplanar and non-parallel, for example, cuts 1606 and 1608' or cuts 1606' and 1608. Non-coplanar facets of resection cuts can include a step-cut 1610 to connect the non-coplanar resection facet surfaces. Selected and/or designed resection dimensions can be achieved using or more selected and/or designed guide tools (e.g., cutting jigs) that guide resectioning (e.g., guide cutting tools) of the patient's biological structure to yield the predetermined resection surface dimensions (e.g., resection surface(s), angles, and/or orientation(s). In certain embodiments, the bone-facing surfaces of the implant components can be designed to include one or more features (e.g., bone cut surface areas, perimeters, angles, and/or orientations) that substantially match one or more of the resection cut or cut facets that were predetermined to enhance the patient's alignment. As shown in FIG. 3, certain combinations of resection cuts can aid in bringing the femoral mechanical axis 1612 and tibial mechanical axis 1614 into alignment 1616.

Alternatively, or in addition, certain implant features, such as different implant thicknesses and/or surface curvatures across two different sides of the plane in which the mechanical axes are misaligned also can aid correcting limb alignment. As described more fully below, independent tibial implant components and/or independent tibial inserts on medial and lateral sides of the tibial implant component can be used to enhance alignment at a patient's knee joint. An implant component can include constant yet different thicknesses in two or more portions of the implant (e.g., a constant medial tibial plateau thickness different from a constant lateral tibial plateau thickness), a gradually increasing thickness across the implant or a portion of the implant, or a combination of constant and gradually increasing thicknesses.

The selection and/or design of one or more femoral resection dimensions, femoral implant component thicknesses, femoral implant component surface curvatures, tibial resection dimensions, tibial implant component thicknesses, tibial implant component insert thicknesses, and/or tibial implant component surface curvatures can be used to adjust the femoral mechanical axis and tibial mechanical axis into alignment in the sagittal plane (e.g., by altering corresponding features across the sagittal plane, for example, by altering anterior features relative to corresponding posterior features). Alignment deformities in both the coronal and sagittal planes, or in multiple planes about the mechanical axes, can be addressed by designing and/or selecting one or more resection dimensions, one or more implant component thicknesses, and/or one or more implant component surface curvatures.

In certain embodiments, an implant component that is preoperatively designed and/or selected to correct a patient's alignment also can be designed or selected to include additional patient-specific or patient-engineered features. For example, the bone-facing surface of an implant or implant component can be designed and/or selected to substantially negatively-match the resected bone surface. As depicted in FIG. 4, the perimeters and areas 1910 of two bone surface areas of a patient's proximal tibia is different for two different bone resection cut depths 1920. Similarly, FIG. 5 depicts a distal view of the femur in which two different resection cuts are applied. As shown, the resected perimeters and surface areas for two distal facet resection depths are different for each of the medial condyle distal cut facet 1930 and the lateral condyle distal cut facet 1940.

If resection dimensions are angled, for example, in the coronal plane and/or in the sagittal plane, various features of the implant component, for example, the component bone-facing surface, can be designed and/or selected based on an angled orientation into the joint rather than on a perpendicular orientation. For example, the perimeter of tibial implant or implant component that substantially positively-matches the perimeter of the patient's cut tibial bone has a different shape depending on the angle of the cut. Similarly, with a femoral implant component, the depth or angle of the distal condyle resection on the medial and/or lateral condyle can be designed and/or selected to correct a patient alignment deformity. However, in so doing, one or more of the implant or implant component condyle width, length, curvature, and angle of impact against the tibia can be altered. Accordingly in certain embodiments, one or more implant or implant component features, such as implant perimeter, condyle length, condyle width, curvature, and angle is designed and/or selected relative to the a sloping and/or non-coplanar resection cut.

Preserving Bone, Cartilage or Ligament

Traditional orthopedic implants incorporate bone cuts. These bone cuts achieve two objectives: they establish a shape of the bone that is adapted to the implant and they help achieve a normal or near normal axis alignment. For example, bone cuts can be used with a knee implant to correct an underlying varus of valgus deformity and to shape the articular surface of the bone to fit a standard, bone-facing surface of a traditional implant component. With a traditional implant, multiple bone cuts are placed. However, since traditional implants are manufactured off-the-shelf without use of patient-specific information, these bone cuts are pre-set for a given implant without taking into consideration the unique shape of the patient. Thus, by cutting the patient's bone to fit the traditional implant, more bone is discarded than is necessary with an implant that is specifically designed and/or selected to address the particularly patient's structures and deficiencies.

In certain embodiments, resection cuts are optimized to preserve the maximum amount of bone for each individual patient, based on a series of two-dimensional images or a three-dimensional representation of the patient's articular anatomy and geometry and the desired limb alignment and/or desired deformity correction. Resection cuts on two opposing articular surfaces can be optimized to achieve the minimum amount of bone resected from one or both articular surfaces.

By adapting resection cuts in the series of two-dimensional images or the three-dimensional representation on two opposing articular surfaces such as, for example, a femoral head and an acetabulum, one or both femoral condyle(s) and a tibial plateau, a trochlea and a patella, a glenoid and a humeral head, a talar dome and a tibial plafond, a distal humerus and a radial head and/or an ulna, or a radius and a scaphoid, certain embodiments allow for patient individualized, bone-preserving implant designs that can assist with proper ligament balancing and that can help avoid "overstuffing" of the joint, while achieving optimal bone preservation on one or more articular surfaces in each patient.

Implant design and modeling also can be used to achieve ligament sparing, for example, with regard to the PCL and/or the ACL. An imaging test can be utilized to identify, for example, the origin and/or the insertion of the PCL and the ACL on the femur and tibia. The origin and the insertion can be identified by visualizing, for example, the ligaments directly, as is possible with MRI or spiral CT arthrography, or by visualizing bony landmarks known to be the origin or insertion of the ligament such as the medial and lateral tibial spines.

An implant system can then be selected or designed based on the image data so that, for example, the femoral component preserves the ACL and/or PCL origin, and the tibial component preserves the ACL and/or PCL attachment. The implant can be selected or designed so that bone cuts adjacent to the ACL or PCL attachment or origin do not weaken the bone to induce a potential fracture.

For ACL preservation, the implant can have two unicompartmental tibial components that can be selected or designed and placed using the image data. Alternatively, the implant can have an anterior bridge component. The width of the anterior bridge in AP dimension, its thickness in the supero-inferior dimension or its length in mediolateral dimension can be selected or designed using the imaging data and, specifically, the known insertion of the ACL and/or PCL.

As can be seen in FIGS. 6A and 6B, the posterior margin of an implant component, e.g. a polyethylene- or metal-backed tray with polyethylene inserts, can be selected and/or designed using the imaging data or shapes derived from the imaging data so that the implant component does not interfere with and stay clear of the PCL. This can be achieved, for example, by including concavities in the outline of the implant that are specifically designed or selected or adapted to avoid the ligament insertion.

Any implant component can be selected and/or adapted in shape so that it stays clear of ligament structures. Imaging data can help identify or derive shape or location information on such ligamentous structures. For example, the lateral femoral condyle of a unicompartmental, bicompartmental or total knee system can include a concavity or divet to avoid the popliteus tendon. In a shoulder, the glenoid component can include a shape or concavity or divet to avoid a subscapularis tendon or a biceps tendon. In a hip, the femoral component can be selected or designed to avoid an iliopsoas or adductor tendons.

Establishing Normal or Near-Normal Joint Kinematics

In certain embodiments, bone cuts and implant shape including at least one of a bone-facing or a joint-facing surface of the implant can be designed or selected to achieve normal joint kinematics.

In certain embodiments, a computer program simulating biomotion of one or more joints, such as, for example, a knee joint, or a knee and ankle joint, or a hip, knee and/or ankle joint can be utilized. In certain embodiments, patient-specific imaging data can be fed into this computer program. For example, a series of two-dimensional images of a patient's knee joint or a three-dimensional representation of a patient's knee joint can be entered into the program. Additionally, two-dimensional images or a three-dimensional representation of the patient's ankle joint and/or hip joint may be added.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters listed above. The biomotion model can simulate various activities of daily life including normal gait, stair climbing, descending stairs, running, kneeling, squatting, sitting and any other physical activity. The biomotion model can start out with standardized activities, typically derived from reference databases. These reference databases can be, for example, generated using biomotion measurements using force plates and motion trackers using radiofrequency or optical markers and video equipment.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in the preceding optimizations, for example, limb alignment, deformity correction, bone preservation on one or more articular surfaces, can be introduced into the model. The resultant biomotion data can be used to further optimize the implant design with the objective to establish normal or near normal kinematics. The implant optimizations can include one or multiple implant components. Implant optimizations based on patient-specific data including image based biomotion data include, but are not limited to:

Changes to external, joint-facing implant shape in coronal plane

Changes to external, joint-facing implant shape in sagittal plane

Changes to external, joint-facing implant shape in axial plane

Changes to external, joint-facing implant shape in multiple planes or three dimensions Changes to internal, bone-facing implant shape in coronal plane Changes to internal, bone-facing implant shape in sagittal plane Changes to internal, bone-facing implant shape in axial plane Changes to internal, bone-facing implant shape in multiple planes or three dimensions Changes to one or more bone cuts, for example with regard to depth of cut, orientation of cut Any single one or combinations of the above or all of the above on at least one articular surface or implant component or multiple articular surfaces or implant components.

When changes are made on multiple articular surfaces or implant components, these can be made in reference to or linked to each other. For example, in the knee, a change made to a femoral bone cut based on patient-specific biomotion data can be referenced to or linked with a concomitant change to a bone cut on an opposing tibial surface, for example, if less femoral bone is resected, the computer program may elect to resect more tibial bone.

Similarly, if a femoral implant shape is changed, for example on an external surface, this can be accompanied by a change in the tibial component shape. This is, for example, particularly applicable when at least portions of the tibial bearing surface negatively-match the femoral joint-facing surface.

Similarly, if the footprint of a femoral implant is broadened, this can be accompanied by a widening of the bearing surface of a tibial component. Similarly, if a tibial implant shape is changed, for example on an external surface, this can be accompanied by a change in the femoral component shape. This is, for example, particularly applicable when at least portions of the femoral bearing surface negatively-match the tibial joint-facing surface.

If a patellar component radius is widened, this can be accompanied by a widening of an opposing trochlear bearing surface radius or vice versa.

Similarly, in a hip, if a femoral implant shape is changed, for example on an external surface, this can be accompanied by a change in an acetabular component shape. This is, for example, particularly applicable when at least portions of the acetabular bearing surface substantially negatively-match the femoral joint facing surface. For example, the acetabular rim can be altered, for example via reaming or cutting. These surgical changes and resultant change on cortical bone profile can be virtually simulated and a new resultant peripheral margin(s) can be derived. The derived peripheral bone margin or shape can then be used to design or select an implant that substantially matches, in at least a portion, the altered rim or joint margin or edge.

Similarly, in a shoulder, if a glenoid implant shape is changed, for example on an external surface, this can be accompanied by a change in a humeral component shape. This is, for example, particularly applicable when at least portions of the humeral bearing surface substantially negatively-match the glenoid joint facing surface, or vice versa.

By optimizing implant shape in this manner, it is possible to establish normal or near normal kinematics. Moreover, it is possible to avoid implant related complications, including but not limited to anterior notching, notch impingement, posterior femoral component impingement in high flexion, and other complications associated with existing implant designs.

Biomotion models for a particular patient can be supplemented with patient-specific data and/or finite element modeling or other biomechanical models known in the art. Resultant forces in the knee joint can be calculated for each component for each specific patient. The implant can be engineered to the patient's load and force demands. For instance, a 125 lb. patient may not need a tibial plateau as thick as a 280 lb patient. Similarly, the polyethylene can be adjusted in shape, thickness and material properties for each patient. For example, a 3 mm polyethylene insert can be used in a light patient with low force and a heavier or more active patient may need an 8 mm polymer insert or similar device.

Complex Modeling

As described herein, certain embodiments can apply modeling, for example, virtual modeling and/or mathematical modeling, to identify optimum implant component features and measurements, and optionally resection features and measurements, to achieve or advance one or more parameter targets or thresholds. For example, a model of patient's joint or limb can be used to identify, select, and/or design one or more optimum features and/or feature measurements relative to selected parameters for an implant component and, optionally, for corresponding resection cuts and/or guide tools. In certain embodiments, a physician, clinician, or other user can select one or more parameters, parameter thresholds or targets, and/or relative weightings for the parameters included in the model. Alternatively or in addition, clinical data, for example obtained from clinical trials, or intraoperative data, can be included in selecting parameter targets or thresholds, and/or in determining optimum features and/or feature measurements for an implant component, resection cut, and/or guide tool.

Any combination of one or more of the above-identified parameters and/or one or more additional parameters can be used in the design and/or selection of a patient-adapted (e.g., patient-specific and/or patient-engineered) implant component and, in certain embodiments, in the design and/or selection of corresponding patient-adapted resection cuts and/or patient-adapted guide tools. In particular assessments, a patient's biological features and feature measurements are used to select and/or design one or more implant component features and feature measurements, resection cut features and feature measurements, and/or guide tool features and feature measurements.

The optimization of joint kinematics can include, as another parameter, the goal of not moving the joint line postoperatively or minimizing any movements of the joint line, or any threshold values or cut off values for moving the joint line superiorly or inferiorly. The optimization of joint kinematics can also include ligament loading or function during motion.

As described herein, implants of various sizes, shapes, curvatures and thicknesses with various types and locations and orientations and number of bone cuts can be selected and/or designed and manufactured. The implant designs and/or implant components can be selected from, catalogued in, and/or stored in a library. The library can be a virtual library of implants, or components, or component features that can be combined and/or altered to create a final implant. The library can include a catalogue of physical implant components. In certain embodiments, physical implant components can be identified and selected using the library. The library can include previously-generated implant components having one or more patient-adapted features, and/or components with standard or blank features that can be altered to be patient-adapted. Accordingly, implants and/or implant features can be selected from the library.

Accordingly, in certain embodiments an implant can include one or more features designed patient-specifically and one or more features selected from one or more library sources. For example, in designing an implant for a total knee replacement comprising a femoral component and a tibial component, one component can include one or more patient-specific features and the other component can be selected from a library. Table 4 includes an exemplary list of possible combinations.

TABLE 4

Illustrative Combinations of Patient-Specific and Library-Derived Components

| Implant component(s) | Implant component(s) having a patient-specific feature | Implant component(s) having a library derived feature |
|---|---|---|
| Femoral, Tibial | Femoral and Tibial | Femoral and Tibial |
| Femoral, Tibial | Femoral | Femoral and Tibial |
| Femoral, Tibial | Tibial | Femoral and Tibial |
| Femoral, Tibial | Femoral and Tibial | Femoral |
| Femoral, Tibial | Femoral and Tibial | Tibial |
| Femoral, Tibial | Femoral and Tibial | none |

In certain embodiments, a library can be generated to include images from a particular patient at one or more ages prior to the time that the patient needs a joint implant. For example, a method can include identifying patients eliciting one or more risk factors for a joint problem, such as low bone mineral density score, and collecting one or more images of the patient's joints into a library. In certain embodiments, all patients below a certain age, for example, all patients below 40 years of age can be scanned to collect one or more images of the patient's joint. The images and data collected from the patient can be banked or stored in a patient-specific database. For example, the articular shape of the patient's joint or joints can be stored in an electronic database until the time when the patient needs an implant. Then, the images and data in the patient-specific database can be accessed and a patient-specific and/or patient-engineered partial or total joint replacement implant using the patient's originally anatomy, not affected by arthritic deformity yet, can be generated. This process results is a more functional and more anatomic implant.

Tibial Implant Component Features

In various embodiments described herein, one or more features of a tibial implant component are designed and/or selected, optionally in conjunction with an implant procedure, so that the tibial implant component fits the patient. For example, in certain embodiments, one or more features of a tibial implant component and/or implant procedure are designed and/or selected, based on patient-specific data, so that the tibial implant component substantially matches (e.g., substantially negatively-matches and/or substantially positively-matches) one or more of the patient's biological structures. Alternatively or in addition, one or more features of a tibial implant component and/or implant procedure can be preoperatively engineered based on patient-specific data to provide to the patient an optimized fit with respect to one or more parameters, for example, one or more of the parameters described above. For example, in certain embodiments, an engineered bone preserving tibial implant component can be designed and/or selected based on one or more of the patient's joint dimensions as seen, for example, on a series of two-dimensional images or a three-dimensional representation generated, for example, from a CT scan or MRI scan. Alternatively or in addition, an engineered tibial implant component can be designed and/or selected, at least in part, to provide to the patient an optimized fit with respect to the engaging, joint-facing surface of a corresponding femoral implant component.

Certain embodiments include a tibial implant component having one or more patient-adapted (e.g., patient-specific or patient-engineered) features and, optionally, one or more standard features. Optionally, the one or more patient-adapted features can be designed and/or selected to fit the patient's resected tibial surface. For example, depending on the patient's anatomy and desired postoperative geometry or alignment, a patient's lateral and/or medial tibial plateaus may be resected independently and/or at different depths, for example, so that the resected surface of the lateral plateau is higher (e.g., 1 mm, greater than 1 mm, 2 mm, and/or greater than 2 mm higher) or lower (e.g., 1 mm, greater than 1 mm, 2 mm, and/or greater than 2 mm lower) than the resected surface of the medial tibial plateau.

Accordingly, in certain embodiments, tibial implant components can be independently designed and/or selected for each of the lateral and/or medial tibial plateaus. For example, the perimeter of a lateral tibial implant component and the perimeter of a medial tibial implant component can be independently designed and/or selected to substantially match the perimeter of the resection surfaces for each of the lateral and medial tibial plateaus. FIGS. 7A and B show exemplary unicompartmental medial and lateral tibial implant components without (FIG. 7A) and with (FIG. 7B) a polyethylene layer or insert. As shown, the lateral tibial implant component and the medial tibial implant component have different perimeters shapes, each of which substantially matches the perimeter of the corresponding resection surface (see arrows). In addition, the polyethylene layers or inserts 6010 for the lateral tibial implant component and the medial tibial implant component have perimeter shapes that correspond to the respective implant component perimeter shapes. In certain embodiments, one or both of the implant components can be made entirely of a plastic or polyethylene (rather than having a having a polyethylene layer or insert) and each entire implant component can include a perimeter shape that substantially matches the perimeter of the corresponding resection surface.

Moreover, the height of a lateral tibial implant component and the height of a medial tibial implant component can be independently designed and/or selected to maintain or alter the relative heights generated by different resection surfaces for each of the lateral and medial tibial plateaus. For example, the lateral tibial implant component can be thicker (e.g., 1 mm, greater than 1 mm, 2 mm, and/or greater than 2 mm thicker) or thinner (e.g., 1 mm, greater than 1 mm, 2 mm, and/or greater than 2 mm thinner) than the medial tibial implant component to maintain or alter, as desired, the relative height of the joint-facing surface of each of the lateral and medial tibial implant components. As shown in FIGS. 7A and B, the relative heights of the lateral and medial resection surfaces 6020 is maintained using lateral and medial implant components (and lateral and medial polyethylene layers or inserts) that have the same thickness. Alternatively, the lateral implant component (and/or the lateral polyethylene layer or insert) can have a different thickness than the medial implant component (and/or the medial polyethylene layer or insert). For embodiments having one or both of the lateral and medial implant components made entirely of a plastic or polyethylene (rather than having a having a polyethylene layer or insert) the thickness of one implant component can be different from the thickness of the other implant component.

Different medial and lateral tibial cut heights also can be applied with a one piece implant component, e.g., a monolithically formed, tibial implant component. In this case, the tibial implant component and the corresponding resected surface of the patient's femur can have an angled surface or a step cut connecting the medial and the lateral surface facets. For example, FIGS. 8A-C depict three different types of step cuts 6110 separating medial and lateral resection cut facets on a patient's proximal tibia. In certain embodiments, the bone-facing surface of the tibial implant component is selected and/or designed to match these surface depths and the step cut angle, as well as other optional features such as perimeter shape.

Tibial components also can include the same medial and lateral cut height.

In certain embodiments, the medial tibial plateau facet can be oriented at an angle different than the lateral tibial plateau facet or it can be oriented at the same angle. One or both of the medial and the lateral tibial plateau facets can be at an angle that is patient-specific, for example, similar to the original slope or slopes of the medial and/or lateral tibial plateaus, for example, in the sagittal plane. Moreover, the medial slope can be patient-specific, while the lateral slope is fixed or preset or vice versa, as exemplified in Table 5.

TABLE 5

Exemplary designs for tibial slopes

| MEDIAL SIDE IMPLANT SLOPE | LATERAL SIDE IMPLANT SLOPE |
|---|---|
| Patient-matched to medial plateau | Patient-matched to lateral plateau |
| Patient-matched to medial plateau | Patient-matched to medial plateau |
| Patient-matched to lateral plateau | Patient-matched to lateral plateau |
| Patient-matched to medial plateau | Not patient-matched, e.g., preset, fixed or intraoperatively adjusted |
| Patient-matched to lateral plateau | Not patient-matched, e.g., preset, fixed or intraoperatively adjusted |
| Not patient matched, e.g. preset, fixed or intraoperatively adjusted | Patient-matched to lateral plateau |
| Not patient matched, e.g., preset, fixed or intraoperatively adjusted | Patient-matched to medial plateau |
| Not patient matched, e.g. preset, fixed or intraoperatively adjusted | Not patient-matched, e.g. preset, fixed or intraoperatively adjusted |

The exemplary combinations described in Table 5 are applicable to implants that use two unicompartmental tibial implant components with or without metal backing, one medial and one lateral. They also can be applicable to implant systems that use a single tibial implant component including all plastic designs or metal backed designs with inserts (optionally a single insert for the medial and lateral plateau, or two inserts, e.g., one medial and one lateral), for example PCL retaining, posterior stabilized, or ACL and PCL retaining implant components. The slope preferably is between 0 and 7 degrees, but other embodiments with other slope angles outside that range can be used. The slope can vary across one or both tibial facets from anterior to posterior. For example, a lesser slope, e.g., 0-1 degrees, can be used anteriorly, and a greater slope can be used posteriorly, e.g., 4-5 degrees. Variable slopes across at least one of a medial or a lateral tibial facet can be accomplished, for example, with use of burrs (for example guided by a robot) or with use of two or more bone cuts on at least one of the tibial facets. In certain embodiments, two separate slopes can be used medially and laterally. Independent tibial slope designs can be useful for achieving bone preservation. In addition, independent slope designs can be advantageous in achieving implant kinematics that are more natural and closer to the performance of a normal knee or the patient's knee.

Figure 9A:
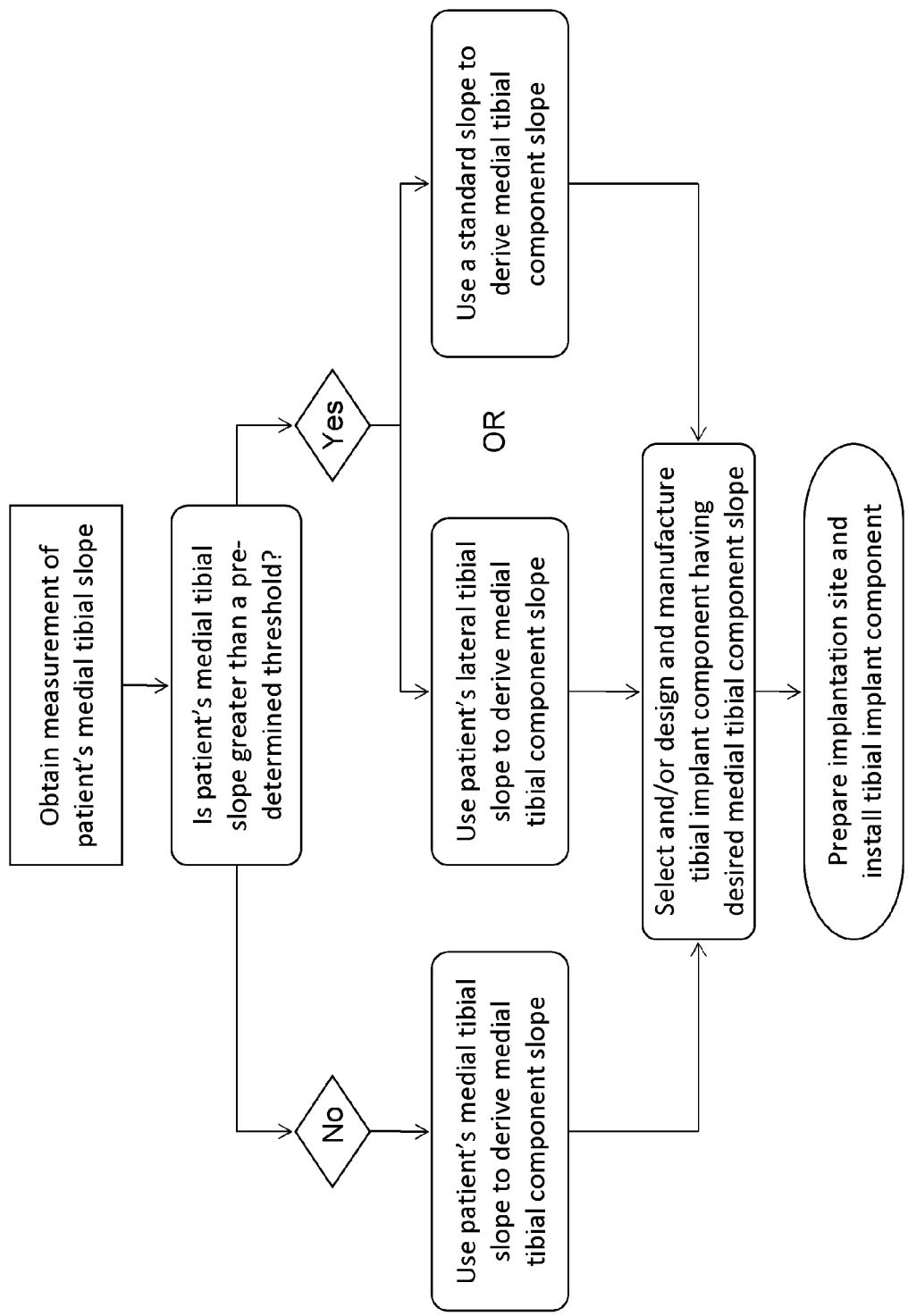
FIGS. 9A and 9B show exemplary flow charts for deriving a medial tibial component slope (FIG. 9A) and/or a lateral tibial component slope (FIG. 9B) for a tibial implant component.
Figure 9B:
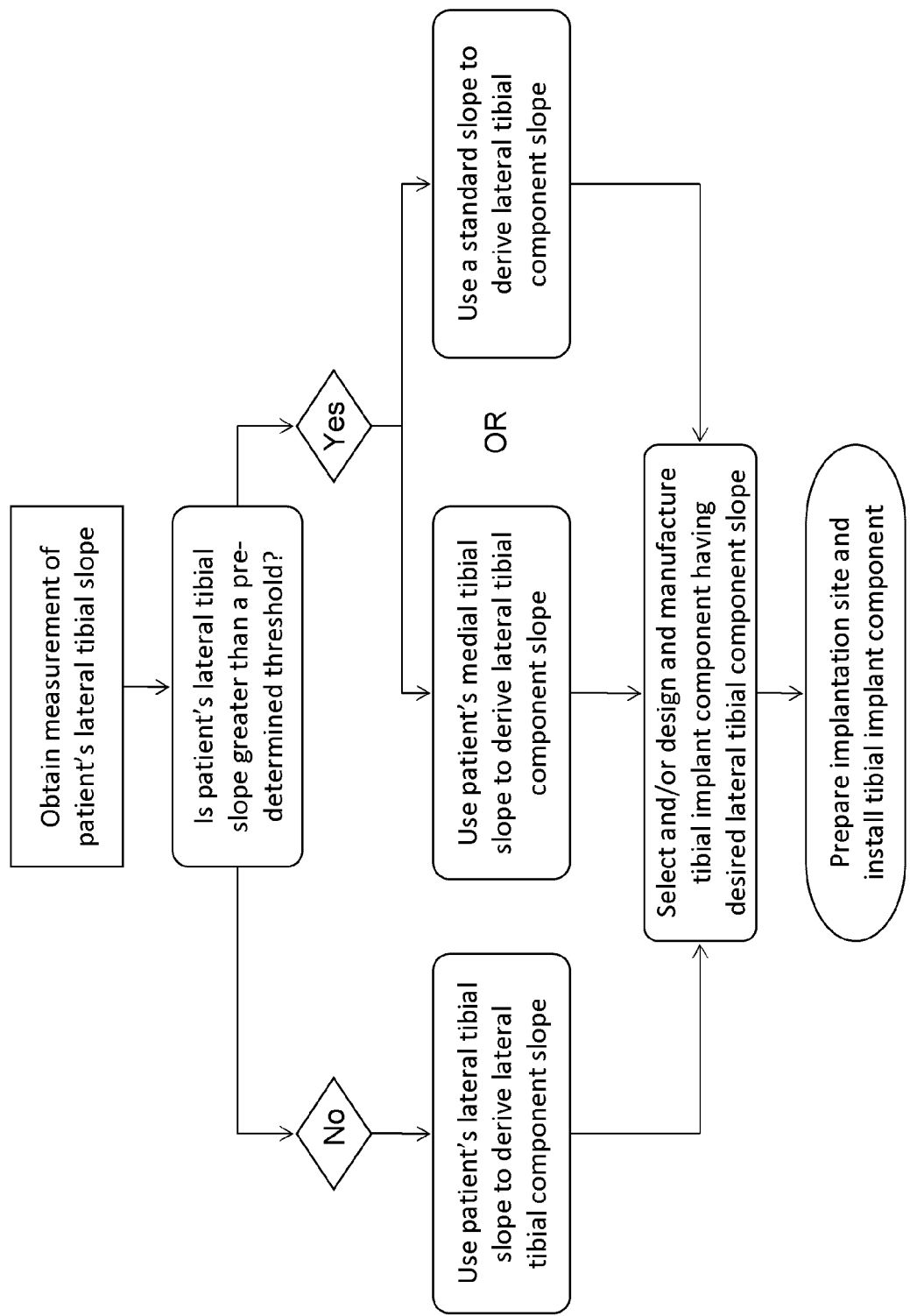

In certain embodiments, the slope can be fixed, e.g. at 3, 5 or 7 degrees in the sagittal plane. In certain embodiments, the slope, either medial or lateral or both, can be patient-specific. The patient's medial slope can be used to derive the medial tibial component slope and, optionally, the lateral component slope, in either a single or a two-piece tibial implant component. The patient's lateral slope can be used to derive the lateral tibial component slope and, optionally, the medial component slope, in either a single or a two-piece tibial implant component. A patient's slope typically is between 0 and 7 degrees. In select instances, a patient may show a medial or a lateral slope that is greater than 7 degrees. In this case, if the patient's medial slope has a higher value than 7 degrees or some other pre-selected threshold, the patient's lateral slope can be applied to the medial tibial implant component or to the medial side of a single tibial implant component. If the patient's lateral slope has a higher value than 7 degrees or some other pre-selected threshold, the patient's medial slope can be applied to the lateral tibial implant component or to the lateral side of a single tibial implant component. Alternatively, if the patient's slope on one or both medial and lateral sides exceeds a pre-selected threshold value, e.g., 7 degrees or 8 degrees or 10 degrees, a fixed slope can be applied to the medial component or side, to the lateral component or side, or both. The fixed slope can be equal to the threshold value, e.g., 7 degrees or it can be a different value. FIGS. 9A and B show exemplary flow charts for deriving a medial tibial component slope (FIG. 9A) and/or a lateral tibial component slope (FIG. 9B) for a tibial implant component.

A fixed tibial slope can be used in any of the embodiments described herein.

In another embodiment, a mathematical function can be applied to derive a medial implant slope and/or a lateral implant slope, or both (wherein both can be the same). In certain embodiments, the mathematical function can include a measurement derived from one or more of the patient's joint dimensions as seen, for example, on a series of two-dimensional images or a three-dimensional representation generated, for example, from a CT scan or MRI scan. For example, the mathematical function can include a ratio between a geometric measurement of the patient's femur and the patient's tibial slope. Alternatively or in addition, the mathematical function can be or include the patient's tibial slope divided by a fixed value. In certain embodiments, the mathematical function can include a measurement derived from a corresponding implant component for the patient, for example, a femoral implant component, which itself can include patient-specific, patient-engineered, and/or standard features. Many different possibilities to derive the patient's slope using mathematical functions can be applied by someone skilled in the art.

In certain embodiments, the medial and lateral tibial plateau can be resected at the same angle. For example, a single resected cut or the same multiple resected cuts can be used across both plateaus. In other embodiments, the medial and lateral tibial plateau can be resected at different angles. Multiple resection cuts can be used when the medial and lateral tibial plateaus are resected at different angles. Optionally, the medial and the lateral tibia also can be resected at a different distance relative to the tibial plateau. In this setting, the two horizontal plane tibial cuts medially and laterally can have different slopes and/or can be accompanied by one or two vertical or oblique resection cuts, typically placed medial to the tibial plateau components. FIG. 3 and FIGS. 8A-C show several exemplary tibial resection cuts, which can be used in any combination for the medial and lateral plateaus.

The medial tibial implant component plateau can have a flat, convex, concave, or dished surface and/or it can have a thickness different than the lateral tibial implant component plateau. The lateral tibial implant component plateau can have a flat, convex, concave, or dished surface and/or it can have a thickness different than the medial tibial implant component plateau. The different thickness can be achieved using a different material thickness, for example, metal thickness or polyethylene or insert thickness on either side. In certain embodiments, the lateral and medial surfaces are selected and/or designed to closely resemble the patient's anatomy prior to developing the arthritic state.

The height of the medial and/or lateral tibial implant component plateau, e.g., metal only, ceramic only, metal backed with polyethylene or other insert, with single or dual inserts and single or dual tray configurations can be determined based on the patient's tibial shape, for example using an imaging test.

Alternatively, the height of the medial and/or lateral tibial component plateau, e.g. metal only, ceramic only, metal backed with polyethylene or other insert, with single or dual inserts and single or dual tray configurations can be determined based on the patient's femoral shape. For example, if the patient's lateral condyle has a smaller radius than the medial condyle and/or is located more superior than the medial condyle with regard to its bearing surface, the height of the tibial component plateau can be adapted and/or selected to ensure an optimal articulation with the femoral bearing surface. In this example, the height of the lateral tibial component plateau can be adapted and/or selected so that it is higher than the height of the medial tibial component plateau. Since polyethylene is typically not directly visible on standard x-rays, metallic or other markers can optionally be included in the inserts in order to indicate the insert location or height, in particular when asymmetrical medial and lateral inserts or inserts of different medial and lateral thickness are used.

Alternatively, the height of the medial and/or lateral tibial component plateau, e.g. metal only, ceramic only, metal backed with polyethylene or other insert, with single or dual inserts and single or dual tray configurations can be determined based on the shape of a corresponding implant component, for example, based on the shape of certain features of the patient's femoral implant component. For example, if the femoral implant component includes a lateral condyle having a smaller radius than the medial condyle and/or is located more superior than the medial condyle with regard to its bearing surface, the height of the tibial implant component plateaus can be adapted and/or selected to ensure an optimal articulation with the bearing surface(s) of the femoral implant component. In this example, the height of the lateral tibial implant component plateau can be adapted and/or selected to be higher than the height of the medial tibial implant component plateau.

Moreover, the surface shape, e.g. mediolateral or anteroposterior curvature or both, of the tibial insert(s) can reflect the shape of the femoral component. For example, the medial insert shape can be matched to one or more radii on the medial femoral condyle of the femoral component. The lateral insert shape can be matched to one or more radii on the lateral femoral condyle of the femoral component. The lateral insert may optionally also be matched to the medial condyle. The matching can occur, for example, in the coronal plane. This has benefits for wear optimization. A pre-manufactured insert can be selected for a medial tibia that matches the medial femoral condyle radii in the coronal plane with a pre-selected ratio, e.g. 1:5 or 1:7 or 1:10. Any combination is possible. A pre-manufactured insert can be selected for a lateral tibia that matches the lateral femoral condyle radii in the coronal plane with a pre-selected ratio, e.g. 1:5 or 1:7 or 1:10. Any combination is possible. Alternatively, a lateral insert can also be matched to a medial condyle or a medial insert shape can also be matched to a lateral condyle. These combinations are possible with single and dual insert systems with metal backing. Someone skilled in the art can recognize that these matchings also can be applied to implants that use all polyethylene tibial components, for example, the radii on all polyethylene tibial components can be matched to the femoral radii in a similar manner.

The matching of radii can also occur in the sagittal plane. For example, a cutter can be used to cut a fixed coronal curvature into a tibial insert or all polyethylene tibia that is matched to or derived from a femoral implant or patient geometry. The path and/or depth that the cutter is taking can be driven based on the femoral implant geometry or based on the patient's femoral geometry prior to the surgery. Medial and lateral sagittal geometry can be the same on the tibial inserts or all poly tibia. Alternatively, each can be cut separately. By adapting or matching the tibial poly geometry to the sagittal geometry of the femoral component or femoral condyle, a better functional result may be achieved. For example, more physiologic tibiofemoral motion and kinematics can be enabled.

Figure 10G:
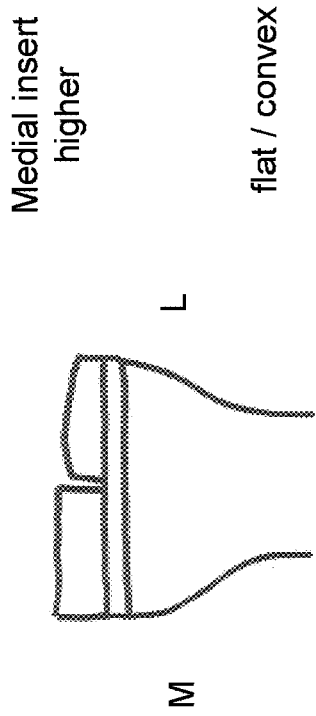
FIGS. 10A-O show exemplary tibial implants designs that include a tibial tray with dual inserts.
FIGS. 10P-AD show exemplary tibial implants designs that include a tibial tray with a single inserts, with a range of insert surface shapes.
Figure 10H:
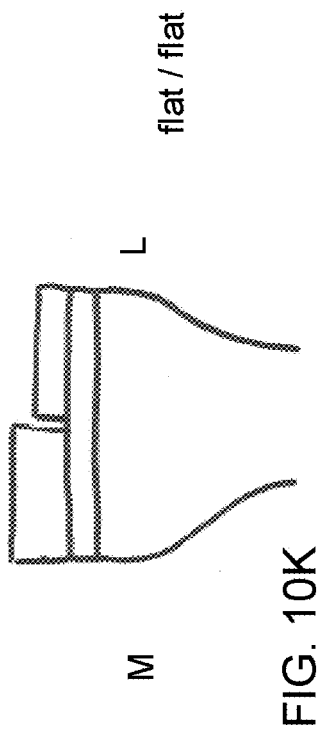
Figure 10I:
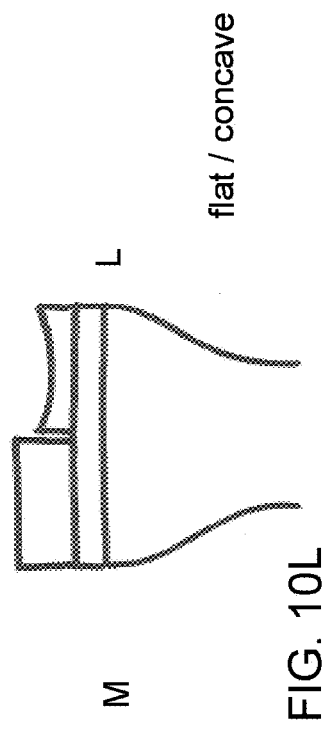
Figure 10J:
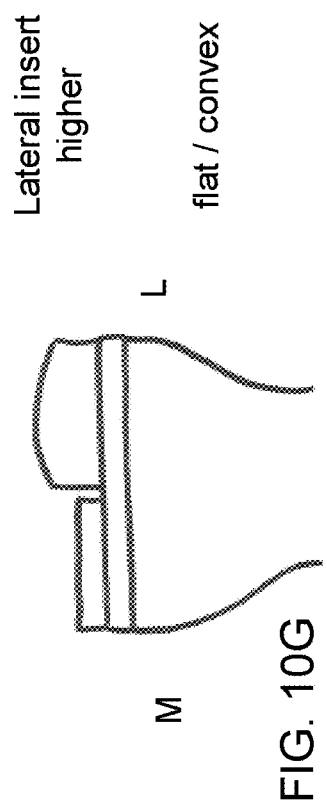
Figure 10K:
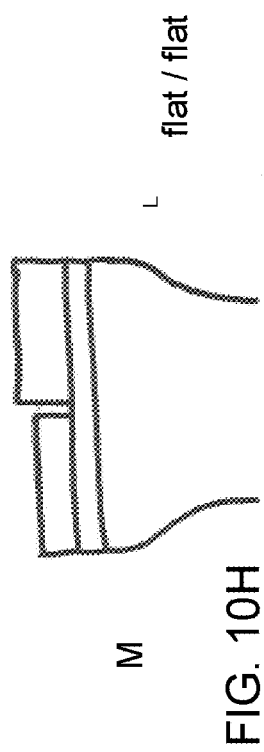
Figure 10L:
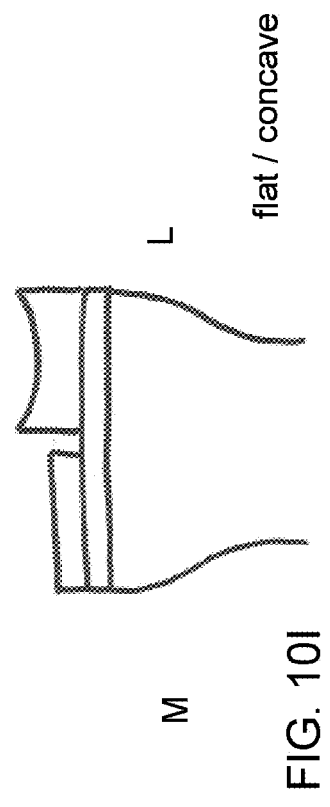
Figures 10S, 10T, 10U:
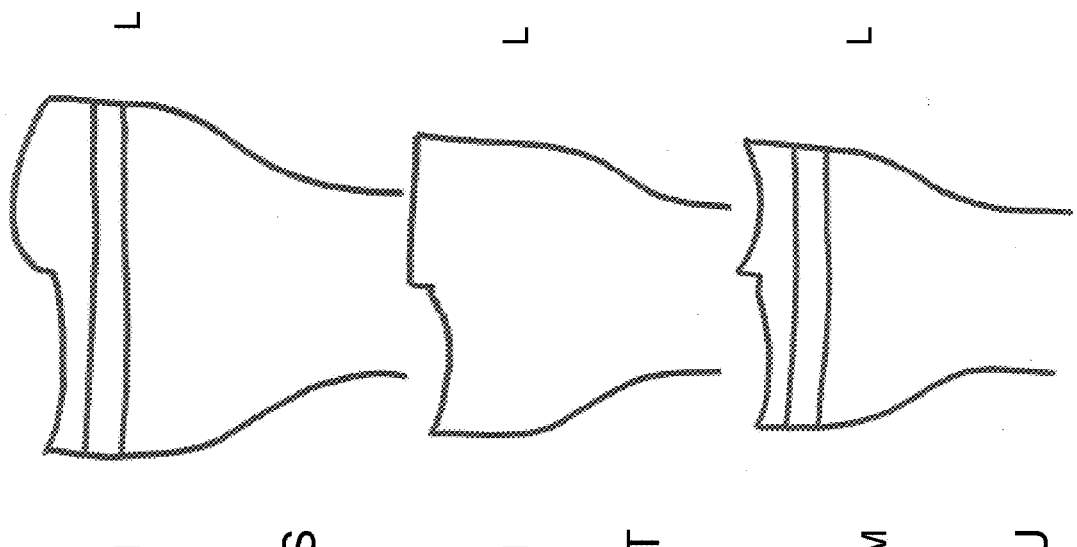
Figures 10V, 10W, 10X:
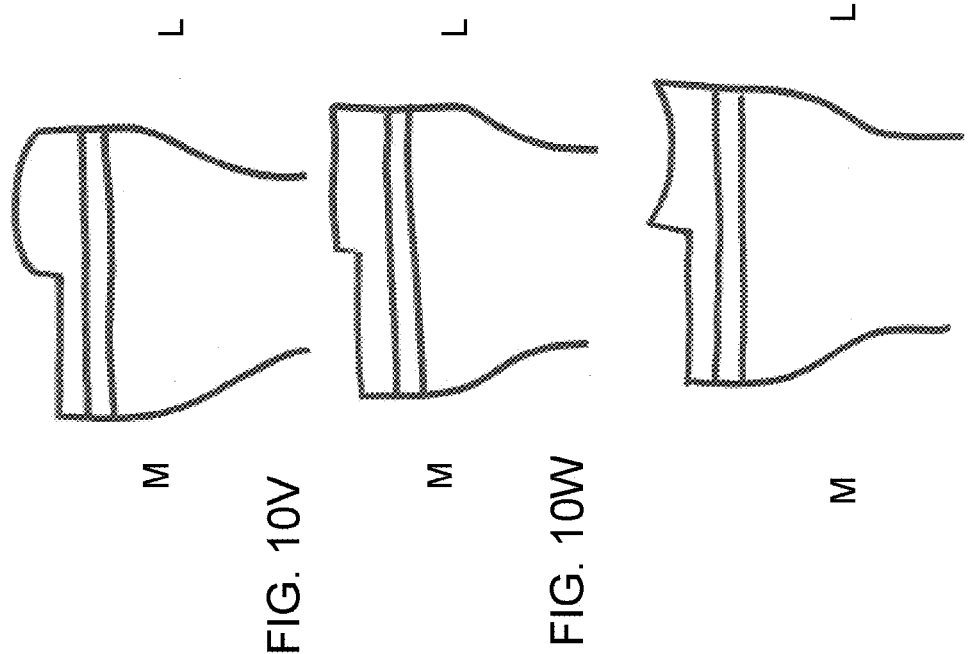

The medial and/or the lateral component can include a trough. The medial component can be dish shaped, while the lateral component includes a trough. The lateral component can be dish shaped, while the medial component includes a trough. The lateral component can be convex, while the medial component includes a trough. The shape of the medial or lateral component can be patient derived or patient matched in one, two or three dimensions, for example as it pertains to its perimeter as well as its surface shape. The convex shape of the lateral component can be patient derived or patient matched in one, two or three dimensions. The trough can be straight. The trough can also be curved. The curvature of the trough can have a constant radius of curvature or it can include several radii of curvature. The radii can be patient matched or patient derived, for example based on the femoral geometry or on the patient's kinematics. These designs can be applied with a single-piece tibial polyethylene or other plastic insert or with two-piece tibial polyethylene or other plastic inserts. FIGS. 10A-AD show exemplary combinations of tibial tray designs having dual inserts (FIGS. 10A-O) and single inserts (FIGS. 10P-AD) with different medial and lateral surface shapes.

One- and Two-Piece Tibial Inserts

In a preferred embodiment, the tray component is able to accept either a one piece insert or a two piece insert. The two piece insert can be one piece insert cut in half at the approximate medial-lateral midpoint of the insert. This can create a medial insert and a lateral insert that each exhibit all of the features described in the one piece insert described herein. Alternatively, each piece can be formed separately, with different surface shapes and also different locking mechanisms. One of the benefits to using a two piece insert over a one piece insert is the ability to use different thicknesses for each of the medial insert and the lateral insert, to accommodate specific geometries of the patient's specific joint. Thus, the surgeon may intraoperatively optimize ligament balancing or soft-tissue balancing by, for example, selecting a thicker piece on one side when compared to the other side. Moreover, the surgeon can intraoperatively select pieces with different profiles, which may help with joint kinematics and which can also assist with ligament or soft-tissue balancing. For example, the medial insert can have a substantially concave shape. The lateral insert can have a convex shape. Alternatively, the lateral insert can have a concave shape in mediolateral direction that is, however, substantially straight in anteroposterior direction. Alternatively, the lateral insert can have a concave shape in mediolateral direction that follows the contour of the normal gliding path of the lateral condyle on the lateral tibial plateau in AP direction. Similarly, the medial insert can have a substantially concave shape in mediolateral direction that follows the contour of the normal gliding path of the medial condyle on the medial tibial plateau in AP direction. Optionally, one or both inserts can be flat.

The following are examples of possible combinations of medial and lateral inserts with dual inserts (Table 6):

TABLE 6

Examples of possible medial and lateral two-piece insert combinations (additionally illustrated in FIGS. 10A-O):

| Insert Thickness | Medial | Lateral |
|---|---|---|
| Medial thickness = lateral thickness | Concave | Convex |
| Medial thickness = lateral thickness | Concave | Flat |
| Medial thickness = lateral thickness | Concave | Concave |
| Medial thickness = lateral thickness | Flat | Convex |
| Medial thickness = lateral thickness | Flat | Flat |
| Medial thickness = lateral thickness | Flat | Concave |
| Medial thickness = lateral thickness | Convex | Convex |
| Medial thickness = lateral thickness | Convex | Flat |
| Medial thickness = lateral thickness | Convex | Concave |
| Medial thickness less than lateral thickness | Concave | Convex |
| Medial thickness less than lateral thickness | Concave | Flat |
| Medial thickness less than lateral thickness | Concave | Concave |
| Medial thickness less than lateral thickness | Flat | Convex |
| Medial thickness less than lateral thickness | Flat | Flat |
| Medial thickness less than lateral thickness | Flat | Concave |
| Medial thickness less than lateral thickness | Convex | Convex |
| Medial thickness less than lateral thickness | Convex | Flat |
| Medial thickness less than lateral thickness | Convex | Concave |
| Medial thickness greater than lateral thickness | Concave | Convex |
| Medial thickness greater than lateral thickness | Concave | Flat |
| Medial thickness greater than lateral thickness | Concave | Concave |
| Medial thickness greater than lateral thickness | Flat | Convex |
| Medial thickness greater than lateral thickness | Flat | Flat |
| Medial thickness greater than lateral thickness | Flat | Concave |
| Medial thickness greater than lateral thickness | Convex | Convex |
| Medial thickness greater than lateral thickness | Convex | Flat |
| Medial thickness greater than lateral thickness | Convex | Concave |

The same surface profiles or similar surface profiles can be used with a single piece insert. The following are examples of possible combinations of medial and lateral implant surface profiles with a single piece tibial insert (Table 7):

TABLE 7

Examples of possible medial and lateral implant surface profiles with a single piece tibial insert (additionally illustrated in FIGS. 10P-AD):

| Insert Thickness | Medial | Lateral |
|---|---|---|
| Medial thickness = lateral thickness | Concave | Convex |
| Medial thickness = lateral thickness | Concave | Flat |
| Medial thickness = lateral thickness | Concave | Concave |
| Medial thickness = lateral thickness | Flat | Convex |
| Medial thickness = lateral thickness | Flat | Flat |
| Medial thickness = lateral thickness | Flat | Concave |
| Medial thickness = lateral thickness | Convex | Convex |
| Medial thickness = lateral thickness | Convex | Flat |
| Medial thickness = lateral thickness | Convex | Concave |
| Medial thickness less than lateral thickness | Concave | Convex |
| Medial thickness less than lateral thickness | Concave | Flat |
| Medial thickness less than lateral thickness | Concave | Concave |
| Medial thickness less than lateral thickness | Flat | Convex |
| Medial thickness less than lateral thickness | Flat | Flat |
| Medial thickness less than lateral thickness | Flat | Concave |
| Medial thickness less than lateral thickness | Convex | Convex |
| Medial thickness less than lateral thickness | Convex | Flat |
| Medial thickness less than lateral thickness | Convex | Concave |
| Medial thickness greater than lateral thickness | Concave | Convex |
| Medial thickness greater than lateral thickness | Concave | Flat |
| Medial thickness greater than lateral thickness | Concave | Concave |
| Medial thickness greater than lateral thickness | Flat | Convex |
| Medial thickness greater than lateral thickness | Flat | Flat |
| Medial thickness greater than lateral thickness | Flat | Concave |
| Medial thickness greater than lateral thickness | Convex | Convex |
| Medial thickness greater than lateral thickness | Convex | Flat |
| Medial thickness greater than lateral thickness | Convex | Concave |

Figure 11A:
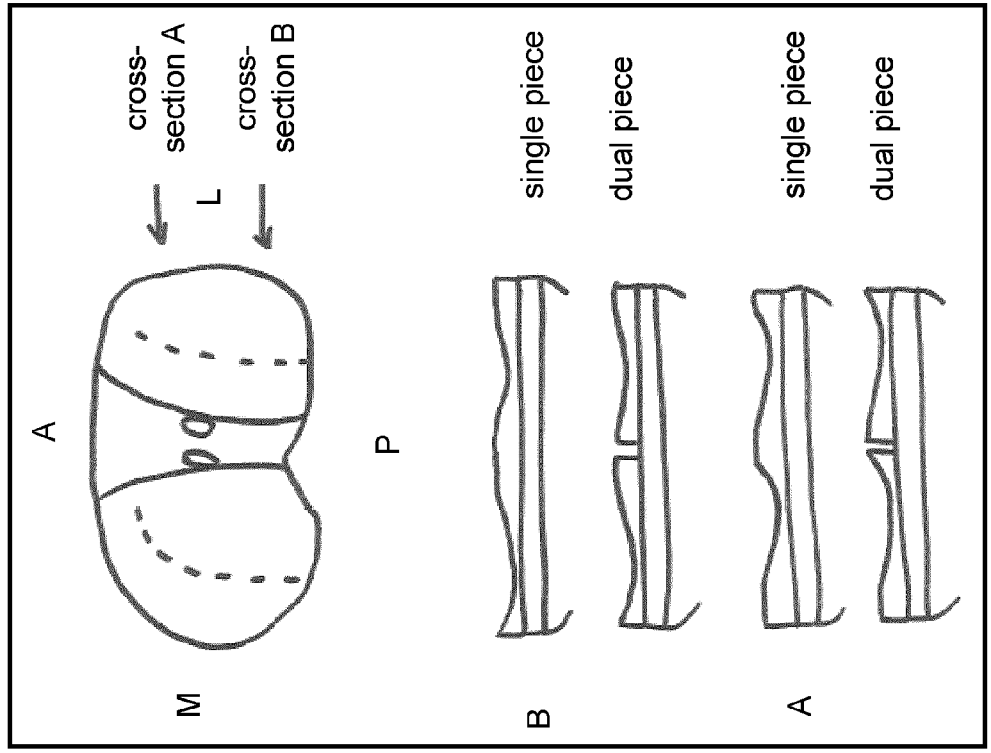
FIGS. 11A-C depict exemplary medial and lateral gliding paths for tibial implant components and related single and dual piece insert surfaces.
Figure 11B:
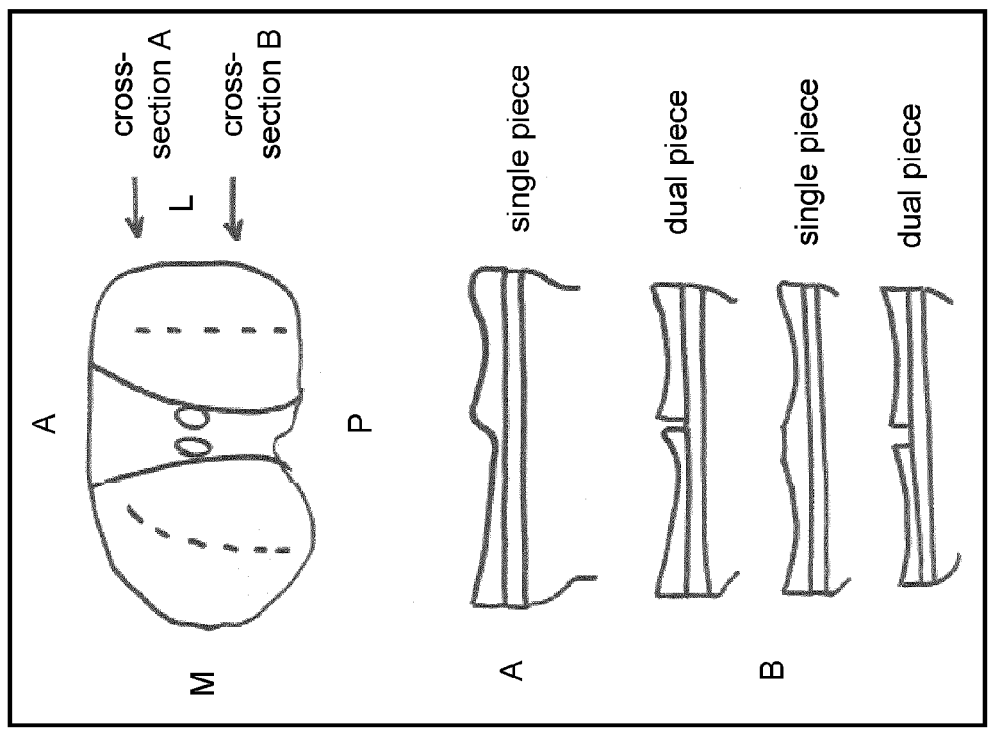
Figure 12:
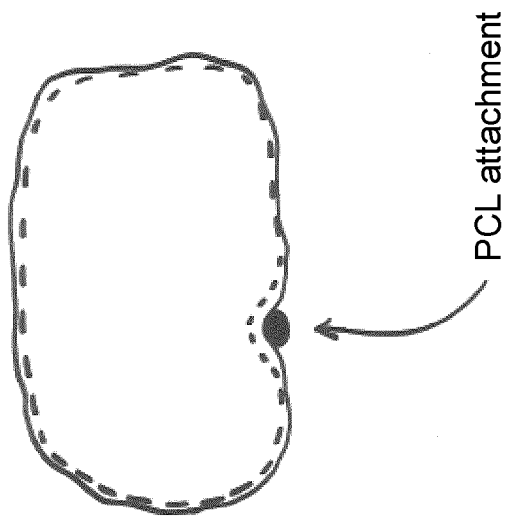
FIG. 12 depicts an embodiments of a tibial implant component that is ligament retaining.
Figure 11C:
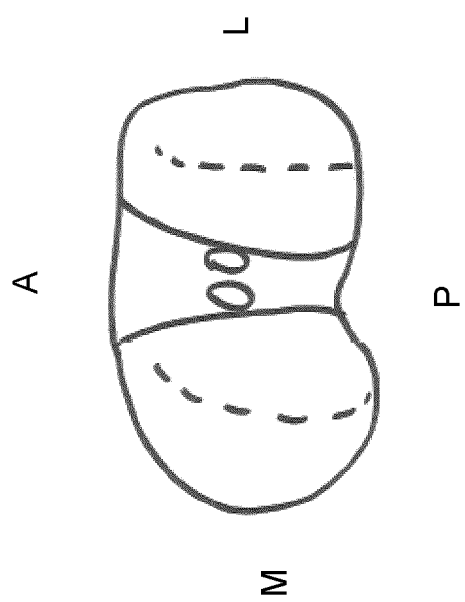

Referring to FIGS. 11A-C, medial and lateral gliding paths can be estimated based on population data that can include information on age, gender, race, body weight, BMI and other demographic data. Alternatively, medial and lateral gliding paths can be estimated based on kinematic modeling. Kinematic modeling can also be database based. Kinematic modeling can include the inclusion of patient specific data, e.g. age, gender, race, body weight, BMI and other demographic data as well as patient specific anatomy or geometry, for example derived from an imaging test. In certain embodiments, at least one of a medial or lateral tibial implant profile or both can be adapted so that the coronal curvature, e.g. convex or concave, follows this glide path at least in part.

Of note, several of the above embodiments describe an implant system that uses a metal backing with a single or two piece plastic inserts. The same surface profile and thickness combinations shown in Tables 6 and 7 are applicable to tibial implants that have no metal backing, and that have attachment mechanisms incorporated into their base. Such tibial implant systems can be composed of plastics including polyethylene and ceramics or composites or combinations thereof; they can include components that replace the entire tibial plateau or combinations of a medial and a lateral unicompartmental tibial component.

Surface profiles can be patient-derived or patient-adapted. For example, the sagittal radius of a femoral component can be patient specific, e.g., derived based on the patient's subchondral bone or cartilage shape in at least a portion of the femoral component. The coronal radius of the femoral component can be engineered. The mating tibial component can include, at least in part, a sagittal radius derived from said patient specific femoral component radius, e.g. slightly widened, as well as an engineered coronal radius derived from said engineered femoral coronal radius and, preferably, slightly widened relative to said engineered femoral coronal radius. Any combination of patient specific and engineered femoral and tibial radii is possible. Similarly, any combination of patient specific and engineered radii is possible in other joints.

An additional benefit of a two piece insert over a one piece insert is ease of use. A one piece insert is often difficult to place into a knee joint during surgery due to the size of the insert and the spatial constraints of the joint. Each piece of the two piece insert is not only smaller in size than a full one piece insert, but it also enables insertion of the lateral side or the medial side of the insert into the joint first, depending on the size constraints of the joint.

An important goal of arthroplasty is the balancing of soft-tissue and ligaments for different pose angles of the joint. In the knee, this balancing can be achieved for different degrees of knee flexion and extension. The surgeon has several options available for soft-tissue and ligament balancing. These include, for example, (1) selecting placement of bone cuts including height, depth and orientation of bone cuts (e.g. tibial slope) for optimizing soft-tissue and ligament balancing; (2) selecting removal of osteophytes; and/or (3) soft-tissue and partial or complete ligament releases, e.g., release of the medial collateral ligament or lateral collateral ligament. However, once these steps have been performed, the surgeon typically has no further means of optimizing ligament or soft-tissue balance at his disposal. Thus, if it turns out that a knee is too loose on one side or both sides in flexion or extension, the surgeon has no means of correcting this with traditional knee implants. Thus, in certain embodiments, the surgeon will be provided with several different single piece insert systems. Each piece has a different thickness and/or medial or lateral surface profile. The insert systems can be accompanied by matching trials that can be inserted into the locking system and easily be removed. The surgeon can trial different insert systems for different degrees of knee flexion and extension to correct for any remaining ligament imbalance.

In some embodiments, the surgeon can use a two insert piece system. Each insert, medial and lateral, can be provided with different thicknesses and/or different implant profiles. Trial medial and lateral insert systems can be provided that can be inserted into the metal backing and lock and that can be readily removed from the lock after testing. The surgeon can trial different combinations of medial and lateral insert systems and can optimize ligament and soft-tissue balancing by selecting a combination of medial and lateral inserts that yields the best balancing result for different flexion and extension angles.

All of the embodiments described herein can be compatible with tibial components that (1) preserve the anterior and posterior cruciate ligament; (2) preserve the posterior cruciate ligament only; or (3) are posterior stabilized (i.e., sacrifice both cruciate ligaments).

Ligament-Retaining

Referring to FIGS. 6A-B, 12, and 13A-B, examples of ligament-retaining tibial implants are shown. For example, the implant can provide space ligaments of the knee, for example the posterior cruciate ligament (PCL), and allows the components to be shaped so as to avoid interference with the ligament. Optionally, the PCL origin and insertion can be identified in the imaging study, e.g., an ultrasound, CT scan, MRI scan, optical scan, laser scan, photoacoustic imaging and others. The PCL origin and insertion as well as the ligament proper can be identified directly on the imaging study, for example when an MRI is used. Alternatively, the origin and/or insertion can be identified by determining bony landmarks such as a groove on the posterior aspect of the tibia that are representative of the bone attachment site. In this manner, the tibial tray can be shaped so that the ligament is avoided and can remain intact after the surgery. For example, the tibial tray, e.g., the metal backing or insert or both or an all poly component can be shaped to include a groove that is recessed relative to the PCL insertion and that is slightly wider than the PCL and its insertion.

Additionally, the tibial tray can be configured or selected to account for the anterior cruciate ligament (ACL), and allows the components to be shaped so as to avoid interference with the ligament. Optionally, the ACL origin and insertion can be identified in the imaging study, e.g. an ultrasound, CT scan, MRI scan, optical scan, laser scan, photoacoustic imaging and others. The ACL origin and insertion as well as the ligament proper can be identified directly on the imaging study, for example when an MRI is used. Alternatively, the origin and or insertion can be identified by determining bony landmarks such as a groove or bony irregularity on the femur or tibia that are representative of the bone attachment site. In this manner, the tibial tray can be shaped so that the ligament is avoided and can remain intact after the surgery. Thus, embodiments described herein allow for shaping/designing and/or selecting tibial implant components that are adapted to the patient's anatomy in order to avoid any interference with ligaments and to preserve these ligaments. This is applicable to single and dual component systems, with metal backing or without metal backing.

Moreover, the tibial and femoral components can be shaped so that any soft-tissue interference is avoided using, for example, imaging data. Other soft-tissue structures or bony landmarks related to these soft-tissue structures can be identified, for example on imaging data of the patient. For example, referring to FIGS. 14A-B, in the knee, the popliteus tendon, medial capsule, lateral capsule, posterior capsule, Hoffa's fat pad, plicae and other soft-tissue structures can be identified. The femoral and/or tibial implant components can be designed, shaped or selected so that they avoid interference with or impingement on one or more of these or other soft-tissue structures.

The joint can be moved virtually into different pose angles, including kinematic simulation, in order to detect any potential ligament or soft-tissue interference or impingement. The implant components can be designed or adapted to avoid ligament or soft-tissue interference or impingement for different degrees of flexion and extension, abduction and adduction, elevation, rotation, and/or other positions.

Similarly, in a hip the femoral and acetabular components can be shaped so that any soft-tissue interference is avoided using, for example, imaging data. Other soft-tissue structures or bony landmarks related to these soft-tissue structures can be identified, for example on imaging data of the patient. For example, medial capsule, lateral capsule, posterior capsule, anterior capsule, iliopsoas tendon and other soft-tissue structures can be identified. The femoral and/or acetabular implant components can be designed, shaped or selected so that they avoid interference with or impingement on one or more of these or other soft-tissue structures.

Similarly, in a shoulder the humeral and glenoid components can be shaped so that any soft-tissue interference is avoided using, for example, imaging data. Other soft-tissue structures or bony landmarks related to these soft-tissue structures can be identified, for example on imaging data of the patient. For example, medial capsule, lateral capsule, posterior capsule, anterior capsule, rotator cuff including the supraspinatus tendon, infraspinatus tendon, teres minor and subscapularis and other soft-tissue structures can be identified. The humeral and/or glenoid implant components can be designed, shaped or selected so that they avoid interference with or impingement on one or more of these or other soft-tissue structures.

Figure 15A:
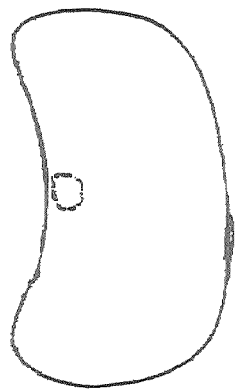
FIGS. 15A-C depict steps in a process for designing a PCL-retaining tibial insert.
Figure 15B:
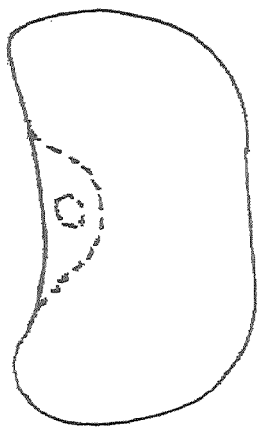
Figure 15C:
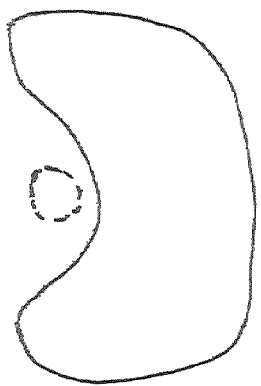

Various methods can be employed for designing a cruciate—retaining implant. For example, FIGS. 15A-C depict one exemplary method for designing a PCL retaining ligament. In FIG. 15A, a tibial implant perimeter is designed based on the perimeter shape of the planned resected tibial surface. In FIG. 15B, the implant perimeter design is altered so that the PCL is maintained. FIG. 15C depicts the resulting shape of the PCL-retaining tibial implant component, with the PCL shown as a circle.

Cruciate Substitution

Figure 16A:
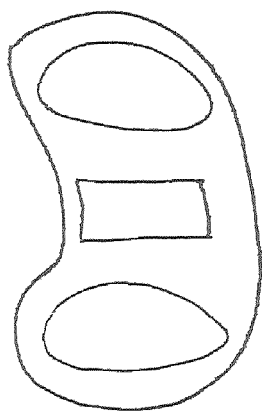
FIGS. 16A-C depict three perspectives of an exemplary tibial implant component that includes a stabilizing fin (e.g., a PCL-sacrificing patient-specific tibial implant component)
Figure 16B:
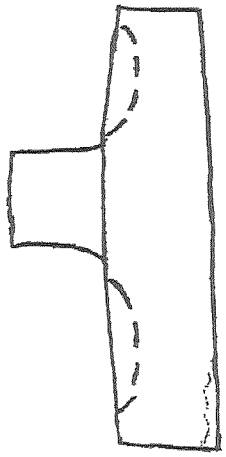
Figure 16C:
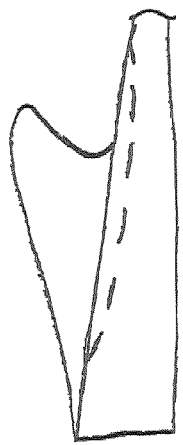

In addition to the implant component features described above, certain embodiments can include features and designs for cruciate substitution. These features and designs can include, for example, a keel, post, or projection that projects from the bone-facing surface of the tibial implant component and engage a corresponding intercondylar housing, receptacle, or bars on the corresponding femoral implant component. FIGS. 16A-C depict a tibial implant component that includes a stabilizing fin to help stabilize a cruciate-sacrificing knee replacement.

Figure 17B:
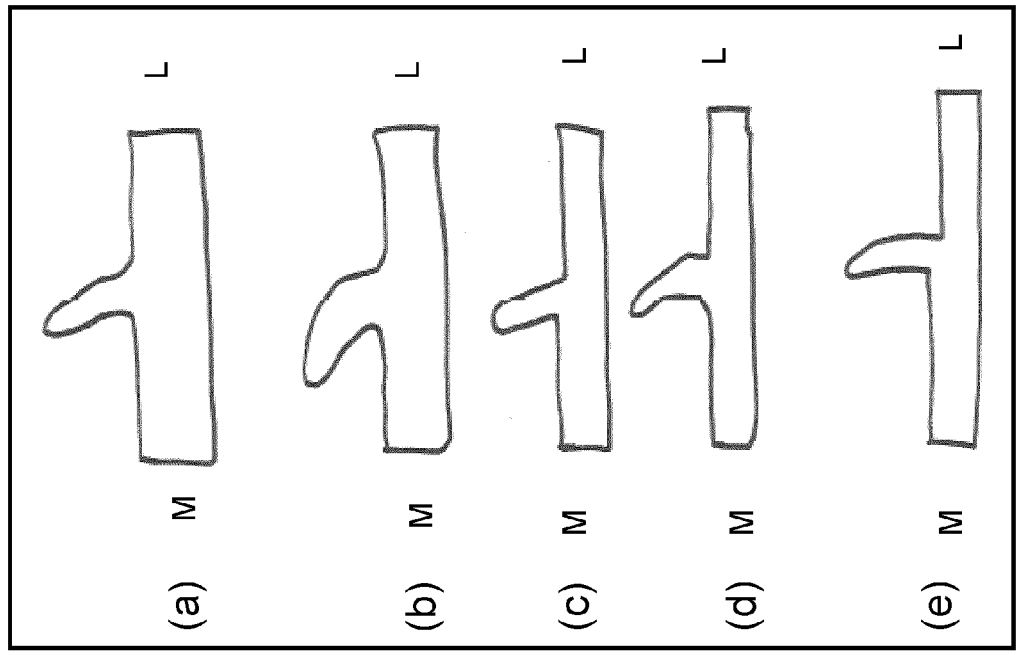
FIGS. 17A and 17B depict exemplary cross-sections of tibial implant components having a post (or keel or projection) projecting from the surface of the implant component.
Figure 17A:
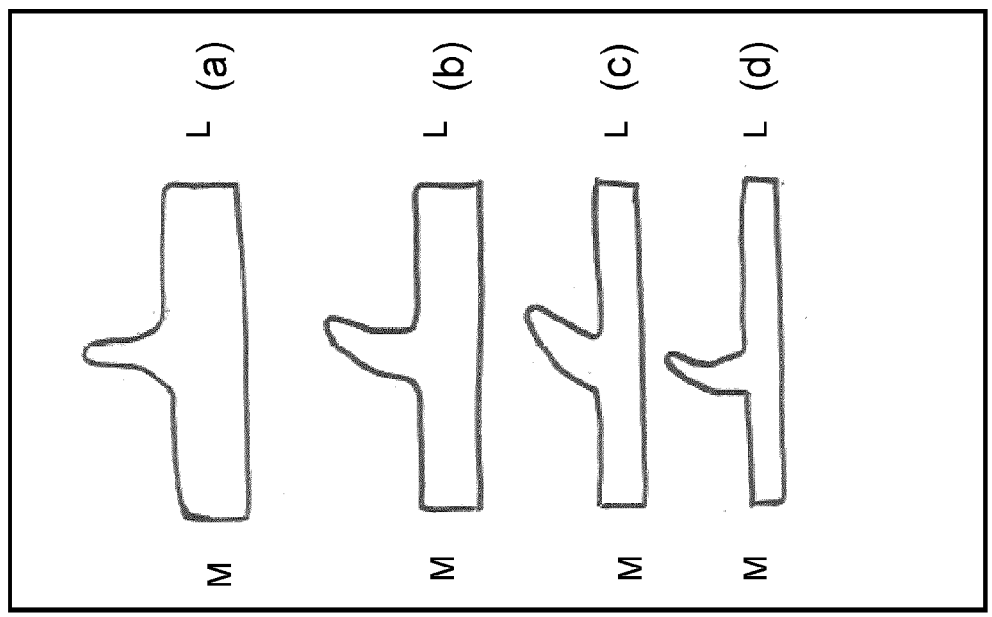

FIGS. 17A and 17B depict exemplary cross-sections of tibial implant components having a post (or keel or projection) projecting from the surface of the implant component. In particular, FIG. 17A shows (a) a tibial implant component with a straight post or projection and (b)-(d) tibial implant components having posts or projections oriented laterally, with varying thicknesses, lengths, and curvatures. FIG. 17B shows (a)-(e) tibial implant components having posts or projections oriented medially, with varying thicknesses, lengths, and curvatures.

As shown in the figures, the upper surface of the tray component has a "keel type" structure in between the concave surfaces that are configured to mate with the femoral condyle surfaces of a femoral implant. This "keel type" structure can be configured to slide within a groove in the femoral implant. The groove can comprise stopping mechanisms at each end of the groove to keep the "keel type" structure within the track of the groove. This "keel type" structure and groove arrangement may be used in situations where a patient's posterior cruciate ligament is removed as part of the surgical process and there is a need to posteriorly stabilize the implant within the joint.

In certain embodiments, the tibial implant component can be designed and manufactured to include the post or projection as a permanently integrated feature of the implant component. However, in certain embodiments, the post or projection can be modular. For example, the post or projection can be designed and/or manufactured separate from the tibial implant component and optionally joined with the component, either prior to (e.g., preoperatively) or during the implant procedure. For example, a modular post or projection and a tibial implant component can be mated using an integrating mechanism such as respective male and female screw threads, other male-type and female-type locking mechanisms, or other mechanism capable of integrating the post or projection into or onto the tibial implant component and providing stability to the post or projection during normal wear. A modular post or projection can be joined to a tibial implant component at the option of the surgeon or practitioner, for example, by removing a plug or other device that covers the integrating mechanism and attaching the modular post or projection at the uncovered integrating mechanism.

The post or projection can include features that are patient-adapted (e.g., patient-specific or patient-engineered). In certain embodiments, the post or projection includes one or more features that are designed and/or selected preoperatively, based on patient-specific data including imaging data, to substantially match one or more of the patient's biological features. For example, the length, width, height, and/or curvature of one or more portions of the post or projection can be designed and/or selected to be patient-specific, for example, with respect to the patient's intercondylar distance or depth, femoral shape, and/or condyle shape. Alternatively or in addition, one or more features of the post or projection can be engineered based on patient-specific data to provide to the patient an optimized fit. For example, the length, width, height, and/or curvature of one or more portions of the post or projection can be designed and/or selected to be patient-engineered. One or more thicknesses of the housing, receptacle, or bar can be matched to patient-specific measurements. One or more dimensions of the post or projection can be adapted based on one or more implant dimensions (e.g., one or more dimensions of the housing, receptacle or bar on the corresponding femoral implant component), which can be patient-specific, patient-engineered or standard. One or more dimensions of the post or projection can be adapted based on one or more of patient weight, height, sex, and body mass index. In addition, one or more features of the post or projection can be standard.

Optionally, referring to FIGS. 17A and 17B, an exemplary "keel type" structure or post can be adapted to the patient's anatomy. For example, the post can be shaped to enable a more normal, physiologic glide path of the femur relative to the tibia. Thus, the post can deviate medially or lateral as it extends from its base to its tip. This medial or lateral deviation can be designed to achieve a near physiologic rolling and rotating action of the knee joint. The medial and lateral bending of the post can be adapted based on patient specific imaging data. For example, the mediolateral curve or bend of the post or keel can be patient-derived or patient-matched (e.g., to match the physical or force direction of PCL or ACL). Alternatively or in addition, the post or keel can deviate at a particular AP angle or bend, for example, the sagittal curve of the post or keel can be reflection of PCL location and orientation or combinations of ACL and PCL location and orientation. The post can optionally taper or can have different diameters and cross-sectional profiles, e.g. round, elliptical, ovoid, square, rectangular at different heights from its base.

Different dimensions of the post or projection can be shaped, adapted, or selected based on different patient dimensions and implant dimensions. Examples of different technical implementations are provided in Table 8. These examples are in no way meant to be limiting. Someone skilled in the art can recognize other means of shaping, adapting or selecting a tibial implant post or projection based on the patient's geometry including imaging data.

TABLE 8

Examples of different technical implementations of a cruciate-sacrificing tibial implant component

| Post or projection feature | Corresponding patient anatomy, e.g., derived from imaging studies or intraoperative measurements |
| --- | --- |
| Mediolateral width | Maximum mediolateral width of patient intercondylar notch or fraction thereof |
| Mediolateral width | Average mediolateral width of intercondylar notch |
| Mediolateral width | Median mediolateral width of intercondylar notch |
| Mediolateral width | Mediolateral width of intercondylar notch in select regions, e.g. most inferior zone, most posterior zone, superior one third zone, mid zone, and/or other zones |
| Superoinferior height | Maximum superoinferior height of patient intercondylar notch or fraction thereof |
| Superoinferior height | Average superoinferior height of intercondylar notch |
| Superoinferior height | Median superoinferior height of intercondylar notch |
| Superoinferior height | Superoinferior height of intercondylar notch in select regions, e.g. most medial zone, most lateral zone, central zone, and/or other zones |
| Anteroposterior length | Maximum anteroposterior length of patient intercondylar notch or fraction thereof |
| Anteroposterior length | Average anteroposterior length of intercondylar notch |
| Anteroposterior length | Median anteroposterior length of intercondylar notch |
| Anteroposterior length | Anteroposterior length of intercondylar notch in select regions, e.g. most anterior zone, most posterior zone, central zone, anterior one third zone, posterior one third zone, and/or other zones |

The height or M-L width or A-P length of the intercondylar notch can not only influence the length but also the position or orientation of a post or projection from the tibial implant component.

The dimensions of the post or projection can be shaped, adapted, or selected not only based on different patient dimensions and implant dimensions, but also based on the intended implantation technique, for example, the intended tibial component slope or rotation and/or the intended femoral component flexion or rotation. For example, at least one of an anteroposterior length or superoinferior height can be adjusted if a tibial implant is intended to be implanted at a 7 degrees slope as compared to a 0 degrees slope, reflecting the relative change in patient or trochlear or intercondylar notch or femoral geometry when the tibial component is implanted. Moreover, at least one of an anteroposterior length or superoinferior height can be adjusted if the femoral implant is intended to be implanted in flexion, for example, in 7 degrees flexion as compared to 0 degrees flexion. The corresponding change in post or projection dimension can be designed or selected to reflect the relative change in patient or trochlear or intercondylar notch or femoral geometry when the femoral component is implanted in flexion.

In another example, the mediolateral width can be adjusted if one or both of the tibial and/or femoral implant components are intended to be implanted in internal or external rotation, reflecting, for example, an effective elongation of the intercondylar dimensions when a rotated implantation approach is chosen. Features of the post or projection can be oblique or curved to match corresponding features of the femoral component housing, receptacle or bar. For example, the superior portion of the post projection can be curved, reflecting a curvature in the roof of the femoral component housing, receptacle, or bar, which itself may reflect a curvature of the intercondylar roof In another example, a side of a post or projection may be oblique to reflect an obliquity of a side wall of the housing or receptacle of the femoral component, which itself may reflect an obliquity of one or more condylar walls. Accordingly, an obliquity or curvature of a post or projection can be adapted based on at least one of a patient dimension or a femoral implant dimension. Alternatively, the post or projection of the tibial implant component can be designed and/or selected based on generic or patient-derived or patient-desired or implant-desired kinematics in one, two, three or more dimensions. Then, the corresponding surface(s) of the femoral implant housing or receptacle can be designed and/or selected to mate with the tibial post or projection, e.g., in the ML plane. Alternatively, the post or projection of the femoral receptacle or box or bar or housing can be designed and/or selected based on generic or patient-derived or patient-desired or implant-desired kinematics in one, two, three or more dimensions. Then, the corresponding surface(s) of the post or projection of the tibial implant can be designed and/or selected to mate with the tibial post or projection, e.g., in the ML plane.

The tibial post or projection can be straight. Alternatively, the tibial post or projection can have a curvature or obliquity in one, two or three dimensions, which can optionally be, at least in part, reflected in the internal shape of the box. One or more tibial projection or post dimensions can be matched to, designed to, adapted to, or selected based on one or more patient dimensions or measurements. Any combination of planar and curved surfaces is possible.

In certain embodiments, the position and/or dimensions of the tibial implant component post or projection can be adapted based on patient-specific dimensions. For example, the post or projection can be matched with the position of the posterior cruciate ligament or the PCL insertion. It can be placed at a predefined distance from anterior or posterior cruciate ligament or ligament insertion, from the medial or lateral tibial spines or other bony or cartilaginous landmarks or sites. By matching the position of the post with the patient's anatomy, it is possible to achieve a better functional result, better replicating the patient's original anatomy.

Matching Features of a Tibial Implant Component

The perimeter of the tibial component, metal backed, optionally poly inserts, or all plastic or other material, can be matched to and/or derived from the patient's tibial shape, and can be optimized for different cut heights and/or tibial slopes. In a preferred embodiment, the shape is matched to the cortical bone of the cut surface. The surface topography of the tibial bearing surface can be designed or selected to match or reflect at least a portion of the tibial geometry, in one or more planes, e.g., a sagittal plane or a coronal plane, or both. The medial tibial implant surface topography can be selected or designed to match or reflect all or portions of the medial tibial geometry in one or more planes, e.g., sagittal and coronal. The lateral tibial implant surface topography can be selected or designed to match or reflect all or portions of the lateral tibial geometry in one or more planes, e.g., sagittal and coronal. The medial tibial implant surface topography can be selected or designed to match or reflect all or portions of the lateral tibial geometry in one or more planes, e.g., sagittal and coronal. The lateral tibial implant surface topography can be selected or designed to match or reflect all or portions of the medial tibial geometry in one or more planes, e.g., sagittal and coronal.

The surface topography of the tibial bearing surface(s) can be designed or selected to match or reflect at least portions of the femoral geometry or femoral implant geometry, in one or more planes, e.g., a sagittal plane or a coronal plane, or both. The medial implant surface topography can be selected or designed to match or reflect all or portions of the medial femoral geometry or medial femoral implant geometry in one or more planes. The lateral implant surface topography can be selected or designed to match or reflect all or portions of the lateral femoral geometry or lateral femoral implant geometry in one or more planes. The medial implant surface topography can be selected or designed to match or reflect all or portions of the lateral femoral geometry or lateral femoral implant geometry in one or more planes. The lateral implant surface topography can be selected or designed to match or reflect all or portions of the medial femoral geometry or medial femoral implant geometry in one or more planes. The medial and/or the lateral surface topography can be fixed in one, two or all dimensions. The latter can typically be used when at least one femoral geometry, e.g., the coronal curvature, is also fixed.

The implant surface topography can include one or more of the following:

Curvature of convexity in sagittal plane, optionally patient derived or matched, e.g., based on tibial or femoral geometry Curvature of convexity in coronal plane, optionally patient derived or matched, e.g., based on tibial or femoral geometry Curvature of concavity in sagittal plane, optionally patient derived or matched, e.g., based on tibial or femoral geometry Curvature of concavity in coronal plane, optionally patient derived or matched, e.g., based on tibial or femoral geometry Single sagittal radius of curvature, optionally patient derived or matched, e.g., based on tibial or femoral geometry Multiple sagittal radii of curvature, optionally patient derived or matched, e.g., based on tibial or femoral geometry Single coronal radius of curvature, optionally patient derived or matched, e.g., based on tibial or femoral geometry Multiple coronal radii of curvature, optionally patient derived or matched, e.g., based on tibial or femoral geometry Depth of dish, optionally patient derived or matched, e.g., based on tibial or femoral geometry AP length of dish, optionally patient derived or matched, e.g., based on tibial or femoral geometry ML width of dish, optionally patient derived or matched, e.g., based on tibial or femoral geometry Depth of trough, optionally patient derived or matched, e.g., based on tibial or femoral geometry AP length of trough, optionally patient derived or matched, e.g., based on tibial or femoral geometry ML width of trough, optionally patient derived or matched, e.g., based on tibial or femoral geometry Curvature of trough, optionally patient derived or matched, e.g., based on tibial or femoral geometry All of the tibial designs discussed can be applied with a:

single piece tibial polyethylene insert, for example with a single metal backed component single piece tibial insert of other materials, for example with a single metal backed component two piece tibial polyethylene inserts, for example with a single metal backed component two piece tibial inserts of other materials, for example with a single metal backed component single piece all polyethylene tibial implant two piece all polyethylene tibial implant, e.g. medial and lateral single piece metal tibial implant (e.g., metal on metal or metal on ceramic)

two piece metal tibial implant, e.g., medial and lateral (e.g., metal on metal or metal on ceramic)

single piece ceramic tibial implant two piece ceramic tibial implant, e.g., medial and lateral Any material or material combination currently known in the art and developed in the future can be used.

Certain embodiments of tibial trays can have the following features, although other embodiments are possible: modular insert system (polymer); cast cobalt chrome; standard blanks (cobalt portion and/or modular insert) can be made in advance, then shaped patient-specific to order; thickness based on size (saves bone, optimizes strength); allowance for 1-piece or 2-piece insert systems; and/or different medial and lateral fins.

In certain embodiments, the tibial tray is designed or cut from a blank so that the tray periphery matches the edge of the cut tibial bone, for example, the patient-matched peripheral geometry achieves >70%, >80%, >90%, or >95% cortical coverage. In certain embodiments, the tray periphery is designed to have substantially the same shape, but be slightly smaller, than the cortical area.

If a shape, such as perimeter shape, of a tibial tray or insert is derived based on the shape of cortical bone, portions or the entire implant contour can be directly matched to the derived cortical bone surface. If the tibial shape is derived based on deriving the shape of endosteal or trabecular bone or bone marrow, the implant contour can be matched to the edge of the tibial plateau by adding, for example, an offset to the periphery of the endosteal bone or trabecular bone or bone marrow. This offset can be selected to be similar to the thickness of the cortical bone in the area, e.g. 1 mm, 1.5 mm, 2 mm, 2.5 mm etc. The offset can optionally be derived using a mathematical function.

The patient-adapted tibial implants of certain embodiments allow for design flexibility. For example, inserts can be designed to compliment an associated condyle of a corresponding femoral implant component, and can vary in dimensions to optimize design, for example, one or more of height, shape, curvature (preferably flat to concave), and location of curvature to accommodate natural or engineered wear pattern.

In the knee, a tibial cut can be selected so that it is, for example, 90 degrees perpendicular to the tibial mechanical axis or to the tibial anatomical axis. The cut can be referenced, for example, by finding the intersect with the lowest medial or lateral point on the plateau.

The slope for tibial cuts typically is between 0 and 7 or 0 and 8 degrees in the sagittal plane. Rarely, a surgeon may elect to cut the tibia at a steeper slope. The slope can be selected or designed into a patient-specific cutting jig using a preoperative imaging test. The slope can be similar to the patient's preoperative slope on at least one of a medial or one of a lateral side. The medial and lateral tibia can be cut with different slopes. The slope also can be different from the patient's preoperative slope on at least one of a medial or one of a lateral side.

The tibial cut height can differ medially and laterally, as shown in FIG. 3 and FIGS. 8A-C. In some patients, the uncut lateral tibia can be at a different height, for example, higher or lower, than the uncut medial tibia. In this instance, the medial and lateral tibial cuts can be placed at a constant distance from the uncut medial and the uncut lateral tibial plateau, resulting in different cut heights medially or laterally. Alternatively, they can be cut at different distances relative to the uncut medial and lateral tibial plateau, resulting in the same cut height on the remaining tibia. Alternatively, in this setting, the resultant cut height on the remaining tibia can be elected to be different medially and laterally. In certain embodiments, independent design of the medial and lateral tibial resection heights, resection slopes, and/or implant component (e.g., tibial tray and/or tibial tray insert), can enhance bone perseveration on the medial and/or lateral sides of the proximal tibia as well as on the opposing femoral condyles.

Figure 18:
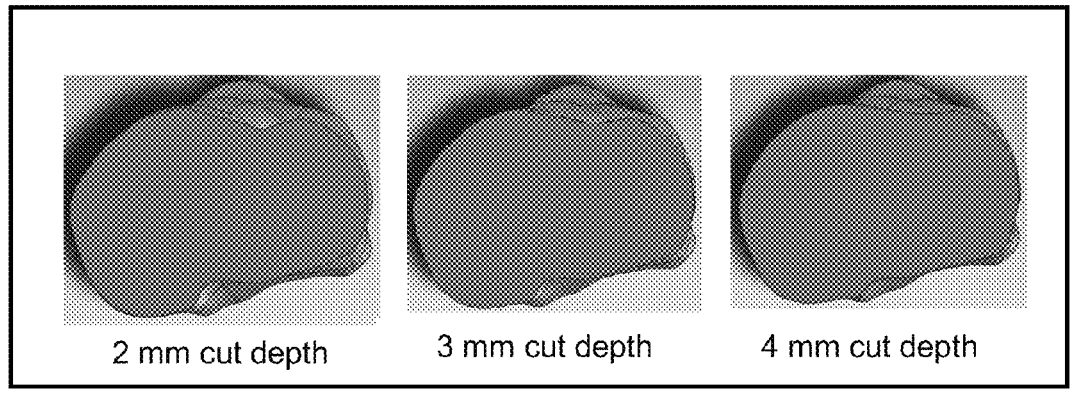
FIG. 18 shows proximal tibial resection cut depths of 2 mm, 3 mm and 4 mm.

In certain embodiments, a patient-specific proximal tibia cut (and the corresponding bone-facing surface of the tibial component) is designed by: (1) finding the tibial axis perpendicular plane ("TAPP"); (2) lowering the TAPP, for example, 2 mm below the lowest point of the medial tibial plateau; (3) sloping the lowered TAPP 5 degrees posteriorly (with no additional slope on the proximal surface of the insert); (4) fixing the component posterior slope, for example, at 5 degrees; and (5) using the tibial anatomic axis derived from Cobb or other measurement technique for tibial implant rotational alignment. As shown in FIG. 18, resection cut depths deeper than 2 mm below the lowest point of the patient's uncut medial or lateral plateau (e.g., medial plateau) may be selected and/or designed, for example, if the patient's anatomy includes an abnormality or diseased tissue below this point, or if the surgeon prefers a lower cut. For example, resection cut depths of 2.5 mm, 3 mm, 3.5 mm, 4 mm, 4.5 mm, or 5 mm can be selected and/or designed and, optionally, one or more corresponding tibial and/or femoral implant thicknesses can be selected and/or designed based on this patient-specific information.

In certain embodiments, a patient-specific proximal tibial cut (and the corresponding bone-facing surface of the tibial component) uses the preceding design except for determining the A-P slope of the cut. In certain embodiments, a patient-specific A-P slope can be used, for example, if the patient's anatomic slope is between 0 degrees and 7 degrees, or between 0 degrees and 8 degrees, or between 0 degrees and 9 degrees; a slope of 7 degrees can be used if the patient's anatomic slope is between 7 degrees and 10 degrees, and a slope of 10° can be used if the patient's anatomic slope is greater than 10 degrees.

In certain embodiments, a patient-specific A-P slope is used if the patient's anatomic slope is between 0 and 7 degrees and a slope of 7 degrees is used if the patient's anatomic slope is anything over 7 degrees. Someone skilled in the art can recognize other methods for determining the tibial slope and for adapting it during implant and jig design to achieve a desired implant slope.

A different tibial slope can be applied on the medial and the lateral side. A fixed slope can be applied on one side, while the slope on the other side can be adapted based on the patient's anatomy. For example, a medial slope can be fixed at 5 degrees, while a lateral slope matches that of the patient's tibia. In this setting, two unicondylar tibial inserts or trays can be used. Alternatively, a single tibial component, optionally with metal backing, can be used wherein said component does not have a flat, bone-facing surface, but includes, for example, an oblique portion to connect the medial to the lateral side substantially negatively-match resected lateral and medial tibial surfaces as shown, for example, in FIG. 3 and FIGS. 8A-C.

In certain embodiments, the axial profile (e.g., perimeter shape) of the tibial implant can be designed to match the axial profile of the patient's cut tibia, for example as described in U.S. Patent Application Publication No. 2009/0228113. Alternatively or in addition, in certain embodiments, the axial profile of the tibial implant can be designed to maintain a certain percentage or distance in its perimeter shape relative to the axial profile of the patient's cut tibia. Alternatively or in addition, in certain embodiments, the axial profile of the tibial implant can be designed to maintain a certain percentage or overhang in its perimeter shape relative to the axial profile of the patient's cut tibia.

Figure 19:
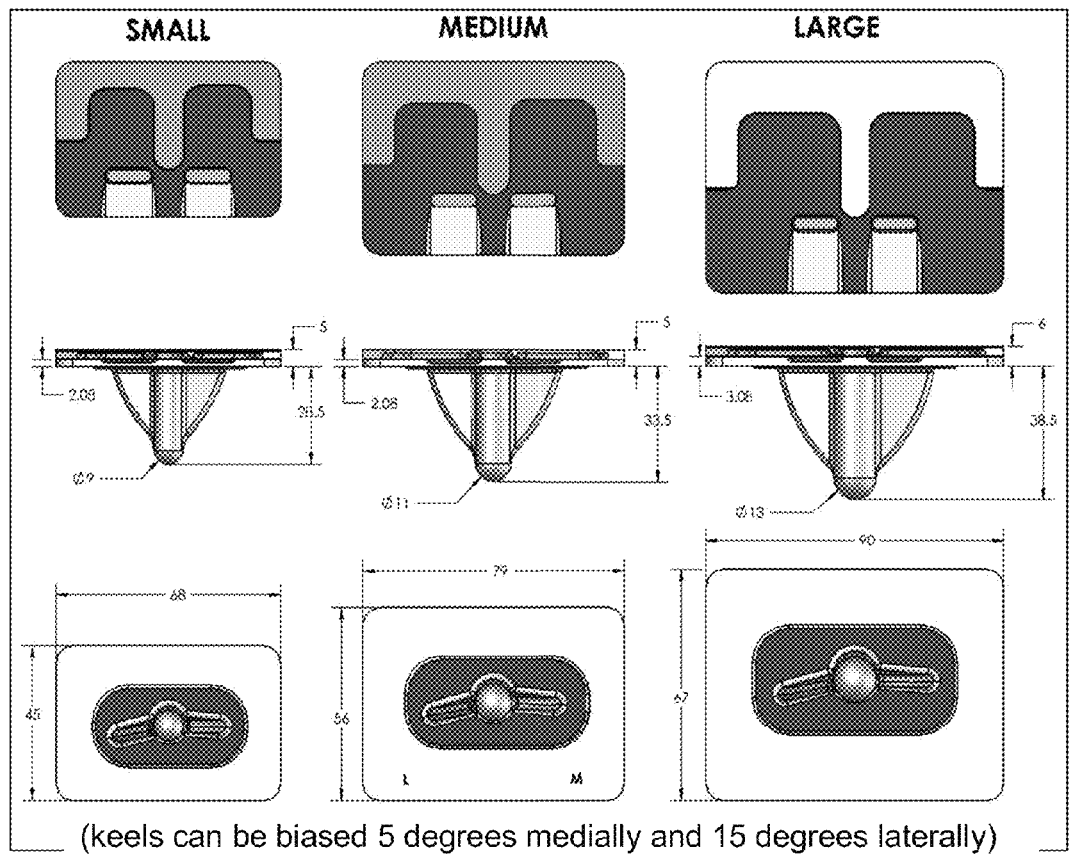
FIG. 19 shows exemplary small, medium and large blank tibial trays.

Tibial tray designs can include patient-specific, patient-engineered, and/or standard features. For example, in certain embodiments the tibial tray can have a front-loading design that can be seated using minimal impaction force. The trays can come in various standard or standard blank designs, for example, small, medium and large standard or standard blank tibial trays can be provided. FIG. 19 shows exemplary small, medium and large blank tibial trays. As shown, the tibial tray perimeters include a blank perimeter shape that can be designed based on the design of the patient's resected proximal tibia surface. In certain embodiments, small and medium trays can include a base thickness of 2 mm (e.g., such that a patient's natural joint line may be raised 3-4 mm if the patient has 2-3 mm of cartilage on the proximal tibia prior to the disease state). Large trays can have a base thickness of 3 mm (such that in certain embodiments it may be beneficial to resect an additional 1 mm of bone so that the joint line is raised no more than 2-3 mm (assuming 2-3 mm of cartilage on the patient's proximal tibia prior to the disease state).

Figure 20A:
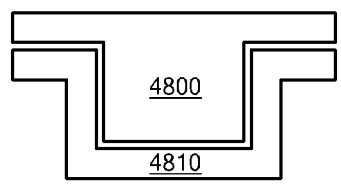
FIGS. 20A-C depict three exemplary combinations of a tibial tray and tibial tray insert manufactured and/or machined to include matching perimeters.
Figure 20B:
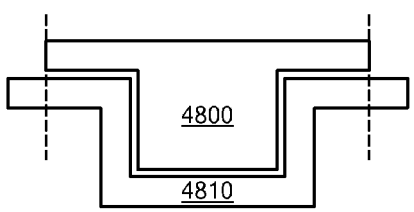
Figure 20C:
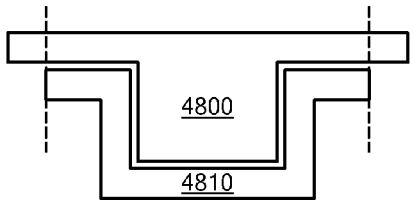

Any of the tibial implant components described herein can be derived from a blank that is cut to include one or more patient-specific features. For example, certain embodiments include a pre-existing repair system wherein a stock of "standard" tray components with the upper surface of the tray component machined with the walls, grooves, and receptacles outlined above, are kept. Similarly, a stock of standard tray inserts with the locking mechanism already machined in with the walls, grooves, receptacles can be kept. A patient's imaging data and anatomy information may then be used to shape a "standard" tray component so that at least one of the perimeter, shape, stem location, stem size, peg location, peg size, lock location, cement pocket location and cement pocket size of the tray component can be adapted for that specific patient. A "standard" insert component is then similarly shaped, according to the patient's individual imaging data and anatomy, to mate with the tray component that is specific to that patient. The insert component may also be initially configured to be larger than the tray component and then shaped to match the exact perimeter of the tray component to ensure there is no metal on metal scorching between the femoral component and the tibial component. FIGS. 20A-C depict three exemplary combinations of a tibial tray 4800 and tibial tray insert 4810 manufactured and/or machined to include matching perimeters. In FIG. 20A, the tray and tray insert are manufactured to have the same perimeter, e.g., same patient-specific, sam2e patient-derived, or same standard perimeter. In FIG. 20B, an oversized, e.g., standard or blank, tray is machined to include a perimeter that matches the tibial tray insert perimeter, e.g., matching patient-specific, matching patient-derived, or matching standard perimeter. In FIG. 20C, an oversized, e.g., standard or blank, tray insert is machined to include a perimeter that matches the tibial tray perimeter, e.g., matching patient-specific, matching patient-derived, or matching standard perimeter.

Figure 21A:
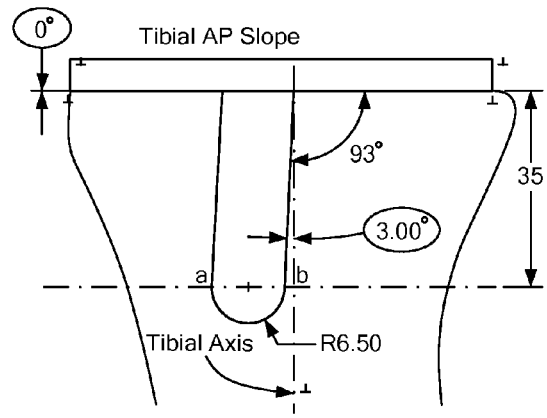
FIGS. 21A-C depict exemplary A-P and peg angles for tibial trays.
Figure 21B:
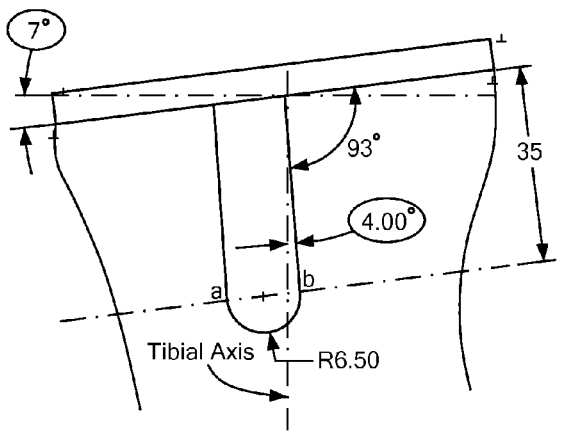
Figure 21C:
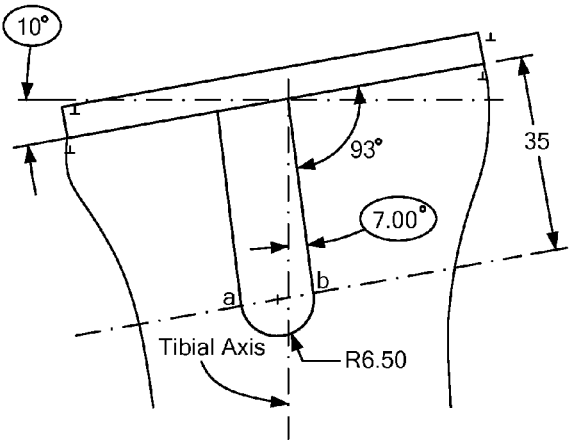

A patient-specific peg alignment (e.g., either aligned to the patient's mechanical axis or aligned to another axis) can be combined with a patient-specific A-P cut plane. For example, in certain embodiments the peg alignment can tilt anteriorly at the same angle that the A-P slope is designed. In certain embodiments, the peg can be aligned in relation to the patient's sagittal mechanical axis, for example, at a predetermined angle relative to the patient's mechanical axis. FIGS. 21A-21C show exemplary A-P and peg angles for tibial trays. In particular, in FIG. 21A, the A-P slope is 0 degrees and the tray tilts posteriorly 3 degrees; in FIG. 21B, the A-P slope is 7 degrees and the tray tilts posteriorly 4 degrees; and in FIG. 21C, the A-P slope is 10 degrees and the tray tilts posteriorly 7 degrees. The stem can be designed with a standard or patient-adapted tilt, e.g., a posterior tilt. For example, the stem can be designed to have a standard three degree tilt relative to the tray tilt, as shown in FIGS. 21A-C.

The joint-facing surface of a tibial implant component includes a medial bearing surface and a lateral bearing surface. Like the femoral implant bearing surface(s) described above, a bearing surface on a tibial implant (e.g., a groove or depression or a convex portion (on the lateral side) in the tibial surface that receives contact from a femoral component condyle) can be of standard design, for example, available in 6 or 7 different shapes, with a single radius of curvature or multiple radii of curvature in one dimension or more than one dimension. Alternatively, a bearing surface can be standardized in one or more dimensions and patient-adapted in one or more dimensions. A single radius of curvature and/or multiple radii of curvature can be selected in one dimension or multiple dimensions. Some of the radii can be patient-adapted.

Each of the two contact areas of the polyethylene insert of the tibial implant component that engage the femoral medial and lateral condyle surfaces can be any shape, for example, convex, flat, or concave, and can have any radii of curvature. In certain embodiments, any one or more of the curvatures of the medial or lateral contact areas can include patient-specific radii of curvature. Specifically, one or more of the coronal curvature of the medial contact area, the sagittal curvature of the medial contact area, the coronal curvature of the lateral contact area, and/or the sagittal curvature of the lateral contact area can include, at least in part, one or more patient-specific radii of curvature. In certain embodiments, the tibial implant component is designed to include one or both medial and lateral bearing surfaces having a sagittal curvature with, at least in part, one or more patient-specific radii of curvature and a standard coronal curvature. In certain embodiments, the bearing surfaces on one or both of the medial and lateral tibial surfaces can include radii of curvature derived from (e.g., the same length or slightly larger, such as 0-10% larger than) the radii of curvature on the corresponding femoral condyle. Having patient-adapted sagittal radii of curvature, at least in part, can help achieve normal kinematics with full range of motion.

Alternatively, the coronal curvature can be selected, for example, by choosing from a family of standard curvatures the one standard curvature having the radius of curvature or the radii of curvature that is most similar to the coronal curvature of the patient's uncut femoral condyle or that is most similar to the coronal curvature of the femoral implant component.

In preferred embodiments, one or both tibial medial and lateral contact areas have a standard concave coronal radius that is larger, for example slightly larger, for example, between 0 and 1 mm, between 0 and 2 mm, between 0 and 4 mm, between 1 and 2 mm, and/or between 2 and 4 mm larger, than the convex coronal radius on the corresponding femoral component. By using a standard or constant coronal radius on a femoral condyle with a matching standard or constant coronal radius or slightly larger on a tibial insert, for example, with a tibial radius of curvature of from about 1.05× to about 2×, or from about 1.05× to about 1.5×, or from about 1.05× to about 1.25×, or from about 1.05× to about 1.10×, or from about 1.05× to about 1.06×, or about 1.06× of the corresponding femoral implant coronal curvature. The relative convex femoral coronal curvature and slightly larger concave tibial coronal curvature can be selected and/or designed to be centered to each about the femoral condylar centers.

In the sagittal plane, one or both tibial medial and lateral concave curvatures can have a standard curvature slightly larger than the corresponding convex femoral condyle curvature, for example, between 0 and 1 mm, between 0 and 2 mm, between 0 and 4 mm, between 1 and 2 mm, and/or between 2 and 4 mm larger, than the convex sagittal radius on the corresponding femoral component. For example, the radius of curvature for one or both of the medial and lateral sides can be from about 1.1× to about 2×, or from about 1.2× to about 1.5×, or from about 1.25× to about 1.4×, or from about 1.30× to about 1.35×, or about 1.32× of the corresponding femoral implant sagittal curvature. In certain embodiments, the depth of the curvature into the tibial surface material can depend on the height of the surface into the joint gap. As mentioned, the height of the medial and lateral tibial component joint-facing surfaces can be selected and/or designed independently. In certain embodiments, the medial and lateral tibial heights are selected and/or designed independently based on the patient's medial and lateral condyle height difference. In addition or alternatively, in certain embodiments, a threshold minimum or maximum tibial height and/or tibial insert thickness can be used. For example, in certain embodiments, a threshold minimum insert thickness of 6 mm is employed so that no less than a 6 mm medial tibial insert is used.

By using a tibial contact surface sagittal and/or coronal curvature selected and/or designed based on the curvature(s) of the corresponding femoral condyles or a portion thereof (e.g., the bearing portion), the kinematics and wear of the implant can be optimized For example, this approach can enhance the wear characteristics a polyethylene tibial insert. This approach also has some manufacturing benefits.

Figure 22B:
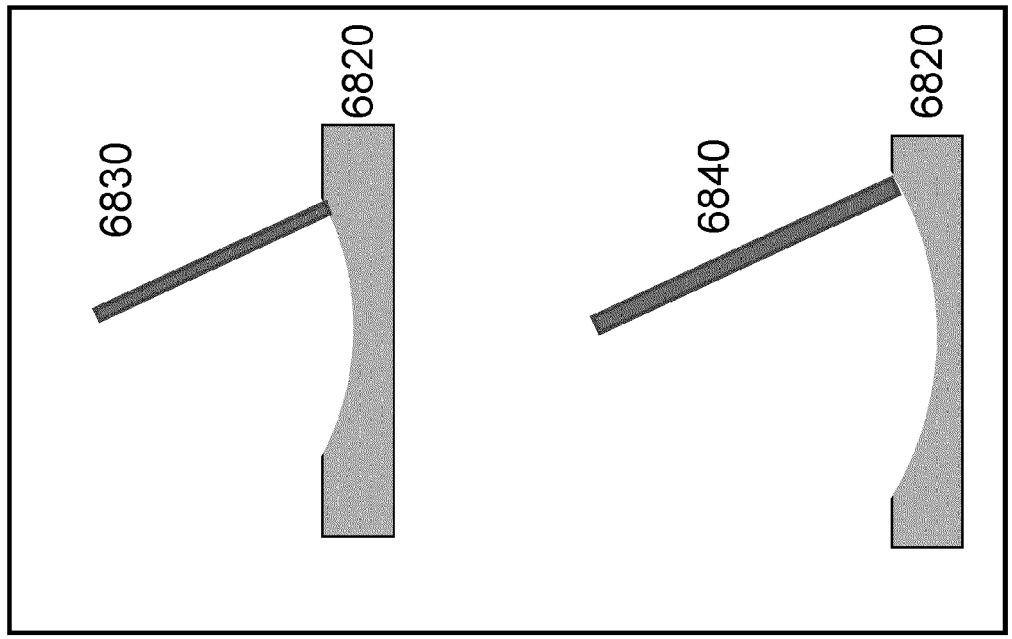
FIG. 22B shows a sagittal view of two exemplary tools sweeping from different distances into the polyethylene insert.
Figure 22A:
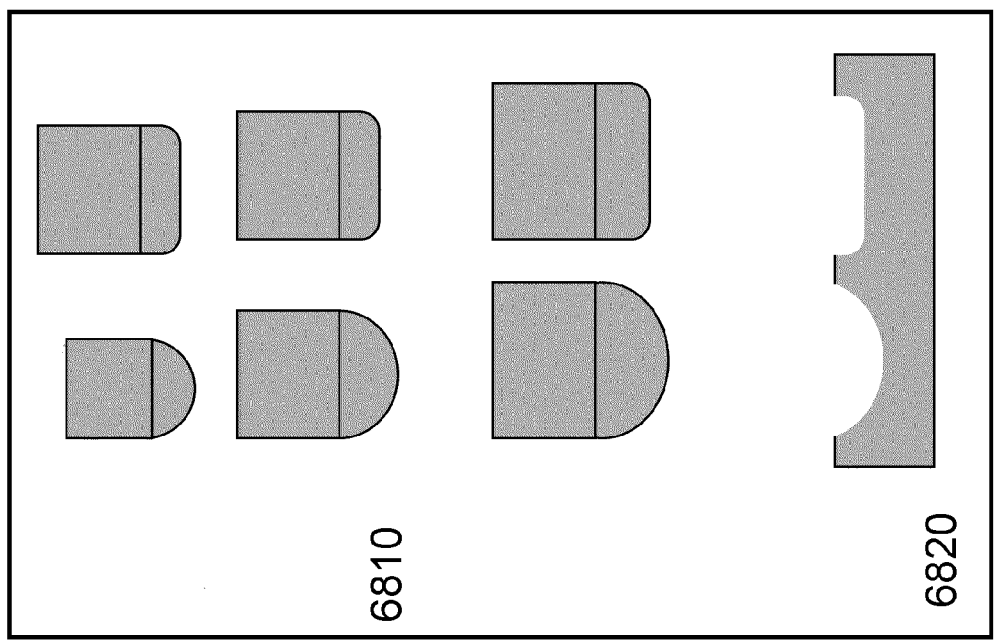
FIG. 22A shows six exemplary tool tips for making a polymer (e.g., polyethylene) insert for a tibial implant component.

For example, a set of different-sized tools can be produced wherein each tool corresponds to one of the pre-selected standard coronal curvatures. The corresponding tool then can be used in the manufacture of a polyethylene insert of the tibial implant component, for example, to create a curvature in the polyethylene insert. FIG. 22A shows six exemplary tool tips 6810 and a polyethylene insert 6820 in cross-section in the coronal view. The size of the selected tool can be used to generate a polyethylene insert having the desired coronal curvature. In addition, FIG. 22A shows an exemplary polyethylene insert 6820 having two different coronal curvatures created by two different tool tips. The action of the selected tool on the polyethylene insert, for example, a sweeping arc motion by the tool at a fixed point above the insert, can be used to manufacture a standard or patient-specific sagittal curvature. FIG. 22B shows a sagittal view of two exemplary tools 6830, 6840 sweeping from different distances into the polyethylene insert 6820 of a tibial implant component to create different sagittal curvatures in the polyethylene insert 6820.

In certain embodiments, one or both of the tibial contact areas includes a concave groove having an increasing or decreasing radius along its sagittal axis, for example, a groove with a decreasing radius from anterior to posterior.

Figure 23B:
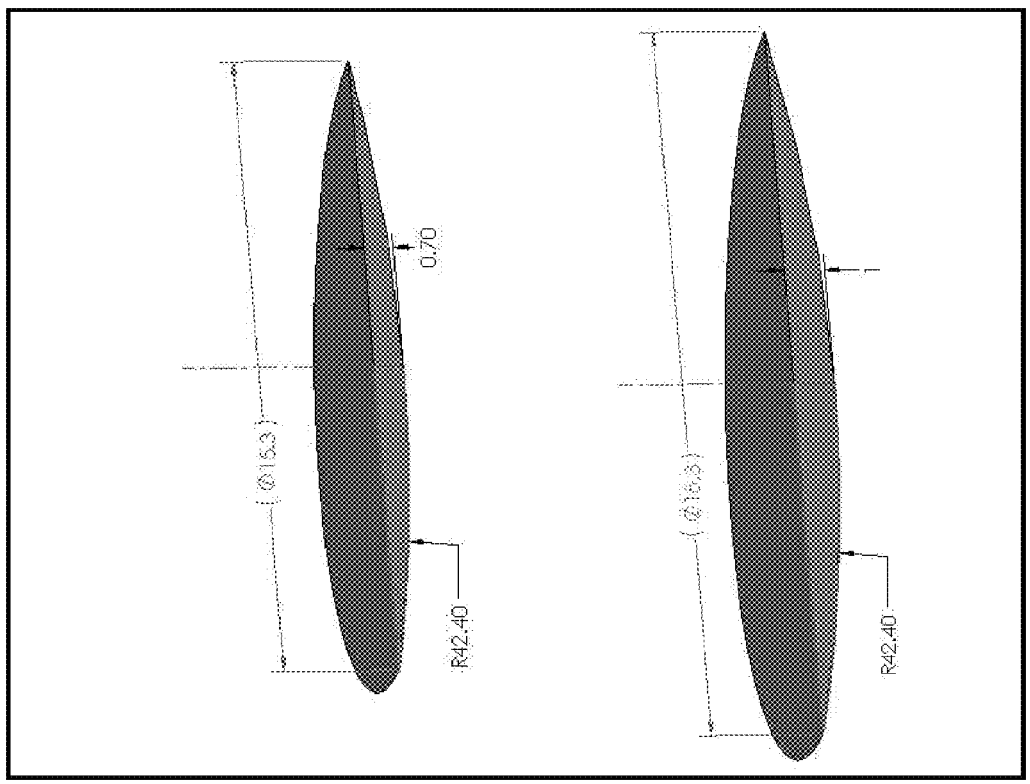
FIG. 23B illustrates two exemplary concavity dimensions for the bearing surface of a tibial implant component.
Figure 23A:
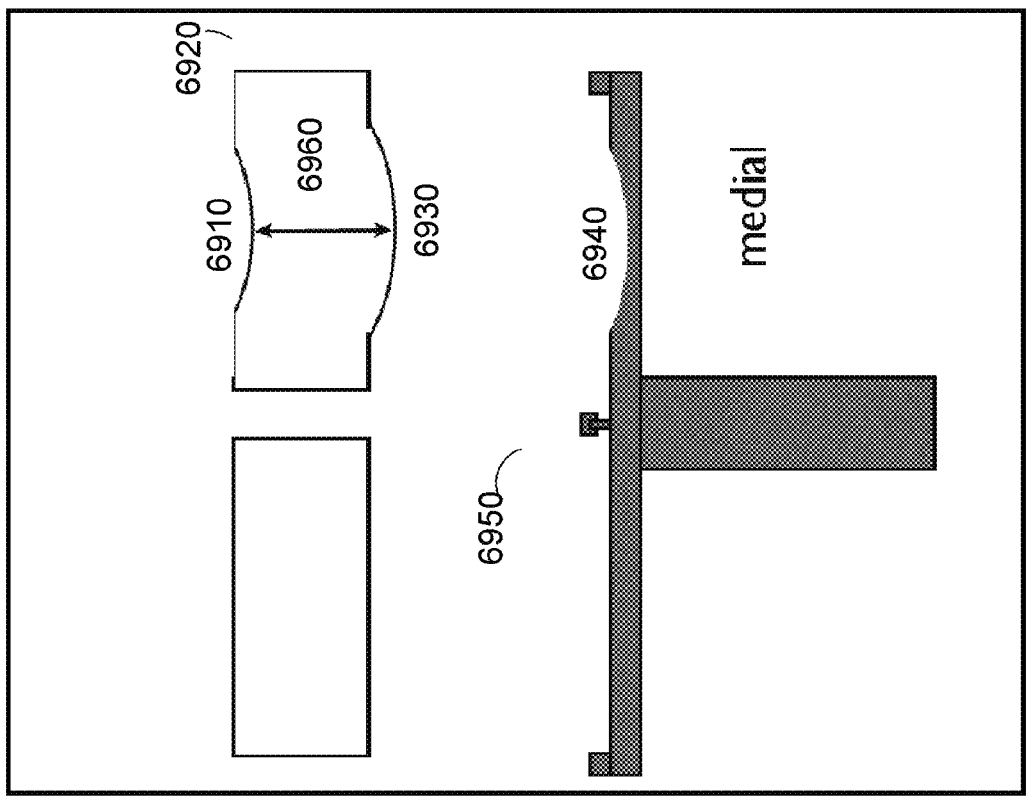
FIG. 23A shows an embodiment in which the shape of the concave groove on the medial side of the joint-facing surface of the tibial insert is matched by a convex shape on the opposing surface of the insert and by a concavity on the engaging surface of the tibial tray.

As shown in FIG. 23A, in certain embodiments the shape of the concave groove 6910 on the lateral and/or on the medial sides of the joint-facing surface of the tibial insert 6920 can be matched by a convex shape 6930 on the opposing side surface of the insert and, optionally, by a concavity 6940 on the engaging surface of the tibial tray 6950. This can allow the thickness of the component to remain constant 6960, even though the surfaces are not flat, and thereby can help maintain a minimum thickness of the material, for example, plastic material such as polyethylene. For example, an implant insert can maintain a constant material thickness (e.g., less than 5.5 mm, 5.5 mm, 5.6 mm, 5.7 mm, 5.8 mm, 5.9 mm, 6.0 mm, 6.1 mm, or greater than 6.1 mm) even though the insert includes a groove on the joint-facing surface. The constant material thickness can help to minimize overall minimum implant thickness while achieving or maintaining a certain mechanical strength (as compared to a thicker implant). The matched shape on the metal backing can serve the purpose of maintaining a minimum polyethylene thickness. It can, however, also include design features to provide a locking mechanism between the polyethylene or other insert and the metal backing. Such locking features can include ridges, edges, or interference fit. In the case of an interference fit, the polyethylene can have slightly larger dimensions at the undersurface convexity than the matching concavity on the metal tray. This can be stabilized against rails or dove tail locking mechanisms in the center or the sides of the metal backing. Other design options are possible. For example, the polyethylene extension can have a saucer shape that can snap into a matching recess on the metal backing. In addition, as shown in FIG. 23A, any corresponding pieces of the component, such as a metal tray, also can include a matching groove to engage the curved surface of the plastic material. Two exemplary concavity dimensions are shown in FIG. 23B. As shown in the figure, the concavities or scallops have depths of 1.0 and 0.7 mm, based on a coronal geometry of R42.4 mm At a 1.0 mm depth, the footprint width is 18.3 mm. At a 0.70 mm depth, the footprint width is 15.3 mm. These dimensions are only of exemplary nature. Other configurations are possible.

Figure 24B:
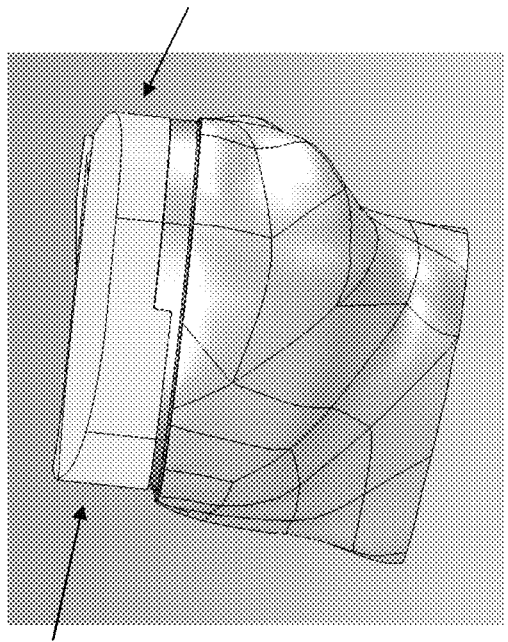
FIGS. 24A and B illustrates two embodiments of tibial implant components having sloped sagittal J-curves.
Figure 24A:
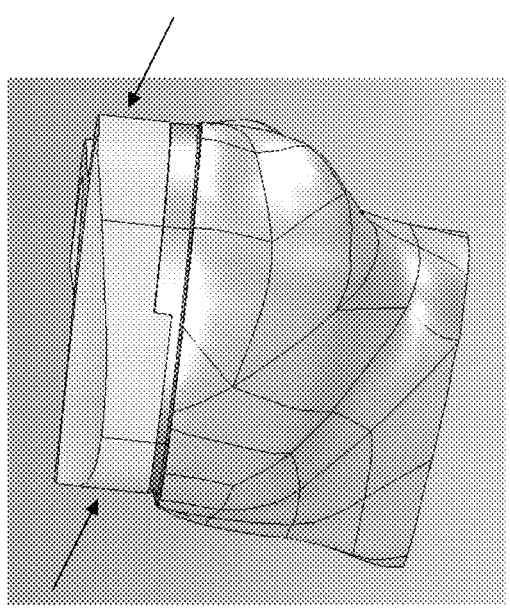

In certain embodiments, the sagittal curvature of the femoral component can be designed to be tilted, as suggested by FIGS. 24A and B. The corresponding curvature of the tibial surface can be tilted by that same slope, which can allow for thicker material on the corresponding tibial implant, for example, thicker poly at the anterior or posterior aspect of the tibial implant. The femoral component J-curve, and optionally the corresponding curvature for the tibial component, can be tilted by the same slope in both the medial and lateral condyles, just in the medial condyle or just in the lateral condyle or both independently or coupled. In certain embodiments, some additional material can be removed or the material thickness can be adapted from the posterior aspect of the femoral and/or tibial curvatures to allow for rotation.

Locking Mechanisms

Various embodiments of tibial trays include a scaffold or stage with one or more polymer inserts that can be inserted and locked into the scaffold. One embodiment is a tibial implant for a knee joint that is configured to be implanted onto a patient's proximal tibia. The tibial implant comprises at least two components: a first component that rests on the tibia; and a second component that is configured to articulate with the femoral condyle components of a femoral implant.

The tibial resting component is shaped as a tray (tray component) that sits on the patient's proximal tibia that is preferably surgically cut to become substantially flat. There may be situations in which the tibia needs to be cut at an angle, in a multi-tiered fashion or even contoured. This disclosure is not intended to be limited to any one of these and is able to accommodate each of them. In some embodiments, the tray component has a peripheral geometry that matches the patient's existing bone and in a further preferred embodiment the tray achieves significant coverage of the tibial plateau, e.g., 80, 85, 90 or 95 percent cortical coverage in AP or ML dimension or perimeter coverage or area of resected bone coverage. The tray component has an upper surface and a lower surface, a medial side, a lateral side, an anterior or front side and a posterior or rear side. The tray component can be attached to the patient's proximal tibia by way of a central stem or post integrated into the lower surface of the tray component. Other attachment mechanisms known in the art can be used. As will be appreciated by those of skill in the art, the stem or post may be attached to the tray component to provide the shape of the bone surface. For example, if the tibial surface is substantially flat, the stem or post may be attached substantially perpendicular to the tray component so that the tray component is positioned horizontal to the tibial axis. If, for example, the tibial surface is at an angle, the stem or post may be attached to the tray component at an angle so that the resulting position of the tray component is horizontal to the tibial axis. The angle can be selected based on the patient's unique anatomy, e.g. using an imaging test. The stem or post may have fins attached to it for further stabilization of the tray component. In one embodiment, the fins are aligned asymmetrically, i.e., they are placed at different angles from the horizontal middle of the tray component. The fins can also have different lengths, e.g., the fins can be longer on the medial side than on the lateral side or vice versa. By varying the fin angle and length, access to the bone, in particular posterior to the fins, can be facilitated when the surgeon performs a revision surgery and, for example, cuts the bone with a bone saw. In one embodiment, the stem is 13 mm in diameter and 40 mm long. The fins can be 2 or 3 or 4 mm wide, with the lateral side, for example, biased 15 degrees from horizontal and the medial side biased 5 degrees from horizontal. To aid fixation, a pocket or cut-out can be included in the lower surface of the tray component to incorporate additional adhesive means such as bone cement. The dimensions of the pocket or cut out can be adapted to the patient's anatomy, for example by deriving a bone shape using an imaging test.

The interior of the upper surface of the tray component can be substantially flat or can have at least one or more curved portions. There can be a wall that spans the posterior perimeter of the upper surface, from approximately halfway up the medial side to approximately halfway down the lateral side of the upper surface. This wall can optionally contain grooves along the inner surface for accepting an insert component of the implant. The wall can extend into the middle of the upper surface of the tray component from the posterior side towards the anterior side, approximately halfway between the medial and lateral sides, creating a peninsular wall on the upper surface. The outward facing sides of this peninsular wall can optionally be sloped inward from the top of the wall to the bottom of the wall, for mating with the insert component of the implant. Towards the end of the peninsular wall, receptacles can optionally be cut into either side of the wall for receiving an optional locking member formed into the surface of the insert of the implant. Perpendicular to the peninsular wall there can be one or more grooves cut into the upper surface of the tray component for accepting a notched portion extending from the lower surface of the insert of the implant. The anterior side of the upper surface of the tray component can contain at least one slanted surface that acts as a ramp to assist with proper alignment and insertion of the implant component into the tray component.

The articulating component, or insert component, has an upper surface, a lower surface, a medial side, a lateral side and anterior or front side and a posterior or rear side. The upper surface of the insert component can be flat or can be shaped to align with the geometry of the joint or the bearing surface of the opposite implant component by having one or more concave surfaces that are articulate with the convex surfaces of the femoral component of an implant, but other configurations are possible, such as a flat surface, a curved surface on a medial side and flat surface on a lateral side, a curved surface on a lateral side and a flat surface on a tibial side, or other configurations and combinations.

The lower surface of the insert component can be flat and is configured to mate with the tray component of the implant. The posterior side of the implant can be cut out from approximately half way up the medial side of the implant to approximately halfway down the lateral side of the implant to align with the geometrically matched wall of the upper surface of the tray component. The remaining structure on the lower surface of the implant can have a ledge extending along the medial and posterior sides of the surface for lockably mating with the grooves of the interior walls of the upper surface of the tray component. Approximately halfway between the medial side and the lateral side of the implant, a canal can be formed from the posterior side of the implant towards the anterior side of the implant, for mating with the peninsular wall of the upper surface of the tray component. This canal can run approximately ¾ the length of the implant from the posterior to anterior of the lower surface of the implant. The exterior walls of this canal can be sloped inward from the bottom of the canal to the top of the canal creating a surface that dovetails with the sloped peninsular walls of the upper surface of the tray component. This dovetail joint can assist with proper alignment of the insert into the tray component and then locks the insert into the tray component once fully inserted. At the anterior end of the canal, there can be a locking mechanism consisting of bendable fingers that snap optionally into the receptacles cut into the interior of the peninsular walls upon insertion of the insert into the tray component of the implant, thereby locking the implant component into the tray component. Perpendicular to the canal running ¾ the length of the lower surface of the insert can be at least one notch for mating with the at least one groove cut out of the upper surface of the tray component.

Thus, multiple locking mechanisms can be designed into the opposing surfaces of the walls and canal of the insert and the tray component, as well as the notch and groove and they can help to lock the insert into place on the tray component and resist against anterior-posterior motion within the knee as well as against medial-lateral motion. The bendable fingers can assist in preventing any lifting motion between the insert and tray component as pressure is applied to various parts of the joint.

Manufacturing and Machining

The tray component can be machined, molded, casted, manufactured through additive techniques such as laser sintering or electron beam melting or otherwise constructed out of a metal or metal alloy such as cobalt chromium. Similarly, the insert component may be machined, molded, manufactured through rapid prototyping or additive techniques or otherwise constructed out of a plastic polymer such as ultra high molecular weight polyethylene. Other known materials, such as ceramics including ceramic coating, may be used as well, for one or both components, or in combination with the metal, metal alloy and polymer described above. It can be appreciated by those of skill in the art that an implant may be constructed as one piece out of any of the above, or other, materials, or in multiple pieces out of a combination of materials. For example, a tray component constructed of a polymer with a two-piece insert component constructed one piece out of a metal alloy and the other piece constructed out of ceramic.

Each of the components may be constructed as a "standard" or "blank" in various sizes or may be specifically formed for each patient based on their imaging data and anatomy. Computer modeling may be used and a library of virtual standards may be created for each of the components. A library of physical standards may also be amassed for each of the components.

Imaging data including shape, geometry, e.g., M-L, A-P, and S-I dimensions, then can be used to select the standard component, e.g., a femoral component or a tibial component or a humeral component and a glenoid component that most closely approximates the select features of the patient's anatomy. Typically, these components are selected so that they are slightly larger than the patient's articular structure that are be replaced in at least one or more dimensions. The standard component is then adapted to the patient's unique anatomy, for example by removing overhanging material, e.g. using machining.

Figure 25:
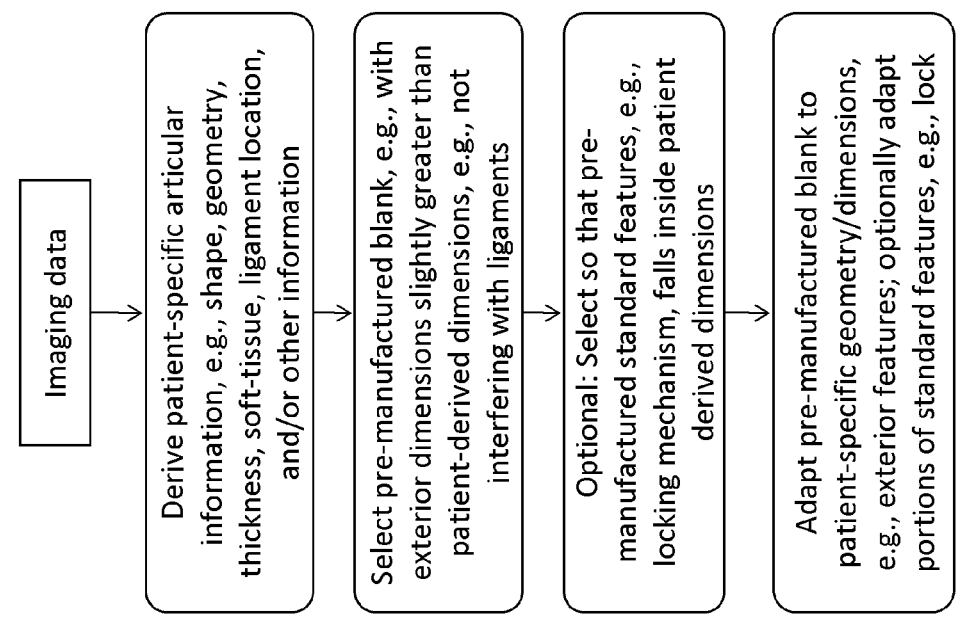
FIG. 25 is a flow chart for adapting a blank implant component for a particular patient.

Thus, referring to the flow chart shown in FIG. 25, in a first step, the imaging data is analyzed, either manually or with computer assistance, to determine the patient specific parameters relevant for placing the implant component. These parameters can include patient specific articular dimensions and geometry and also information about ligament location, size, and orientation, as well as potential soft-tissue impingement, and, optionally, kinematic information.

In a second step, one or more standard components, e.g., a femoral component or a tibial component or tibial insert, are selected. These are selected so that they are at least slightly greater than one or more of the derived patient specific articular dimensions and so that they can be shaped to the patient specific articular dimensions. Alternatively, these are selected so that they do not interfere with any adjacent soft-tissue structures. Combinations of both are possible.

If an implant component is used that includes an insert, e.g., a polyethylene insert and a locking mechanism in a metal or ceramic base, the locking mechanism can be adapted to the patient's specific anatomy in at least one or more dimensions. The locking mechanism can also be patient adapted in all dimensions. The location of locking features can be patient adapted while the locking feature dimensions, for example between a femoral component and a tibial component, can be fixed. Alternatively, the locking mechanism can be pre-fabricated; in this embodiment, the location and dimensions of the locking mechanism also is considered in the selection of the pre-fabricated components, so that any adaptations to the metal or ceramic backing relative to the patient's articular anatomy do not compromise the locking mechanism. Thus, the components can be selected so that after adaptation to the patient's unique anatomy a minimum material thickness of the metal or ceramic backing is maintained adjacent to the locking mechanism.

In some embodiments, a pre-manufactured metal backing blank can be selected so that it's exterior dimensions are slightly greater than the derived patient specific dimensions or geometry in at least one or more directions, while, optionally, at the same time not interfering with ligaments, e.g. the PCL. The pre-manufactured metal backing blank can include a pre-manufactured locking mechanism for an insert, e.g. a polyethylene insert. The locking mechanism can be completely pre-manufactured, i.e. not requiring any patient adaptation. Alternatively, the locking mechanism can have pre-manufactured components, e.g. an anterior locking tab or feature, with other locking features that will be machined later based on patient specific dimensions, e.g. a posterior locking tab or feature at a distance from the anterior locking feature that is derived from patient specific imaging data. In this setting, the pre-manufactured metal blank will be selected so that at least the anterior locking feature will fall inside the derived patient specific articular dimensions. In a preferred embodiment, all pre-manufactured locking features on the metal backing and an insert will fall inside the derived patient specific articular dimensions. Thus, when the blank is adapted to the patient's specific geometry, the integrity of the lock is not compromised and will remain preserved. An exemplary, by no means limiting, process flow is provided below:

Access imaging data, e.g. CT, MRI scan, digital tomosynthesis, cone beam CT, ultrasound, optical imaging, laser imaging, photoacoustic imaging etc.

Derive patient specific articular dimensions/geometry, e.g. at least one of an AP, ML, SI dimension, e.g. an AP and/or ML dimension of a tibial plateau and/or an AP and/or ML dimension of a distal femur Determine preferred resection location and orientation (e.g. tibial slope) on at least one or two articular surface(s)
In one dimension/direction, e.g. ML
In two dimensions/directions, e.g. ML and AP
In three dimensions/directions, e.g. ML, AP and sagittal tibial slope Optionally, optimize resection location and orientation across two opposing articular surface, e.g. one or more femoral condyles and a tibial plateau or a femoral head/femoral neck and acetabulum Derive/identify cortical edges or edges or margins of resected articular bones, e.g. femoral condyle(s) and tibial plateau Derive dimensions of resected bones, e.g. AP and ML dimension(s) of femoral condyles post resection and tibial plateau post resection Identify implant component blanks with exterior dimensions greater than the derived dimension(s) of the resected bone, e.g. femoral blank with ML and/or AP dimension greater than derived ML and/or AP dimension of femoral condyles at simulated resection level or tibial blank with ML and/or AP dimension greater than derived ML and/or AP dimension at simulated resection level Identify subset of implant component blanks found in step (g) with pre-manufactured lock feature(s) and sufficient material thickness adjacent to lock feature(s) located inside the derived dimension(s) of the resected bone, e.g. tibial blank with ML and/or AP dimension greater than derived ML and/or AP dimension at simulated resection level and pre-manufactured lock feature(s) plus sufficient material thickness adjacent to lock feature located inside the derived dimension(s) of the resected bone, e.g. ML and/or AP dimension of the resected bone.

Adapt implant component blank to derived patient specific dimensions of resected bone(s), e.g. remove overhanging material from femoral component blank relative to medial and lateral cortical edge or anterior and posterior cortical edge or remove overhanging material from tibial blank relative to medial, lateral, anterior or posterior cortical margin and, optionally, relative to adjacent soft-tissue structures, e.g. PCL.

Optionally adapt lock features(s) to patient specific geometry, e.g. on a tibial tray or polyethylene insert, adapt distance between a posterior lock feature to be machined and a pre-manufactured anterior lock feature based on patient specific geometry. Or on a tibial tray or polyethylene insert, adapt distance between a lateral lock feature to be machined and a pre-manufactured medial lock feature based on patient specific geometry.

Those of skill in the art will appreciate that not all of these process steps will be required to design, select or adapt an implant to the patient's geometry. Moreover, additional steps may be added, for example kinematic adaptations or finite element modeling of implant components including locks. Finite element modeling can be performed based on patient specific input data including patient specific articular geometry and virtually derived implant component shapes.

Clearly, all combinations of pre-manufactured and patient adapted lock features are possible, including pre-manufactured lock features on a medial insert and patient specific lock features on a lateral insert or the reverse. Other locations of lock features are possible.

A locking mechanism for a tibial tray, for example, can:

Be completely standard with only the exterior dimensions of the metal blank and/or insert adapted to the patient's articular geometry.

Have standard lock features at standard locations and patient individualized lock features, e.g. standard anterior lock feature and distance between anterior and posterior lock feature on a metal tray and/or insert patient adapted.

Have completely individualized features on a metal tray and insert, e.g. the location of each lock feature on a metal tray or insert is individualized based on the patient's geometry. However, even in this embodiment, certain lock components will have standard features, e.g. a standard distance or location between interlocking pieces on the metal tray and the tibial insert or standard distance or location between the lock and an adjacent implant wall on the metal tray or the insert.

Adapting implant component blank(s) to derived patient specific dimensions of resected bone(s) can involve (1) a metal tray only, (2) an insert only, or (3) a metal tray and an insert. When no metal tray is used, the adaptation can involve a single material component, e.g. a tibial implant manufactured of polyethylene, wherein one or more dimensions are adapted to a patient specific geometry.

Figure 26:
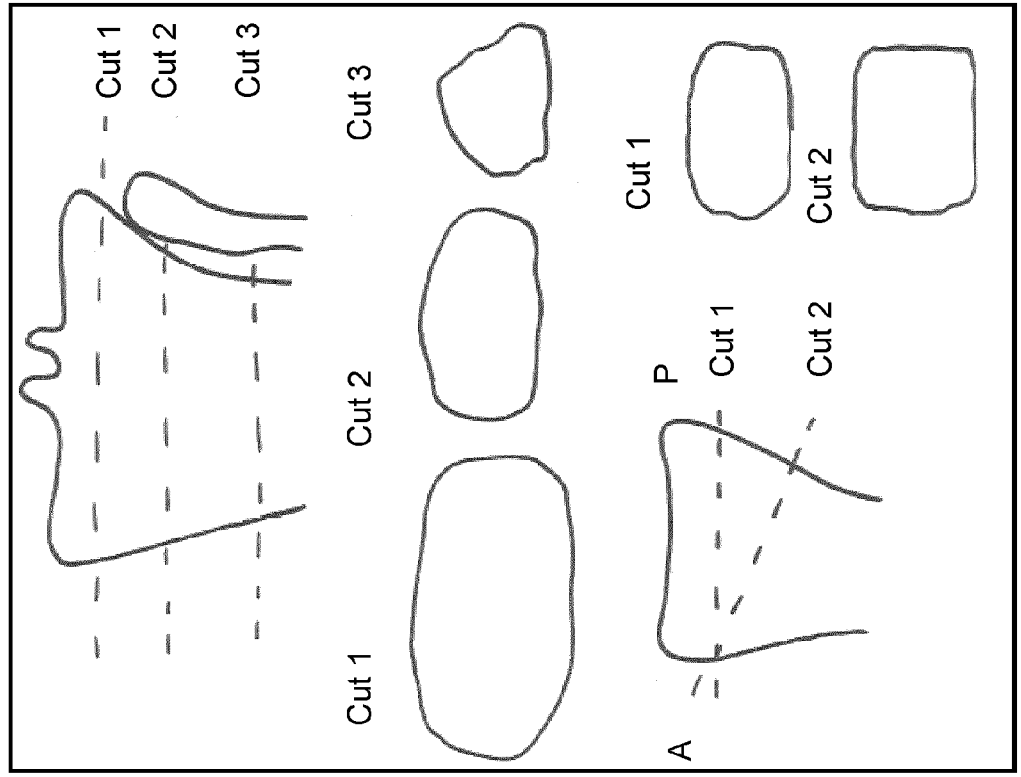
FIG. 26 illustrates various tibial cuts and corresponding surface features.

Since the tibia has the shape of a champagne glass, e.g., it tapers distally from the knee joint space down, moving the tibial cut distally can result in a smaller resultant cross-section of the cut tibial plateau, e.g., the ML and/or AP dimension of the cut tibia is smaller. For example, referring to FIG. 26, increasing the slope of the cut can result in an elongation of the AP dimension of the cut surface—requiring a resultant elongation of a patient matched tibial component. Thus, in one embodiment it is possible to select an optimal standard, pre-made tibial blank for a given resection height and/or slope. This selection can involve (1) patient-adapted metal with a standard poly insert; or (2) metal and poly insert, wherein both are adapted to patient anatomy. The metal can be selected so that based on cut tibial dimensions there is a certain minimum metal perimeter (in one, two or three dimensions) guaranteed after patient adaptation so that a lock mechanism does not fail. Optionally, one can determine minimal metal perimeter based on finite element modeling (FEA) (once during initial design of standard lock features, or patient specific every time e.g. via patient specific FEA modeling).

The tibial tray can be selected (or a metal base for other joints) to optimize percent cortical bone coverage at resection level. This selection can be (1) based on one dimension, e.g., ML; (2) based on two dimensions, e.g. ML and AP; and/or (3) based on three dimensions, e.g., ML, AP, SI or slope.

Figure 27:
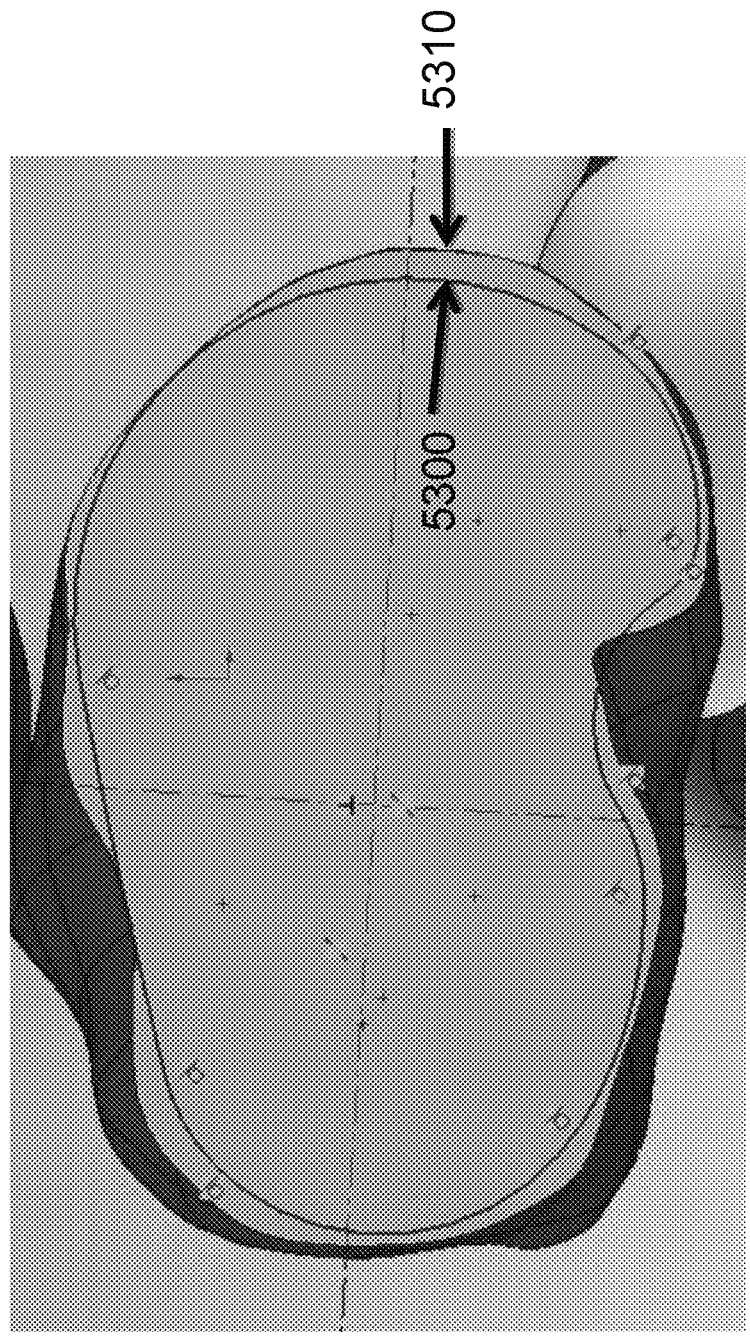
FIG. 27 depicts a resected proximal tibial surface perimeter and a smoothed perimeter line for designing a tibial implant perimeter.

The selection can be performed to achieve a target percentage coverage of the resected bone (e.g. area) or cortical edge or margin at the resection level (e.g. AP, ML, perimeter), e.g. 85%, 90%, 95%, 98% or 100%. Optionally, a smoothing function can be applied to the derived contour of the patient's resected bone or the resultant selected, designed or adapted implant contour so that the implant does not extend into all irregularities or crevaces of the virtually and then later surgically cut bone perimeter. FIG. 27 depicts a resected proximal tibial surface perimeter 5300 and a smoothed perimeter line 5310 for a tibial implant perimeter, the smoothed perimeter line 5310 and subsequent implant perimeter being derived from the patient's resected tibial perimeter.

Optionally, a function can be included for deriving the desired implant shape that allows changing the tibial implant perimeter if the implant overhangs the cortical edge in a convex outer contour portion or in a concave outer contour portion (e.g. "crevace"). These changes can subsequently be included in the implant shape, e.g. by machining select features into the outer perimeter.

Those of skill in the art can appreciate that a combination of standard and customized components may be used in conjunction with each other. For example, a standard tray component may be used with an insert component that has been individually constructed for a specific patient based on the patient's anatomy and joint information.

Another embodiment incorporates a tray component with one half of a two-piece insert component integrally formed with the tray component, leaving only one half of the two-piece insert to be inserted during surgery. For example, the tray component and medial side of the insert component may be integrally formed, with the lateral side of the insert component remaining to be inserted into the tray component during surgery. Of course, the reverse can also be used, wherein the lateral side of the insert component is integrally formed with the tray component leaving the medial side of the insert component for insertion during surgery.

Each of these alternatives results in a tray component and an insert component shaped so that once combined, they create a uniformly shaped implant matching the geometries of the patient's specific joint.

The above embodiments are applicable to all joints of a body, e.g., ankle, foot, elbow, hand, wrist, shoulder, hip, spine, or other joint. For example, in a hip, an acetabular component can be designed or selected or adapted so that its peripheral margin can be closely matched to the patient-specific acetabular rim or perimeter. Optionally, reaming can be simulated for placement of an acetabular cup and the implant then can be designed and/or selected or adapted so that it closely matches the resultant acetabular rim after reaming. Thus, the exterior dimensions of the implant can be matched to the patient's geometry in this fashion. Optionally, standard, round dimensions of a polyethylene insert can be used with this embodiment. Similarly, a glenoid component can be matched to the glenoid rim, optionally after surgically preparing or resectioning all or portions of the glenoid rim. Thus, edge matching, designing, selecting or adapting implants including, optionally lock features, can be performed for implants used in any joint of the body.

An implant component can include a fixed bearing design or a mobile bearing design. With a fixed bearing design, a platform of the implant component is fixed and does not rotate. However, with a mobile bearing design, the platform of the implant component is designed to rotate e.g., in response to the dynamic forces and stresses on the joint during motion.

A rotating platform mobile bearing on the tibial implant component allows the implant to adjust and accommodate in an additional dimension during joint motion. However, the additional degree of motion can contribute to soft tissue impingement and dislocation. Mobile bearings are described elsewhere, for example, in U.S. Patent Application Publication No. 2007/0100462.

In certain embodiments, an implant can include a mobile-bearing implant that includes one or more patient-specific features, one or more patient-engineered features, and/or one or more standard features. For example, for a knee implant, the knee implant can include a femoral implant component having a patient-specific femoral intercondylar distance; a tibial component having standard mobile bearing and a patient-engineered perimeter based on the dimensions of the perimeter of the patient's cut tibia and allowing for rotation without significant extension beyond the perimeter of the patient's cut tibia; and a tibial insert or top surface that is patient-specific for at least the patient's intercondylar distance between the tibial insert dishes to accommodate the patient-specific femoral intercondylar distance of the femoral implant.

As another example, in certain embodiments a knee implant can include a femoral implant component that is patient-specific with respect to a particular patient's M-L dimension and standard with respect to the patient's femoral intercondylar distance; a tibial component having a standard mobile bearing and a patient-engineered perimeter based on the dimensions of the perimeter of the patient's cut tibia and allowing for rotation without significant extension beyond the perimeter of the patient's cut tibia; and a tibial insert or top surface that includes a standard intercondylar distance between the tibial insert dishes to accommodate the standard femoral intercondylar distance of the femoral implant.

The step of designing an implant component and/or guide tool as described herein can include both configuring one or more features, measurements, and/or dimensions of the implant and/or guide tool (e.g., derived from patient-specific data from a particular patient and adapted for the particular patient) and manufacturing the implant. In certain embodiments, manufacturing can include making the implant component and/or guide tool from starting materials, for example, metals and/or polymers or other materials in solid (e.g., powders or blocks) or liquid form. In addition or alternatively, in certain embodiments, manufacturing can include altering (e.g., machining) an existing implant component and/or guide tool, for example, a standard blank implant component and/or guide tool or an existing implant component and/or guide tool (e.g., selected from a library). The manufacturing techniques to making or altering an implant component and/or guide tool can include any techniques known in the art today and in the future. Such techniques include, but are not limited to additive as well as subtractive methods, i.e., methods that add material, for example to a standard blank, and methods that remove material, for example from a standard blank.

Various technologies appropriate for this purpose are known in the art, for example, as described in *Wohlers Report 2009, State of the Industry Annual Worldwide Progress Report on Additive Manufacturing*, Wohlers Associates, 2009 (ISBN 0-9754429-5-3), available from the web www.wohlersassociates.com; Pham and Dimov, *Rapid manufacturing*, Springer-Verlag, 2001 (ISBN 1-85233-360-X); Grenda, *Printing the Future, The 3D Printing and Rapid Prototyping Source Book*, Castle Island Co., 2009; *Virtual Prototyping & Bio Manufacturing in Medical Applications*, Bidanda and Bartolo (Eds.), Springer, Dec. 17, 2007 (ISBN: 10: 0387334297; 13: 978-0387334295); *Bio-Materials and Prototyping Applications in Medicine*, Bartolo and Bidanda (Eds.), Springer, Dec. 10, 2007 (ISBN: 10: 0387476822; 13: 978-0387476827); Liou, *Rapid Prototyping and Engineering Applications: A Toolbox for Prototype Development*, CRC, Sep. 26, 2007 (ISBN: 10: 0849334098; 13: 978-0849334092); *Advanced Manufacturing Technology for Medical Applications: Reverse Engineering, Software Conversion and Rapid Prototyping*, Gibson (Ed.), Wiley, January 2006 (ISBN: 10: 0470016884; 13: 978-0470016886); and Branner et al., "Coupled Field Simulation in Additive Layer Manufacturing," 3rd International Conference PMI, 2008 (10 pages).

EXAMPLES

Example 1 illustrates a patient-adapted implant design for an implant having a femoral component and a patella component. Example 2 describes and exemplary tibial implant design and related resection techniques. Example 3 describes exemplary tibial tray and insert designs and related jigs and cutting designs. Example 4 describes an exemplary design for a tibial implant component. Example 5 illustrates a set of jigs for guiding patient-specific bone cuts in a femur-first technique. Example 6 illustrates a set of jigs for guiding patient-specific bone cuts in a tibia-first technique.

Example 1

A Patient-Specific Engineered Trochlea Design

This example describes a patient-specific trochlea design that is optimized for proper kinematics of the patella-femoral ("PF") joint.

1.1 Method

Figure 29:
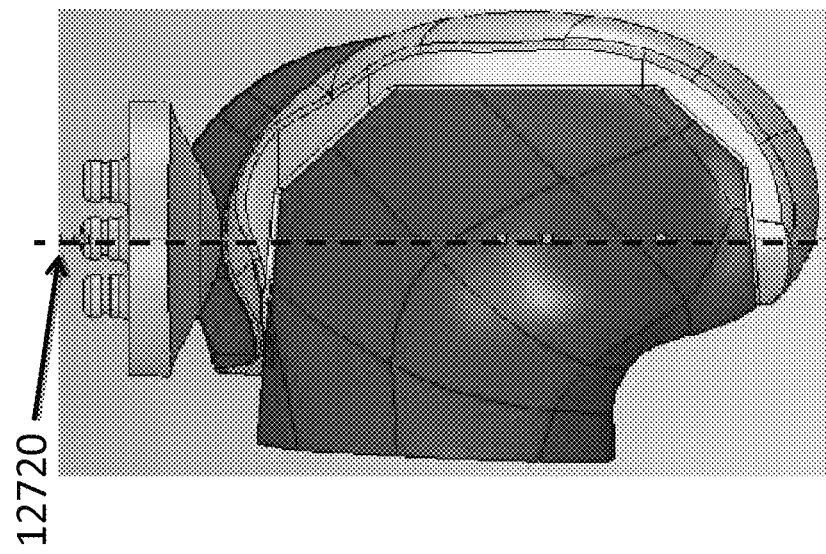
FIGS. 28 to 33 illustrate an exemplary design of a knee implant, including a femoral component and a patella component.
Figure 28:
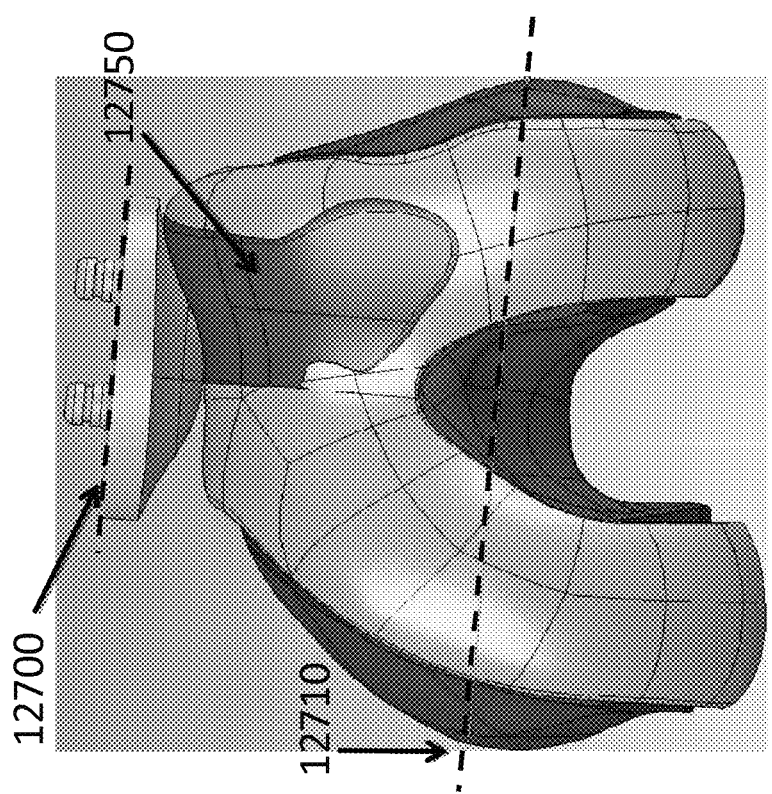
Figure 31:
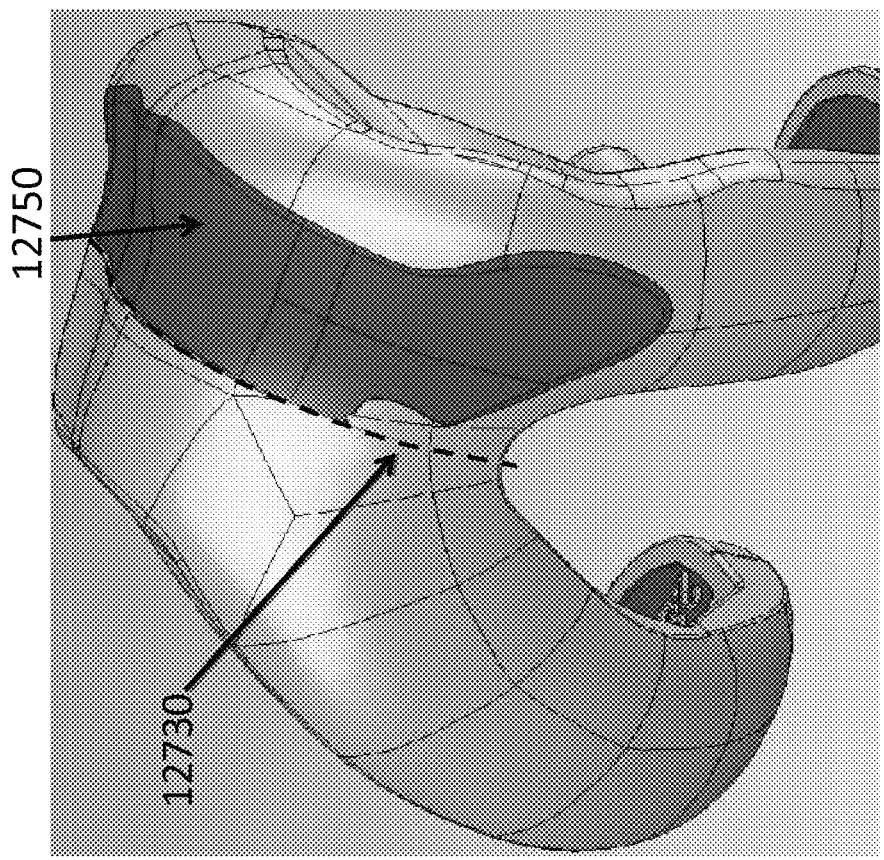
Figure 30:
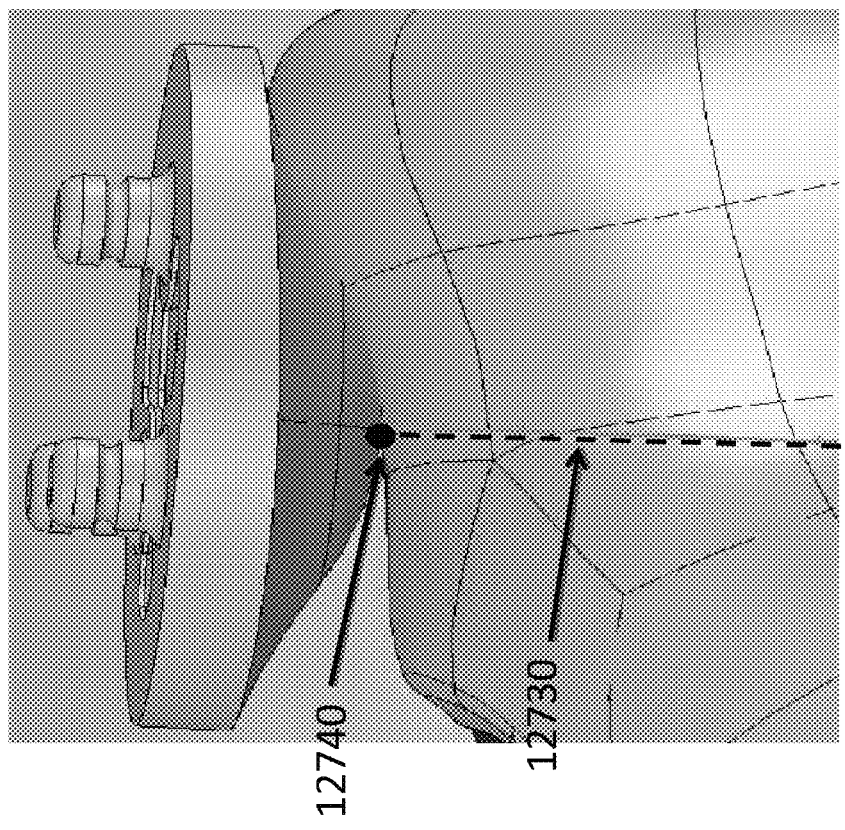
Figure 33:
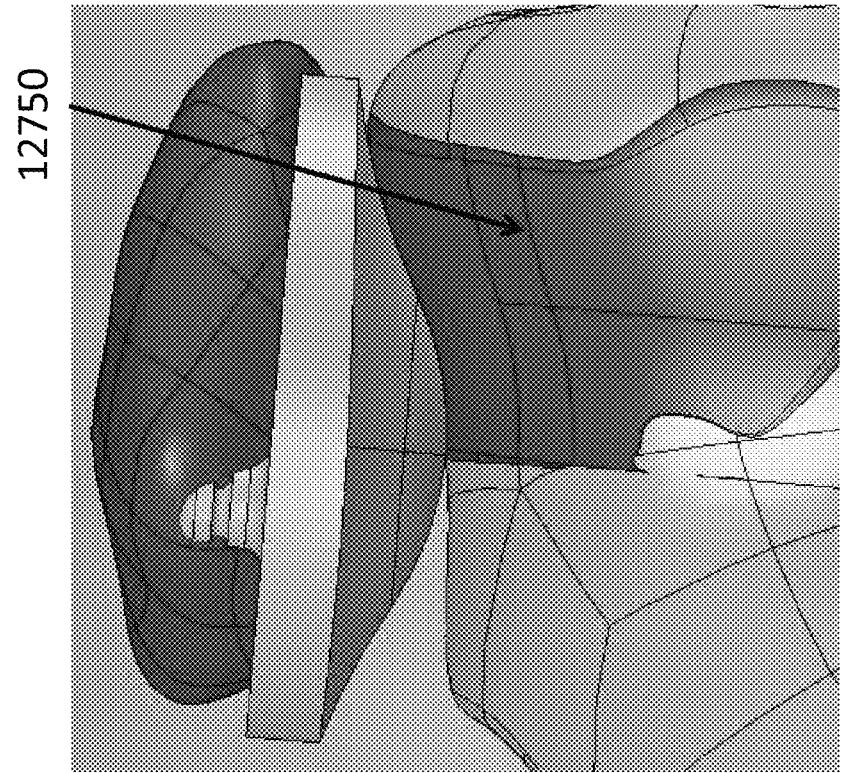
Figure 32:
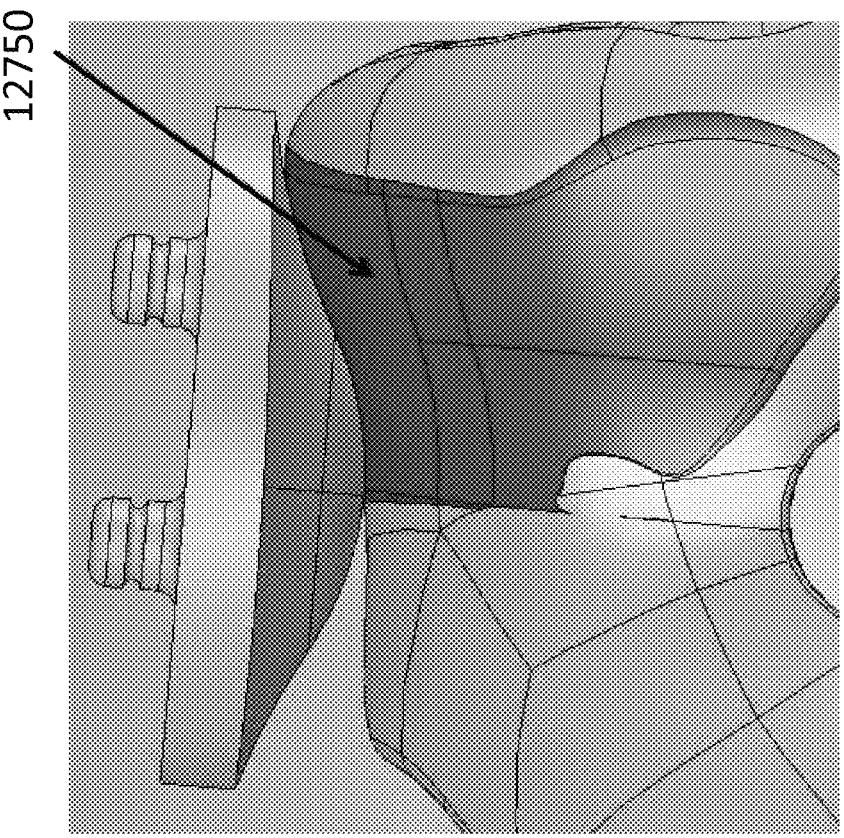

FIGS. 28 to 33 show an exemplary design of a knee implant, including a femoral component and a patella component, with a material cutaway region highlighted (darker) in certain figures. The placement of the patella and material removal was as follows: As shown in FIG. 28, the flat bone-bearing surface of the patella 12700, was made parallel to the epicondylar axis 12710 in the coronal view. As shown in FIG. 29, the center plane of the patella implant was made collinear with the epicondylar axis 12720. This allows for general positioning at the peak area of the trochlea. As shown in FIG. 30, in this position the medial-lateral center or sulcus of the trochlea is identified 12730, and the patella implant component is brought down so the lowest points are coincident 12740. As shown in FIGS. 31 through 33, the patella profile is swept along the sagittal curve of the trochlear region 12750.

1.2 Results and Discussion

This exemplary implant design uses a patient-specific sagittal curvature and an engineered coronal curvature to allow the patella component to track properly in the trochlear groove. This exemplary implant design for the femoral component and a patella component can allow various advantages including a reduction of lateral overstuffing of the P-F joint and a post-operative patella tracking that is normal or close to the patient's pre-operative and/or pre-disease state. In certain embodiments, the lateral peak can be retained, which may minimize dislocation events. In certain embodiments, the patella implant bone-bearing surface can be or appear to be approximately parallel to the osteochondral junction of the native patella.

Example 2

Tibial Implant Design and Bone Cuts

Figure 34A:
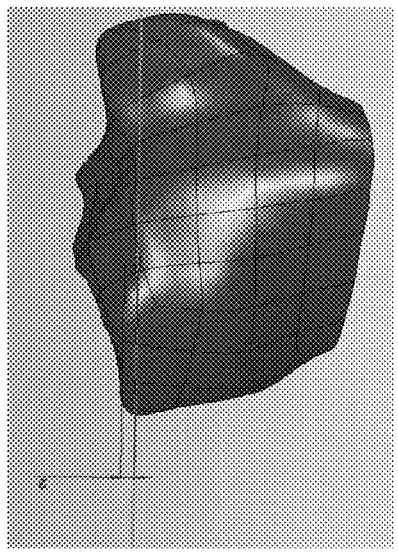
FIG. 34A illustrates a tibial proximal resection cut that can be selected and/or designed to be a certain distance below a particular location on the patient's tibial plateau.
Figure 34B:
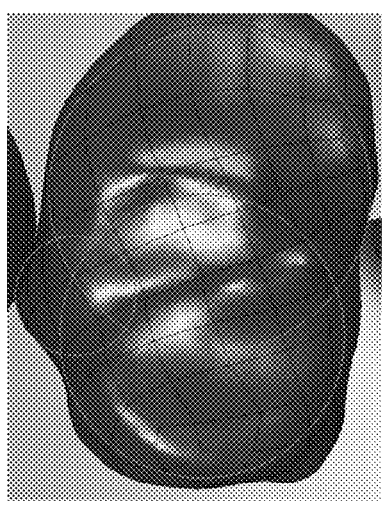
FIG. 34B illustrates anatomic sketches (e.g., using a CAD program to manipulate a model of the patient's biological structure) overlaid with the patient's tibial plateau.
Figure 34C:
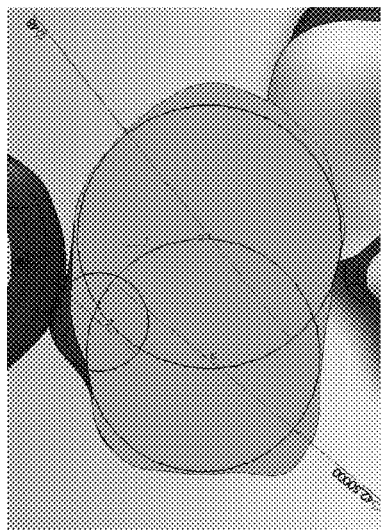
FIG. 34C illustrates sketched overlays used to identify the centers of tubercles and the centers of one or both of the lateral and medial plateaus.
Figure 35A:
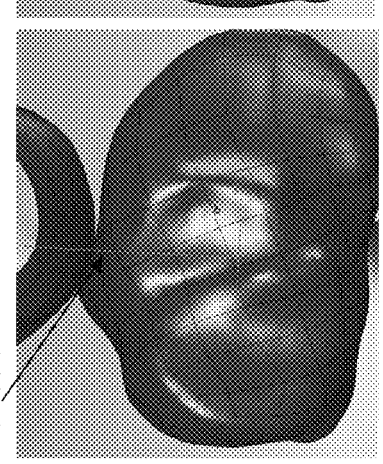
FIGS. 35A to 35C illustrate one or more axes that can be derived from anatomic sketches.
Figure 35B:
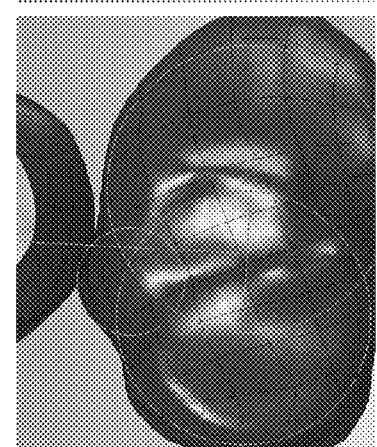
Figure 35C:
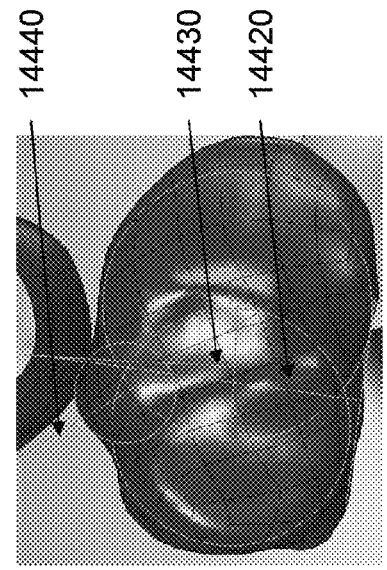

This example illustrates tibial implant components and related designs. This example also describes methods and devices for performing a series of tibial bone cuts to prepare a patient's tibia for receiving a tibial implant component. Patient data, such scans of the patient's joint, can be used to locate the point and features used to identify planes, axes and slopes associated with the patient's joint. As shown in FIG. 34A, the tibial proximal cut can be selected and/or designed to be a certain distance below a particular location on the patient's tibial plateau. For example, the tibial proximal cut height can be selected and/or designed to be 1 mm, 1.5 mm, 2 mm, 2.5 mm, 3 mm, 3.5 mm, or 4 mm or more below the lowest point on the patient's tibial plateau or below the lowest point on the patient's medial tibial plateau or below the lowest point on the patient's lateral tibial plateau. In this example, the tibial proximal cut height was selected and designed to be 2 mm below the lowest point on the patient's medial tibial plateau. For example, as shown in FIG. 34B, anatomic sketches (e.g., using a CAD program to manipulate a model of the patient's biological structure) can be overlaid with the patient's tibial plateau. As shown in FIG. 34C, these sketched overlays can be used to identify the centers of tubercles and the centers of one or both of the lateral and medial plateaus. In addition, as shown in FIGS. 35A-C, one or more axes such as the patient's anatomic tibial axis 14420, posterior condylar axis 14430, and/or sagittal axis 14440 can be derived from anatomic sketches, e.g., based on a defined a midpoint line 14450 between the patient's lateral condyle center and medial condyle center.

Figure 36A:
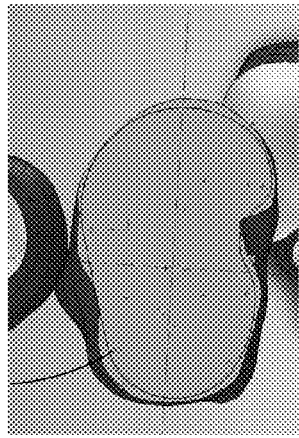
FIG. 36A depicts a proximal tibial resection made at 2 mm below the lowest point of the patient's medial tibial plateau with a an A-P slope cut that matched the A-P slope.
Figure 36B:
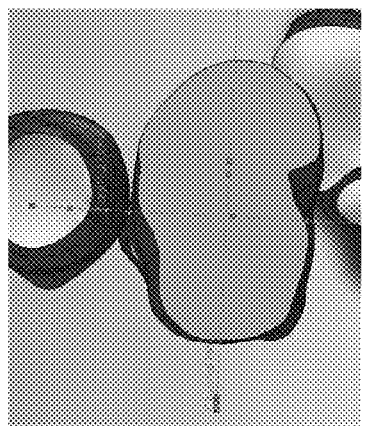
FIGS. 36B and 36C illustrate an implant selected and/or designed to have 90% coverage of the patient's cut tibial surface.
Figure 36C:
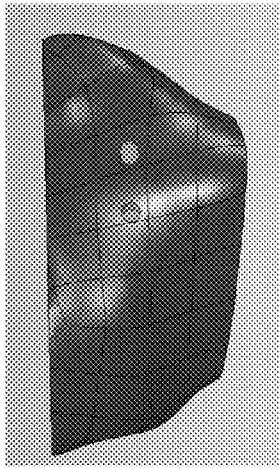
Figure 37B:
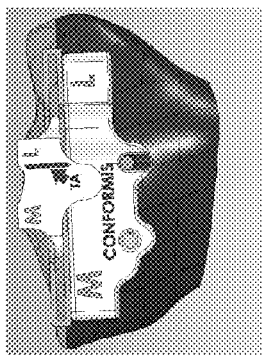
Figure 38B:
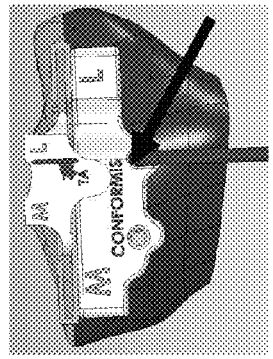

As shown in FIG. 36A, the proximal tibial resection was made a 2 mm below the lowest point of the patient's medial tibial plateau with a an A-P slope cut that matched the A-P slope on the patient's medial tibial plateau. As shown in FIGS. 36B and 36C, an implant profile 14500 was selected and/or designed to have 90% coverage of the patient's cut tibial surface. In certain embodiments, the tibial implant profile can be selected and/or designed such that tibial implant is supported entirely or substantially by cortical bone and/or such that implant coverage of the cut tibial surface exceeds 100% and/or has no support on cortical bone.

Figure 37A:
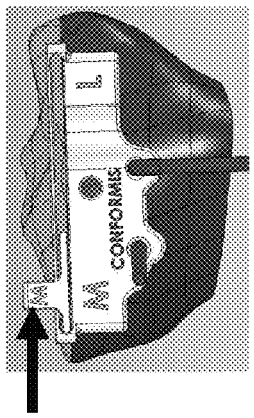
FIGS. 37A to 47C describe exemplary steps for performing resection cuts to the tibia using the anatomical references identified above.
Figure 38A:
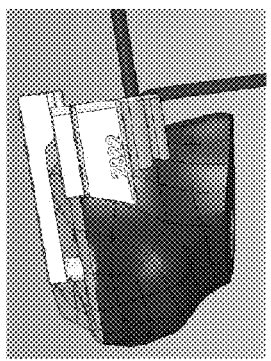
Figure 42:
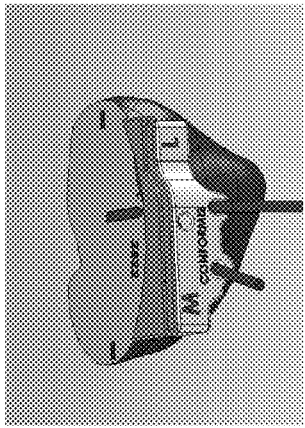
Figure 46:
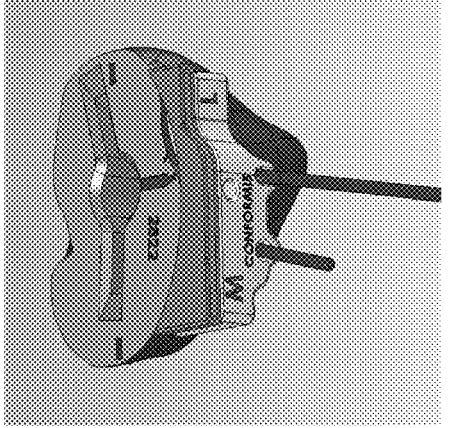
Figure 41:
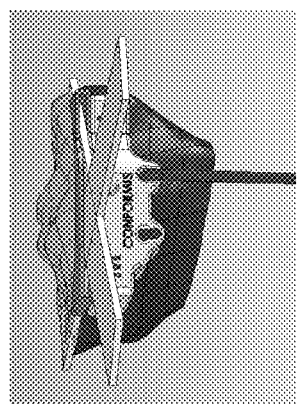
Figure 45:
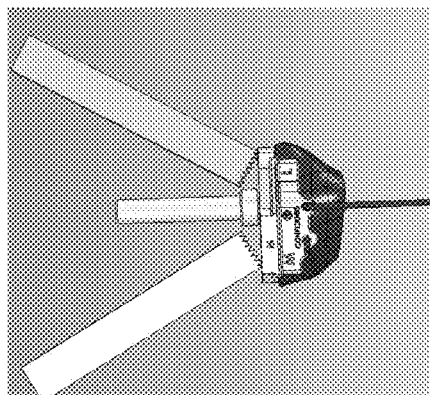
Figure 40:
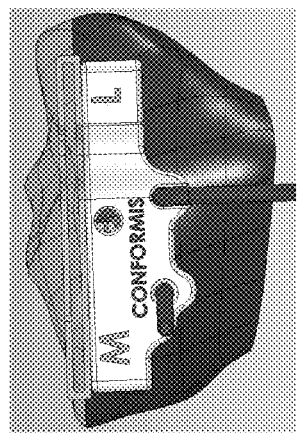
Figure 44:
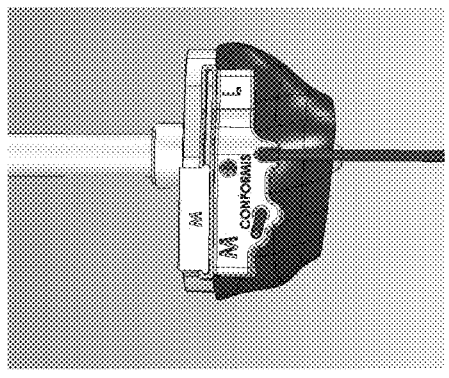
Figure 39:
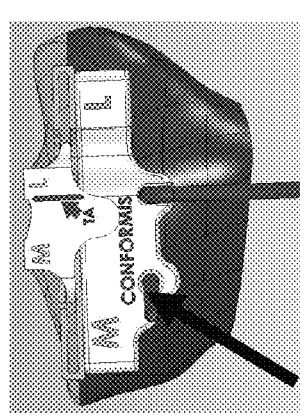
Figure 43:
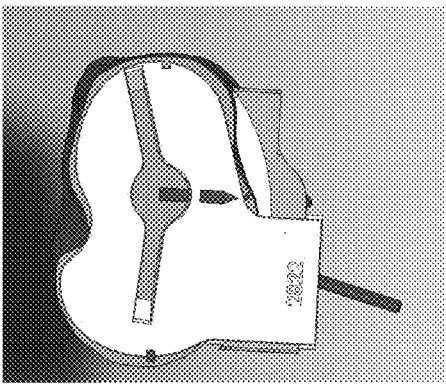
Figure 47C:
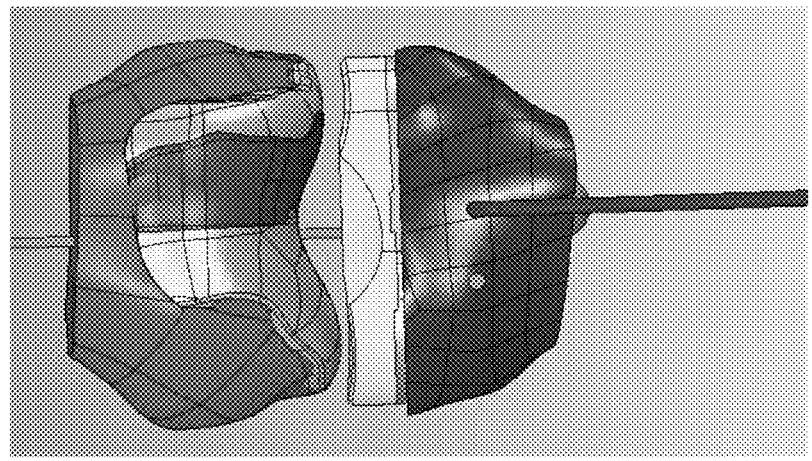
Figure 47B:
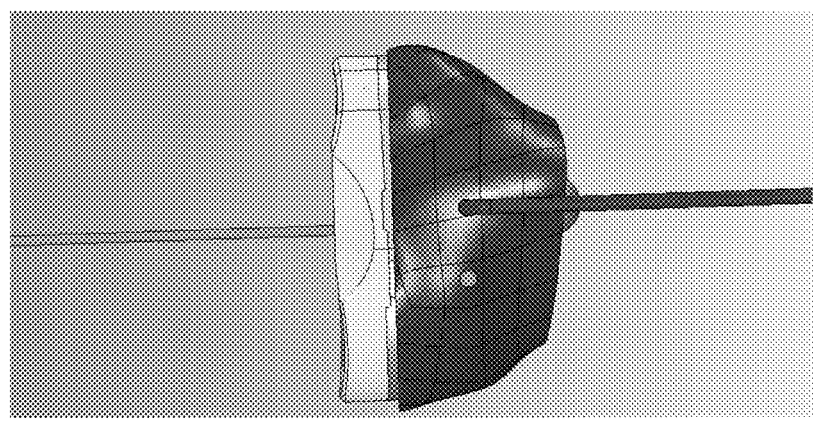
Figure 47A:
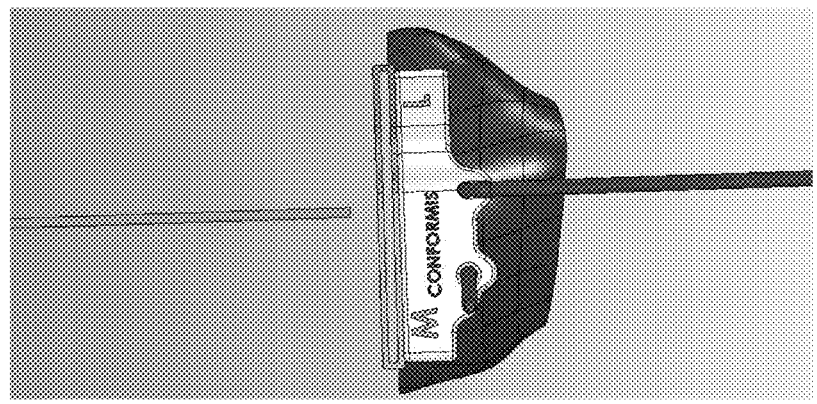

FIGS. 37A to 47C describe exemplary steps for performing resection cuts to the tibia using the anatomical references identified above. For example, as shown in FIGS. 37A and B, one step can include aligning the top of the tibial jig stylus to the top of the patient's medial and lateral spines (see arrow). As shown in FIGS. 38A and B, a second step can include drilling and pinning the tibial axis (see arrow). As shown in FIG. 39, a third step can include drilling and pinning the medial pin (see arrow). As shown in FIG. 40, a fourth step can include removing the stylus. As shown in FIG. 41, a fifth step can include sawing 2 mm of tibial bone from the patient's tibial plateau with the patient's medial AP slope. As shown in FIG. 42, a sixth step can include removing the resected portion of the patient's tibial plateau. As shown in FIG. 43, a seventh step can include assembling stem and keel guide(s) onto the tibial cut guide. As shown in FIG. 44, an eighth step can include drilling, e.g., using a 14 mm drill bit (13 mm×40 mm stem) to drill a central hole into the proximal tibial surface. As shown in FIG. 45, a ninth step can include using a saw or osteotome to create a keel slot, for example, a 3.5 mm wide keel slot. FIG. 46 shows the finished tibial plateau with guide tools still in place. FIGS. 47A-C show each of a guide tool (FIG. 47A), a tibial implant component (FIG. 47B), and tibial and femoral implant components (FIG. 47C) in the aligned position in the knee.

This example shows that using a patient's joint axes (e.g., as identified from patient-specific data and optionally from a model of the patient's joint) to select and/or design resection cuts, e.g., the tibia, and corresponding guide tools can create resection cuts perpendicular to the patient's tibial axis and based on the patient's medial AP slope. In addition, one or more features of the corresponding implant components (e.g., tibial tray implant thickness) can be selected and/or designed to align the tibial axis with the femoral axis and thereby correct the patient's alignment.

Example 3

Tibial Tray and Insert Designs

This example illustrates exemplary designs and implant components for tibial trays and inserts for certain embodiments described herein. In particular, this example describes a standard blank tibial tray and insert and a method for altering the standard blanks based on patient-specific data to include a patient-adapted feature (e.g., a patient-adapted tray and insert perimeter that substantially match the perimeter of the patient's resected tibia).

FIGS. 48A-E illustrate various aspects of an embodiment of a standard blank tibial implant component, including a bottom view (FIG. 48A) of a standard blank tibial tray, a top view (FIG. 48B) of the standard blank tibial tray, a bottom view (FIG. 48C) of a standard blank tibial insert, a top-front (i.e., proximal-anterior) perspective view (FIG. 48D) of the standard blank tibial tray, and a bottom front (i.e., distal anterior) perspective view (FIG. 48E) of a patient-adapted tibial insert. In this example and in certain embodiments, the top surface of the tibial tray can receive a one-piece tibial insert or two-piece tibial inserts. The tibial inserts can include one or more patient-adapted features (e.g., patient-matched or patient-engineered perimeter profile, thickness, and/or joint-facing surface) and/or one or more standard features, in addition to a standard locking mechanism to engage the tibial tray. With reference to FIGS. 48D and E, in certain embodiments the locking mechanism on the tray and insert can include, for example, one or more of: (1) a posterior interlock, (2) a central dovetail interlock, (3) an anterior snap, (4) an anterior interlock, and (5) an anterior wedge.

Standard blank tibial trays and/or inserts can be prepared in multiple sizes, e.g., having various AP dimensions, ML dimensions, and/or stem and keel dimensions and configurations. For example, in certain-sized embodiments, the stem can be 13 mm in diameter and 40 mm long and the keel can be 35 mm wide, 15 degrees biased on the lateral side and 5 degrees biased on the medial side. However, in other-sized embodiments (e.g., having larger or small tray ML and/or AP dimensions, the step and keel can be larger, smaller, or have a different configuration.

As mentioned above, in this example and in certain embodiments, the tibial tray can receive a one-piece tibial insert or two-piece tibial inserts. FIGS. 49A-C show aspects of an embodiment of a tibial implant component that includes a tibial tray and a one-piece insert. FIGS. 50A-C show aspects of an embodiment of a tibial implant component that includes a tibial tray and a one-piece insert. Alternatively, a two-piece tibial insert can be used with a two-piece tibial tray. Alternatively, a one-piece tibial insert can be used with a two-piece tibial tray.

Figures 51A, 51B, 51C:
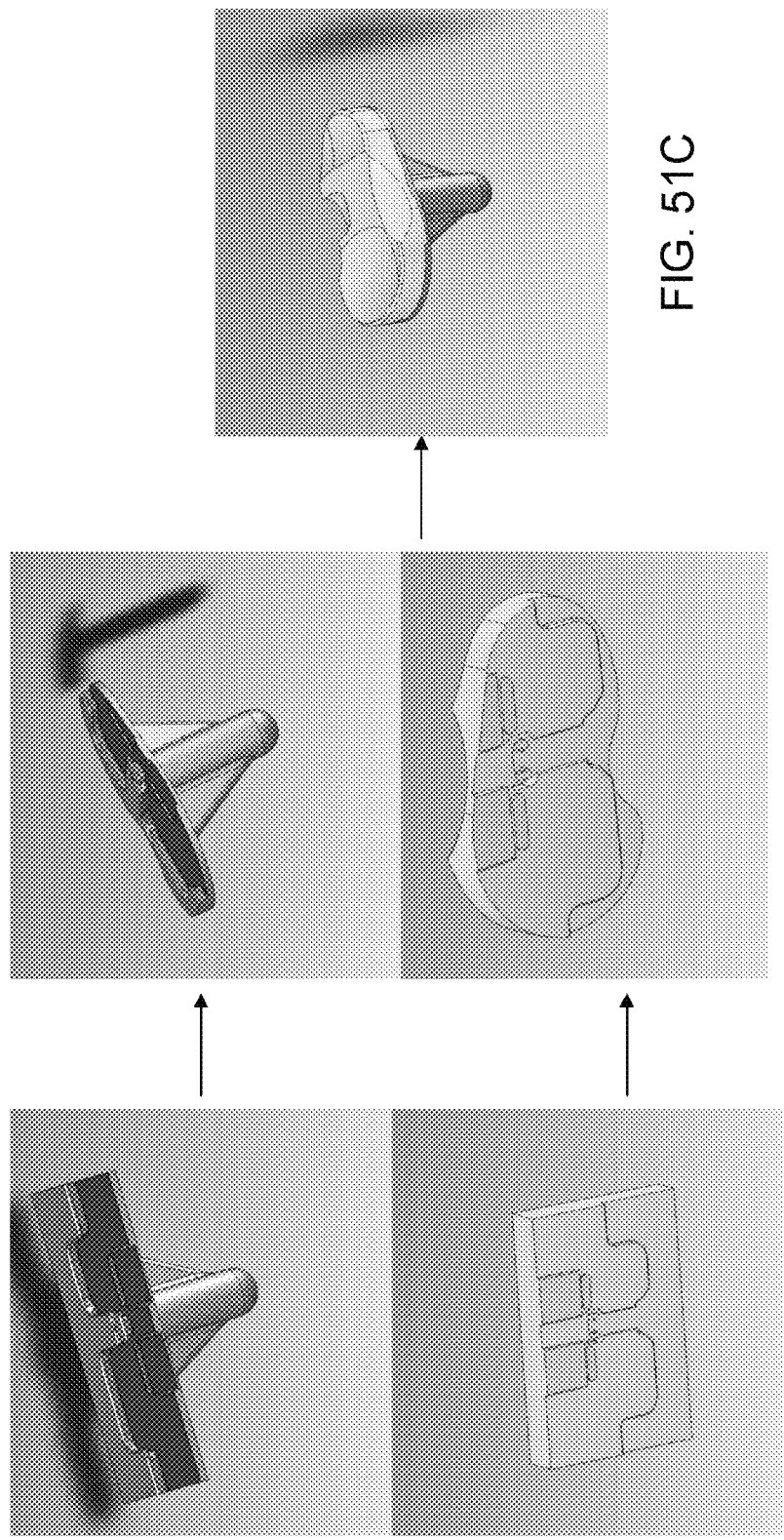
FIGS. 51A-C show exemplary steps for altering a blank tibial tray and a blank tibial insert to each include a patient-adapted profile, for example, to substantially match the profile of the patient's resected tibial surface.

FIGS. 51A-C show exemplary steps for altering a blank tibial tray and a blank tibial insert to each include a patient-adapted profile, for example, to substantially match the profile of the patient's resected tibial surface. In particular, as shown in FIG. 51A, standard cast tibial tray blanks and standard machined insert blanks (e.g., having standard locking mechanisms) can be finished, e.g., using CAM machining technology, to alter the blanks to include one or more patient-adapted features. For example, as shown in FIG. 51B, the blank tray and insert can be finish machined to match or optimize one or more patient-specific features based on patient-specific data. The patient-adapted features machined into the blanks can include for example, a patient-specific perimeter profile and/or one or more medial coronal, medial sagittal, lateral coronal, lateral sagittal bone-facing insert curvatures. FIG. 51C illustrates a finished tibial implant component that includes a patient-specific perimeter profile and/or one or more patient-adapted bone-facing insert curvatures.

Example 4

Tibial Implant Component Design

This example illustrates tibial implant component selection and/or design to address tibial rotation. FIGS. 52A and B describe exemplary techniques for determining tibial rotation for a patient and FIG. 52C shows resulting alignment data for the second technique.

Figure 53:
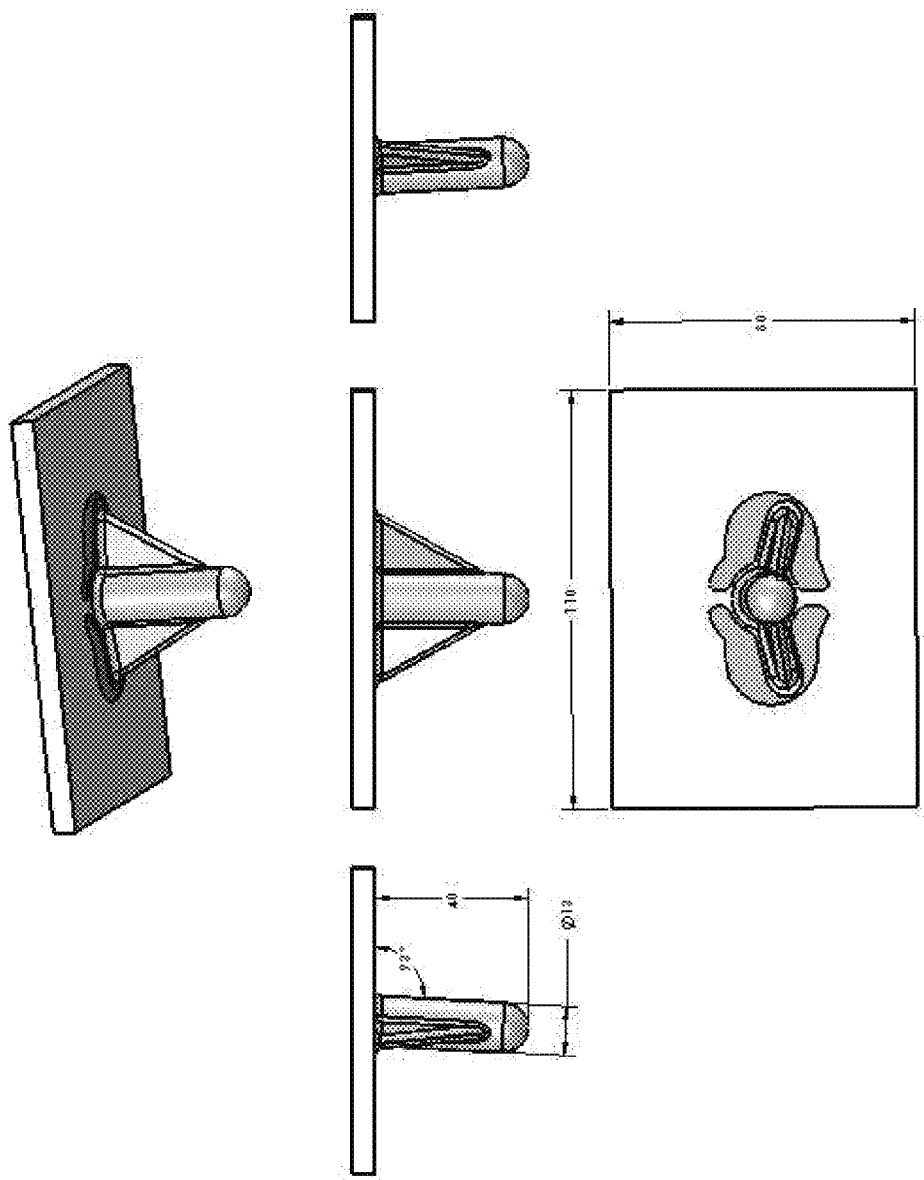
FIG. 53 illustrates exemplary stem design options for a tibial tray.

Various tibial implant component features can optimized to ensure proper tibial rotation. For example, FIG. 53 illustrates exemplary stem design options for a tibial tray including using stem and keel dimensions that increase or decrease depending on the size of the tibial implant component (e.g., in the ML and/or AP dimension). Moreover, cement pockets can be employed to enhance stabilization upon implantation, In addition, patient-specific stem and keel guide tools can be selected and/or designed so that the prepared stem and keel holes in a patient's proximal tibia are properly sized, which can minimize rotation (e.g., of a keel in a keel hole that is too large).

Figure 54A:
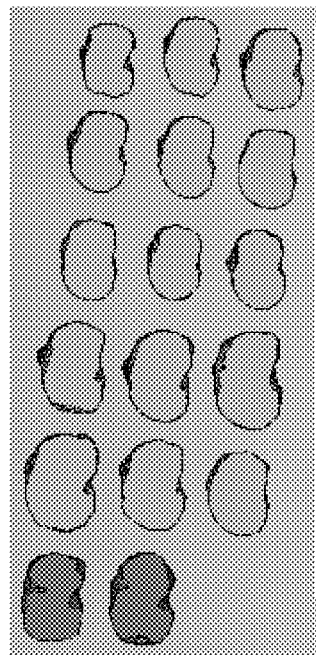
FIGS. 54A and B show an approach in certain embodiments for identifying a tibial implant perimeter profile based on the depth and angle of the proximal tibial resection, which can applied in the selection and/or design of the tibial tray perimeter profile and/or the tibial insert perimeter profile.
Figure 54B:
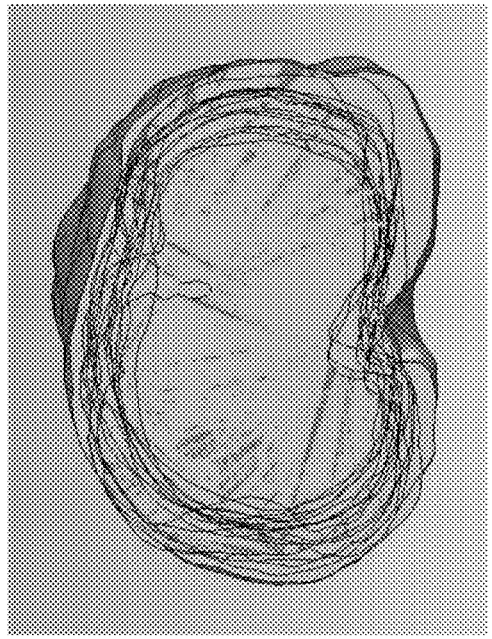
Figure 55A:
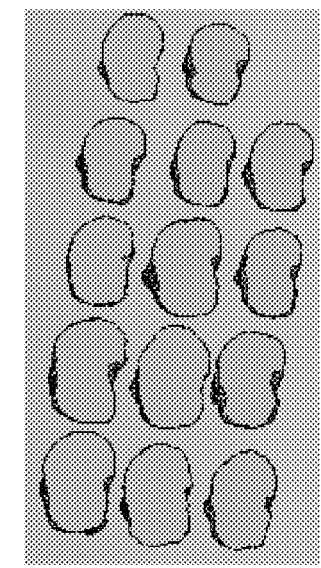
FIGS. 55A and B show the same approach as described for FIGS. 54A and B, but applied to a different patient having a smaller tibia (e.g., smaller diameter and perimeter length)
Figure 55B:
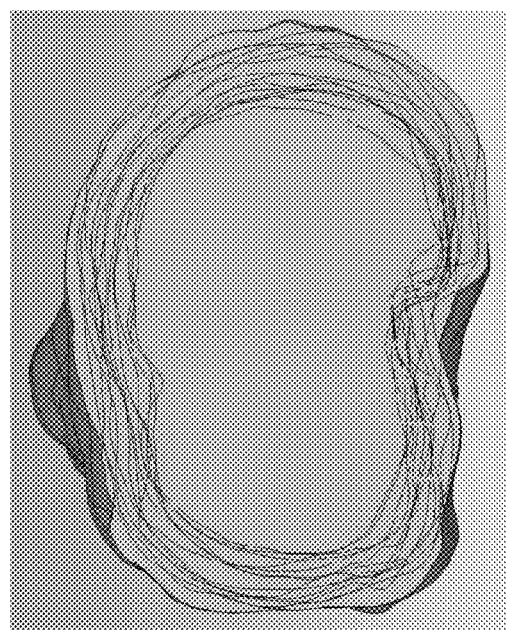
Figure 56A:
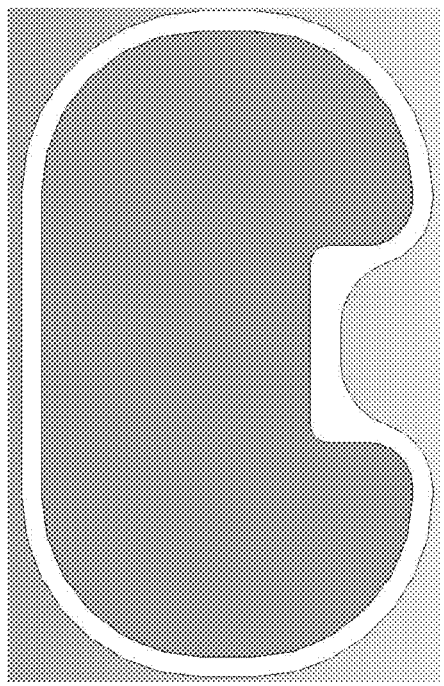
FIGS. 56A-D show four different exemplary tibial implant profiles, for example, having different medial and lateral condyle perimeter shapes.
Figure 56B:
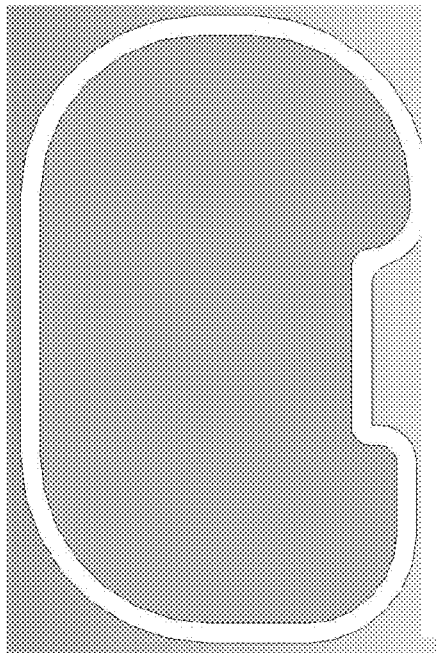
Figure 56C:
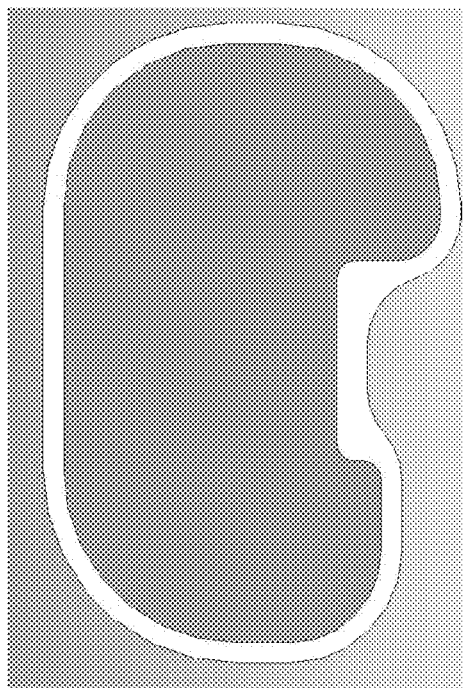
Figure 56D:
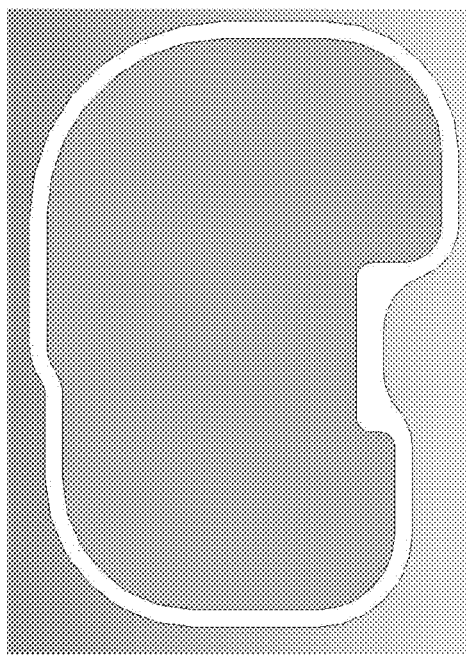

Another tibial implant component that can be used to address tibial rotation is selecting and/or designing a tibial tray perimeter profile and/or a tibial insert perimeter profile that minimizes overhang from the patient's bone (which may catch and cause rotation) and, optionally, that maximizes seating of the implant component on cortical bone. Accordingly, in certain embodiments, the tibial tray perimeter profile and/or a tibial insert perimeter profile is preoperatively selected and/or designed to substantially match the perimeter profile of the patient's resected tibial surface. FIGS. 54A and B show an approach for identifying the patient's tibial implant perimeter profile based on the depth and angle of the proximal tibial resection, which can applied in the selection and/or design of the tibial tray perimeter profile and/or the tibial insert perimeter profile. As shown in the bottom image, the lines inside the perimeter of the cut surface represent the perimeters of the various cuts in the top image taken at various depths from the patient's tibial surface. FIGS. 55A and B show the same approach as described for FIGS. 54A and B, but applied to a different patient having a smaller tibia (e.g., smaller diameter and perimeter length).

Similarly, FIGS. 56A-D show four different exemplary tibial implant profiles, for example, having different medial and lateral condyle perimeter shapes that generally match various different relative medial and lateral condyle perimeter dimensions. In certain embodiments, a tibial tray and/or insert can be selected (e.g., preoperatively or intraoperatively) from a collection or library of implants for a particular patient (e.g., to best-match the perimeter of the patient's cut tibial surface) and implanted without further alteration to the perimeter profile. However, in certain embodiments, these different tibial tray and/or insert perimeter profiles can serve as blanks. For example, one of these tibial tray and/or insert profiles can be selected preoperatively from a library (e.g., an actual or virtual library) for a particular patient to best-match the perimeter of the patient's cut tibial surface. Then, the selected implant perimeter can be designed or further altered based on patient-specific data, for example, to substantially match the perimeter of the patient's cut tibial surface.

As described in this example, various features of a tibial implant component can be designed or altered based on patient-specific data. For example, the tibial implant component design or alterations can be made to maximize coverage and extend to cortical margins; maximize medial compartment coverage; minimize overhang from the medial compartment; avoid internal rotation of tibial components to avoid patellar dislocation; and avoid excessive external rotation to avoid overhang laterally and impingement on the popliteus tendon.

Example 5

Bone Cuts Using a Femur-First Jig Set

This example describes methods and devices for performing a series of bone cuts to receive a patient-specific implant. Specifically, a set of jigs is designed in connection with the design of a patient-specific implant component. The designed jigs guide the surgeon in performing one or more patient-specific cuts to the bone so that those cut bone surface(s) negatively-match the patient-specific bone cuts of the implant component. The set of jigs described in this example are designed for a femur-first cut technique.

Figure 57A:
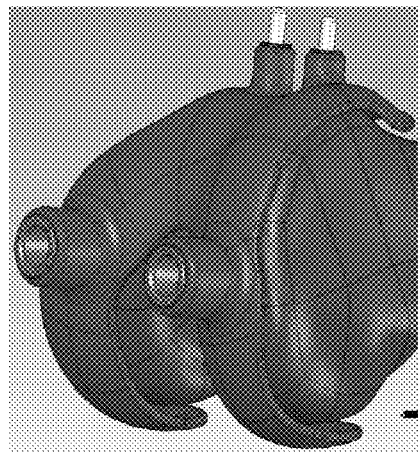
FIGS. 57A and B illustrate a first femur jig used to establish peg holes and pin placements for a subsequent jig used for a distal cut.
Figure 57B:
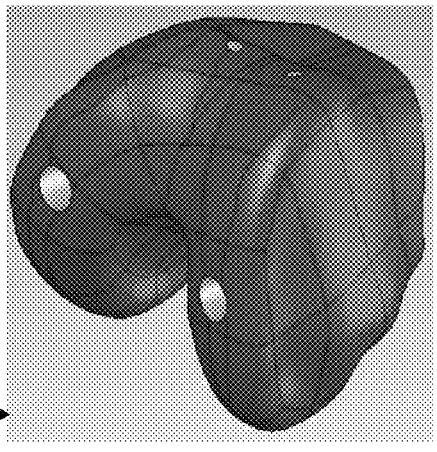
Figure 58A:
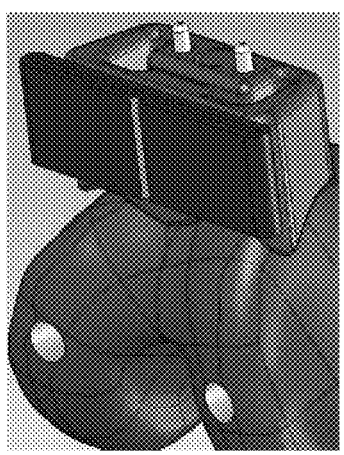
FIGS. 58A and B illustrate a distal femoral resection cut performed with a second femur jig.
Figure 58B:
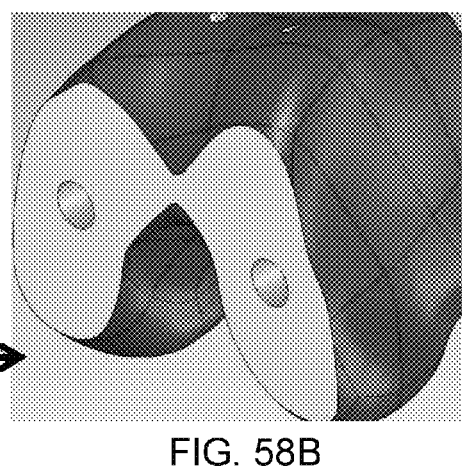
Figure 59A:
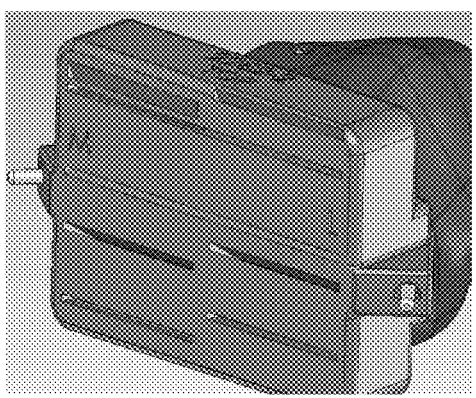
FIG. 59A illustrates an anterior cut, posterior cut, and chamfer cut performed with a third femur jig.
Figure 59B:
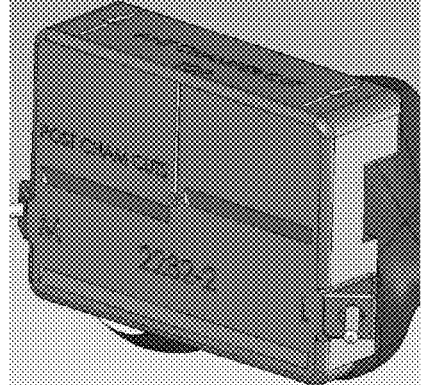
FIG. 59B illustrate an additional femoral jig for making additional resection cuts.

In a first step, shown in FIGS. 57A and B, a first femur jig is used to establish peg holes and pin placements for a subsequent jig used for a distal cut. In this example, the first jig is designed to circumvent 3 mm of cartilage thickness. In a second step, shown in FIGS. 58A and B, the distal cut is performed with a second femur jig. In this example, the second jig is patient-specific. However, in certain embodiments that apply a traditional distal cut, a standard jig can be used. In a third step, as shown in FIG. 59A, the anterior cut, the posterior cut, and the chamfer cuts are performed with a third femur jig. In this example, the jig includes slots that are 1.5 mm wide to allow for a saw blade thickness. As shown in FIG. 59B, in certain embodiments, for implant component designs having six or more inner, bone-facing surfaces, for example, having one or two additional chamfer cuts, the additional cuts can be performed using one or more additional jigs. In this example, the additional jig is designed to accommodate two steep additional chamfer cuts.

Figure 60A:
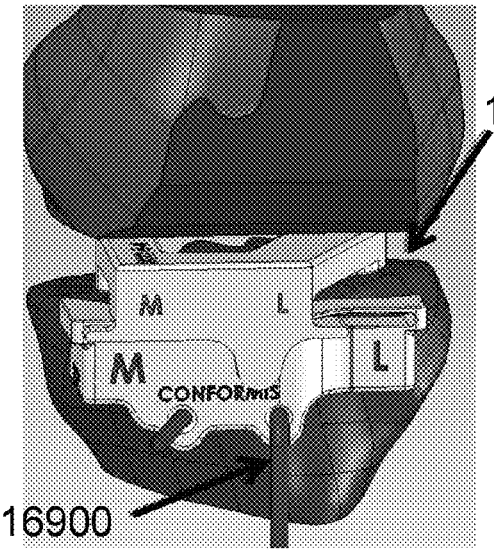
FIGS. 60A and 60B illustrate and exemplary tibial jig.
Figure 60B:
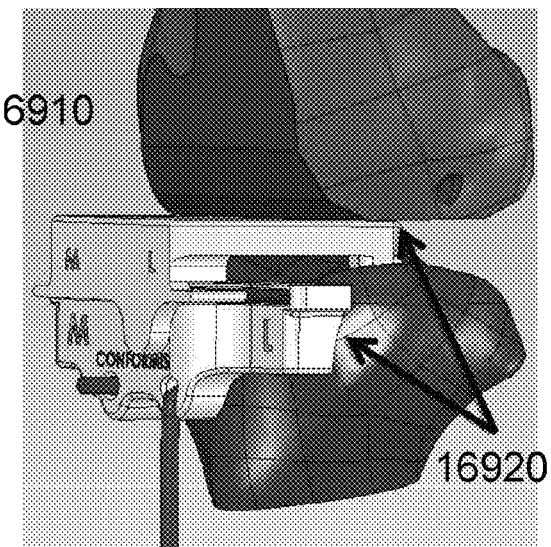

Next, the tibia is cut using one or more jigs designed to make patient-specific cuts to the tibia. An exemplary tibial jig is depicted in FIGS. 60A and B. A tibial alignment pin 16900 is used to help properly orient the jig. The portion 16910 of the jig inserted between the femur and tibia can have a variable thickness. In certain embodiments, the tibial jig can be designed to accommodate for composite thickness from the distal cut femur 16920. Alternatively or additionally, a balancing chip can be used to address differences in the distance between the tibia and femur surfaces. For example, in certain embodiments a tibia jig may be designed to rest on 2 mm of cartilage, while a balancing chip is designed to rest on the distal cut femur.

Figure 61:
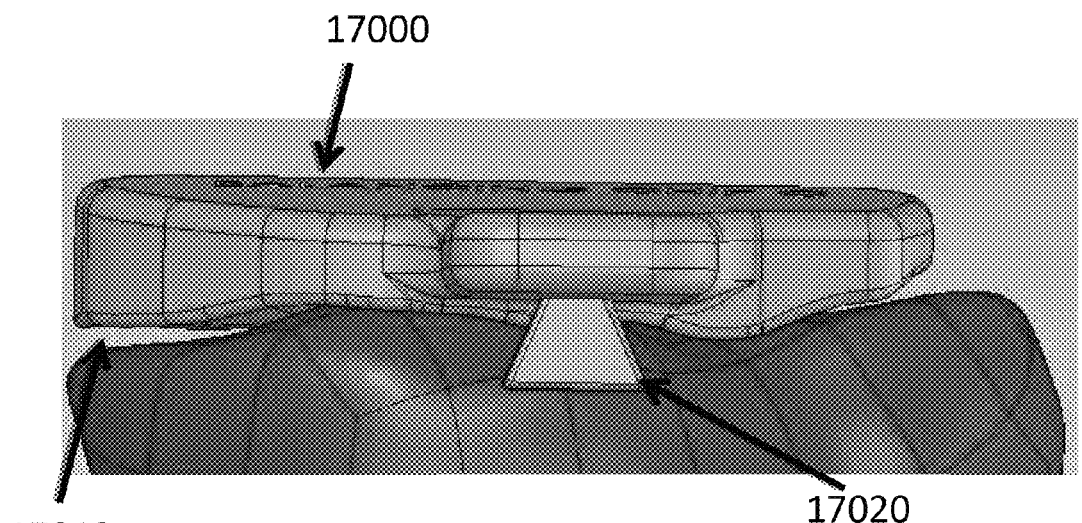
FIG. 61 illustrates and exemplary balancing chip.
Figure 62A:
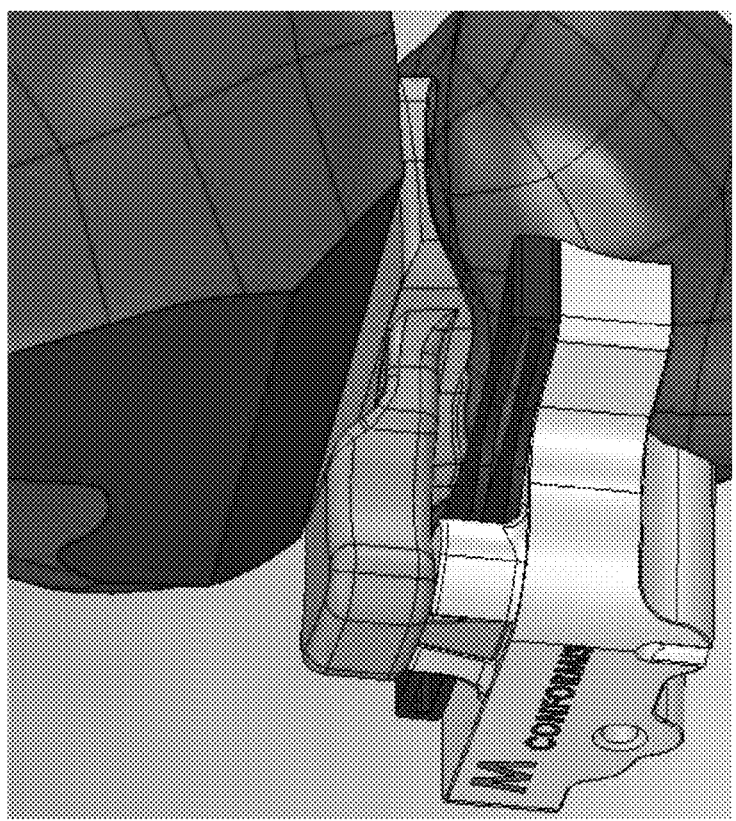
FIGS. 62A and B illustrate an exemplary balancing chip attached to a tibial jig.
Figure 62B:
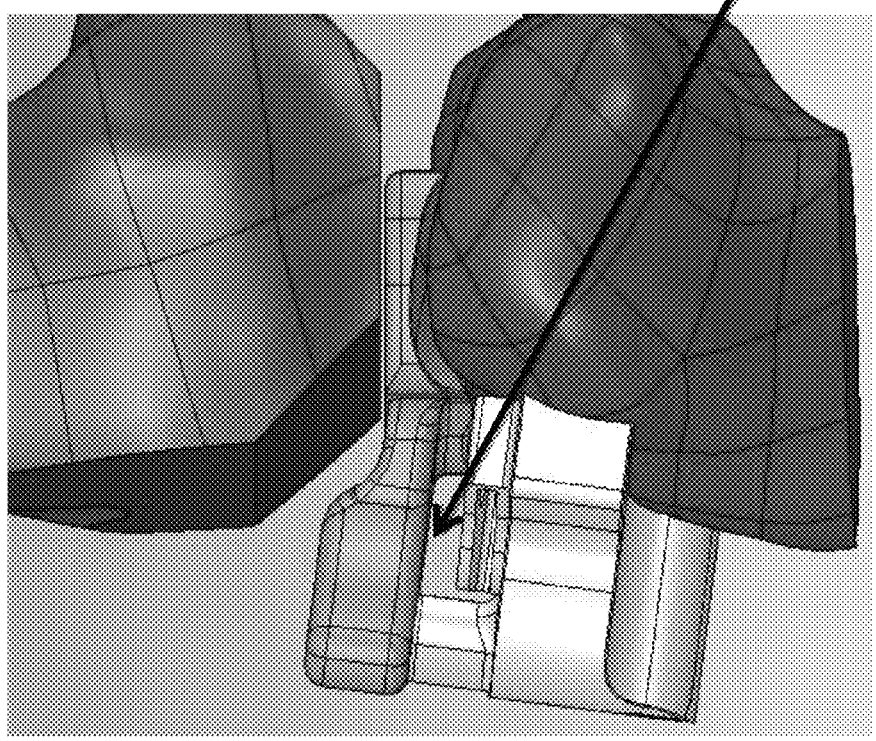

A balancing chip is shown in FIG. 61. If a varus deformity of the knee is observed, virtual realignment can be addressed by including added thickness to the balancing chip in the area that would produce a leg in neutral alignment 17010. For a grossly mal-aligned contra-lateral leg, correction can be per a surgeon's order. The balancing chip can include a feature 17020 to attach it to the tibia jig, and thereby allow for accurate distal placement of the tibial cut while at the same time accommodating for composite thickness. An exemplary balancing chip attached to a tibia jig is shown in FIGS. 62A and B. To facilitate attachment, the balancing chip handle 18000 matches the tibial slope designed into the tibial cut and tibial implant. Preferably, the balancing chip is designed to enter into the joint easily.

Example 6

Bone Cuts Using a Tibial-First Jig Set

This example describes methods and devices for performing a series of bone cuts to receive a patient-specific implant. Specifically, a set of jigs is designed in connection with the design of a patient-specific implant component. The designed jigs guide the surgeon in performing one or more patient-specific cuts to the bone so that those cut bone surface(s) negatively-match the patient-specific bone cuts of the implant component. The set of jigs described in this example are designed for cuts to a femoral implant component in a tibia-first cut technique.

Figure 63:
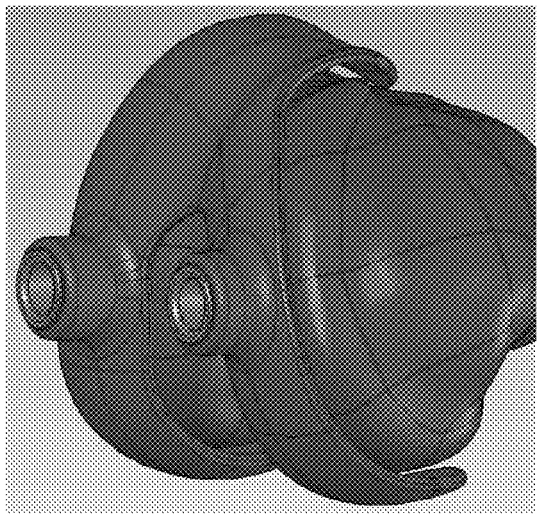
FIG. 63 illustrates a first jig used to establish placement and alignment of femoral implant peg holes.
Figure 64:
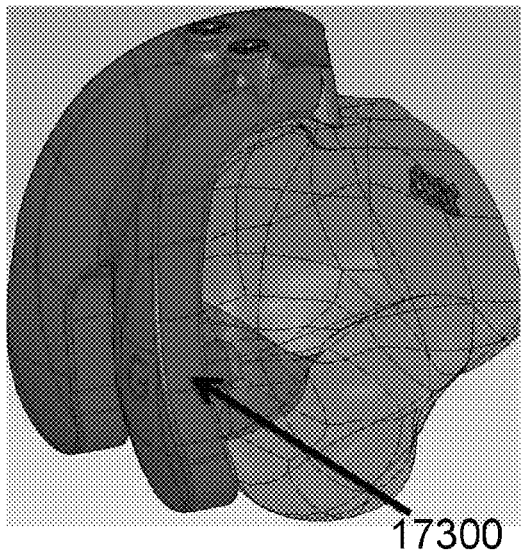
FIG. 64 illustrates a second jig used to establish placement pins for the distal cut jig.
Figure 65:
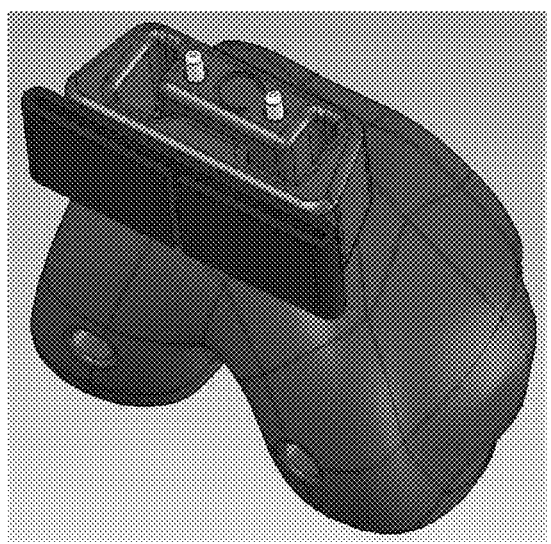
FIG. 65 illustrates a distal cut jig positioned based on the placement established by the previous jig.
Figure 66:
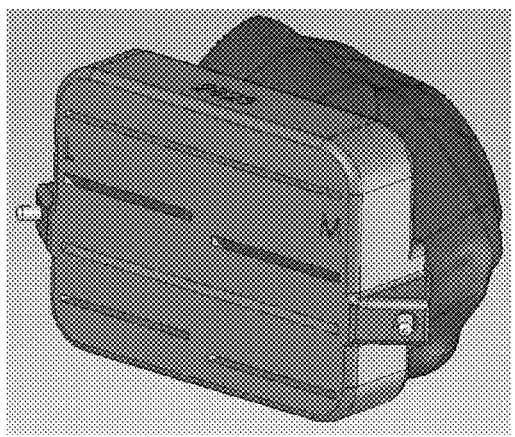
FIG. 66 illustrates remaining resection cuts performed with a chamfer cut jig.

In a first step, shown in FIG. 63, a first jig is used to establish placement and alignment of femoral implant peg holes. In the example, the placement is flexed 5 degrees with respect to the sagittal femoral axis. In a second step, shown in FIG. 64, a second jig is used to establish placement pins for the distal cut jig. The second jig can have different thicknesses 17300 to accommodate composite thickness from the cut tibial surface. In a third step, as shown in FIG. 65, a distal cut jig is positioned based on the placement established by the previous jig. The distal cut jig can be patient-specific or standard. Lastly, as shown in FIG. 66, remaining cuts are performed with a chamfer cut jig. In the example, the anterior cut is not oblique.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A tibial implant for a knee arthroplasty in a patient, the tibial implant comprising:
   (a) a tibial tray sized and shaped generally for placement on a proximal surface of a tibia of the patient and having at least one insert locking mechanism;
   (b) a first insert comprising a first reciprocal locking mechanism, a first bottom surface for engaging a surface of the tibial tray, a first articular surface portion generally opposite the first bottom surface, and a first thickness extending in a generally perpendicular direction between the first bottom surface and the first articular surface portion; and
   (c) a second insert comprising a second reciprocal locking mechanism, a second bottom surface for engaging a surface of the tibial tray, a second articular surface portion generally opposite the second bottom surface, and a second thickness extending in a generally perpendicular direction between the second bottom surface and the second articular surface portion;
   wherein the first thickness is greater than the second thickness, wherein the first articular surface portion or the second articular surface portion, or both, includes patient-adapted sagittal radii or curvature.

2. The tibial tray of claim 1, wherein the first and second thicknesses are measured from geographic centers of the first and second contact areas of the first and second articular surface portions, respectively.

3. The tibial tray of claim 1, wherein the first and second thicknesses are measured from corresponding edges of first and second contact areas of the first and second articular surface portions, respectively.

4. The tibial tray of claim 1, wherein the first and second thicknesses are measured from central points of the first and second articular surface portions, respectively.

5. The tibial tray of claim 1, wherein the first and second thicknesses are measured from the point of the first and second articular surfaces that are closest to the first and second bottom surface portions, respectively.

6. The tibial tray of claim 1, wherein the first and second thicknesses are measured from the point of the first and second articular surfaces that are furthest from the first and second bottom surface portions, respectively.

7. The tibial tray of claim 1, wherein the first and second thicknesses are average thicknesses of the first and second inserts, respectively.

8. The tibial tray of claim 1, wherein the first thickness is substantially greater than the second thickness.

9. The tibial tray of claim 1, wherein a difference in the thickness of the first and second thicknesses is a statistically significant difference.

10. The tibial tray of claim 1, wherein a difference in the thickness of the first and second thicknesses is a clinically significant difference.

11. The tibial tray of claim 1, wherein a difference in the thickness of the first and second thicknesses is sufficient to induce a clinical effect.

12. The tibial tray of claim 11, wherein the clinical effect is an alignment of at least a portion of the knee.

13. The tibial tray of claim 11, wherein the clinical effect is a balancing of at least a portion of the knee.

14. The tibial tray of claim 1, wherein the first and second inserts have different curvatures on respective articular surface portions.

15. The tibial tray of claim 1, wherein the first and second inserts have different slopes on respective articular surface portions.

16. A tibial implant for knee arthroplasty in a patient, the tibial implant comprising:
    (a) a medial tibial insert comprising (i) a substantially planar inner surface for engaging a medial tibial tray face and (ii) an articular surface comprising an articular surface plateau and disposed therein a curved portion for opposing an articular surface of a medial femoral condyle; and
    (b) a lateral tibial insert comprising (i) a substantially planar inner surface for engaging a lateral tibial tray face and (ii) an articular surface comprising an articular surface plateau and disposed therein a curved portion for opposing an articular surface of a lateral femoral condyle;
    wherein the distance from the inner surface to the articular surface of the medial tibial insert is different from the distance from the inner surface to the articular surface of the lateral tibial insert, and wherein the articular surface of the medical tibial insert, or the articular surface of the lateral tibial insert, or both, includes patient-adapted sagittal radii or curvature.

17. The tibial implant of claim 16, wherein the minimum distance from the inner surface to the articular surface of the medial tibial insert is different from the minimum distance from the inner surface to the articular surface of the lateral tibial insert.

18. The tibial implant of claim 16, wherein the maximum distance from the inner surface to the articular surface of the medial tibial insert is different from the maximum distance from the inner surface to the articular surface of the lateral tibial insert.

19. The tibial implant of claim 16, wherein the average distance from the inner surface to the articular surface of the medial tibial insert is different from the average distance from the inner surface to the articular surface of the lateral tibial insert.

20. The tibial implant of claim 16, wherein the distance from the inner surface to the articular surface of the medial tibial insert is substantially different from the distance from the inner surface to the articular surface of the lateral tibial insert.

21. The tibial implant of claim 16, wherein the distance from the inner surface to the articular surface of the medial tibial insert is significantly different from the distance from the inner surface to the articular surface of the lateral tibial insert.

22. The tibial implant of claim 16, wherein the distance from the inner surface to a central point of the articular surface of the medial tibial insert is different from the distance from the inner surface to a central point of the articular surface of the lateral tibial insert.

23. The tibial implant of claim 16, wherein the distance from the inner surface to a central point of a contact area of the articular surface of the medial tibial insert is different from the distance from the inner surface to a central point of a contact area of the articular surface of the lateral tibial insert.

24. The tibial implant of claim 16, wherein the distance from the inner surface to an edge of the articular surface of the medial tibial insert is different from the distance from the inner surface to an edge of the articular surface of the lateral tibial insert.

25. The tibial implant of claim 16, wherein a first tibial tray comprises the medial tibial tray face and a second tibial tray comprises the lateral tibial tray face.

26. The tibial implant of claim 16, wherein the medial and lateral tibial inserts have different curvatures in the respective curved portions.

27. The tibial implant of claim 16, wherein the medial and lateral tibial inserts have different articular surface plateau slopes.

28. The tibial implant of claim 16, wherein the slope for the articular surface plateau of the medial tibial insert is patient-matched to the patient's medial tibial plateau slope.

29. The tibial implant of claim 16, wherein the slope for the articular surface plateau of the medial tibial insert is patient-matched to the patient's lateral tibial plateau slope.

30. The tibial implant of claim 16, wherein the slope for the articular surface plateau of the lateral tibial insert is patient-matched to the patient's lateral tibial plateau slope.

31. The tibial implant of claim 16, wherein the slope for the articular surface plateau of the lateral tibial insert is patient-matched to the patient's medial tibial plateau slope.

32. A method for implanting a knee implant in a patient's knee joint, the method comprising the steps of:
    (a) preparing a proximal end of a tibia to receive an implant including at least one tibial implant; and
    (b) inserting the at least one tibial implant onto the prepared proximal end of the tibia such that a first articular surface of the at least one tibial implant engages a first articular surface of a femoral implant and a second articular surface of the at least one tibial implant engages a second articular surface of the femoral implant;
    wherein the first articular surface is higher than the second articular surface relative to an anatomical axis of the tibia, wherein the first articular surface, or the second articular surface, or both, includes patient-adapted sagittal radii or curvature.

33. The method of claim 32, wherein the at least one tibial implant comprises a single tibial implant tray.

34. The method of claim 33, further comprising a single tibial insert.

35. The method of claim 33, further comprising dual tibial inserts.

36. The method of claim 32, wherein the at least one tibial implant comprises two tibial implant trays.

37. The method of claim 36, further comprising a single tibial insert for each of the two tibial implant trays.

38. The method of claim 32, further comprising adjusting height of the first articular surface relative to the second articular surface.

39. The method of claim 32, further comprising aligning the patient's knee joint.

40. The method of claim 39, further comprising assessing the alignment of the patient's knee joint.

41. The method of claim 39, further comprising adjusting alignment of the patient's knee joint.

42. The method of claim 32, further comprising adjusting rotational alignment of the patient's knee joint.

43. The method of claim 32, further comprising adjusting linear alignment of the patient's knee joint.

44. The method of claim 32, further comprising adjusting alignment of the patient's femur and tibia.

45. The method of claim 32, further comprising adjusting a biomechanical axis of the patient's knee joint.

46. The method of claim 32, further comprising adjusting an anatomical axis of the patient's knee joint.

47. The method of claim 32, further comprising balancing a patient's knee joint.

48. The method of claim 47, further comprising assessing the balance of the patient's knee joint.

49. The method of claim 47, further comprising adjusting the balance of the patient's knee joint.

50. The method of claim 47, wherein balancing of the patient's knee joint comprises balancing of the patient's knee joint in extension.

51. The method of claim 47, wherein balancing of the patient's knee joint comprises balancing of the patient's knee joint in flexion.

52. The method of claim 32, further comprising planning a surgical procedure based on electronic image data of the patient's knee joint.

53. The method of claim 52, further comprising performing the surgical procedure.

54. The method of claim 52, further comprising planning the surgical procedure based on electronic image data of the patient's knee in order to achieve a predetermined surgical result.

55. The method of claim 54, wherein step (b) substantially achieves the predetermined surgical result.

56. The method of claim 54, wherein the surgical result includes joint balancing.

57. The method of claim 54, wherein the surgical result includes joint alignment.

58. The method of claim 32, wherein step (b) comprises inserting a first insert.

59. The method of claim 58, further comprising adjusting balance with a second insert.

60. The method of claim 58, further comprising adjusting alignment with a second insert.

61. The method of claim 58, further comprising inserting a second insert.

62. The method of claim 61, further comprising replacing the second insert with a third insert.

63. The method of claim 62, further comprising adjusting balance with the third insert.

64. The method of claim 62, further comprising adjusting alignment with the third insert.

65. A kit for implanting a tibial implant in a patient in need of knee replacement, the kit comprising:
 (a) a tibial tray comprising a first surface for affixing the tray to the patient's tibia and an opposing second surface for engaging a medial tibial insert; and
 (b) two or more medial tibial inserts having different thicknesses from which to select one medial tibial insert for engaging with the tibial tray, wherein the two or more medial tibial inserts include an articular surface that has patient-adapted sagittal radii or curvature.

66. A kit for implanting a tibial implant in a patient in need of knee replacement, the kit comprising:
 (a) a tibial tray comprising a first surface for affixing the tray to the patient's tibia and an opposing second surface for engaging a lateral tibial insert; and
 (b) two or more lateral tibial inserts having different thicknesses from which to select one lateral tibial insert for engaging with the tibial tray, wherein the two or more lateral tibial inserts include an articular surface that has patient-adapted sagittal radii or curvature.

* * * * *